US008188036B2

(12) United States Patent
Abad et al.

(10) Patent No.: US 8,188,036 B2
(45) Date of Patent: *May 29, 2012

(54) GENES ENCODING NOVEL PROTEINS WITH PESTICIDAL ACTIVITY AGAINST COLEOPTERANS

(75) Inventors: Andre R. Abad, West Des Moines, IA (US); Nicholas B. Duck, Apex, NC (US); Xiang Feng, West Des Moines, IA (US); Ronald D. Flannagan, Grimes, IA (US); Theodore W. Kahn, Johnston, IA (US); Lynne E. Sims, Polk City, IA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 101 days.

This patent is subject to a terminal disclaimer.

(21) Appl. No.: 12/472,997

(22) Filed: May 27, 2009

(65) Prior Publication Data

US 2009/0291896 A1    Nov. 26, 2009

Related U.S. Application Data

(62) Division of application No. 10/032,717, filed on Oct. 23, 2001, now Pat. No. 7,605,304.

(60) Provisional application No. 60/242,838, filed on Oct. 24, 2000.

(51) Int. Cl.
*A01N 37/18* (2006.01)
(52) U.S. Cl. ...................................... 514/4.5
(58) Field of Classification Search .................. None
See application file for complete search history.

(56) References Cited

U.S. PATENT DOCUMENTS

| | | | |
|---|---|---|---|
| 5,554,534 A | 9/1996 | Michaels et al. | |
| 5,659,123 A | 8/1997 | Van Rie et al. | |
| 6,313,378 B1 | 11/2001 | Baum et al. | |
| 7,105,332 B2 | 9/2006 | Abad et al. | |
| 7,339,092 B2 * | 3/2008 | Abad et al. | 800/302 |
| 7,378,499 B2 * | 5/2008 | Abad et al. | 530/350 |
| 7,462,760 B2 * | 12/2008 | Abad et al. | 800/302 |
| 7,473,821 B2 * | 1/2009 | Abad et al. | 800/302 |
| 7,556,936 B2 | 7/2009 | Abad et al. | |
| 7,629,449 B2 | 12/2009 | Abad et al. | |
| 7,910,807 B2 * | 3/2011 | Abad et al. | 800/302 |
| 2009/0317891 A1 | 12/2009 | Abad et al. | |

FOREIGN PATENT DOCUMENTS

WO    93/15206    8/1993

OTHER PUBLICATIONS de Maagd et al, 1999, Appl. Environ. Microbiol. 65:4369-4374.*
Tounsi et al, 2003, J. Appl. Microbiol. 95:23-28.*
Aaronson et al (2001, FEMS Microbiol. Lett. 195:1-8).*
De Maagd et al (2001, Trends Genet. 17:193-199).*
Guo et al (2004, Proc. Natl. Acad. Sci. USA 101: 9205-9210).*

Angsuthanasombat, C., et al., "Effects on Toxicity of Eliminating a Cleavage Site in a Predicted Interhelical Loop in *Bacillus thuringiensis* CryIVB δ-Endotoxin," *FEMS Microbiology Letters*, 1993, pp. 255-262, vol. 111, Elsevier Science, UK.
Aronson, A., and Y. Shai, "Why *Bacillus thuringiensis* Insecticidal Toxins are so Effective: Unique Features of Their Mode of Action," *FEMS Microbiology Letters*, 2001, pp. 1-8, vol. 195, Elsevier Science, UK.
Bravo et al., "Characterization of *cry* Genes in a Mexican *Bacillus thuringiensis* Strain Collection," *Applied and Environmental Microbiology*, 1998, pp. 4965-4972, vol. 64(12).
Carroll, J., et al., "Intramolecular Proteolytic Cleavage of *Bacillus thuringiensis* Cry3A δ-Endotoxin May Facilitate its Coleopteran Toxicity," *Journal of Invertebrate Pathology*, 1997, pp. 41-49, vol. 70, Academic Press.
Chen, X., et al., "Mutations in Domain I of *Bacillus thuringiensis* δ-Endotoxin CryIAb Reduce the Irreversible Binding of Toxin in *Manduca sexta* Brush Border Membrane Vesicles," *Journal of Biological Chemistry*, 1995, pp. 6412-6419, vol. 270(11), USA.
Gazit, E., et al.,"The Structure and Organization Within the Membrane of the Helices Composing the Pore-Forming Domain of *Bacillus thuringiensis* δ-Endotoxin are Consistent with an "Umbrella-Like" Structure of the Pore," *Proc. Natl. Acad. Sci USA*, 1998, pp. 12289-12294, vol. 951.
Koiwa, H., et al., "A Plant Defensive Cystatin (Soyacystatin) Targets Cathepsin L-like Digestive Cysteine Proteinases (DvCALs) in the larval Midgut of Western Corn Rootworm (*Diabrotica virgifera virgifera*)," *FEBS Letters 471*, 2000, pp. 67-70.
Li, J., et al.,"Crystal Structure of Insecticidal δ-Endotoxin from *Bacillus thuringiensis* at 2.5 ÅResolution," *Nature*, 1991, pp. 815-821, vol. 353.
Masson, L., et al., "Helix 4 of the *Bacillus thuringiensis* Cry1Aa Toxin Lines the Lumen of the Ion Channel," *Journal of Biological Chemistry*, 1999, pp. 31996-32000, vol. 274(45).
Melo, R.L., et al., "Synthesis and Hydrolysis by Cysteine and Serine Proteases of Short Internally Quenched Fluorogenic Peptides," *Analytical Biochemistry*, 2001, pp. 71-77, vol. 23.
Naidu et al., "Screening of *Bacillus thuringiensis* Serotypes by Polymerase Chain Reaction (PCR) for Insecticidal Crystal Genes Toxic Against Coffee Berry Borer," *Indian Journal of Experimental Biology*, 2001, pp. 148-154, vol. 39.
Oppert, B., "Protease Interactions with *Bacillus thuringiensis* Insecticidal Toxins," *Arch. Insect Biochem. Physiol*. 1999, pp. 1-12, vol. 42, Wiley-Liss, Inc., USA.

(Continued)

*Primary Examiner* — Anne Kubelik
(74) *Attorney, Agent, or Firm* — Alston & Bird LLP

(57) ABSTRACT

The invention provides nucleic acids, and variants and fragments thereof, obtained from strains of *Bacillus thuringiensis* encoding δ-endotoxins having pesticidal activity against pests of the order Coleoptera. The invention further provides mutagenized nucleic acids that have been modified to encode endotoxins having improved pesticidal activity and/or altered pest specificity. Particular embodiments of the invention provide isolated nucleic acids encoding pesticidal proteins, pesticidal compositions, expression cassettes, and transformed microorganisms and plants comprising a nucleic acid of the invention. These compositions find use in methods for controlling pests, especially plant pests.

12 Claims, No Drawings

OTHER PUBLICATIONS

Purcell, J.P., et al., "Examination of Midgut Luminal Proteinase Activities in Six Economically Important Insects," *Insect Biochem. Molec. Biol.*, 1992, pp. 41-47, vol. 22(1).

Schwartz, J., et al., "Restriction of Intramolecular Movements Within the CrylAa Toxin Molecule of *Bacillus thuringiensis* Through Disulfide Bond Engineering," *FEBS Letters*, 1997, pp. 397-402, vol. 410.

Shiba, H., et al., "Involvement of Cathepsin B- and L-Like Proteinases in Silk Gland Histolysis During Metamorphosis of *Bombyx mori*," *Archives of Biochemistry and Biophysics*, 2001, pp. 28-34, vol. 390(1).

Sun et al., "Recent Developments in the Biotechnology of *Bacillus thuringiensis*," *Biotechnology Advances*, 2000, pp. 143-145, vol. 18(2).

Wu, D. and A. Aronson, "Localized Mutagenesis Defines Regions of the *Bacillus thuringiensis* δ-Endotoxin Involved in Toxicity and Specificity," *Journal of Biological Chemistry*, 1992, pp. 2311-2317, vol. 267(4).

Wu, S., et al., "Enhanced Toxicity of *Bacillus thuringiensis* Cry3A δ-Endotoxin in Coleopterans by Mutagenesis in a Receptor Binding Loop," *FEBS Letters*, 2000, pp. 227-232, vol. 473.

\* cited by examiner

SEQUENCE LISTING

```
<160> NUMBER OF SEQ ID NOS: 48

<210> SEQ ID NO 1
<211> LENGTH: 3621
<212> TYPE: DNA
<213> ORGANISM: Bacillus thuringiensis
<220> FEATURE:
<221> NAME/KEY: misc_feature
<223> OTHER INFORMATION: Cry1218-1
```

```
<220> FEATURE:
<221> NAME/KEY: CDS
<222> LOCATION: (1)..(3621)

<400> SEQUENCE: 1 atg agt cca aat aat caa aat gaa tat gaa att ata gat gcg aca cct       48
Met Ser Pro Asn Asn Gln Asn Glu Tyr Glu Ile Ile Asp Ala Thr Pro
1               5                   10                  15 tct act tct gta tcc aat gat tct aac aga tac cct ttt gcg aat gag       96
Ser Thr Ser Val Ser Asn Asp Ser Asn Arg Tyr Pro Phe Ala Asn Glu
            20                  25                  30 cca aca aat gcg cta caa aat atg gat tat aaa gat tat tta aaa atg      144
Pro Thr Asn Ala Leu Gln Asn Met Asp Tyr Lys Asp Tyr Leu Lys Met
        35                  40                  45 tct gcg gga aat gct agt gaa tac cct ggt tca cct gaa gta ctt gtt      192
Ser Ala Gly Asn Ala Ser Glu Tyr Pro Gly Ser Pro Glu Val Leu Val
    50                  55                  60 agc gga caa gat gca gct aag gcc gca att gat ata gta ggt aaa tta      240
Ser Gly Gln Asp Ala Ala Lys Ala Ala Ile Asp Ile Val Gly Lys Leu
65                  70                  75                  80 cta tca ggt tta ggg gtc cca ttt gtt ggg ccg ata gtg agt ctt tat      288
Leu Ser Gly Leu Gly Val Pro Phe Val Gly Pro Ile Val Ser Leu Tyr
                85                  90                  95 act caa ctt att gat att ctg tgg cct tca ggg gaa aag agt caa tgg      336
Thr Gln Leu Ile Asp Ile Leu Trp Pro Ser Gly Glu Lys Ser Gln Trp
            100                 105                 110 gaa att ttt atg gaa caa gta gaa gaa ctc att aat caa aaa ata gca      384
Glu Ile Phe Met Glu Gln Val Glu Glu Leu Ile Asn Gln Lys Ile Ala
        115                 120                 125 gaa tat gca agg aat aaa gcg ctt tcg gaa tta gaa gga tta ggt aat      432
Glu Tyr Ala Arg Asn Lys Ala Leu Ser Glu Leu Glu Gly Leu Gly Asn
    130                 135                 140 aat tac caa tta tat cta act gcg ctt gaa gaa tgg gaa gaa aat cca      480
Asn Tyr Gln Leu Tyr Leu Thr Ala Leu Glu Glu Trp Glu Glu Asn Pro
145                 150                 155                 160 aat ggt tca aga gcc tta cga gat gtg cga aat cga ttt gaa atc ctg      528
Asn Gly Ser Arg Ala Leu Arg Asp Val Arg Asn Arg Phe Glu Ile Leu
                165                 170                 175 gat agt tta ttt acg caa tat atg cca tct ttt aga gtg aca aat ttt      576
Asp Ser Leu Phe Thr Gln Tyr Met Pro Ser Phe Arg Val Thr Asn Phe
            180                 185                 190 gaa gta cca ttc ctt act gta tat gca atg gca gcc aac ctt cat tta      624
Glu Val Pro Phe Leu Thr Val Tyr Ala Met Ala Ala Asn Leu His Leu
        195                 200                 205 ctg tta tta aag gac gcg tca att ttt gga gaa gaa tgg gga tgg tca      672
Leu Leu Leu Lys Asp Ala Ser Ile Phe Gly Glu Glu Trp Gly Trp Ser
    210                 215                 220 aca act act att aat aac tat tat gat cgt caa atg aaa ctt act gca      720
Thr Thr Thr Ile Asn Asn Tyr Tyr Asp Arg Gln Met Lys Leu Thr Ala
225                 230                 235                 240 gaa tat tct gat cac tgt gta aag tgg tat gaa act ggt tta gca aaa      768
Glu Tyr Ser Asp His Cys Val Lys Trp Tyr Glu Thr Gly Leu Ala Lys
                245                 250                 255 tta aaa ggc acg agc gct aaa caa tgg gtt gac tat aac caa ttc cgt      816
Leu Lys Gly Thr Ser Ala Lys Gln Trp Val Asp Tyr Asn Gln Phe Arg
            260                 265                 270 aga gaa atg aca ctg gcg gtt tta gat gtt gtt gca tta ttc cca aat      864
Arg Glu Met Thr Leu Ala Val Leu Asp Val Val Ala Leu Phe Pro Asn
        275                 280                 285 tat gac aca cgc acg tac cca atg gaa acg aaa gca caa cta aca agg      912
Tyr Asp Thr Arg Thr Tyr Pro Met Glu Thr Lys Ala Gln Leu Thr Arg
```

|          |          |          |          |          |          |          |          |          |          |          |          |          |          |          |          |      |
|----------|----------|----------|----------|----------|----------|----------|----------|----------|----------|----------|----------|----------|----------|----------|----------|------|
|          |          |          | 290      |          |          |          | 295      |          |          |          | 300      |          |          |          |          |      |
| gaa      | gta      | tat      | aca      | gat      | cca      | ctg      | ggc      | gcg      | gta      | aac      | gtg      | tct      | tca      | att      | ggt      | 960  |
| Glu      | Val      | Tyr      | Thr      | Asp      | Pro      | Leu      | Gly      | Ala      | Val      | Asn      | Val      | Ser      | Ser      | Ile      | Gly      |      |
| 305      |          |          |          |          | 310      |          |          |          |          | 315      |          |          |          |          | 320      |      |
| tcc      | tgg      | tat      | gac      | aaa      | gca      | cct      | tct      | ttc      | gga      | gtg      | ata      | gaa      | tca      | tcc      | gtt      | 1008 |
| Ser      | Trp      | Tyr      | Asp      | Lys      | Ala      | Pro      | Ser      | Phe      | Gly      | Val      | Ile      | Glu      | Ser      | Ser      | Val      |      |
|          |          |          |          | 325      |          |          |          |          | 330      |          |          |          |          | 335      |          |      |
| att      | cga      | cca      | ccc      | cat      | gta      | ttt      | gat      | tat      | ata      | acg      | gga      | ctc      | aca      | gtg      | tat      | 1056 |
| Ile      | Arg      | Pro      | Pro      | His      | Val      | Phe      | Asp      | Tyr      | Ile      | Thr      | Gly      | Leu      | Thr      | Val      | Tyr      |      |
|          |          |          | 340      |          |          |          |          | 345      |          |          |          |          | 350      |          |          |      |
| aca      | caa      | tca      | aga      | agc      | att      | tct      | tcc      | gct      | cgc      | tat      | ata      | aga      | cat      | tgg      | gct      | 1104 |
| Thr      | Gln      | Ser      | Arg      | Ser      | Ile      | Ser      | Ser      | Ala      | Arg      | Tyr      | Ile      | Arg      | His      | Trp      | Ala      |      |
|          |          |          |          | 355      |          |          |          |          | 360      |          |          |          |          | 365      |          |      |
| ggt      | cat      | caa      | ata      | agc      | tac      | cat      | cgt      | gtc      | agt      | agg      | ggt      | agt      | aat      | ctt      | caa      | 1152 |
| Gly      | His      | Gln      | Ile      | Ser      | Tyr      | His      | Arg      | Val      | Ser      | Arg      | Gly      | Ser      | Asn      | Leu      | Gln      |      |
|          | 370      |          |          |          |          | 375      |          |          |          |          | 380      |          |          |          |          |      |
| caa      | atg      | tat      | gga      | act      | aat      | caa      | aat      | cta      | cac      | agc      | act      | agt      | acc      | ttt      | gat      | 1200 |
| Gln      | Met      | Tyr      | Gly      | Thr      | Asn      | Gln      | Asn      | Leu      | His      | Ser      | Thr      | Ser      | Thr      | Phe      | Asp      |      |
| 385      |          |          |          |          | 390      |          |          |          |          | 395      |          |          |          |          | 400      |      |
| ttt      | acg      | aat      | tat      | gat      | att      | tac      | aag      | act      | cta      | tca      | aag      | gat      | gca      | gta      | ctc      | 1248 |
| Phe      | Thr      | Asn      | Tyr      | Asp      | Ile      | Tyr      | Lys      | Thr      | Leu      | Ser      | Lys      | Asp      | Ala      | Val      | Leu      |      |
|          |          |          |          | 405      |          |          |          |          | 410      |          |          |          |          | 415      |          |      |
| ctt      | gat      | att      | gtt      | tac      | cct      | ggt      | tat      | acg      | tat      | ata      | ttt      | ttt      | gga      | atg      | cca      | 1296 |
| Leu      | Asp      | Ile      | Val      | Tyr      | Pro      | Gly      | Tyr      | Thr      | Tyr      | Ile      | Phe      | Phe      | Gly      | Met      | Pro      |      |
|          |          |          | 420      |          |          |          |          | 425      |          |          |          |          | 430      |          |          |      |
| gaa      | gtc      | gag      | ttt      | ttc      | atg      | gta      | aac      | caa      | ttg      | aat      | aat      | acc      | aga      | aag      | acg      | 1344 |
| Glu      | Val      | Glu      | Phe      | Phe      | Met      | Val      | Asn      | Gln      | Leu      | Asn      | Asn      | Thr      | Arg      | Lys      | Thr      |      |
|          |          | 435      |          |          |          |          | 440      |          |          |          |          | 445      |          |          |          |      |
| tta      | aag      | tat      | aat      | cca      | gtt      | tcc      | aaa      | gat      | att      | ata      | gcg      | agt      | aca      | aga      | gat      | 1392 |
| Leu      | Lys      | Tyr      | Asn      | Pro      | Val      | Ser      | Lys      | Asp      | Ile      | Ile      | Ala      | Ser      | Thr      | Arg      | Asp      |      |
| 450      |          |          |          |          | 455      |          |          |          |          | 460      |          |          |          |          |          |      |
| tcg      | gaa      | tta      | gaa      | tta      | cct      | cca      | gaa      | act      | tca      | gat      | caa      | cca      | aat      | tat      | gag      | 1440 |
| Ser      | Glu      | Leu      | Glu      | Leu      | Pro      | Pro      | Glu      | Thr      | Ser      | Asp      | Gln      | Pro      | Asn      | Tyr      | Glu      |      |
| 465      |          |          |          |          | 470      |          |          |          |          | 475      |          |          |          |          | 480      |      |
| tca      | tat      | agc      | cat      | aga      | tta      | tgt      | cat      | atc      | aca      | agt      | att      | ccc      | gcg      | acg      | ggt      | 1488 |
| Ser      | Tyr      | Ser      | His      | Arg      | Leu      | Cys      | His      | Ile      | Thr      | Ser      | Ile      | Pro      | Ala      | Thr      | Gly      |      |
|          |          |          |          | 485      |          |          |          |          | 490      |          |          |          |          | 495      |          |      |
| aac      | act      | acc      | gga      | tta      | gta      | cct      | gta      | ttt      | tct      | tgg      | aca      | cat      | cga      | agt      | gca      | 1536 |
| Asn      | Thr      | Thr      | Gly      | Leu      | Val      | Pro      | Val      | Phe      | Ser      | Trp      | Thr      | His      | Arg      | Ser      | Ala      |      |
|          |          |          | 500      |          |          |          |          | 505      |          |          |          |          | 510      |          |          |      |
| gat      | tta      | aac      | aat      | aca      | ata      | tat      | tca      | gat      | aaa      | atc      | act      | caa      | att      | ccg      | gcc      | 1584 |
| Asp      | Leu      | Asn      | Asn      | Thr      | Ile      | Tyr      | Ser      | Asp      | Lys      | Ile      | Thr      | Gln      | Ile      | Pro      | Ala      |      |
|          |          |          |          | 515      |          |          |          |          | 520      |          |          |          |          | 525      |          |      |
| gtt      | aaa      | tgt      | tgg      | gat      | aat      | tta      | ccg      | ttt      | gtt      | cca      | gtg      | gta      | aaa      | gga      | cca      | 1632 |
| Val      | Lys      | Cys      | Trp      | Asp      | Asn      | Leu      | Pro      | Phe      | Val      | Pro      | Val      | Val      | Lys      | Gly      | Pro      |      |
| 530      |          |          |          |          | 535      |          |          |          |          | 540      |          |          |          |          |          |      |
| gga      | cat      | aca      | gga      | ggg      | gat      | tta      | tta      | cag      | tat      | aat      | aga      | agt      | act      | ggt      | tct      | 1680 |
| Gly      | His      | Thr      | Gly      | Gly      | Asp      | Leu      | Leu      | Gln      | Tyr      | Asn      | Arg      | Ser      | Thr      | Gly      | Ser      |      |
| 545      |          |          |          |          | 550      |          |          |          |          | 555      |          |          |          |          | 560      |      |
| gta      | gga      | acc      | tta      | ttt      | cta      | gct      | cga      | tat      | ggc      | cta      | gca      | tta      | gaa      | aaa      | gca      | 1728 |
| Val      | Gly      | Thr      | Leu      | Phe      | Leu      | Ala      | Arg      | Tyr      | Gly      | Leu      | Ala      | Leu      | Glu      | Lys      | Ala      |      |
|          |          |          |          | 565      |          |          |          |          | 570      |          |          |          |          | 575      |          |      |
| ggg      | aaa      | tat      | cgt      | gta      | aga      | ctg      | aga      | tat      | gct      | act      | gat      | gca      | gat      | att      | gta      | 1776 |
| Gly      | Lys      | Tyr      | Arg      | Val      | Arg      | Leu      | Arg      | Tyr      | Ala      | Thr      | Asp      | Ala      | Asp      | Ile      | Val      |      |
|          |          |          | 580      |          |          |          |          | 585      |          |          |          |          | 590      |          |          |      |
| ttg      | cat      | gta      | aac      | gat      | gct      | cag      | att      | cag      | atg      | cca      | aaa      | aca      | atg      | aac      | cca      | 1824 |
| Leu      | His      | Val      | Asn      | Asp      | Ala      | Gln      | Ile      | Gln      | Met      | Pro      | Lys      | Thr      | Met      | Asn      | Pro      |      |
|          |          |          |          | 595      |          |          |          |          | 600      |          |          |          |          | 605      |          |      |
| ggt      | gag      | gat      | ctg      | aca      | tct      | aaa      | act      | ttt      | aaa      | gtt      | gca      | gat      | gct      | atc      | aca      | 1872 |
| Gly      | Glu      | Asp      | Leu      | Thr      | Ser      | Lys      | Thr      | Phe      | Lys      | Val      | Ala      | Asp      | Ala      | Ile      | Thr      |      |

```
                    610                 615                 620
aca tta aat tta gca aca gat agt tcg cta gca ttg aaa cat aat tta    1920
Thr Leu Asn Leu Ala Thr Asp Ser Ser Leu Ala Leu Lys His Asn Leu
625                 630                 635                 640 ggt gaa gac cct aat tca aca tta tct ggt ata gtt tac gtt gac cga    1968
Gly Glu Asp Pro Asn Ser Thr Leu Ser Gly Ile Val Tyr Val Asp Arg
                645                 650                 655 atc gaa ttc atc cca gta gat gag aca tat gaa gcg gaa caa gat tta    2016
Ile Glu Phe Ile Pro Val Asp Glu Thr Tyr Glu Ala Glu Gln Asp Leu
            660                 665                 670 gaa gca gcg aag aaa gca gtg aat gcc ttg ttt acg aat aca aaa gat    2064
Glu Ala Ala Lys Lys Ala Val Asn Ala Leu Phe Thr Asn Thr Lys Asp
        675                 680                 685 ggc tta cga cca ggc gta acg gat tat gaa gtg aat caa gcg gca aac    2112
Gly Leu Arg Pro Gly Val Thr Asp Tyr Glu Val Asn Gln Ala Ala Asn
    690                 695                 700 tta gtg gaa tgc cta tcg gat gat ttg tat cca aat gaa aaa cga ttg    2160
Leu Val Glu Cys Leu Ser Asp Asp Leu Tyr Pro Asn Glu Lys Arg Leu
705                 710                 715                 720 tta ttt gat gca gtg aga gag gca aaa cgc ctc agt gag gca cgt aat    2208
Leu Phe Asp Ala Val Arg Glu Ala Lys Arg Leu Ser Glu Ala Arg Asn
                725                 730                 735 ttg ctt caa gat cca gat ttc caa gag ata aat gga gaa aat ggc tgg    2256
Leu Leu Gln Asp Pro Asp Phe Gln Glu Ile Asn Gly Glu Asn Gly Trp
            740                 745                 750 acg gca agt acg gga att gag gtt ata gaa ggg gat gct tta ttc aaa    2304
Thr Ala Ser Thr Gly Ile Glu Val Ile Glu Gly Asp Ala Leu Phe Lys
        755                 760                 765 ggg cgt tat cta cgc cta cca ggt gcg aga gaa ata gat acg gaa acg    2352
Gly Arg Tyr Leu Arg Leu Pro Gly Ala Arg Glu Ile Asp Thr Glu Thr
    770                 775                 780 tat cca acg tat ctg tat caa aaa gta gag gaa ggt gta tta aaa cca    2400
Tyr Pro Thr Tyr Leu Tyr Gln Lys Val Glu Glu Gly Val Leu Lys Pro
785                 790                 795                 800 tac aca aga tat aga ttg aga ggg ttt gtc gga agc agt caa gga ttg    2448
Tyr Thr Arg Tyr Arg Leu Arg Gly Phe Val Gly Ser Ser Gln Gly Leu
                805                 810                 815 gaa att ttc aca att cgt cat caa acg aac cga att gta aaa aat gta    2496
Glu Ile Phe Thr Ile Arg His Gln Thr Asn Arg Ile Val Lys Asn Val
            820                 825                 830 ccg gat gat ttg ctg cca gat gta tct cct gtt aac tcg gat ggt agt    2544
Pro Asp Asp Leu Leu Pro Asp Val Ser Pro Val Asn Ser Asp Gly Ser
        835                 840                 845 atc aat cga tgc agc gaa caa aag tat gtg aat agc cgt tta gaa gta    2592
Ile Asn Arg Cys Ser Glu Gln Lys Tyr Val Asn Ser Arg Leu Glu Val
    850                 855                 860 gaa aac cgt tct ggt gaa gcg cat gag ttc tct att cct att gat aca    2640
Glu Asn Arg Ser Gly Glu Ala His Glu Phe Ser Ile Pro Ile Asp Thr
865                 870                 875                 880 ggt gaa atc gat tac aat gaa aat gca gga ata tgg gtt gga ttt aag    2688
Gly Glu Ile Asp Tyr Asn Glu Asn Ala Gly Ile Trp Val Gly Phe Lys
                885                 890                 895 att acg gac cca gag gga tat gca aca ctc gga aac cta gaa ttg gtc    2736
Ile Thr Asp Pro Glu Gly Tyr Ala Thr Leu Gly Asn Leu Glu Leu Val
            900                 905                 910 gaa gag gga cct tta tca gga gac gca tta gaa cgc ttg caa aga gaa    2784
Glu Glu Gly Pro Leu Ser Gly Asp Ala Leu Glu Arg Leu Gln Arg Glu
        915                 920                 925 gaa caa cag tgg aag att caa atg aca aga aga cgt gaa gaa aca gat    2832
Glu Gln Gln Trp Lys Ile Gln Met Thr Arg Arg Arg Glu Glu Thr Asp
```

```
                    930             935             940
aga agg tat atg gca tcg aaa caa gcg gta gat cgt tta tat gcc gat      2880
Arg Arg Tyr Met Ala Ser Lys Gln Ala Val Asp Arg Leu Tyr Ala Asp
945                 950                 955                 960 tat cag gat cag caa ctg aat cct gat gta gag att aca gat ctt act      2928
Tyr Gln Asp Gln Gln Leu Asn Pro Asp Val Glu Ile Thr Asp Leu Thr
                965                 970                 975 gcg gcc caa gat ctg ata cag tcc att cct tac gta tat aac gaa atg      2976
Ala Ala Gln Asp Leu Ile Gln Ser Ile Pro Tyr Val Tyr Asn Glu Met
            980                 985                 990 ttc cca gaa ata cca ggg atg aac tat acg aag ttt aca gaa tta aca      3024
Phe Pro Glu Ile Pro Gly Met Asn Tyr Thr Lys Phe Thr Glu Leu Thr
        995                 1000                1005 gat cga ctc caa caa gcg tgg agt ttg tat gat cag cga aat gcc          3069
Asp Arg Leu Gln Gln Ala Trp Ser Leu Tyr Asp Gln Arg Asn Ala
    1010                1015                1020 ata cca aat ggt gat ttt cga aat ggg tta agt aat tgg aat gca          3114
Ile Pro Asn Gly Asp Phe Arg Asn Gly Leu Ser Asn Trp Asn Ala
1025                1030                1035 acg cct ggc gta gaa gta caa caa atc aat cat aca tct gtc ctt          3159
Thr Pro Gly Val Glu Val Gln Gln Ile Asn His Thr Ser Val Leu
        1040                1045                1050 gtg att cca aac tgg gat gag caa gtt tcg caa cag ttt aca gtt          3204
Val Ile Pro Asn Trp Asp Glu Gln Val Ser Gln Gln Phe Thr Val
    1055                1060                1065 caa ccg aat caa aga tat gtg tta cga gtt act gcg aga aaa gaa          3249
Gln Pro Asn Gln Arg Tyr Val Leu Arg Val Thr Ala Arg Lys Glu
1070                1075                1080 ggg gta gga aat gga tat gta agt atc cgt gat ggt gga aat caa          3294
Gly Val Gly Asn Gly Tyr Val Ser Ile Arg Asp Gly Gly Asn Gln
        1085                1090                1095 aca gaa acg ctt act ttt agt gca agc gat tat gat aca aat gga          3339
Thr Glu Thr Leu Thr Phe Ser Ala Ser Asp Tyr Asp Thr Asn Gly
    1100                1105                1110 atg tat aat acg caa gtg tcc aat aca aat gga tat aac aca aat          3384
Met Tyr Asn Thr Gln Val Ser Asn Thr Asn Gly Tyr Asn Thr Asn
1115                1120                1125 aat gcg tat aat aca caa gca tcg agt aca aac gga tat aac gca          3429
Asn Ala Tyr Asn Thr Gln Ala Ser Ser Thr Asn Gly Tyr Asn Ala
        1130                1135                1140 aat aat atg tat aat acg caa gca tcg aat aca aac gga tat aac          3474
Asn Asn Met Tyr Asn Thr Gln Ala Ser Asn Thr Asn Gly Tyr Asn
    1145                1150                1155 aca aat agt gtg tac aat gat caa acc ggc tat atc aca aaa aca          3519
Thr Asn Ser Val Tyr Asn Asp Gln Thr Gly Tyr Ile Thr Lys Thr
1160                1165                1170 gtg aca ttc atc ccg tat aca gat caa atg tgg att gag atg agt          3564
Val Thr Phe Ile Pro Tyr Thr Asp Gln Met Trp Ile Glu Met Ser
        1175                1180                1185 gag aca gaa ggt aca ttc tat ata gaa agt gta gaa ttg att gta          3609
Glu Thr Glu Gly Thr Phe Tyr Ile Glu Ser Val Glu Leu Ile Val
    1190                1195                1200 gac gta gag taa                                                      3621
Asp Val Glu
    1205

<210> SEQ ID NO 2
<211> LENGTH: 1206
<212> TYPE: PRT
<213> ORGANISM: Bacillus thuringiensis
```

<400> SEQUENCE: 2

```
Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Glu Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Ala Met Ala Ala Asn Leu His Leu
        195                 200                 205

Leu Leu Leu Lys Asp Ala Ser Ile Phe Gly Glu Glu Trp Gly Trp Ser
210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Ala Val Leu Asp Val Val Ala Leu Phe Pro Asn
        275                 280                 285

Tyr Asp Thr Arg Thr Tyr Pro Met Glu Thr Lys Ala Gln Leu Thr Arg
290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Val Ser Arg Gly Ser Asn Leu Gln
370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415
```

-continued

```
Leu Asp Ile Val Tyr Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
            435                 440                 445

Leu Lys Tyr Asn Pro Val Ser Lys Asp Ile Ile Ala Ser Thr Arg Asp
450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Asn Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
            515                 520                 525

Val Lys Cys Trp Asp Asn Leu Pro Phe Val Pro Val Lys Gly Pro
530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
                565                 570                 575

Gly Lys Tyr Arg Val Arg Leu Arg Tyr Ala Thr Asp Ala Asp Ile Val
            580                 585                 590

Leu His Val Asn Asp Ala Gln Ile Gln Met Pro Lys Thr Met Asn Pro
            595                 600                 605

Gly Glu Asp Leu Thr Ser Lys Thr Phe Lys Val Ala Asp Ala Ile Thr
            610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655

Ile Glu Phe Ile Pro Val Asp Glu Thr Tyr Glu Ala Glu Gln Asp Leu
            660                 665                 670

Glu Ala Ala Lys Lys Ala Val Asn Ala Leu Phe Thr Asn Thr Lys Asp
            675                 680                 685

Gly Leu Arg Pro Gly Val Thr Asp Tyr Glu Val Asn Gln Ala Ala Asn
690                 695                 700

Leu Val Glu Cys Leu Ser Asp Asp Leu Tyr Pro Asn Glu Lys Arg Leu
705                 710                 715                 720

Leu Phe Asp Ala Val Arg Glu Ala Lys Arg Leu Ser Glu Ala Arg Asn
                725                 730                 735

Leu Leu Gln Asp Pro Asp Phe Gln Glu Ile Asn Gly Gln Asn Gly Trp
            740                 745                 750

Thr Ala Ser Thr Gly Ile Glu Val Ile Glu Gly Asp Ala Leu Phe Lys
            755                 760                 765

Gly Arg Tyr Leu Arg Leu Pro Gly Ala Arg Glu Ile Asp Thr Glu Thr
770                 775                 780

Tyr Pro Thr Tyr Leu Tyr Gln Lys Val Glu Glu Gly Val Leu Lys Pro
785                 790                 795                 800

Tyr Thr Arg Tyr Arg Leu Arg Gly Phe Val Gly Ser Ser Gln Gly Leu
                805                 810                 815

Glu Ile Phe Thr Ile Arg His Gln Thr Asn Arg Ile Val Lys Asn Val
            820                 825                 830

Pro Asp Asp Leu Leu Pro Asp Val Ser Pro Val Asn Ser Asp Gly Ser
            835                 840                 845
```

Ile Asn Arg Cys Ser Glu Gln Lys Tyr Val Asn Ser Arg Leu Glu Val
    850                 855                 860

Glu Asn Arg Ser Gly Glu Ala His Glu Phe Ser Ile Pro Ile Asp Thr
865                 870                 875                 880

Gly Glu Ile Asp Tyr Asn Glu Asn Ala Gly Ile Trp Val Gly Phe Lys
                885                 890                 895

Ile Thr Asp Pro Glu Gly Tyr Ala Thr Leu Gly Asn Leu Glu Leu Val
            900                 905                 910

Glu Glu Gly Pro Leu Ser Gly Asp Ala Leu Glu Arg Leu Gln Arg Glu
        915                 920                 925

Glu Gln Gln Trp Lys Ile Gln Met Thr Arg Arg Glu Glu Thr Asp
    930                 935                 940

Arg Arg Tyr Met Ala Ser Lys Gln Ala Val Asp Arg Leu Tyr Ala Asp
945                 950                 955                 960

Tyr Gln Asp Gln Gln Leu Asn Pro Asp Val Glu Ile Thr Asp Leu Thr
                965                 970                 975

Ala Ala Gln Asp Leu Ile Gln Ser Ile Pro Tyr Val Tyr Asn Glu Met
            980                 985                 990

Phe Pro Glu Ile Pro Gly Met Asn Tyr Thr Lys Phe Thr Glu Leu Thr
        995                 1000                1005

Asp Arg Leu Gln Gln Ala Trp Ser Leu Tyr Asp Gln Arg Asn Ala
    1010                1015                1020

Ile Pro Asn Gly Asp Phe Arg Asn Gly Leu Ser Asn Trp Asn Ala
    1025                1030                1035

Thr Pro Gly Val Glu Val Gln Gln Ile Asn His Thr Ser Val Leu
    1040                1045                1050

Val Ile Pro Asn Trp Asp Glu Gln Val Ser Gln Gln Phe Thr Val
    1055                1060                1065

Gln Pro Asn Gln Arg Tyr Val Leu Arg Val Thr Ala Arg Lys Glu
    1070                1075                1080

Gly Val Gly Asn Gly Tyr Val Ser Ile Arg Asp Gly Gly Asn Gln
    1085                1090                1095

Thr Glu Thr Leu Thr Phe Ser Ala Ser Asp Tyr Asp Thr Asn Gly
    1100                1105                1110

Met Tyr Asn Thr Gln Val Ser Asn Thr Asn Gly Tyr Asn Thr Asn
    1115                1120                1125

Asn Ala Tyr Asn Thr Gln Ala Ser Ser Thr Asn Gly Tyr Asn Ala
    1130                1135                1140

Asn Asn Met Tyr Asn Thr Gln Ala Ser Asn Thr Asn Gly Tyr Asn
    1145                1150                1155

Thr Asn Ser Val Tyr Asn Asp Gln Thr Gly Tyr Ile Thr Lys Thr
    1160                1165                1170

Val Thr Phe Ile Pro Tyr Thr Asp Gln Met Trp Ile Glu Met Ser
    1175                1180                1185

Glu Thr Glu Gly Thr Phe Tyr Ile Glu Ser Val Glu Leu Ile Val
    1190                1195                1200

Asp Val Glu
    1205

<210> SEQ ID NO 3
<211> LENGTH: 3633
<212> TYPE: DNA
<213> ORGANISM: Bacillus thuringiensis
<220> FEATURE:
<221> NAME/KEY: misc_feature
<223> OTHER INFORMATION: Cry1218-2
<220> FEATURE:
<221> NAME/KEY: CDS
<222> LOCATION: (1)..(3633)

<400> SEQUENCE: 3

```
atg agt cca aat aat caa aat gaa tat gaa att ata gat gcg aca cct      48
Met Ser Pro Asn Asn Gln Asn Glu Tyr Glu Ile Ile Asp Ala Thr Pro
1               5                  10                  15 tct act tct gta tcc aat gat tct aac aga tac cct ttt gcg aat gag      96
Ser Thr Ser Val Ser Asn Asp Ser Asn Arg Tyr Pro Phe Ala Asn Glu
            20                  25                  30 cca aca aat gcg cta caa aat atg gat tat aaa gat tat tta aaa atg     144
Pro Thr Asn Ala Leu Gln Asn Met Asp Tyr Lys Asp Tyr Leu Lys Met
        35                  40                  45 tct gcg gga aat gct agt gaa tac cct ggt tca cct gaa gta ctt gtt     192
Ser Ala Gly Asn Ala Ser Glu Tyr Pro Gly Ser Pro Glu Val Leu Val
    50                  55                  60 agc gga caa gat gca gct aag gcc gca att gat ata gta ggt aaa tta     240
Ser Gly Gln Asp Ala Ala Lys Ala Ala Ile Asp Ile Val Gly Lys Leu
65                  70                  75                  80 cta tca ggt tta ggg gtc cca ttt gtt ggg ccg ata gtg agt ctt tat     288
Leu Ser Gly Leu Gly Val Pro Phe Val Gly Pro Ile Val Ser Leu Tyr
                85                  90                  95 act caa ctt att gat att ctg tgg cct tca ggg caa aag agt caa tgg     336
Thr Gln Leu Ile Asp Ile Leu Trp Pro Ser Gly Gln Lys Ser Gln Trp
            100                 105                 110 gag att ttt atg gaa caa gta gaa gaa ctc ata aat caa aaa ata gca     384
Glu Ile Phe Met Glu Gln Val Glu Glu Leu Ile Asn Gln Lys Ile Ala
        115                 120                 125 gaa tat gca agg aat aaa gcg ctt tcg gaa tta gaa gga tta ggt aat     432
Glu Tyr Ala Arg Asn Lys Ala Leu Ser Glu Leu Glu Gly Leu Gly Asn
    130                 135                 140 aat tac caa tta tat cta act gcg ctt gaa gaa tgg aaa gaa aat cca     480
Asn Tyr Gln Leu Tyr Leu Thr Ala Leu Glu Glu Trp Lys Glu Asn Pro
145                 150                 155                 160 aat ggt tca aga gcc tta cga gat gtg cga aat cga ttt gaa atc ctg     528
Asn Gly Ser Arg Ala Leu Arg Asp Val Arg Asn Arg Phe Glu Ile Leu
                165                 170                 175 gat agt tta ttt acg caa tac atg cca tct ttt cga gtg aca aat ttt     576
Asp Ser Leu Phe Thr Gln Tyr Met Pro Ser Phe Arg Val Thr Asn Phe
            180                 185                 190 gaa gta cca ttc ctt aca gta tat aca cag gca gcc aac ctt cat tta     624
Glu Val Pro Phe Leu Thr Val Tyr Thr Gln Ala Ala Asn Leu His Leu
        195                 200                 205 ctg tta tta aag gac gct tca att ttt gga gaa gaa tgg gga tgg tct     672
Leu Leu Leu Lys Asp Ala Ser Ile Phe Gly Glu Glu Trp Gly Trp Ser
    210                 215                 220 aca acc act att aat aac tat tat gat cgt caa atg aaa ctt act gca     720
Thr Thr Thr Ile Asn Asn Tyr Tyr Asp Arg Gln Met Lys Leu Thr Ala
225                 230                 235                 240 gaa tat tct gat cac tgt gta aag tgg tat gaa act ggt tta gca aaa     768
Glu Tyr Ser Asp His Cys Val Lys Trp Tyr Glu Thr Gly Leu Ala Lys
                245                 250                 255 tta aaa ggc acg agc gct aaa caa tgg gtc gac tat aac caa ttc cgt     816
Leu Lys Gly Thr Ser Ala Lys Gln Trp Val Asp Tyr Asn Gln Phe Arg
            260                 265                 270 aga gaa atg aca ctg acg gtt tta gat gtt gtt gca tta ttc cca aat     864
Arg Glu Met Thr Leu Thr Val Leu Asp Val Val Ala Leu Phe Pro Asn
        275                 280                 285 tat gac aca cgc acg tac cca atg gaa acg aaa gca caa cta aca agg     912
```

```
                Tyr Asp Thr Arg Thr Tyr Pro Met Glu Thr Lys Ala Gln Leu Thr Arg
                    290                 295                 300 gaa gta tat aca gat cca ctg ggc gcg gta aac gtg tct tca att ggt        960
Glu Val Tyr Thr Asp Pro Leu Gly Ala Val Asn Val Ser Ser Ile Gly
305                 310                 315                 320 tcc tgg tat gac aaa gca cct tct ttc gga gtg ata gaa tca tcc gtt       1008
Ser Trp Tyr Asp Lys Ala Pro Ser Phe Gly Val Ile Glu Ser Ser Val
                325                 330                 335 att cga cca ccc cat gta ttt gat tat ata acg gga ctc aca gtg tat       1056
Ile Arg Pro Pro His Val Phe Asp Tyr Ile Thr Gly Leu Thr Val Tyr
            340                 345                 350 aca caa tca aga agc att tct tcc gct cgc tat ata aga cat tgg gct       1104
Thr Gln Ser Arg Ser Ile Ser Ser Ala Arg Tyr Ile Arg His Trp Ala
        355                 360                 365 ggt cat caa ata agc tat cat cgg att ttt agt gat aat att ata aaa       1152
Gly His Gln Ile Ser Tyr His Arg Ile Phe Ser Asp Asn Ile Ile Lys
    370                 375                 380 cag atg tat gga act aat caa aat cta cac agc act agt acc ttt gat       1200
Gln Met Tyr Gly Thr Asn Gln Asn Leu His Ser Thr Ser Thr Phe Asp
385                 390                 395                 400 ttt acg aat tat gat att tac aag acg tta tca aaa gat gcg gtg ctc       1248
Phe Thr Asn Tyr Asp Ile Tyr Lys Thr Leu Ser Lys Asp Ala Val Leu
                405                 410                 415 ctt gat att gtt ttt cct ggt tat acg tat ata ttt ttt gga atg cca       1296
Leu Asp Ile Val Phe Pro Gly Tyr Thr Tyr Ile Phe Phe Gly Met Pro
            420                 425                 430 gaa gtc gag ttt ttc atg gta aac caa ttg aat aat acc aga aag acg       1344
Glu Val Glu Phe Phe Met Val Asn Gln Leu Asn Asn Thr Arg Lys Thr
        435                 440                 445 tta aag tat aat ccg gtt tcc aaa gat att ata gcg ggg aca aga gat       1392
Leu Lys Tyr Asn Pro Val Ser Lys Asp Ile Ile Ala Gly Thr Arg Asp
    450                 455                 460 tcg gaa tta gaa tta cct cca gaa act tca gat caa cca aat tat gag       1440
Ser Glu Leu Glu Leu Pro Pro Glu Thr Ser Asp Gln Pro Asn Tyr Glu
465                 470                 475                 480 tca tat agc cat aga tta tgt cat atc aca agt att ccc gcg acg ggt       1488
Ser Tyr Ser His Arg Leu Cys His Ile Thr Ser Ile Pro Ala Thr Gly
                485                 490                 495 tca act acc gga tta gta cct gta ttt tct tgg aca cat cgg agt gcc       1536
Ser Thr Thr Gly Leu Val Pro Val Phe Ser Trp Thr His Arg Ser Ala
            500                 505                 510 gat ctt ata aat gca gtt cat tca gat aaa att act cag att ccg gtc       1584
Asp Leu Ile Asn Ala Val His Ser Asp Lys Ile Thr Gln Ile Pro Val
        515                 520                 525 gta aag gtt tct gat ttg gct ccc tct ata aca gga ggg cca aat aat       1632
Val Lys Val Ser Asp Leu Ala Pro Ser Ile Thr Gly Gly Pro Asn Asn
    530                 535                 540 acc gtt gta tcg ggt cct gga ttt aca ggg ggg ggg ata ata aaa gta       1680
Thr Val Val Ser Gly Pro Gly Phe Thr Gly Gly Gly Ile Ile Lys Val
545                 550                 555                 560 ata aga aat gga gta att ata tca cat atg cgt gtt aaa att tca gac       1728
Ile Arg Asn Gly Val Ile Ile Ser His Met Arg Val Lys Ile Ser Asp
                565                 570                 575 att aac aaa gaa tat agt atg agg att cgg tat gct tcc gct aat aat       1776
Ile Asn Lys Glu Tyr Ser Met Arg Ile Arg Tyr Ala Ser Ala Asn Asn
            580                 585                 590 act gaa ttt tat ata aat cct tct gaa gaa aac gtt aaa tct cac gct       1824
Thr Glu Phe Tyr Ile Asn Pro Ser Glu Glu Asn Val Lys Ser His Ala
        595                 600                 605 caa aaa act atg aat aga ggt gaa gct tta aca tat aat aaa ttt aat       1872
```

```
                Gln Lys Thr Met Asn Arg Gly Glu Ala Leu Thr Tyr Asn Lys Phe Asn
                610                 615                 620 tat gcg act ttg ccc cct att aaa ttt acg aca acc gaa cct ttc att          1920
Tyr Ala Thr Leu Pro Pro Ile Lys Phe Thr Thr Thr Glu Pro Phe Ile
625                 630                 635                 640 act cta ggg gct ata ttt gaa gcg gaa gac ttt ctt gga att gaa gct          1968
Thr Leu Gly Ala Ile Phe Glu Ala Glu Asp Phe Leu Gly Ile Glu Ala
                645                 650                 655 tat ata gac cga atc gaa ttt atc cca gta gat gag aca tat gaa gcg          2016
Tyr Ile Asp Arg Ile Glu Phe Ile Pro Val Asp Glu Thr Tyr Glu Ala
            660                 665                 670 gaa caa gat tta gaa gca gcg aag aaa gca gtg aat gcc ttg ttt acg          2064
Glu Gln Asp Leu Glu Ala Ala Lys Lys Ala Val Asn Ala Leu Phe Thr
        675                 680                 685 aat aca aaa gat ggc tta cga cca ggc gta acg gat tat gaa gtg aat          2112
Asn Thr Lys Asp Gly Leu Arg Pro Gly Val Thr Asp Tyr Glu Val Asn
690                 695                 700 caa gcg gca aac tta gtg gaa tgc cta tcg gat gat ttg tat cca aat          2160
Gln Ala Ala Asn Leu Val Glu Cys Leu Ser Asp Asp Leu Tyr Pro Asn
705                 710                 715                 720 gaa aaa cga ttg tta ttt gat gca gtg aga gag gca aaa cgc ctc agt          2208
Glu Lys Arg Leu Leu Phe Asp Ala Val Arg Glu Ala Lys Arg Leu Ser
                725                 730                 735 gag gca cgt aat ttg ctt caa gat cca gat ttc caa gag ata aat gga          2256
Glu Ala Arg Asn Leu Leu Gln Asp Pro Asp Phe Gln Glu Ile Asn Gly
                740                 745                 750 gaa aat ggc tgg acg gca agt acg gga att gag gtt ata gaa ggg gat          2304
Glu Asn Gly Trp Thr Ala Ser Thr Gly Ile Glu Val Ile Glu Gly Asp
            755                 760                 765 gct tta ttc aaa ggg cgt tat cta cgc cta cca ggt gcg aga gaa ata          2352
Ala Leu Phe Lys Gly Arg Tyr Leu Arg Leu Pro Gly Ala Arg Glu Ile
770                 775                 780 gat acg gaa acg tat cca acg tat ctg tat caa aaa gta gag gaa ggt          2400
Asp Thr Glu Thr Tyr Pro Thr Tyr Leu Tyr Gln Lys Val Glu Glu Gly
785                 790                 795                 800 gta tta aaa cca tac aca aga tat aga ttg aga ggg ttt gtc gga agc          2448
Val Leu Lys Pro Tyr Thr Arg Tyr Arg Leu Arg Gly Phe Val Gly Ser
                805                 810                 815 agt caa gga ttg gaa att ttc aca att cgt cat caa acg aac cga att          2496
Ser Gln Gly Leu Glu Ile Phe Thr Ile Arg His Gln Thr Asn Arg Ile
                820                 825                 830 gta aaa aat gta ccg gat gat ttg ctg cca gat gta tct cct gtt aac          2544
Val Lys Asn Val Pro Asp Asp Leu Leu Pro Asp Val Ser Pro Val Asn
            835                 840                 845 tcg gat ggt agt atc aat cga tgc agc gaa caa aag tat gtg aat agc          2592
Ser Asp Gly Ser Ile Asn Arg Cys Ser Glu Gln Lys Tyr Val Asn Ser
850                 855                 860 cgt tta gaa gta gaa aac cgt tct ggt gaa gcg cat gag ttc tct att          2640
Arg Leu Glu Val Glu Asn Arg Ser Gly Glu Ala His Glu Phe Ser Ile
865                 870                 875                 880 cct att gat aca ggt gaa atc gat tac aat gaa aat gca gga ata tgg          2688
Pro Ile Asp Thr Gly Glu Ile Asp Tyr Asn Glu Asn Ala Gly Ile Trp
                885                 890                 895 gtt gga ttt aag att acg gac cca gag gga tat gca aca ctc gga aac          2736
Val Gly Phe Lys Ile Thr Asp Pro Glu Gly Tyr Ala Thr Leu Gly Asn
                900                 905                 910 cta gaa ttg gtc gaa gag gga cct tta tca gga gac gca tta gaa cgc          2784
Leu Glu Leu Val Glu Glu Gly Pro Leu Ser Gly Asp Ala Leu Glu Arg
            915                 920                 925 ttg caa aga gaa gaa caa cag tgg aag att caa atg aca aga aga cgt          2832
```

```
Leu Gln Arg Glu Glu Gln Gln Trp Lys Ile Gln Met Thr Arg Arg
        930                 935                 940 gaa gaa aca gat aga agg tat atg gca tcg aaa caa gcg gta gat cgt    2880
Glu Glu Thr Asp Arg Arg Tyr Met Ala Ser Lys Gln Ala Val Asp Arg
945                 950                 955                 960 tta tat gcc gat tat cag gat cag caa ctg aat cct gat gta gag att    2928
Leu Tyr Ala Asp Tyr Gln Asp Gln Gln Leu Asn Pro Asp Val Glu Ile
                965                 970                 975 aca gat ctt act gcg gcc caa gat ctg ata cag tcc att cct tac gta    2976
Thr Asp Leu Thr Ala Ala Gln Asp Leu Ile Gln Ser Ile Pro Tyr Val
            980                 985                 990 tat aac gaa atg ttc cca gaa ata cca ggg atg aac tat acg aag ttt    3024
Tyr Asn Glu Met Phe Pro Glu Ile Pro Gly Met Asn Tyr Thr Lys Phe
        995                 1000                1005 aca gaa tta aca gat cga ctc caa caa gcg tgg agt ttg tat gat        3069
Thr Glu Leu Thr Asp Arg Leu Gln Gln Ala Trp Ser Leu Tyr Asp
    1010                1015                1020 cag cga aat gcc ata cca aat ggt gat ttt cga aat ggg tta agt        3114
Gln Arg Asn Ala Ile Pro Asn Gly Asp Phe Arg Asn Gly Leu Ser
1025                1030                1035 aat tgg aat gca acg cct ggc gta gaa gta caa caa atc aat cat        3159
Asn Trp Asn Ala Thr Pro Gly Val Glu Val Gln Gln Ile Asn His
1040                1045                1050 aca tct gtc ctt gtg att cca aac tgg gat gag caa gtt tcg caa        3204
Thr Ser Val Leu Val Ile Pro Asn Trp Asp Glu Gln Val Ser Gln
1055                1060                1065 cag ttt aca gtt caa ccg aat caa aga tat gtg tta cga gtt act        3249
Gln Phe Thr Val Gln Pro Asn Gln Arg Tyr Val Leu Arg Val Thr
1070                1075                1080 gcg aga aaa gaa ggg gta gga aat gga tat gta agt atc cgt gat        3294
Ala Arg Lys Glu Gly Val Gly Asn Gly Tyr Val Ser Ile Arg Asp
1085                1090                1095 ggt gga aat caa aca gaa acg ctt act ttt agt gca agc gat tat        3339
Gly Gly Asn Gln Thr Glu Thr Leu Thr Phe Ser Ala Ser Asp Tyr
1100                1105                1110 gat aca aat gga atg tat aat acg caa gtg tcc aat aca aat gga        3384
Asp Thr Asn Gly Met Tyr Asn Thr Gln Val Ser Asn Thr Asn Gly
1115                1120                1125 tat aac aca aat aat gcg tat aat aca caa gca tcg agt aca aac        3429
Tyr Asn Thr Asn Asn Ala Tyr Asn Thr Gln Ala Ser Ser Thr Asn
1130                1135                1140 gga tat aac gca aat aat atg tat aat acg caa gca tcg aat aca        3474
Gly Tyr Asn Ala Asn Asn Met Tyr Asn Thr Gln Ala Ser Asn Thr
1145                1150                1155 aac gga tat aac aca aat agt gtg tac aat gat caa acc ggc tat        3519
Asn Gly Tyr Asn Thr Asn Ser Val Tyr Asn Asp Gln Thr Gly Tyr
1160                1165                1170 atc aca aaa aca gtg aca ttc atc ccg tat aca gat caa atg tgg        3564
Ile Thr Lys Thr Val Thr Phe Ile Pro Tyr Thr Asp Gln Met Trp
1175                1180                1185 att gag atg agt gag aca gaa ggt aca ttc tat ata gaa agt gta        3609
Ile Glu Met Ser Glu Thr Glu Gly Thr Phe Tyr Ile Glu Ser Val
1190                1195                1200 gaa ttg att gta gac gta gag taa                                    3633
Glu Leu Ile Val Asp Val Glu
1205                1210

<210> SEQ ID NO 4
<211> LENGTH: 1210
<212> TYPE: PRT
<213> ORGANISM: Bacillus thuringiensis
```

<400> SEQUENCE: 4

```
Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Gln Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Gln Ala Ala Asn Leu His Leu
        195                 200                 205

Leu Leu Leu Lys Asp Ala Ser Ile Phe Gly Glu Glu Trp Gly Trp Ser
210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Thr Val Leu Asp Val Val Ala Leu Phe Pro Asn
        275                 280                 285

Tyr Asp Thr Arg Thr Tyr Pro Met Glu Thr Lys Ala Gln Leu Thr Arg
290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Ile Phe Ser Asp Asn Ile Ile Lys
370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415
```

```
Leu Asp Ile Val Phe Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
            435                 440                 445

Leu Lys Tyr Asn Pro Val Ser Lys Asp Ile Ile Ala Gly Thr Arg Asp
450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Ile Asn Ala Val His Ser Asp Lys Ile Thr Gln Ile Pro Val
            515                 520                 525

Val Lys Val Ser Asp Leu Ala Pro Ser Ile Thr Gly Gly Pro Asn Asn
530                 535                 540

Thr Val Val Ser Gly Pro Gly Phe Thr Gly Gly Ile Ile Lys Val
545                 550                 555                 560

Ile Arg Asn Gly Val Ile Ile Ser His Met Arg Val Lys Ile Ser Asp
                565                 570                 575

Ile Asn Lys Glu Tyr Ser Met Arg Ile Arg Tyr Ala Ser Ala Asn Asn
            580                 585                 590

Thr Glu Phe Tyr Ile Asn Pro Ser Glu Glu Asn Val Lys Ser His Ala
            595                 600                 605

Gln Lys Thr Met Asn Arg Gly Glu Ala Leu Thr Tyr Asn Lys Phe Asn
610                 615                 620

Tyr Ala Thr Leu Pro Pro Ile Lys Phe Thr Thr Thr Glu Pro Phe Ile
625                 630                 635                 640

Thr Leu Gly Ala Ile Phe Glu Ala Glu Asp Phe Leu Gly Ile Glu Ala
                645                 650                 655

Tyr Ile Asp Arg Ile Glu Phe Ile Pro Val Asp Glu Thr Tyr Glu Ala
            660                 665                 670

Glu Gln Asp Leu Glu Ala Ala Lys Lys Ala Val Asn Ala Leu Phe Thr
            675                 680                 685

Asn Thr Lys Asp Gly Leu Arg Pro Gly Val Thr Asp Tyr Glu Val Asn
690                 695                 700

Gln Ala Ala Asn Leu Val Glu Cys Leu Ser Asp Asp Leu Tyr Pro Asn
705                 710                 715                 720

Glu Lys Arg Leu Leu Phe Asp Ala Val Arg Glu Ala Lys Arg Leu Ser
                725                 730                 735

Glu Ala Arg Asn Leu Leu Gln Asp Pro Asp Phe Gln Glu Ile Asn Gly
            740                 745                 750

Glu Asn Gly Trp Thr Ala Ser Thr Gly Ile Glu Val Ile Glu Gly Asp
            755                 760                 765

Ala Leu Phe Lys Gly Arg Tyr Leu Arg Leu Pro Gly Ala Arg Glu Ile
770                 775                 780

Asp Thr Glu Thr Tyr Pro Thr Tyr Leu Tyr Gln Lys Val Glu Glu Gly
785                 790                 795                 800

Val Leu Lys Pro Tyr Thr Arg Tyr Arg Leu Arg Gly Phe Val Gly Ser
                805                 810                 815

Ser Gln Gly Leu Glu Ile Phe Thr Ile Arg His Gln Thr Asn Arg Ile
            820                 825                 830

Val Lys Asn Val Pro Asp Asp Leu Leu Pro Asp Val Ser Pro Val Asn
```

```
                835                 840                 845
Ser Asp Gly Ser Ile Asn Arg Cys Ser Glu Gln Lys Tyr Val Asn Ser
850                 855                 860

Arg Leu Glu Val Glu Asn Arg Ser Gly Glu Ala His Glu Phe Ser Ile
865                 870                 875                 880

Pro Ile Asp Thr Gly Glu Ile Asp Tyr Asn Glu Asn Ala Gly Ile Trp
                885                 890                 895

Val Gly Phe Lys Ile Thr Asp Pro Glu Gly Tyr Ala Thr Leu Gly Asn
                900                 905                 910

Leu Glu Leu Val Glu Glu Gly Pro Leu Ser Gly Asp Ala Leu Glu Arg
                915                 920                 925

Leu Gln Arg Glu Glu Gln Gln Trp Lys Ile Gln Met Thr Arg Arg Arg
                930                 935                 940

Glu Glu Thr Asp Arg Arg Tyr Met Ala Ser Lys Gln Ala Val Asp Arg
945                 950                 955                 960

Leu Tyr Ala Asp Tyr Gln Asp Gln Gln Leu Asn Pro Asp Val Glu Ile
                965                 970                 975

Thr Asp Leu Thr Ala Ala Gln Asp Leu Ile Gln Ser Ile Pro Tyr Val
                980                 985                 990

Tyr Asn Glu Met Phe Pro Glu Ile Pro Gly Met Asn Tyr Thr Lys Phe
                995                 1000                1005

Thr Glu Leu Thr Asp Arg Leu Gln Gln Ala Trp Ser Leu Tyr Asp
1010                1015                1020

Gln Arg Asn Ala Ile Pro Asn Gly Asp Phe Arg Asn Gly Leu Ser
1025                1030                1035

Asn Trp Asn Ala Thr Pro Gly Val Glu Val Gln Gln Ile Asn His
1040                1045                1050

Thr Ser Val Leu Val Ile Pro Asn Trp Asp Glu Gln Val Ser Gln
1055                1060                1065

Gln Phe Thr Val Gln Pro Asn Gln Arg Tyr Val Leu Arg Val Thr
1070                1075                1080

Ala Arg Lys Glu Gly Val Gly Asn Gly Tyr Val Ser Ile Arg Asp
1085                1090                1095

Gly Gly Asn Gln Thr Glu Thr Leu Thr Phe Ser Ala Ser Asp Tyr
1100                1105                1110

Asp Thr Asn Gly Met Tyr Asn Thr Gln Val Ser Asn Thr Asn Gly
1115                1120                1125

Tyr Asn Thr Asn Asn Ala Tyr Asn Thr Gln Ala Ser Ser Thr Asn
1130                1135                1140

Gly Tyr Asn Ala Asn Asn Met Tyr Asn Thr Gln Ala Ser Asn Thr
1145                1150                1155

Asn Gly Tyr Asn Thr Asn Ser Val Tyr Asn Asp Gln Thr Gly Tyr
1160                1165                1170

Ile Thr Lys Thr Val Thr Phe Ile Pro Tyr Thr Asp Gln Met Trp
1175                1180                1185

Ile Glu Met Ser Glu Thr Glu Gly Thr Phe Tyr Ile Glu Ser Val
1190                1195                1200

Glu Leu Ile Val Asp Val Glu
1205                1210

<210> SEQ ID NO 5
<211> LENGTH: 2003
<212> TYPE: DNA
<213> ORGANISM: Bacillus thuringiensis (truncated)
<220> FEATURE:
```

<221> NAME/KEY: misc_feature
<223> OTHER INFORMATION: 1218-1
<220> FEATURE:
<221> NAME/KEY: CDS
<222> LOCATION: (1)..(2001)

<400> SEQUENCE: 5

| | | | | | | | | | | | | | | | | |
|---|---|---|---|---|---|---|---|---|---|---|---|---|---|---|---|---|
| atg | agt | cca | aat | aat | caa | aat | gaa | tat | gaa | att | ata | gat | gcg | aca | cct | 48 |
| Met | Ser | Pro | Asn | Asn | Gln | Asn | Glu | Tyr | Glu | Ile | Ile | Asp | Ala | Thr | Pro | |
| 1 | | | | 5 | | | | | 10 | | | | | 15 | | |

| tct | act | tct | gta | tcc | aat | gat | tct | aac | aga | tac | cct | ttt | gcg | aat | gag | 96 |
|---|---|---|---|---|---|---|---|---|---|---|---|---|---|---|---|---|
| Ser | Thr | Ser | Val | Ser | Asn | Asp | Ser | Asn | Arg | Tyr | Pro | Phe | Ala | Asn | Glu | |
| | | | 20 | | | | | 25 | | | | | 30 | | | |

| cca | aca | aat | gcg | cta | caa | aat | atg | gat | tat | aaa | gat | tat | tta | aaa | atg | 144 |
|---|---|---|---|---|---|---|---|---|---|---|---|---|---|---|---|---|
| Pro | Thr | Asn | Ala | Leu | Gln | Asn | Met | Asp | Tyr | Lys | Asp | Tyr | Leu | Lys | Met | |
| | | 35 | | | | | 40 | | | | | 45 | | | | |

| tct | gcg | gga | aat | gct | agt | gaa | tac | cct | ggt | tca | cct | gaa | gta | ctt | gtt | 192 |
|---|---|---|---|---|---|---|---|---|---|---|---|---|---|---|---|---|
| Ser | Ala | Gly | Asn | Ala | Ser | Glu | Tyr | Pro | Gly | Ser | Pro | Glu | Val | Leu | Val | |
| | 50 | | | | | 55 | | | | | 60 | | | | | |

| agc | gga | caa | gat | gca | gct | aag | gcc | gca | att | gat | ata | gta | ggt | aaa | tta | 240 |
|---|---|---|---|---|---|---|---|---|---|---|---|---|---|---|---|---|
| Ser | Gly | Gln | Asp | Ala | Ala | Lys | Ala | Ala | Ile | Asp | Ile | Val | Gly | Lys | Leu | |
| 65 | | | | | 70 | | | | | 75 | | | | | 80 | |

| cta | tca | ggt | tta | ggg | gtc | cca | ttt | gtt | ggg | ccg | ata | gtg | agt | ctt | tat | 288 |
|---|---|---|---|---|---|---|---|---|---|---|---|---|---|---|---|---|
| Leu | Ser | Gly | Leu | Gly | Val | Pro | Phe | Val | Gly | Pro | Ile | Val | Ser | Leu | Tyr | |
| | | | | 85 | | | | | 90 | | | | | 95 | | |

| act | caa | ctt | att | gat | att | ctg | tgg | cct | tca | ggg | gaa | aag | agt | caa | tgg | 336 |
|---|---|---|---|---|---|---|---|---|---|---|---|---|---|---|---|---|
| Thr | Gln | Leu | Ile | Asp | Ile | Leu | Trp | Pro | Ser | Gly | Glu | Lys | Ser | Gln | Trp | |
| | | | 100 | | | | | 105 | | | | | 110 | | | |

| gaa | att | ttt | atg | gaa | caa | gta | gaa | gaa | ctc | att | aat | caa | aaa | ata | gca | 384 |
|---|---|---|---|---|---|---|---|---|---|---|---|---|---|---|---|---|
| Glu | Ile | Phe | Met | Glu | Gln | Val | Glu | Glu | Leu | Ile | Asn | Gln | Lys | Ile | Ala | |
| | | | 115 | | | | | 120 | | | | | 125 | | | |

| gaa | tat | gca | agg | aat | aaa | gcg | ctt | tcg | gaa | tta | gaa | gga | tta | ggt | aat | 432 |
|---|---|---|---|---|---|---|---|---|---|---|---|---|---|---|---|---|
| Glu | Tyr | Ala | Arg | Asn | Lys | Ala | Leu | Ser | Glu | Leu | Glu | Gly | Leu | Gly | Asn | |
| | 130 | | | | | 135 | | | | | 140 | | | | | |

| aat | tac | caa | tta | tat | cta | act | gcg | ctt | gaa | gaa | tgg | gaa | gaa | aat | cca | 480 |
|---|---|---|---|---|---|---|---|---|---|---|---|---|---|---|---|---|
| Asn | Tyr | Gln | Leu | Tyr | Leu | Thr | Ala | Leu | Glu | Glu | Trp | Glu | Glu | Asn | Pro | |
| 145 | | | | | 150 | | | | | 155 | | | | | 160 | |

| aat | ggt | tca | aga | gcc | tta | cga | gat | gtg | cga | aat | cga | ttt | gaa | atc | ctg | 528 |
|---|---|---|---|---|---|---|---|---|---|---|---|---|---|---|---|---|
| Asn | Gly | Ser | Arg | Ala | Leu | Arg | Asp | Val | Arg | Asn | Arg | Phe | Glu | Ile | Leu | |
| | | | | 165 | | | | | 170 | | | | | 175 | | |

| gat | agt | tta | ttt | acg | caa | tat | atg | cca | tct | ttt | aga | gtg | aca | aat | ttt | 576 |
|---|---|---|---|---|---|---|---|---|---|---|---|---|---|---|---|---|
| Asp | Ser | Leu | Phe | Thr | Gln | Tyr | Met | Pro | Ser | Phe | Arg | Val | Thr | Asn | Phe | |
| | | | 180 | | | | | 185 | | | | | 190 | | | |

| gaa | gta | cca | ttc | ctt | act | gta | tat | gca | atg | gca | gcc | aac | ctt | cat | tta | 624 |
|---|---|---|---|---|---|---|---|---|---|---|---|---|---|---|---|---|
| Glu | Val | Pro | Phe | Leu | Thr | Val | Tyr | Ala | Met | Ala | Ala | Asn | Leu | His | Leu | |
| | | | | 195 | | | | | 200 | | | | | 205 | | |

| ctg | tta | tta | aag | gac | gcg | tca | att | ttt | gga | gaa | gaa | tgg | gga | tgg | tca | 672 |
|---|---|---|---|---|---|---|---|---|---|---|---|---|---|---|---|---|
| Leu | Leu | Leu | Lys | Asp | Ala | Ser | Ile | Phe | Gly | Glu | Glu | Trp | Gly | Trp | Ser | |
| | 210 | | | | | 215 | | | | | 220 | | | | | |

| aca | act | act | att | aat | aac | tat | tat | gat | cgt | caa | atg | aaa | ctt | act | gca | 720 |
|---|---|---|---|---|---|---|---|---|---|---|---|---|---|---|---|---|
| Thr | Thr | Thr | Ile | Asn | Asn | Tyr | Tyr | Asp | Arg | Gln | Met | Lys | Leu | Thr | Ala | |
| 225 | | | | | 230 | | | | | 235 | | | | | 240 | |

| gaa | tat | tct | gat | cac | tgt | gta | aag | tgg | tat | gaa | act | ggt | tta | gca | aaa | 768 |
|---|---|---|---|---|---|---|---|---|---|---|---|---|---|---|---|---|
| Glu | Tyr | Ser | Asp | His | Cys | Val | Lys | Trp | Tyr | Glu | Thr | Gly | Leu | Ala | Lys | |
| | | | | 245 | | | | | 250 | | | | | 255 | | |

| tta | aaa | ggc | acg | agc | gct | aaa | caa | tgg | gtt | gac | tat | aac | caa | ttc | cgt | 816 |
|---|---|---|---|---|---|---|---|---|---|---|---|---|---|---|---|---|
| Leu | Lys | Gly | Thr | Ser | Ala | Lys | Gln | Trp | Val | Asp | Tyr | Asn | Gln | Phe | Arg | |
| | | | 260 | | | | | 265 | | | | | 270 | | | |

| aga | gaa | atg | aca | ctg | gcg | gtt | tta | gat | gtt | gtt | gca | tta | ttc | cca | aat | 864 |
|---|---|---|---|---|---|---|---|---|---|---|---|---|---|---|---|---|
| Arg | Glu | Met | Thr | Leu | Ala | Val | Leu | Asp | Val | Val | Ala | Leu | Phe | Pro | Asn | |
| | | 275 | | | | | 280 | | | | | 285 | | | | |

| | | |
|---|---|---|
| tat gac aca cgc acg tac cca atg gaa acg aaa gca caa cta aca agg<br>Tyr Asp Thr Arg Thr Tyr Pro Met Glu Thr Lys Ala Gln Leu Thr Arg<br>290                            295                       300 | | 912 |
| gaa gta tat aca gat cca ctg ggc gcg gta aac gtg tct tca att ggt<br>Glu Val Tyr Thr Asp Pro Leu Gly Ala Val Asn Val Ser Ser Ile Gly<br>305                    310                      315                     320 | | 960 |
| tcc tgg tat gac aaa gca cct tct ttc gga gtg ata gaa tca tcc gtt<br>Ser Trp Tyr Asp Lys Ala Pro Ser Phe Gly Val Ile Glu Ser Ser Val<br>                      325                      330                     335 | | 1008 |
| att cga cca ccc cat gta ttt gat tat ata acg gga ctc aca gtg tat<br>Ile Arg Pro Pro His Val Phe Asp Tyr Ile Thr Gly Leu Thr Val Tyr<br>                   340                     345                     350 | | 1056 |
| aca caa tca aga agc att tct tcc gct cgc tat ata aga cat tgg gct<br>Thr Gln Ser Arg Ser Ile Ser Ser Ala Arg Tyr Ile Arg His Trp Ala<br>               355                     360                     365 | | 1104 |
| ggt cat caa ata agc tac cat cgt gtc agt agg ggt agt aat ctt caa<br>Gly His Gln Ile Ser Tyr His Arg Val Ser Arg Gly Ser Asn Leu Gln<br>370                            375                       380 | | 1152 |
| caa atg tat gga act aat caa aat cta cac agc act agt acc ttt gat<br>Gln Met Tyr Gly Thr Asn Gln Asn Leu His Ser Thr Ser Thr Phe Asp<br>385                           390                     395                   400 | | 1200 |
| ttt acg aat tat gat att tac aag act cta tca aag gat gca gta ctc<br>Phe Thr Asn Tyr Asp Ile Tyr Lys Thr Leu Ser Lys Asp Ala Val Leu<br>                         405                     410                     415 | | 1248 |
| ctt gat att gtt tac cct ggt tat acg tat ata ttt ttt gga atg cca<br>Leu Asp Ile Val Tyr Pro Gly Tyr Thr Tyr Ile Phe Phe Gly Met Pro<br>                   420                     425                     430 | | 1296 |
| gaa gtc gag ttt ttc atg gta aac caa ttg aat aat acc aga aag acg<br>Glu Val Glu Phe Phe Met Val Asn Gln Leu Asn Asn Thr Arg Lys Thr<br>               435                     440                     445 | | 1344 |
| tta aag tat aat cca gtt tcc aaa gat att ata gcg agt aca aga gat<br>Leu Lys Tyr Asn Pro Val Ser Lys Asp Ile Ile Ala Ser Thr Arg Asp<br>450                           455                     460 | | 1392 |
| tcg gaa tta gaa tta cct cca gaa act tca gat caa cca aat tat gag<br>Ser Glu Leu Glu Leu Pro Pro Glu Thr Ser Asp Gln Pro Asn Tyr Glu<br>465                           470                     475                   480 | | 1440 |
| tca tat agc cat aga tta tgt cat atc aca agt att ccc gcg acg ggt<br>Ser Tyr Ser His Arg Leu Cys His Ile Thr Ser Ile Pro Ala Thr Gly<br>                         485                     490                     495 | | 1488 |
| aac act acc gga tta gta cct gta ttt tct tgg aca cat cga agt gca<br>Asn Thr Thr Gly Leu Val Pro Val Phe Ser Trp Thr His Arg Ser Ala<br>                   500                     505                     510 | | 1536 |
| gat tta aac aat aca ata tat tca gat aaa atc act caa att ccg gcc<br>Asp Leu Asn Asn Thr Ile Tyr Ser Asp Lys Ile Thr Gln Ile Pro Ala<br>               515                     520                     525 | | 1584 |
| gtt aaa tgt tgg gat aat tta ccg ttt gtt cca gtg gta aaa gga cca<br>Val Lys Cys Trp Asp Asn Leu Pro Phe Val Pro Val Val Lys Gly Pro<br>530                           535                     540 | | 1632 |
| gga cat aca gga ggg gat tta tta cag tat aat aga agt act ggt tct<br>Gly His Thr Gly Gly Asp Leu Leu Gln Tyr Asn Arg Ser Thr Gly Ser<br>545                           550                     555                   560 | | 1680 |
| gta gga acc tta ttt cta gct cga tat ggc cta gca tta gaa aaa gca<br>Val Gly Thr Leu Phe Leu Ala Arg Tyr Gly Leu Ala Leu Glu Lys Ala<br>                         565                     570                     575 | | 1728 |
| ggg aaa tat cgt gta aga ctg aga tat gct act gat gca gat att gta<br>Gly Lys Tyr Arg Val Arg Leu Arg Tyr Ala Thr Asp Ala Asp Ile Val<br>                   580                     585                     590 | | 1776 |
| ttg cat gta aac gat gct cag att cag atg cca aaa aca atg aac cca<br>Leu His Val Asn Asp Ala Gln Ile Gln Met Pro Lys Thr Met Asn Pro<br>               595                     600                     605 | | 1824 |

```
ggt gag gat ctg aca tct aaa act ttt aaa gtt gca gat gct atc aca    1872
Gly Glu Asp Leu Thr Ser Lys Thr Phe Lys Val Ala Asp Ala Ile Thr
610                 615                 620 aca tta aat tta gca aca gat agt tcg cta gca ttg aaa cat aat tta    1920
Thr Leu Asn Leu Ala Thr Asp Ser Ser Leu Ala Leu Lys His Asn Leu
625                 630                 635                 640 ggt gaa gac cct aat tca aca tta tct ggt ata gtt tac gtt gac cga    1968
Gly Glu Asp Pro Asn Ser Thr Leu Ser Gly Ile Val Tyr Val Asp Arg
            645                 650                 655 atc gaa ttc atc cca gta gat gag aca tat gaa gc                     2003
Ile Glu Phe Ile Pro Val Asp Glu Thr Tyr Glu
                660                 665
```

<210> SEQ ID NO 6
<211> LENGTH: 667
<212> TYPE: PRT
<213> ORGANISM: Bacillus thuringiensis (truncated)

<400> SEQUENCE: 6

```
Met Ser Pro Asn Asn Gln Asn Glu T

```
Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
            325                 330                 335

Ile Arg Pro Pro His Val Phe Asp Tyr Ile Thr Gly Leu Thr Val Tyr
                340                 345                 350

Thr Gln Ser Arg Ser Ile Ser Ser Ala Arg Tyr Ile Arg His Trp Ala
            355                 360                 365

Gly His Gln Ile Ser Tyr His Arg Val Ser Arg Gly Ser Asn Leu Gln
        370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Tyr Pro Gly Tyr Thr Tyr Ile Phe Phe Gly Met Pro
                420                 425                 430

Glu Val Glu Phe Phe Met Val Asn Gln Leu Asn Asn Thr Arg Lys Thr
            435                 440                 445

Leu Lys Tyr Asn Pro Val Ser Lys Asp Ile Ile Ala Ser Thr Arg Asp
        450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Asn Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Cys Trp Asp Asn Leu Pro Phe Val Pro Val Lys Gly Pro
530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
                565                 570                 575

Gly Lys Tyr Arg Val Arg Leu Arg Tyr Ala Thr Asp Ala Asp Ile Val
                580                 585                 590

Leu His Val Asn Asp Ala Gln Ile Gln Met Pro Lys Thr Met Asn Pro
        595                 600                 605

Gly Glu Asp Leu Thr Ser Lys Thr Phe Lys Val Ala Asp Ala Ile Thr
610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655

Ile Glu Phe Ile Pro Val Asp Glu Thr Tyr Glu
                660                 665
```

<210> SEQ ID NO 7
<211> LENGTH: 2003
<212> TYPE: DNA
<213> ORGANISM: Bacillus thuringiensis (truncated)
<220> FEATURE:
<221> NAME/KEY: misc_feature
<223> OTHER INFORMATION: 1218-2
<220> FEATURE:
<221> NAME/KEY: CDS

<222> LOCATION: (1)..(2001)

<400> SEQUENCE: 7

| | | | | | | | | | | | | | | | | |
|---|---|---|---|---|---|---|---|---|---|---|---|---|---|---|---|---|
| atg | agt | cca | aat | aat | caa | aat | gaa | tat | gaa | att | ata | gat | gcg | aca | cct | 48 |
| Met | Ser | Pro | Asn | Asn | Gln | Asn | Glu | Tyr | Glu | Ile | Ile | Asp | Ala | Thr | Pro | |
| 1 | | | | 5 | | | | | 10 | | | | | 15 | | |

| tct | act | tct | gta | tcc | aat | gat | tct | aac | aga | tac | cct | ttt | gcg | aat | gag | 96 |
|---|---|---|---|---|---|---|---|---|---|---|---|---|---|---|---|---|
| Ser | Thr | Ser | Val | Ser | Asn | Asp | Ser | Asn | Arg | Tyr | Pro | Phe | Ala | Asn | Glu | |
| | | | 20 | | | | | 25 | | | | | 30 | | | |

| cca | aca | aat | gcg | cta | caa | aat | atg | gat | tat | aaa | gat | tat | tta | aaa | atg | 144 |
|---|---|---|---|---|---|---|---|---|---|---|---|---|---|---|---|---|
| Pro | Thr | Asn | Ala | Leu | Gln | Asn | Met | Asp | Tyr | Lys | Asp | Tyr | Leu | Lys | Met | |
| | | 35 | | | | | 40 | | | | | 45 | | | | |

| tct | gcg | gga | aat | gct | agt | gaa | tac | cct | ggt | tca | cct | gaa | gta | ctt | gtt | 192 |
|---|---|---|---|---|---|---|---|---|---|---|---|---|---|---|---|---|
| Ser | Ala | Gly | Asn | Ala | Ser | Glu | Tyr | Pro | Gly | Ser | Pro | Glu | Val | Leu | Val | |
| | 50 | | | | | 55 | | | | | 60 | | | | | |

| agc | gga | caa | gat | gca | gct | aag | gcc | gca | att | gat | ata | gta | ggt | aaa | tta | 240 |
|---|---|---|---|---|---|---|---|---|---|---|---|---|---|---|---|---|
| Ser | Gly | Gln | Asp | Ala | Ala | Lys | Ala | Ala | Ile | Asp | Ile | Val | Gly | Lys | Leu | |
| 65 | | | | | 70 | | | | | 75 | | | | | 80 | |

| cta | tca | ggt | tta | ggg | gtc | cca | ttt | gtt | ggg | ccg | ata | gtg | agt | ctt | tat | 288 |
|---|---|---|---|---|---|---|---|---|---|---|---|---|---|---|---|---|
| Leu | Ser | Gly | Leu | Gly | Val | Pro | Phe | Val | Gly | Pro | Ile | Val | Ser | Leu | Tyr | |
| | | | | 85 | | | | | 90 | | | | | 95 | | |

| act | caa | ctt | att | gat | att | ctg | tgg | cct | tca | ggg | caa | aag | agt | caa | tgg | 336 |
|---|---|---|---|---|---|---|---|---|---|---|---|---|---|---|---|---|
| Thr | Gln | Leu | Ile | Asp | Ile | Leu | Trp | Pro | Ser | Gly | Gln | Lys | Ser | Gln | Trp | |
| | | | 100 | | | | | 105 | | | | | 110 | | | |

| gag | att | ttt | atg | gaa | caa | gta | gaa | gaa | ctc | ata | aat | caa | aaa | ata | gca | 384 |
|---|---|---|---|---|---|---|---|---|---|---|---|---|---|---|---|---|
| Glu | Ile | Phe | Met | Glu | Gln | Val | Glu | Glu | Leu | Ile | Asn | Gln | Lys | Ile | Ala | |
| | | 115 | | | | | 120 | | | | | 125 | | | | |

| gaa | tat | gca | agg | aat | aaa | gcg | ctt | tcg | gaa | tta | gaa | gga | tta | ggt | aat | 432 |
|---|---|---|---|---|---|---|---|---|---|---|---|---|---|---|---|---|
| Glu | Tyr | Ala | Arg | Asn | Lys | Ala | Leu | Ser | Glu | Leu | Glu | Gly | Leu | Gly | Asn | |
| 130 | | | | | 135 | | | | | 140 | | | | | | |

| aat | tac | caa | tta | tat | cta | act | gcg | ctt | gaa | gaa | tgg | aaa | gaa | aat | cca | 480 |
|---|---|---|---|---|---|---|---|---|---|---|---|---|---|---|---|---|
| Asn | Tyr | Gln | Leu | Tyr | Leu | Thr | Ala | Leu | Glu | Glu | Trp | Lys | Glu | Asn | Pro | |
| 145 | | | | | 150 | | | | | 155 | | | | | 160 | |

| aat | ggt | tca | aga | gcc | tta | cga | gat | gtg | cga | aat | cga | ttt | gaa | atc | ctg | 528 |
|---|---|---|---|---|---|---|---|---|---|---|---|---|---|---|---|---|
| Asn | Gly | Ser | Arg | Ala | Leu | Arg | Asp | Val | Arg | Asn | Arg | Phe | Glu | Ile | Leu | |
| | | | 165 | | | | | 170 | | | | | 175 | | | |

| gat | agt | tta | ttt | acg | caa | tac | atg | cca | tct | ttt | cga | gtg | aca | aat | ttt | 576 |
|---|---|---|---|---|---|---|---|---|---|---|---|---|---|---|---|---|
| Asp | Ser | Leu | Phe | Thr | Gln | Tyr | Met | Pro | Ser | Phe | Arg | Val | Thr | Asn | Phe | |
| | | 180 | | | | | 185 | | | | | 190 | | | | |

| gaa | gta | cca | ttc | ctt | aca | gta | tat | aca | cag | gca | gcc | aac | ctt | cat | tta | 624 |
|---|---|---|---|---|---|---|---|---|---|---|---|---|---|---|---|---|
| Glu | Val | Pro | Phe | Leu | Thr | Val | Tyr | Thr | Gln | Ala | Ala | Asn | Leu | His | Leu | |
| | 195 | | | | | 200 | | | | | 205 | | | | | |

| ctg | tta | tta | aag | gac | gct | tca | att | ttt | gga | gaa | gaa | tgg | gga | tgg | tct | 672 |
|---|---|---|---|---|---|---|---|---|---|---|---|---|---|---|---|---|
| Leu | Leu | Leu | Lys | Asp | Ala | Ser | Ile | Phe | Gly | Glu | Glu | Trp | Gly | Trp | Ser | |
| 210 | | | | | 215 | | | | | 220 | | | | | | |

| aca | acc | act | att | aat | aac | tat | tat | gat | cgt | caa | atg | aaa | ctt | act | gca | 720 |
|---|---|---|---|---|---|---|---|---|---|---|---|---|---|---|---|---|
| Thr | Thr | Thr | Ile | Asn | Asn | Tyr | Tyr | Asp | Arg | Gln | Met | Lys | Leu | Thr | Ala | |
| 225 | | | | | 230 | | | | | 235 | | | | | 240 | |

| gaa | tat | tct | gat | cac | tgt | gta | aag | tgg | tat | gaa | act | ggt | tta | gca | aaa | 768 |
|---|---|---|---|---|---|---|---|---|---|---|---|---|---|---|---|---|
| Glu | Tyr | Ser | Asp | His | Cys | Val | Lys | Trp | Tyr | Glu | Thr | Gly | Leu | Ala | Lys | |
| | | | | 245 | | | | | 250 | | | | | 255 | | |

| tta | aaa | ggc | acg | agc | gct | aaa | caa | tgg | gtc | gac | tat | aac | caa | ttc | cgt | 816 |
|---|---|---|---|---|---|---|---|---|---|---|---|---|---|---|---|---|
| Leu | Lys | Gly | Thr | Ser | Ala | Lys | Gln | Trp | Val | Asp | Tyr | Asn | Gln | Phe | Arg | |
| | | | 260 | | | | | 265 | | | | | 270 | | | |

| aga | gaa | atg | aca | ctg | acg | gtt | tta | gat | gtt | gtt | gca | tta | ttc | cca | aat | 864 |
|---|---|---|---|---|---|---|---|---|---|---|---|---|---|---|---|---|
| Arg | Glu | Met | Thr | Leu | Thr | Val | Leu | Asp | Val | Val | Ala | Leu | Phe | Pro | Asn | |
| | | 275 | | | | | 280 | | | | | 285 | | | | |

| tat | gac | aca | cgc | acg | tac | cca | atg | gaa | acg | aaa | gca | caa | cta | aca | agg | 912 |
|---|---|---|---|---|---|---|---|---|---|---|---|---|---|---|---|---|
| Tyr | Asp | Thr | Arg | Thr | Tyr | Pro | Met | Glu | Thr | Lys | Ala | Gln | Leu | Thr | Arg | |
| | 290 | | | | | 295 | | | | | 300 | | | | | |

```
gaa gta tat aca gat cca ctg ggc gcg gta aac gtg tct tca att ggt    960
Glu Val Tyr Thr Asp Pro Leu Gly Ala Val Asn Val Ser Ser Ile Gly
305                 310                 315                 320 tcc tgg tat gac aaa gca cct tct ttc gga gtg ata gaa tca tcc gtt   1008
Ser Trp Tyr Asp Lys Ala Pro Ser Phe Gly Val Ile Glu Ser Ser Val
                325                 330                 335 att cga cca ccc cat gta ttt gat tat ata acg gga ctc aca gtg tat   1056
Ile Arg Pro Pro His Val Phe Asp Tyr Ile Thr Gly Leu Thr Val Tyr
            340                 345                 350 aca caa tca aga agc att tct tcc gct cgc tat ata aga cat tgg gct   1104
Thr Gln Ser Arg Ser Ile Ser Ser Ala Arg Tyr Ile Arg His Trp Ala
        355                 360                 365 ggt cat caa ata agc tat cat cgg att ttt agt gat aat att ata aaa   1152
Gly His Gln Ile Ser Tyr His Arg Ile Phe Ser Asp Asn Ile Ile Lys
    370                 375                 380 cag atg tat gga act aat caa aat cta cac agc act agt acc ttt gat   1200
Gln Met Tyr Gly Thr Asn Gln Asn Leu His Ser Thr Ser Thr Phe Asp
385                 390                 395                 400 ttt acg aat tat gat att tac aag acg tta tca aaa gat gcg gtg ctc   1248
Phe Thr Asn Tyr Asp Ile Tyr Lys Thr Leu Ser Lys Asp Ala Val Leu
                405                 410                 415 ctt gat att gtt ttt cct ggt tat acg tat ata ttt ttt gga atg cca   1296
Leu Asp Ile Val Phe Pro Gly Tyr Thr Tyr Ile Phe Phe Gly Met Pro
            420                 425                 430 gaa gtc gag ttt ttc atg gta aac caa ttg aat aat acc aga aag acg   1344
Glu Val Glu Phe Phe Met Val Asn Gln Leu Asn Asn Thr Arg Lys Thr
        435                 440                 445 tta aag tat aat ccg gtt tcc aaa gat att ata gcg ggg aca aga gat   1392
Leu Lys Tyr Asn Pro Val Ser Lys Asp Ile Ile Ala Gly Thr Arg Asp
    450                 455                 460 tcg gaa tta gaa tta cct cca gaa act tca gat caa cca aat tat gag   1440
Ser Glu Leu Glu Leu Pro Pro Glu Thr Ser Asp Gln Pro Asn Tyr Glu
465                 470                 475                 480 tca tat agc cat aga tta tgt cat atc aca agt att ccc gcg acg ggt   1488
Ser Tyr Ser His Arg Leu Cys His Ile Thr Ser Ile Pro Ala Thr Gly
                485                 490                 495 tca act acc gga tta gta cct gta ttt tct tgg aca cat cgg agt gcc   1536
Ser Thr Thr Gly Leu Val Pro Val Phe Ser Trp Thr His Arg Ser Ala
            500                 505                 510 gat ctt ata aat gca gtt cat tca gat aaa att act cag att ccg gtc   1584
Asp Leu Ile Asn Ala Val His Ser Asp Lys Ile Thr Gln Ile Pro Val
        515                 520                 525 gta aag gtt tct gat ttg gct ccc tct ata aca gga ggg cca aat aat   1632
Val Lys Val Ser Asp Leu Ala Pro Ser Ile Thr Gly Gly Pro Asn Asn
    530                 535                 540 acc gtt gta tcg ggt cct gga ttt aca ggg ggg ggg ata ata aaa gta   1680
Thr Val Val Ser Gly Pro Gly Phe Thr Gly Gly Gly Ile Ile Lys Val
545                 550                 555                 560 ata aga aat gga gta att tca cat atg cgt gtt aaa att tca gac       1728
Ile Arg Asn Gly Val Ile Ser His Met Arg Val Lys Ile Ser Asp
                565                 570                 575 att aac aaa gaa tat agt atg agg att cgg tat gct tcc gct aat aat   1776
Ile Asn Lys Glu Tyr Ser Met Arg Ile Arg Tyr Ala Ser Ala Asn Asn
            580                 585                 590 act gaa ttt tat ata aat cct tct gaa gaa aac gtt aaa tct cac gct   1824
Thr Glu Phe Tyr Ile Asn Pro Ser Glu Glu Asn Val Lys Ser His Ala
        595                 600                 605 caa aaa act atg aat aga ggt gaa gct tta aca tat aat aaa ttt aat   1872
Gln Lys Thr Met Asn Arg Gly Glu Ala Leu Thr Tyr Asn Lys Phe Asn
    610                 615                 620
```

```
tat gcg act ttg ccc cct att aaa ttt acg aca acc gaa cct ttc att    1920
Tyr Ala Thr Leu Pro Pro Ile Lys Phe Thr Thr Thr Glu Pro Phe Ile
625                 630                 635                 640 act cta ggg gct ata ttt gaa gcg gaa gac ttt ctt gga att gaa gct    1968
Thr Leu Gly Ala Ile Phe Glu Ala Glu Asp Phe Leu Gly Ile Glu Ala
                    645                 650                 655 tat ata gac cga atc gaa ttt atc cca gta gat ga                     2003
Tyr Ile Asp Arg Ile Glu Phe Ile Pro Val Asp
            660                 665
```

<210> SEQ ID NO 8
<211> LENGTH: 667
<212> TYPE: PRT
<213> ORGANISM: Bacillus thuringiensis (tru

```
Ser Trp Tyr Asp Lys Ala Pro Ser Phe Gly Val Ile Glu Ser Ser Val
            325                 330                 335

Ile Arg Pro Pro His Val Phe Asp Tyr Ile Thr Gly Leu Thr Val Tyr
        340                 345                 350

Thr Gln Ser Arg Ser Ile Ser Ser Ala Arg Tyr Ile Arg His Trp Ala
    355                 360                 365

Gly His Gln Ile Ser Tyr Arg Ile Phe Ser Asp Asn Ile Ile Lys
370                 375                 380

Gln Met Tyr Gly Thr Asn Gln Asn Leu His Ser Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Phe Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
            435                 440                 445

Leu Lys Tyr Asn Pro Val Ser Lys Asp Ile Ile Ala Gly Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Ile Asn Ala Val His Ser Asp Lys Ile Thr Gln Ile Pro Val
        515                 520                 525

Val Lys Val Ser Asp Leu Ala Pro Ser Ile Thr Gly Gly Pro Asn Asn
    530                 535                 540

Thr Val Ser Pro Gly Phe Thr Gly Gly Ile Ile Lys Val
545                 550                 555                 560

Ile Arg Asn Gly Val Ile Ile Ser His Met Arg Val Lys Ile Ser Asp
                565                 570                 575

Ile Asn Lys Glu Tyr Ser Met Arg Ile Arg Tyr Ala Ser Ala Asn Asn
            580                 585                 590

Thr Glu Phe Tyr Ile Asn Pro Ser Glu Glu Asn Val Lys Ser His Ala
        595                 600                 605

Gln Lys Thr Met Asn Arg Gly Glu Ala Leu Thr Tyr Asn Lys Phe Asn
    610                 615                 620

Tyr Ala Thr Leu Pro Pro Ile Lys Phe Thr Thr Glu Pro Phe Ile
625                 630                 635                 640

Thr Leu Gly Ala Ile Phe Glu Ala Glu Asp Phe Leu Gly Ile Glu Ala
                645                 650                 655

Tyr Ile Asp Arg Ile Glu Phe Ile Pro Val Asp
            660                 665

<210> SEQ ID NO 9
<211> LENGTH: 2010
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Maize-optimized Cry1218-1
<220> FEATURE:
<221> NAME/KEY: misc_feature
<223> OTHER INFORMATION: mo1218-1
<220> FEATURE:
```

```
<221> NAME/KEY: CDS
<222> LOCATION: (1)..(2010)

<400> SEQUENCE: 9 atg tcc ccc aac aac cag aac gag tac gag atc atc gac gcc acc ccc      48
Met Ser Pro Asn Asn Gln Asn Glu Tyr Glu Ile Ile Asp Ala Thr Pro
1               5                   10                  15 tcc acc tcc gtg tcc aac gac tcc aac cgc tac ccc ttc gcc aac gag      96
Ser Thr Ser Val Ser Asn Asp Ser Asn Arg Tyr Pro Phe Ala Asn Glu
            20                  25                  30 ccc acc aac gcc ctc cag aac atg gac tac aag gac tac ctc aag atg     144
Pro Thr Asn Ala Leu Gln Asn Met Asp Tyr Lys Asp Tyr Leu Lys Met
        35                  40                  45 tcc gcc ggc aac gcc tcc gag tac ccc ggc tcc ccc gag gtg ctc gtg     192
Ser Ala Gly Asn Ala Ser Glu Tyr Pro Gly Ser Pro Glu Val Leu Val
50                  55                  60 tcc ggc cag gac gcc gcc aag gcc gcc atc gac atc gtg ggc aag ctc     240
Ser Gly Gln Asp Ala Ala Lys Ala Ala Ile Asp Ile Val Gly Lys Leu
65                  70                  75                  80 ctc tcc ggc ctc ggc gtg ccc ttc gtg ggc ccc atc gtg tcc ctc tac     288
Leu Ser Gly Leu Gly Val Pro Phe Val Gly Pro Ile Val Ser Leu Tyr
                85                  90                  95 acc cag ctc atc gac atc ctc tgg ccc tcc ggc gag aag tcc cag tgg     336
Thr Gln Leu Ile Asp Ile Leu Trp Pro Ser Gly Glu Lys Ser Gln Trp
            100                 105                 110 gaa atc ttc atg gag cag gtg gag gag ctc atc aac cag aag atc gcc     384
Glu Ile Phe Met Glu Gln Val Glu Glu Leu Ile Asn Gln Lys Ile Ala
        115                 120                 125 gag tac gcc cgc aac aag gcc ctc tcc gag ctg gag ggc ctc ggc aac     432
Glu Tyr Ala Arg Asn Lys Ala Leu Ser Glu Leu Glu Gly Leu Gly Asn
    130                 135                 140 aac tac cag ctc tac ctc acc gcc ctg gag gag tgg gag gag aac ccc     480
Asn Tyr Gln Leu Tyr Leu Thr Ala Leu Glu Glu Trp Glu Glu Asn Pro
145                 150                 155                 160 aac ggc tcc cgc gcc ctc cgc gac gtg cgc aac cgc ttc gag atc ctc     528
Asn Gly Ser Arg Ala Leu Arg Asp Val Arg Asn Arg Phe Glu Ile Leu
                165                 170                 175 gac tcc ctc ttc acc cag tac atg ccc tcc ttc cgc gtg acc aac ttc     576
Asp Ser Leu Phe Thr Gln Tyr Met Pro Ser Phe Arg Val Thr Asn Phe
            180                 185                 190 gag gtg ccc ttc ctc acc gtg tac gcc atg gcc gcc aac ctc cac ctc     624
Glu Val Pro Phe Leu Thr Val Tyr Ala Met Ala Ala Asn Leu His Leu
        195                 200                 205 ctc ctc ctc aag gac gcc tcc atc ttc ggc gag gag tgg ggc tgg tcc     672
Leu Leu Leu Lys Asp Ala Ser Ile Phe Gly Glu Glu Trp Gly Trp Ser
    210                 215                 220 acc acc acc atc aac aac tac tac gac cgc cag atg aag ctc acc gcc     720
Thr Thr Thr Ile Asn Asn Tyr Tyr Asp Arg Gln Met Lys Leu Thr Ala
225                 230                 235                 240 gag tac tcc gac cac tgc gtg aag tgg tat gag acc ggc ctc gcc aag     768
Glu Tyr Ser Asp His Cys Val Lys Trp Tyr Glu Thr Gly Leu Ala Lys
                245                 250                 255 ctc aag ggc acc tcc gcc aag cag tgg gtg gac tac aac cag ttc cgc     816
Leu Lys Gly Thr Ser Ala Lys Gln Trp Val Asp Tyr Asn Gln Phe Arg
            260                 265                 270 cgc gag atg acc ctc gcc gtg ctc gac gtg gtg gcc ctc ttc ccc aac     864
Arg Glu Met Thr Leu Ala Val Leu Asp Val Val Ala Leu Phe Pro Asn
        275                 280                 285 tac gac acc cgc acc tac ccc atg gag acc aag gcc cag ctc acc cgc     912
Tyr Asp Thr Arg Thr Tyr Pro Met Glu Thr Lys Ala Gln Leu Thr Arg
    290                 295                 300
```

```
gag gtg tac acc gac ccg ctc ggc gcc gtg aac gtg tcc tcc atc ggc      960
Glu Val Tyr Thr Asp Pro Leu Gly Ala Val Asn Val Ser Ser Ile Gly
305                 310                 315                 320 tct tgg tac gac aag gcc cca agc ttc ggc gtg atc gag tcc tcc gtg     1008
Ser Trp Tyr Asp Lys Ala Pro Ser Phe Gly Val Ile Glu Ser Ser Val
                325                 330                 335 atc cgc ccg ccg cac gtg ttc gac tac atc acc ggc ctc acc gtg tac     1056
Ile Arg Pro Pro His Val Phe Asp Tyr Ile Thr Gly Leu Thr Val Tyr
            340                 345                 350 acc cag tcc cgc tcc atc tcc tcc gcc cgc tac atc cgc cac tgg gcc     1104
Thr Gln Ser Arg Ser Ile Ser Ser Ala Arg Tyr Ile Arg His Trp Ala
        355                 360                 365 ggc cac cag atc tcc tac cac cgc gtg tcc cgc ggc tcc aac ctc cag     1152
Gly His Gln Ile Ser Tyr His Arg Val Ser Arg Gly Ser Asn Leu Gln
    370                 375                 380 cag atg tac ggc acc aac cag aac ctc cac tcc acc tcc acc ttc gac     1200
Gln Met Tyr Gly Thr Asn Gln Asn Leu His Ser Thr Ser Thr Phe Asp
385                 390                 395                 400 ttc acc aac tac gac atc tac aag acc ctc tcc aag gac gcc gtg ctc     1248
Phe Thr Asn Tyr Asp Ile Tyr Lys Thr Leu Ser Lys Asp Ala Val Leu
                405                 410                 415 ctc gac atc gtg tac ccc ggc tac acc tac atc ttc ttc ggc atg ccg     1296
Leu Asp Ile Val Tyr Pro Gly Tyr Thr Tyr Ile Phe Phe Gly Met Pro
            420                 425                 430 gag gtg gag ttc ttc atg gtg aac cag ctc aac aac acc cgc aag acc     1344
Glu Val Glu Phe Phe Met Val Asn Gln Leu Asn Asn Thr Arg Lys Thr
        435                 440                 445 ctc aaa tac aac ccc gtg tcc aag gac atc atc gcc tcc acc cgc gac     1392
Leu Lys Tyr Asn Pro Val Ser Lys Asp Ile Ile Ala Ser Thr Arg Asp
    450                 455                 460 tcc gag ctc gag ctc ccc ccc gag acc tcc gac cag ccc aac tac gag     1440
Ser Glu Leu Glu Leu Pro Pro Glu Thr Ser Asp Gln Pro Asn Tyr Glu
465                 470                 475                 480 tcc tac tcc cac cgc ctc tgc cac atc acc tcc atc ccc gcc acc ggc     1488
Ser Tyr Ser His Arg Leu Cys His Ile Thr Ser Ile Pro Ala Thr Gly
                485                 490                 495 aac acc acc ggc ctc gtg ccg gtg ttc tcc tgg acc cac cgc tct gca     1536
Asn Thr Thr Gly Leu Val Pro Val Phe Ser Trp Thr His Arg Ser Ala
            500                 505                 510 gac ctc aac aac acc atc tac tcc gac aag atc acc cag atc ccc gcc     1584
Asp Leu Asn Asn Thr Ile Tyr Ser Asp Lys Ile Thr Gln Ile Pro Ala
        515                 520                 525 gtg aag tgc tgg gac aac ctc ccc ttc gtg ccc gtg aag ggc ccc         1632
Val Lys Cys Trp Asp Asn Leu Pro Phe Val Pro Val Lys Gly Pro
    530                 535                 540 ggc cac acc ggc ggc gac ctc ctc cag tac aac cgc tcc acc ggc tcc     1680
Gly His Thr Gly Gly Asp Leu Leu Gln Tyr Asn Arg Ser Thr Gly Ser
545                 550                 555                 560 gtg ggc acc ctc ttc ctc gcc cgc tac ggc ctc gcc ctg gag aag gcc     1728
Val Gly Thr Leu Phe Leu Ala Arg Tyr Gly Leu Ala Leu Glu Lys Ala
                565                 570                 575 ggc aag tac cgc gtg cgc ctc cgc tac gcc act gac gcc gac atc gtg     1776
Gly Lys Tyr Arg Val Arg Leu Arg Tyr Ala Thr Asp Ala Asp Ile Val
            580                 585                 590 ctc cac gtg aac gac gcc cag atc cag atg ccc aag acc atg aac ccc     1824
Leu His Val Asn Asp Ala Gln Ile Gln Met Pro Lys Thr Met Asn Pro
        595                 600                 605 ggc gag gac ctc acc tcc aag acc ttc aag gtg gcc gac gcc atc acc     1872
Gly Glu Asp Leu Thr Ser Lys Thr Phe Lys Val Ala Asp Ala Ile Thr
    610                 615                 620
```

```
acc ctc aac ctc gcc acc gac tcc tcc ctc gcc ctc aag cac aac ctc    1920
Thr Leu Asn Leu Ala Thr Asp Ser Ser Leu Ala Leu Lys His Asn Leu
625                 630                 635                 640 ggc gag gac ccc aac tcc acc ctc tcc ggc atc gtg tac gtg gac cgc    1968
Gly Glu Asp Pro Asn Ser Thr Leu Ser Gly Ile Val Tyr Val Asp Arg
            645                 650                 655 atc gag ttc atc ccc gtg gac gag acc tac gag gcc gag tga            2010
Ile Glu Phe Ile Pro Val Asp Glu Thr Tyr Glu Ala Glu
660                 665
```

<210> SEQ ID NO 10
<211> LENGTH: 669
<212> TYPE: PRT
<213> ORGANISM: Artificial Sequence
<220> FEATURE:
<223> OTHER INFORMATION: Synthetic Construct

<400> SEQUENCE: 10

```
Met Ser Pro Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
                20                  25                  30

Pro Thr Asn Ala Leu Gln Asn Met Asp Tyr Lys Asp Tyr Leu Lys Met
            35                  40                  45

Ser Ala Gly Asn Ala Ser Glu Tyr Pro Gly Ser Pro Glu Val Leu Val
50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Glu Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Ala Met Ala Ala Asn Leu His Leu
        195                 200                 205

Leu Leu Leu Lys Asp Ala Ser Ile Phe Gly Glu Glu Trp Gly Trp Ser
210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Ala Val Leu Asp Val Val Ala Leu Phe Pro Asn
        275                 280                 285

Tyr Asp Thr Arg Thr Tyr Pro Met Glu Thr Lys Ala Gln Leu Thr Arg
290                 295                 300
```

```
Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
            325                 330                 335

Ile Arg Pro Pro His Val Phe Asp Tyr Ile Thr Gly Leu Thr Val Tyr
        340                 345                 350

Thr Gln Ser Arg Ser Ile Ser Ser Ala Arg Tyr Ile Arg His Trp Ala
    355                 360                 365

Gly His Gln Ile Ser Tyr His Arg Val Ser Arg Gly Ser Asn Leu Gln
370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
            405                 410                 415

Leu Asp Ile Val Tyr Pro Gly Tyr Thr Tyr Ile Phe Phe Gly Met Pro
        420                 425                 430

Glu Val Glu Phe Phe Met Val Asn Gln Leu Asn Asn Thr Arg Lys Thr
    435                 440                 445

Leu Lys Tyr Asn Pro Val Ser Lys Asp Ile Ile Ala Ser Thr Arg Asp
450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
            485                 490                 495

Asn Thr Thr Gly Leu Val Pro Val Phe Ser Trp Thr His Arg Ser Ala
        500                 505                 510

Asp Leu Asn Asn Thr Ile Tyr Ser Asp Lys Ile Thr Gln Ile Pro Ala
    515                 520                 525

Val Lys Cys Trp Asp Asn Leu Pro Phe Val Pro Val Lys Gly Pro
530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
            565                 570                 575

Gly Lys Tyr Arg Val Arg Leu Arg Tyr Ala Thr Asp Ala Asp Ile Val
        580                 585                 590

Leu His Val Asn Asp Ala Gln Ile Gln Met Pro Lys Thr Met Asn Pro
    595                 600                 605

Gly Glu Asp Leu Thr Ser Lys Thr Phe Lys Val Ala Asp Ala Ile Thr
610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
            645                 650                 655

Ile Glu Phe Ile Pro Val Asp Glu Thr Tyr Glu Ala Glu
        660                 665

<210> SEQ ID NO 11
<211> LENGTH: 2022
<212> TYPE: DNA
<213> ORGANISM: Bacillus thuringiensis (mutated)
<220> FEATURE:
<221> NAME/KEY: CDS
<222> LOCATION: (1)..(2022)
<220> FEATURE:
<221> NAME/KEY: misc_feature
<222>

<223> OTHER INFORMATION: NGSR.N1218-1

<400> SEQUENCE: 11

```
atg agt cca aat aat caa aat gaa tat gaa att ata gat gcg aca cct       48
Met Ser Pro Asn Asn Gln Asn Glu Tyr Glu Ile Ile Asp Ala Thr Pro
1               5                   10                  15 tct act tct gta tcc aat gat tct aac aga tac cct ttt gcg aat gag       96
Ser Thr Ser Val Ser Asn Asp Ser Asn Arg Tyr Pro Phe Ala Asn Glu
            20                  25                  30 cca aca aat gcg cta caa aat atg gat tat aaa gat tat tta aaa atg      144
Pro Thr Asn Ala Leu Gln Asn Met Asp Tyr Lys Asp Tyr Leu Lys Met
        35                  40                  45 tct gcg gga aat gct agt gaa tac cct ggt tca cct gaa gta ctt gtt      192
Ser Ala Gly Asn Ala Ser Glu Tyr Pro Gly Ser Pro Glu Val Leu Val
50                  55                  60 agc gga caa gat gca gct aag gcc gca att gat ata gta ggt aaa tta      240
Ser Gly Gln Asp Ala Ala Lys Ala Ala Ile Asp Ile Val Gly Lys Leu
65                  70                  75                  80 cta tca ggt tta ggg gtc cca ttt gtt ggg ccg ata gtg agt ctt tat      288
Leu Ser Gly Leu Gly Val Pro Phe Val Gly Pro Ile Val Ser Leu Tyr
                85                  90                  95 act caa ctt att gat att ctg tgg cct tca ggg gaa aag agt caa tgg      336
Thr Gln Leu Ile Asp Ile Leu Trp Pro Ser Gly Glu Lys Ser Gln Trp
            100                 105                 110 gaa att ttt atg gaa caa gta gaa gaa ctc att aat caa aaa ata gca      384
Glu Ile Phe Met Glu Gln Val Glu Glu Leu Ile Asn Gln Lys Ile Ala
        115                 120                 125 gaa tat gca agg aat aaa gcg ctt tcg gaa tta gaa gga tta ggt aat      432
Glu Tyr Ala Arg Asn Lys Ala Leu Ser Glu Leu Glu Gly Leu Gly Asn
130                 135                 140 aat tac caa tta tat cta act gcg ctt gaa gaa tgg gaa gaa aat cca      480
Asn Tyr Gln Leu Tyr Leu Thr Ala Leu Glu Glu Trp Glu Glu Asn Pro
145                 150                 155                 160 aat ggt tca aga aat ggt tcc cgg gcc tta cga gat gtg cga aat cga      528
Asn Gly Ser Arg Asn Gly Ser Arg Ala Leu Arg Asp Val Arg Asn Arg
                165                 170                 175 ttt gaa atc ctg gat agt tta ttt acg caa tat atg cca tct ttt aga      576
Phe Glu Ile Leu Asp Ser Leu Phe Thr Gln Tyr Met Pro Ser Phe Arg
            180                 185                 190 gtg aca aat ttt gaa gta cca ttc ctt act gta tat gca atg gca gcc      624
Val Thr Asn Phe Glu Val Pro Phe Leu Thr Val Tyr Ala Met Ala Ala
        195                 200                 205 aac ctt cat tta ctg tta tta aag gac gcg tca att ttt gga gaa gaa      672
Asn Leu His Leu Leu Leu Leu Lys Asp Ala Ser Ile Phe Gly Glu Glu
210                 215                 220 tgg gga tgg tca aca act act att aat aac tat tat gat cgt caa atg      720
Trp Gly Trp Ser Thr Thr Thr Ile Asn Asn Tyr Tyr Asp Arg Gln Met
225                 230                 235                 240 aaa ctt act gca gaa tat tct gat cac tgt gta aag tgg tat gaa act      768
Lys Leu Thr Ala Glu Tyr Ser Asp His Cys Val Lys Trp Tyr Glu Thr
                245                 250                 255 ggt tta gca aaa tta aaa ggc acg agc gct aaa caa tgg gtt gac tat      816
Gly Leu Ala Lys Leu Lys Gly Thr Ser Ala Lys Gln Trp Val Asp Tyr
            260                 265                 270 aac caa ttc cgt aga gaa atg aca ctg gcg gtt tta gat gtt gtt gca      864
Asn Gln Phe Arg Arg Glu Met Thr Leu Ala Val Leu Asp Val Val Ala
        275                 280                 285 tta ttc cca aat tat gac aca cgc acg tac cca atg gaa acg aaa gca      912
Leu Phe Pro Asn Tyr Asp Thr Arg Thr Tyr Pro Met Glu Thr Lys Ala
290                 295                 300
```

```
caa cta aca agg gaa gta tat aca gat cca ctg ggc gcg gta aac gtg      960
Gln Leu Thr Arg Glu Val Tyr Thr Asp Pro Leu Gly Ala Val Asn Val
305                 310                 315                 320 tct tca att ggt tcc tgg tat gac aaa gca cct tct ttc gga gtg ata     1008
Ser Ser Ile Gly Ser Trp Tyr Asp Lys Ala Pro Ser Phe Gly Val Ile
                325                 330                 335 gaa tca tcc gtt att cga cca ccc cat gta ttt gat tat ata acg gga    1056
Glu Ser Ser Val Ile Arg Pro Pro His Val Phe Asp Tyr Ile Thr Gly
            340                 345                 350 ctc aca gtg tat aca caa tca aga agc att tct tcc gct cgc tat ata   1104
Leu Thr Val Tyr Thr Gln Ser Arg Ser Ile Ser Ser Ala Arg Tyr Ile
        355                 360                 365 aga cat tgg gct ggt cat caa ata agc tac cat cgt gtc agt agg ggt   1152
Arg His Trp Ala Gly His Gln Ile Ser Tyr His Arg Val Ser Arg Gly
370                 375                 380 agt aat ctt caa caa atg tat gga act aat caa aat cta cac agc act   1200
Ser Asn Leu Gln Gln Met Tyr Gly Thr Asn Gln Asn Leu His Ser Thr
385                 390                 395                 400 agt acc ttt gat ttt acg aat tat gat att tac aag act cta tca aag   1248
Ser Thr Phe Asp Phe Thr Asn Tyr Asp Ile Tyr Lys Thr Leu Ser Lys
                405                 410                 415 gat gca gta ctc ctt gat att gtt tac cct ggt tat acg tat ata ttt   1296
Asp Ala Val Leu Leu Asp Ile Val Tyr Pro Gly Tyr Thr Tyr Ile Phe
            420                 425                 430 ttt gga atg cca gaa gtc gag ttt ttc atg gta aac caa ttg aat aat   1344
Phe Gly Met Pro Glu Val Glu Phe Phe Met Val Asn Gln Leu Asn Asn
        435                 440                 445 acc aga aag acg tta aag tat aat cca gtt tcc aaa gat att ata gcg   1392
Thr Arg Lys Thr Leu Lys Tyr Asn Pro Val Ser Lys Asp Ile Ile Ala
450                 455                 460 agt aca aga gat tcg gaa tta gaa tta cct cca gaa act tca gat caa   1440
Ser Thr Arg Asp Ser Glu Leu Glu Leu Pro Pro Glu Thr Ser Asp Gln
465                 470                 475                 480 cca aat tat gag tca tat agc cat aga tta tgt cat atc aca agt att   1488
Pro Asn Tyr Glu Ser Tyr Ser His Arg Leu Cys His Ile Thr Ser Ile
                485                 490                 495 ccc gcg acg ggt aac act acc gga tta gta cct gta ttt tct tgg aca   1536
Pro Ala Thr Gly Asn Thr Thr Gly Leu Val Pro Val Phe Ser Trp Thr
            500                 505                 510 cat cga agt gca gat tta aac aat aca ata tat tca gat aaa atc act   1584
His Arg Ser Ala Asp Leu Asn Asn Thr Ile Tyr Ser Asp Lys Ile Thr
        515                 520                 525 caa att ccg gcc gtt aaa tgt tgg gat aat tta ccg ttt gtt cca gtg   1632
Gln Ile Pro Ala Val Lys Cys Trp Asp Asn Leu Pro Phe Val Pro Val
530                 535                 540 gta aaa gga cca gga cat aca gga ggg gat tta tta cag tat aat aga   1680
Val Lys Gly Pro Gly His Thr Gly Gly Asp Leu Leu Gln Tyr Asn Arg
545                 550                 555                 560 agt act ggt tct gta gga acc tta ttt cta gct cga tat ggc cta gca   1728
Ser Thr Gly Ser Val Gly Thr Leu Phe Leu Ala Arg Tyr Gly Leu Ala
                565                 570                 575 tta gaa aaa gca ggg aaa tat cgt gta aga ctg aga tat gct act gat   1776
Leu Glu Lys Ala Gly Lys Tyr Arg Val Arg Leu Arg Tyr Ala Thr Asp
            580                 585                 590 gca gat att gta ttg cat gta aac gat gct cag att cag atg cca aaa   1824
Ala Asp Ile Val Leu His Val Asn Asp Ala Gln Ile Gln Met Pro Lys
        595                 600                 605 aca atg aac cca ggt gag gat ctg aca tct aaa act ttt aaa gtt gca   1872
Thr Met Asn Pro Gly Glu Asp Leu Thr Ser Lys Thr Phe Lys Val Ala
610                 615                 620
```

```
gat gct atc aca aca tta aat tta gca aca gat agt tcg cta gca ttg    1920
Asp Ala Ile Thr Thr Leu Asn Leu Ala Thr Asp Ser Ser Leu Ala Leu
625                 630                 635                 640 aaa cat aat tta ggt gaa gac cct aat tca aca tta tct ggt ata gtt    1968
Lys His Asn Leu Gly Glu Asp Pro Asn Ser Thr Leu Ser Gly Ile Val
                    645                 650                 655 tac gtt gac cga atc gaa ttc atc cca gta gat gag aca tat gaa gcg    2016
Tyr Val Asp Arg Ile Glu Phe Ile Pro Val Asp Glu Thr Tyr Glu Ala
                660                 665                 670 gaa taa                                                             2022
Glu
```

<210> SEQ ID NO 12
<211> LENGTH: 673
<212> TYPE: PRT
<213> ORGANISM: Bacillus thuringiensis (mutated)

<400> SEQUENCE: 12

```
Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
145                 150                 155                 160

Asn Gly Ser Arg Asn Gly Ser Arg Ala Leu Arg Asp Val Arg Asn Arg
                165                 170                 175

Phe Glu Ile Leu Asp Ser Leu Phe Thr Gln Tyr Met Pro Ser Phe Arg
            180                 185                 190

Val Thr Asn Phe Glu Val Pro Phe Leu Thr Val Tyr Ala Met Ala Ala
        195                 200                 205

Asn Leu His Leu Leu Leu Lys Asp Ala Ser Ile Phe Gly Glu Glu
    210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
            260                 265                 270

Asn Gln Phe Arg Arg Glu Met Thr Leu Ala Val Leu Asp Val Val Ala
        275                 280                 285

Leu Phe Pro Asn Tyr Asp Thr Arg Thr Tyr Pro Met Glu Thr Lys Ala
    290                 295                 300
```

```
Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
            325                 330                 335

Glu Ser Ser Val Ile Arg Pro Pro His Val Phe Asp Tyr Ile Thr Gly
        340                 345                 350

Leu Thr Val Tyr Thr Gln Ser Arg Ser Ile Ser Ser Ala Arg Tyr Ile
    355                 360                 365

Arg His Trp Ala Gly His Gln Ile Ser Tyr His Arg Val Ser Arg Gly
370                 375                 380

Ser Asn Leu Gln Gln Met Tyr Gly Thr Asn Gln Asn Leu His Ser Thr
385                 390                 395                 400

Ser Thr Phe Asp Phe Thr Asn Tyr Asp Ile Tyr Lys Thr Leu Ser Lys
                405                 410                 415

Asp Ala Val Leu Leu Asp Ile Val Tyr Pro Gly Tyr Thr Tyr Ile Phe
            420                 425                 430

Phe Gly Met Pro Glu Val Glu Phe Met Val Asn Gln Leu Asn Asn
        435                 440                 445

Thr Arg Lys Thr Leu Lys Tyr Asn Pro Val Ser Lys Asp Ile Ile Ala
450                 455                 460

Ser Thr Arg Asp Ser Glu Leu Glu Leu Pro Pro Glu Thr Ser Asp Gln
465                 470                 475                 480

Pro Asn Tyr Glu Ser Tyr Ser His Arg Leu Cys His Ile Thr Ser Ile
                485                 490                 495

Pro Ala Thr Gly Asn Thr Gly Leu Val Pro Val Phe Ser Trp Thr
            500                 505                 510

His Arg Ser Ala Asp Leu Asn Asn Thr Ile Tyr Ser Asp Lys Ile Thr
        515                 520                 525

Gln Ile Pro Ala Val Lys Cys Trp Asp Asn Leu Pro Phe Val Pro Val
    530                 535                 540

Val Lys Gly Pro Gly His Thr Gly Gly Asp Leu Leu Gln Tyr Asn Arg
545                 550                 555                 560

Ser Thr Gly Ser Val Gly Thr Leu Phe Leu Ala Arg Tyr Gly Leu Ala
                565                 570                 575

Leu Glu Lys Ala Gly Lys Tyr Arg Val Arg Leu Arg Tyr Ala Thr Asp
            580                 585                 590

Ala Asp Ile Val Leu His Val Asn Asp Ala Gln Ile Gln Met Pro Lys
        595                 600                 605

Thr Met Asn Pro Gly Glu Asp Leu Thr Ser Lys Thr Phe Lys Val Ala
    610                 615                 620

Asp Ala Ile Thr Thr Leu Asn Leu Ala Thr Asp Ser Ser Leu Ala Leu
625                 630                 635                 640

Lys His Asn Leu Gly Glu Asp Pro Asn Ser Thr Leu Ser Gly Ile Val
                645                 650                 655

Tyr Val Asp Arg Ile Glu Phe Ile Pro Val Asp Glu Thr Tyr Glu Ala
            660                 665                 670

Glu
```

<210> SEQ ID NO 13
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature -continued

```
<223> OTHER INFORMATION: NGSR Insert
<220> FEATURE:
<221> NAME/KEY: CDS
<222> LOCATION: (1)..(12)

<400> SEQUENCE: 13 aat ggt tcc cgg                                                          12
Asn Gly Ser Arg
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Asn Gly Ser Arg
1

<210> SEQ ID NO 15
<211> LENGTH: 2010
<212> TYPE: DNA
<213> ORGANISM: Bacillus thuringiensis (truncated)
<220> FEATURE:
<221> NAME/KEY: misc_feature
<223> OTHER INFORMATION: 1218-1A
<220> FEATURE:

-continued

```
                      165                 170                 175
gat agt tta ttt acg caa tat atg cca tct ttt aga gtg aca aat ttt     576
Asp Ser Leu Phe Thr Gln Tyr Met Pro Ser Phe Arg Val Thr Asn Phe
        180                 185                 190 gaa gta cca ttc ctt act gta tat gca atg gca gcc aac ctt cat tta     624
Glu Val Pro Phe Leu Thr Val Tyr Ala Met Ala Ala Asn Leu His Leu
            195                 200                 205 ctg tta tta aag gac gcg tca att ttt gga gaa gaa tgg gga tgg tca     672
Leu Leu Leu Lys Asp Ala Ser Ile Phe Gly Glu Glu Trp Gly Trp Ser
210                 215                 220 aca act act att aat aac tat tat gat cgt caa atg aaa ctt act gca     720
Thr Thr Thr Ile Asn Asn Tyr Tyr Asp Arg Gln Met Lys Leu Thr Ala
225                 230                 235                 240 gaa tat tct gat cac tgt gta aag tgg tat gaa act ggt tta gca aaa     768
Glu Tyr Ser Asp His Cys Val Lys Trp Tyr Glu Thr Gly Leu Ala Lys
                245                 250                 255 tta aaa ggc acg agc gct aaa caa tgg gtt gac tat aac caa ttc cgt     816
Leu Lys Gly Thr Ser Ala Lys Gln Trp Val Asp Tyr Asn Gln Phe Arg
            260                 265                 270 aga gaa atg aca ctg gcg gtt tta gat gtt gtt gca tta ttc cca aat     864
Arg Glu Met Thr Leu Ala Val Leu Asp Val Val Ala Leu Phe Pro Asn
        275                 280                 285 tat gac aca cgc acg tac cca atg gaa acg aaa gca caa cta aca agg     912
Tyr Asp Thr Arg Thr Tyr Pro Met Glu Thr Lys Ala Gln Leu Thr Arg
    290                 295                 300 gaa gta tat aca gat cca ctg ggc gcg gta aac gtg tct tca att ggt     960
Glu Val Tyr Thr Asp Pro Leu Gly Ala Val Asn Val Ser Ser Ile Gly
305                 310                 315                 320 tcc tgg tat gac aaa gca cct tct ttc gga gtg ata gaa tca tcc gtt    1008
Ser Trp Tyr Asp Lys Ala Pro Ser Phe Gly Val Ile Glu Ser Ser Val
                325                 330                 335 att cga cca ccc cat gta ttt gat tat ata acg gga ctc aca gtg tat    1056
Ile Arg Pro Pro His Val Phe Asp Tyr Ile Thr Gly Leu Thr Val Tyr
            340                 345                 350 aca caa tca aga agc att tct tcc gct cgc tat ata aga cat tgg gct    1104
Thr Gln Ser Arg Ser Ile Ser Ser Ala Arg Tyr Ile Arg His Trp Ala
        355                 360                 365 ggt cat caa ata agc tac cat cgt gtc agt agg ggt agt aat ctt caa    1152
Gly His Gln Ile Ser Tyr His Arg Val Ser Arg Gly Ser Asn Leu Gln
    370                 375                 380 caa atg tat gga act aat caa aat cta cac agc act agt acc ttt gat    1200
Gln Met Tyr Gly Thr Asn Gln Asn Leu His Ser Thr Ser Thr Phe Asp
385                 390                 395                 400 ttt acg aat tat gat att tac aag act cta tca aag gat gca gta ctc    1248
Phe Thr Asn Tyr Asp Ile Tyr Lys Thr Leu Ser Lys Asp Ala Val Leu
                405                 410                 415 ctt gat att gtt tac cct ggt tat acg tat ata ttt ttt gga atg cca    1296
Leu Asp Ile Val Tyr Pro Gly Tyr Thr Tyr Ile Phe Phe Gly Met Pro
            420                 425                 430 gaa gtc gag ttt ttc atg gta aac caa ttg aat aat acc aga aag acg    1344
Glu Val Glu Phe Phe Met Val Asn Gln Leu Asn Asn Thr Arg Lys Thr
        435                 440                 445 tta aag tat aat cca gtt tcc aaa gat att ata gcg agt aca aga gat    1392
Leu Lys Tyr Asn Pro Val Ser Lys Asp Ile Ile Ala Ser Thr Arg Asp
    450                 455                 460 tcg gaa tta gaa tta cct cca gaa act tca gat caa cca aat tat gag    1440
Ser Glu Leu Glu Leu Pro Pro Glu Thr Ser Asp Gln Pro Asn Tyr Glu
465                 470                 475                 480 tca tat agc cat aga tta tgt cat atc aca agt att ccc gcg acg ggt    1488
Ser Tyr Ser His Arg Leu Cys His Ile Thr Ser Ile Pro Ala Thr Gly
```

|  |  |
|---|---|
| aac act acc gga tta gta cct gta ttt tct tgg aca cat cga agt gca<br>Asn Thr Thr Gly Leu Val Pro Val Phe Ser Trp Thr His Arg Ser Ala<br>        500                 505                 510 | 1536 |
| gat tta aac aat aca ata tat tca gat aaa atc act caa att ccg gcc<br>Asp Leu Asn Asn Thr Ile Tyr Ser Asp Lys Ile Thr Gln Ile Pro Ala<br>        515                 520                 525 | 1584 |
| gtt aaa tgt tgg gat aat tta ccg ttt gtt cca gtg gta aaa gga cca<br>Val Lys Cys Trp Asp Asn Leu Pro Phe Val Pro Val Val Lys Gly Pro<br>        530                 535                 540 | 1632 |
| gga cat aca gga ggg gat tta tta cag tat aat aga agt act ggt tct<br>Gly His Thr Gly Gly Asp Leu Leu Gln Tyr Asn Arg Ser Thr Gly Ser<br>545                 550                 555                 560 | 1680 |
| gta gga acc tta ttt cta gct cga tat ggc cta gca tta gaa aaa gca<br>Val Gly Thr Leu Phe Leu Ala Arg Tyr Gly Leu Ala Leu Glu Lys Ala<br>                        565                 570                 575 | 1728 |
| ggg aaa tat cgt gta aga ctg aga tat gct act gat gca gat att gta<br>Gly Lys Tyr Arg Val Arg Leu Arg Tyr Ala Thr Asp Ala Asp Ile Val<br>                580                 585                 590 | 1776 |
| ttg cat gta aac gat gct cag att cag atg cca aaa aca atg aac cca<br>Leu His Val Asn Asp Ala Gln Ile Gln Met Pro Lys Thr Met Asn Pro<br>                595                 600                 605 | 1824 |
| ggt gag gat ctg aca tct aaa act ttt aaa gtt gca gat gct atc aca<br>Gly Glu Asp Leu Thr Ser Lys Thr Phe Lys Val Ala Asp Ala Ile Thr<br>610                 615                 620 | 1872 |
| aca tta aat tta gca aca gat agt tcg cta gca ttg aaa cat aat tta<br>Thr Leu Asn Leu Ala Thr Asp Ser Ser Leu Ala Leu Lys His Asn Leu<br>625                 630                 635                 640 | 1920 |
| ggt gaa gac cct aat tca aca tta tct ggt ata gtt tac gtt gac cga<br>Gly Glu Asp Pro Asn Ser Thr Leu Ser Gly Ile Val Tyr Val Asp Arg<br>                        645                 650                 655 | 1968 |
| atc gaa ttc atc cca gta gat gag aca tat gaa gcg gaa taa<br>Ile Glu Phe Ile Pro Val Asp Glu Thr Tyr Glu Ala Glu<br>                660                 665 | 2010 |

<210> SEQ ID NO 16
<211> LENGTH: 669
<212> TYPE: PRT
<213> ORGANISM: Bacillus thuringiens

```
Asn Tyr Gln Leu Tyr Leu Thr Ala Leu Glu Glu Trp Glu Asn Pro
145                 150                 155                 160

Asn Gly Ser Arg Ala Leu Arg Asp Val Arg Asn Arg Phe Glu Ile Leu
            165                 170                 175

Asp Ser Leu Phe Thr Gln Tyr Met Pro Ser Phe Arg Val Thr Asn Phe
        180                 185                 190

Glu Val Pro Phe Leu Thr Val Tyr Ala Met Ala Ala Asn Leu His Leu
    195                 200                 205

Leu Leu Leu Lys Asp Ala Ser Ile Phe Gly Glu Glu Trp Gly Trp Ser
210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Ala Val Leu Asp Val Val Ala Leu Phe Pro Asn
        275                 280                 285

Tyr Asp Thr Arg Thr Tyr Pro Met Glu Thr Lys Ala Gln Leu Thr Arg
290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Val Ser Arg Gly Ser Asn Leu Gln
370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Tyr Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Lys Tyr Asn Pro Val Ser Lys Asp Ile Ile Ala Ser Thr Arg Asp
450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Asn Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Cys Trp Asp Asn Leu Pro Phe Val Pro Val Lys Gly Pro
530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
```

```
                    565                 570                 575
Gly Lys Tyr Arg Val Arg Leu Arg Tyr Ala Thr Asp Ala Asp Ile Val
            580                 585                 590

Leu His Val Asn Asp Ala Gln Ile Gln Met Pro Lys Thr Met Asn Pro
        595                 600                 605

Gly Glu Asp Leu Thr Ser Lys Thr Phe Lys Val Ala Asp Ala Ile Thr
    610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655

Ile Glu Phe Ile Pro Val Asp Glu Thr Tyr Glu Ala Glu
            660                 665

<210> SEQ ID NO 17
<211> LENGTH: 2022
<212> TYPE: DNA
<213> ORGANISM: Bacillus thuringiensis (truncated)
<220> FEATURE:
<221> NAME/KEY: misc_feature
<223> OTHER INFORMATION: 1218-2A
<220> FEATURE:
<221> NAME/KEY: CDS
<222> LOCATION: (1)..(2022)

<400> SEQUENCE: 17 atg agt cca aat aat caa aat gaa tat gaa att ata gat gcg aca cct      48
Met Ser Pro Asn Asn Gln Asn Glu Tyr Glu Ile Ile Asp Ala Thr Pro
1               5                   10                  15 tct act tct gta tcc aat gat tct aac aga tac cct ttt gcg aat gag      96
Ser Thr Ser Val Ser Asn Asp Ser Asn Arg Tyr Pro Phe Ala Asn Glu
                20                  25                  30 cca aca aat gcg cta caa aat atg gat tat aaa gat tat tta aaa atg     144
Pro Thr Asn Ala Leu Gln Asn Met Asp Tyr Lys Asp Tyr Leu Lys Met
            35                  40                  45 tct gcg gga aat gct agt gaa tac cct ggt tca cct gaa gta ctt gtt     192
Ser Ala Gly Asn Ala Ser Glu Tyr Pro Gly Ser Pro Glu Val Leu Val
        50                  55                  60 agc gga caa gat gca gct aag gcc gca att gat ata gta ggt aaa tta     240
Ser Gly Gln Asp Ala Ala Lys Ala Ala Ile Asp Ile Val Gly Lys Leu
65                  70                  75                  80 cta tca ggt tta ggg gtc cca ttt gtt ggg ccg ata gtg agt ctt tat     288
Leu Ser Gly Leu Gly Val Pro Phe Val Gly Pro Ile Val Ser Leu Tyr
                85                  90                  95 act caa ctt att gat att ctg tgg cct tca ggg caa aag agt caa tgg     336
Thr Gln Leu Ile Asp Ile Leu Trp Pro Ser Gly Gln Lys Ser Gln Trp
            100                 105                 110 gag att ttt atg gaa caa gta gaa gaa ctc ata aat caa aaa ata gca     384
Glu Ile Phe Met Glu Gln Val Glu Glu Leu Ile Asn Gln Lys Ile Ala
        115                 120                 125 gaa tat gca agg aat aaa gcg ctt tcg gaa tta gaa gga tta ggt aat     432
Glu Tyr Ala Arg Asn Lys Ala Leu Ser Glu Leu Glu Gly Leu Gly Asn
    130                 135                 140 aat tac caa tta tat cta act gcg ctt gaa gaa tgg aaa gaa aat cca     480
Asn Tyr Gln Leu Tyr Leu Thr Ala Leu Glu Glu Trp Lys Glu Asn Pro
145                 150                 155                 160 aat ggt tca aga gcc tta cga gat gtg cga aat cga ttt gaa atc ctg     528
Asn Gly Ser Arg Ala Leu Arg Asp Val Arg Asn Arg Phe Glu Ile Leu
                165                 170                 175 gat agt tta ttt acg caa tac atg cca tct ttt cga gtg aca aat ttt     576
Asp Ser Leu Phe Thr Gln Tyr Met Pro Ser Phe Arg Val Thr Asn Phe
```

```
                         180                 185                 190
gaa gta cca ttc ctt aca gta tat aca cag gca gcc aac ctt cat tta        624
Glu Val Pro Phe Leu Thr Val Tyr Thr Gln Ala Ala Asn Leu His Leu
            195                 200                 205 ctg tta tta aag gac gct tca att ttt gga gaa gaa tgg gga tgg tct        672
Leu Leu Leu Lys Asp Ala Ser Ile Phe Gly Glu Glu Trp Gly Trp Ser
210                 215                 220 aca acc act att aat aac tat tat gat cgt caa atg aaa ctt act gca        720
Thr Thr Thr Ile Asn Asn Tyr Tyr Asp Arg Gln Met Lys Leu Thr Ala
225                 230                 235                 240 gaa tat tct gat cac tgt gta aag tgg tat gaa act ggt tta gca aaa        768
Glu Tyr Ser Asp His Cys Val Lys Trp Tyr Glu Thr Gly Leu Ala Lys
            245                 250                 255 tta aaa ggc acg agc gct aaa caa tgg gtc gac tat aac caa ttc cgt        816
Leu Lys Gly Thr Ser Ala Lys Gln Trp Val Asp Tyr Asn Gln Phe Arg
            260                 265                 270 aga gaa atg aca ctg acg gtt tta gat gtt gtt gca tta ttc cca aat        864
Arg Glu Met Thr Leu Thr Val Leu Asp Val Val Ala Leu Phe Pro Asn
            275                 280                 285 tat gac aca cgc acg tac cca atg gaa acg aaa gca caa cta aca agg        912
Tyr Asp Thr Arg Thr Tyr Pro Met Glu Thr Lys Ala Gln Leu Thr Arg
290                 295                 300 gaa gta tat aca gat cca ctg ggc gcg gta aac gtg tct tca att ggt        960
Glu Val Tyr Thr Asp Pro Leu Gly Ala Val Asn Val Ser Ser Ile Gly
305                 310                 315                 320 tcc tgg tat gac aaa gca cct tct ttc gga gtg ata gaa tca tcc gtt       1008
Ser Trp Tyr Asp Lys Ala Pro Ser Phe Gly Val Ile Glu Ser Ser Val
                325                 330                 335 att cga cca ccc cat gta ttt gat tat ata acg gga ctc aca gtg tat       1056
Ile Arg Pro Pro His Val Phe Asp Tyr Ile Thr Gly Leu Thr Val Tyr
            340                 345                 350 aca caa tca aga agc att tct tcc gct cgc tat ata aga cat tgg gct       1104
Thr Gln Ser Arg Ser Ile Ser Ser Ala Arg Tyr Ile Arg His Trp Ala
            355                 360                 365 ggt cat caa ata agc tat cat cgg att ttt agt gat aat att ata aaa       1152
Gly His Gln Ile Ser Tyr His Arg Ile Phe Ser Asp Asn Ile Ile Lys
370                 375                 380 cag atg tat gga act aat caa aat cta cac agc act agt acc ttt gat       1200
Gln Met Tyr Gly Thr Asn Gln Asn Leu His Ser Thr Ser Thr Phe Asp
385                 390                 395                 400 ttt acg aat tat gat att tac aag acg tta tca aaa gat gcg gtg ctc       1248
Phe Thr Asn Tyr Asp Ile Tyr Lys Thr Leu Ser Lys Asp Ala Val Leu
                405                 410                 415 ctt gat att gtt ttt cct ggt tat acg tat ata ttt ttt gga atg cca       1296
Leu Asp Ile Val Phe Pro Gly Tyr Thr Tyr Ile Phe Phe Gly Met Pro
            420                 425                 430 gaa gtc gag ttt ttc atg gta aac caa ttg aat aat acc aga aag acg       1344
Glu Val Glu Phe Phe Met Val Asn Gln Leu Asn Asn Thr Arg Lys Thr
            435                 440                 445 tta aag tat aat ccg gtt tcc aaa gat att ata gcg ggg aca aga gat       1392
Leu Lys Tyr Asn Pro Val Ser Lys Asp Ile Ile Ala Gly Thr Arg Asp
450                 455                 460 tcg gaa tta gaa tta cct cca gaa act tca gat caa cca aat tat gag       1440
Ser Glu Leu Glu Leu Pro Pro Glu Thr Ser Asp Gln Pro Asn Tyr Glu
465                 470                 475                 480 tca tat agc cat aga tta tgt cat atc aca agt att ccc gcg acg ggt       1488
Ser Tyr Ser His Arg Leu Cys His Ile Thr Ser Ile Pro Ala Thr Gly
                485                 490                 495 tca act acc gga tta gta cct gta ttt tct tgg aca cat cgg agt gcc       1536
Ser Thr Thr Gly Leu Val Pro Val Phe Ser Trp Thr His Arg Ser Ala
```

| | | | | | | | | | | | | | | | | |
|---|---|---|---|---|---|---|---|---|---|---|---|---|---|---|---|---|
| | | | | 500 | | | | | 505 | | | | | 510 | | |
| gat | ctt | ata | aat | gca | gtt | cat | tca | gat | aaa | att | act | cag | att | ccg | gtc | 1584 |
| Asp | Leu | Ile | Asn | Ala | Val | His | Ser | Asp | Lys | Ile | Thr | Gln | Ile | Pro | Val | |
| | 515 | | | | | 520 | | | | | 525 | | | | | |
| gta | aag | gtt | tct | gat | ttg | gct | ccc | tct | ata | aca | gga | ggg | cca | aat | aat | 1632 |
| Val | Lys | Val | Ser | Asp | Leu | Ala | Pro | Ser | Ile | Thr | Gly | Gly | Pro | Asn | Asn | |
| 530 | | | | | 535 | | | | | 540 | | | | | | |
| acc | gtt | gta | tcg | ggt | cct | gga | ttt | aca | ggg | ggg | gga | ata | ata | aaa | gta | 1680 |
| Thr | Val | Val | Ser | Gly | Pro | Gly | Phe | Thr | Gly | Gly | Gly | Ile | Ile | Lys | Val | |
| 545 | | | | | 550 | | | | | 555 | | | | | 560 | |
| ata | aga | aat | gga | gta | att | ata | tca | cat | atg | cgt | gtt | aaa | att | tca | gac | 1728 |
| Ile | Arg | Asn | Gly | Val | Ile | Ile | Ser | His | Met | Arg | Val | Lys | Ile | Ser | Asp | |
| | | | | 565 | | | | | 570 | | | | | 575 | | |
| att | aac | aaa | gaa | tat | agt | atg | agg | att | cgg | tat | gct | tcc | gct | aat | aat | 1776 |
| Ile | Asn | Lys | Glu | Tyr | Ser | Met | Arg | Ile | Arg | Tyr | Ala | Ser | Ala | Asn | Asn | |
| | | | 580 | | | | | 585 | | | | | 590 | | | |
| act | gaa | ttt | tat | ata | aat | cct | tct | gaa | gaa | aac | gtt | aaa | tct | cac | gct | 1824 |
| Thr | Glu | Phe | Tyr | Ile | Asn | Pro | Ser | Glu | Glu | Asn | Val | Lys | Ser | His | Ala | |
| | 595 | | | | | 600 | | | | | 605 | | | | | |
| caa | aaa | act | atg | aat | aga | ggt | gaa | gct | tta | aca | tat | aat | aaa | ttt | aat | 1872 |
| Gln | Lys | Thr | Met | Asn | Arg | Gly | Glu | Ala | Leu | Thr | Tyr | Asn | Lys | Phe | Asn | |
| 610 | | | | | 615 | | | | | 620 | | | | | | |
| tat | gcg | act | ttg | ccc | cct | att | aaa | ttt | acg | aca | acc | gaa | cct | ttc | att | 1920 |
| Tyr | Ala | Thr | Leu | Pro | Pro | Ile | Lys | Phe | Thr | Thr | Thr | Glu | Pro | Phe | Ile | |
| 625 | | | | | 630 | | | | | 635 | | | | | 640 | |
| act | cta | ggg | gct | ata | ttt | gaa | gcg | gaa | gac | ttt | ctt | gga | att | gaa | gct | 1968 |
| Thr | Leu | Gly | Ala | Ile | Phe | Glu | Ala | Glu | Asp | Phe | Leu | Gly | Ile | Glu | Ala | |
| | | | | 645 | | | | | 650 | | | | | 655 | | |
| tat | ata | gac | cga | atc | gaa | ttt | atc | cca | gta | gat | gag | aca | tat | gaa | gcg | 2016 |
| Tyr | Ile | Asp | Arg | Ile | Glu | Phe | Ile | Pro | Val | Asp | Glu | Thr | Tyr | Glu | Ala | |
| | | | 660 | | | | | 665 | | | | | 670 | | | |
| gaa | taa | | | | | | | | | | | | | | | 2022 |
| Glu | | | | | | | | | | | | | | | | |

<210> SEQ ID NO 18
<211> LENGTH: 673
<212> TYPE: PRT
<213> ORGANISM: Bacillus thuringiensis (truncated)

<400> SEQUENCE: 18

Met Ser Pro Asn Asn Gln Asn Gl

```
Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
            165                 170                 175

Asp Ser Leu Phe Thr Gln Tyr Met Pro Ser Phe Arg Val Thr Asn Phe
        180                 185                 190

Glu Val Pro Phe Leu Thr Val Tyr Thr Gln Ala Ala Asn Leu His Leu
    195                 200                 205

Leu Leu Leu Lys Asp Ala Ser Ile Phe Gly Glu Glu Trp Gly Trp Ser
210             215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Thr Val Leu Asp Val Val Ala Leu Phe Pro Asn
        275                 280                 285

Tyr Asp Thr Arg Thr Tyr Pro Met Glu Thr Lys Ala Gln Leu Thr Arg
    290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
        340                 345                 350

Thr Gln Ser Arg Ser Ile Ser Ser Ala Arg Tyr Ile Arg His Trp Ala
    355                 360                 365

Gly His Gln Ile Ser Tyr His Arg Ile Phe Ser Asp Asn Ile Ile Lys
370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Phe Pro Gly Tyr Thr Tyr Ile Phe Phe Gly Met Pro
        420                 425                 430

Glu Val Glu Phe Phe Met Val Asn Gln Leu Asn Asn Thr Arg Lys Thr
    435                 440                 445

Leu Lys Tyr Asn Pro Val Ser Lys Asp Ile Ile Ala Gly Thr Arg Asp
450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
        500                 505                 510

Asp Leu Ile Asn Ala Val His Ser Asp Lys Ile Thr Gln Ile Pro Val
    515                 520                 525

Val Lys Val Ser Asp Leu Ala Pro Ser Ile Thr Gly Gly Pro Asn Asn
530                 535                 540

Thr Val Val Ser Gly Pro Gly Phe Thr Gly Gly Ile Ile Lys Val
545                 550                 555                 560

Ile Arg Asn Gly Val Ile Ile Ser His Met Arg Val Lys Ile Ser Asp
                565                 570                 575
```

```
Ile Asn Lys Glu Tyr Ser Met Arg Ile Arg Tyr Ala Ser Ala Asn Asn
            580                 585                 590

Thr Glu Phe Tyr Ile Asn Pro Ser Glu Glu Asn Val Lys Ser His Ala
        595                 600                 605

Gln Lys Thr Met Asn Arg Gly Glu Ala Leu Thr Tyr Asn Lys Phe Asn
    610                 615                 620

Tyr Ala Thr Leu Pro Pro Ile Lys Phe Thr Thr Thr Glu Pro Phe Ile
625                 630                 635                 640

Thr Leu Gly Ala Ile Phe Glu Ala Glu Asp Phe Leu Gly Ile Glu Ala
                645                 650                 655

Tyr Ile Asp Arg Ile Glu Phe Ile Pro Val Asp Glu Thr Tyr Glu Ala
                660                 665                 670

Glu

<210> SEQ ID NO 19
<211> LENGTH: 1860
<212> TYPE: DNA
<213> ORGANISM: Bacillus thuringiensis (truncated)
<220> FEATURE:
<221> NAME/KEY: misc_feature
<223> OTHER INFORMATION: 49PVD
<220> FEATURE:
<221> NAME/KEY: CDS
<222> LOCATION: (10)..(1860)

<400> SEQUENCE: 19 tccatgggc atg tct gcg gga aat gct agt gaa tac cct ggt tca cct gaa    51
          Met Ser Ala Gly Asn Ala Ser Glu Tyr Pro Gly Ser Pro Glu
           1               5                  10 gta ctt gtt agc gga caa gat gca gct aag gcc gca att gat ata gta       99
Val Leu Val Ser Gly Gln Asp Ala Ala Lys Ala Ala Ile Asp Ile Val
 15                  20                  25                  30 ggt aaa tta cta tca ggt tta ggg gtc cca ttt gtt ggg ccg ata gtg      147
Gly Lys Leu Leu Ser Gly Leu Gly Val Pro Phe Val Gly Pro Ile Val
                 35                  40                  45 agt ctt tat act caa ctt att gat att ctg tgg cct tca ggg gaa aag      195
Ser Leu Tyr Thr Gln Leu Ile Asp Ile Leu Trp Pro Ser Gly Glu Lys
             50                  55                  60 agt caa tgg gaa att ttt atg gaa caa gta gaa gaa ctc att aat caa      243
Ser Gln Trp Glu Ile Phe Met Glu Gln Val Glu Glu Leu Ile Asn Gln
 65                  70                  75 aaa ata gca gaa tat gca agg aat aaa gcg ctt tcg gaa tta gaa gga      291
Lys Ile Ala Glu Tyr Ala Arg Asn Lys Ala Leu Ser Glu Leu Glu Gly
 80                  85                  90 tta ggt aat aat tac caa tta tat cta act gcg ctt gaa gaa tgg gaa      339
Leu Gly Asn Asn Tyr Gln Leu Tyr Leu Thr Ala Leu Glu Glu Trp Glu
 95                 100                 105                 110 gaa aat cca aat ggt tca aga gcc tta cga gat gtg cga aat cga ttt      387
Glu Asn Pro Asn Gly Ser Arg Ala Leu Arg Asp Val Arg Asn Arg Phe
                115                 120                 125 gaa atc ctg gat agt tta ttt acg caa tat atg cca tct ttt aga gtg      435
Glu Ile Leu Asp Ser Leu Phe Thr Gln Tyr Met Pro Ser Phe Arg Val
            130                 135                 140 aca aat ttt gaa gta cca ttc ctt act gta tat gca atg gca gcc aac      483
Thr Asn Phe Glu Val Pro Phe Leu Thr Val Tyr Ala Met Ala Ala Asn
        145                 150                 155 ctt cat tta ctg tta tta aag gac gcg tca att ttt gga gaa gaa tgg      531
Leu His Leu Leu Leu Leu Lys Asp Ala Ser Ile Phe Gly Glu Glu Trp
    160                 165                 170 gga tgg tca aca act act att aat aac tat tat gat cgt caa atg aaa      579
```

```
Gly Trp Ser Thr Thr Thr Ile Asn Asn Tyr Tyr Asp Arg Gln Met Lys
175                 180                 185                 190 ctt act gca gaa tat tct gat cac tgt gta aag tgg tat gaa act ggt    627
Leu Thr Ala Glu Tyr Ser Asp His Cys Val Lys Trp Tyr Glu Thr Gly
                    195                 200                 205 tta gca aaa tta aaa ggc acg agc gct aaa caa tgg gtt gac tat aac    675
Leu Ala Lys Leu Lys Gly Thr Ser Ala Lys Gln Trp Val Asp Tyr Asn
                210                 215                 220 caa ttc cgt aga gaa atg aca ctg gcg gtt tta gat gtt gtt gca tta    723
Gln Phe Arg Arg Glu Met Thr Leu Ala Val Leu Asp Val Val Ala Leu
            225                 230                 235 ttc cca aat tat gac aca cgc acg tac cca atg gaa acg aaa gca caa    771
Phe Pro Asn Tyr Asp Thr Arg Thr Tyr Pro Met Glu Thr Lys Ala Gln
        240                 245                 250 cta aca agg gaa gta tat aca gat cca ctg ggc gcg gta aac gtg tct    819
Leu Thr Arg Glu Val Tyr Thr Asp Pro Leu Gly Ala Val Asn Val Ser
255                 260                 265                 270 tca att ggt tcc tgg tat gac aaa gca cct tct ttc gga gtg ata gaa    867
Ser Ile Gly Ser Trp Tyr Asp Lys Ala Pro Ser Phe Gly Val Ile Glu
                275                 280                 285 tca tcc gtt att cga cca ccc cat gta ttt gat tat ata acg gga ctc    915
Ser Ser Val Ile Arg Pro Pro His Val Phe Asp Tyr Ile Thr Gly Leu
                290                 295                 300 aca gtg tat aca caa tca aga agc att tct tcc gct cgc tat ata aga    963
Thr Val Tyr Thr Gln Ser Arg Ser Ile Ser Ser Ala Arg Tyr Ile Arg
            305                 310                 315 cat tgg gct ggt cat caa ata agc tac cat cgt gtc agt agg ggt agt   1011
His Trp Ala Gly His Gln Ile Ser Tyr His Arg Val Ser Arg Gly Ser
        320                 325                 330 aat ctt caa caa atg tat gga act aat caa aat cta cac agc act agt   1059
Asn Leu Gln Gln Met Tyr Gly Thr Asn Gln Asn Leu His Ser Thr Ser
335                 340                 345                 350 acc ttt gat ttt acg aat tat gat att tac aag act cta tca aag gat   1107
Thr Phe Asp Phe Thr Asn Tyr Asp Ile Tyr Lys Thr Leu Ser Lys Asp
                355                 360                 365 gca gta ctc ctt gat att gtt tac cct ggt tat acg tat ata ttt ttt   1155
Ala Val Leu Leu Asp Ile Val Tyr Pro Gly Tyr Thr Tyr Ile Phe Phe
                370                 375                 380 gga atg cca gaa gtc gag ttt ttc atg gta aac caa ttg aat aat acc   1203
Gly Met Pro Glu Val Glu Phe Phe Met Val Asn Gln Leu Asn Asn Thr
            385                 390                 395 aga aag acg tta aag tat aat cca gtt tcc aaa gat att ata gcg agt   1251
Arg Lys Thr Leu Lys Tyr Asn Pro Val Ser Lys Asp Ile Ile Ala Ser
400                 405                 410 aca aga gat tcg gaa tta gaa tta cct cca gaa act tca gat caa cca   1299
Thr Arg Asp Ser Glu Leu Glu Leu Pro Pro Glu Thr Ser Asp Gln Pro
415                 420                 425                 430 aat tat gag tca tat agc cat aga tta tgt cat atc aca agt att ccc   1347
Asn Tyr Glu Ser Tyr Ser His Arg Leu Cys His Ile Thr Ser Ile Pro
                435                 440                 445 gcg acg ggt aac act acc gga tta gta cct gta ttt tct tgg aca cat   1395
Ala Thr Gly Asn Thr Thr Gly Leu Val Pro Val Phe Ser Trp Thr His
                450                 455                 460 cga agt gca gat tta aac aat aca ata tat tca gat aaa atc act caa   1443
Arg Ser Ala Asp Leu Asn Asn Thr Ile Tyr Ser Asp Lys Ile Thr Gln
            465                 470                 475 att ccg gcc gtt aaa tgt tgg gat aat tta ccg ttt gtt cca gtg gta   1491
Ile Pro Ala Val Lys Cys Trp Asp Asn Leu Pro Phe Val Pro Val Val
        480                 485                 490 aaa gga cca gga cat aca gga ggg gat tta tta cag tat aat aga agt   1539
```

```
Lys Gly Pro Gly His Thr Gly Gly Asp Leu Leu Gln Tyr Asn Arg Ser
495                 500                 505                 510 act ggt tct gta gga acc tta ttt cta gct cga tat ggc cta gca tta      1587
Thr Gly Ser Val Gly Thr Leu Phe Leu Ala Arg Tyr Gly Leu Ala Leu
                515                 520                 525 gaa aaa gca ggg aaa tat cgt gta aga ctg aga tat gct act gat gca      1635
Glu Lys Ala Gly Lys Tyr Arg Val Arg Leu Arg Tyr Ala Thr Asp Ala
                530                 535                 540 gat att gta ttg cat gta aac gat gct cag att cag atg cca aaa aca      1683
Asp Ile Val Leu His Val Asn Asp Ala Gln Ile Gln Met Pro Lys Thr
                545                 550                 555 atg aac cca ggt gag gat ctg aca tct aaa act ttt aaa gtt gca gat      1731
Met Asn Pro Gly Glu Asp Leu Thr Ser Lys Thr Phe Lys Val Ala Asp
                560                 565                 570 gct atc aca aca tta aat tta gca aca gat agt tcg cta gca ttg aaa      1779
Ala Ile Thr Thr Leu Asn Leu Ala Thr Asp Ser Ser Leu Ala Leu Lys
575                 580                 585                 590 cat aat tta ggt gaa gac cct aat tca aca tta tct ggt ata gtt tac      1827
His Asn Leu Gly Glu Asp Pro Asn Ser Thr Leu Ser Gly Ile Val Tyr
                595                 600                 605 gtt gac cga atc gaa ttc atc cca gta gat taa                          1860
Val Asp Arg Ile Glu Phe Ile Pro Val Asp
                610                 615

<210> SEQ ID NO 20
<211> LENGTH: 616
<212> TYPE: PRT
<213> ORGANISM: Bacillus thuringiensis (truncated)

<400> SEQUENCE: 20

Met Ser Ala Gly Asn Ala Ser Glu Tyr Pro Gly Ser Pro Glu Val Leu
1               5                   10                  15

Val Ser Gly Gln Asp Ala Ala Lys Ala Ala Ile Asp Ile Val Gly Lys
                20                  25                  30

Leu Leu Ser Gly Leu Gly Val Pro Phe Val Gly Pro Ile Val Ser Leu
            35                  40                  45

Tyr Thr Gln Leu Ile Asp Ile Leu Trp Pro Ser Gly Glu Lys Ser Gln
        50                  55                  60

Trp Glu Ile Phe Met Glu Gln Val Glu Leu Ile Asn Gln Lys Ile
65                  70                  75                  80

Ala Glu Tyr Ala Arg Asn Lys Ala Leu Ser Glu Leu Gly Leu Gly
                85                  90                  95

Asn Asn Tyr Gln Leu Tyr Leu Thr Ala Leu Glu Glu Trp Glu Asn
                100                 105                 110

Pro Asn Gly Ser Arg Ala Leu Arg Asp Val Arg Asn Arg Phe Glu Ile
            115                 120                 125

Leu Asp Ser Leu Phe Thr Gln Tyr Met Pro Ser Phe Arg Val Thr Asn
130                 135                 140

Phe Glu Val Pro Phe Leu Thr Val Tyr Ala Met Ala Ala Asn Leu His
145                 150                 155                 160

Leu Leu Leu Leu Lys Asp Ala Ser Ile Phe Gly Glu Glu Trp Gly Trp
                165                 170                 175

Ser Thr Thr Thr Ile Asn Asn Tyr Tyr Asp Arg Gln Met Lys Leu Thr
                180                 185                 190

Ala Glu Tyr Ser Asp His Cys Val Lys Trp Tyr Glu Thr Gly Leu Ala
            195                 200                 205

Lys Leu Lys Gly Thr Ser Ala Lys Gln Trp Val Asp Tyr Asn Gln Phe
        210                 215                 220
```

```
Arg Arg Glu Met Thr Leu Ala Val Leu Asp Val Val Ala Leu Phe Pro
225                 230                 235                 240

Asn Tyr Asp Thr Arg Thr Tyr Pro Met Glu Thr Lys Ala Gln Leu Thr
            245                 250                 255

Arg Glu Val Tyr Thr Asp Pro Leu Gly Ala Val Asn Val Ser Ser Ile
                260                 265                 270

Gly Ser Trp Tyr Asp Lys Ala Pro Ser Phe Gly Val Ile Glu Ser Ser
            275                 280                 285

Val Ile Arg Pro Pro His Val Phe Asp Tyr Ile Thr Gly Leu Thr Val
290                 295                 300

Tyr Thr Gln Ser Arg Ser Ile Ser Ser Ala Arg Tyr Ile Arg His Trp
305                 310                 315                 320

Ala Gly His Gln Ile Ser Tyr His Arg Val Ser Arg Gly Ser Asn Leu
                325                 330                 335

Gln Gln Met Tyr Gly Thr Asn Gln Asn Leu His Ser Thr Ser Thr Phe
            340                 345                 350

Asp Phe Thr Asn Tyr Asp Ile Tyr Lys Thr Leu Ser Lys Asp Ala Val
            355                 360                 365

Leu Leu Asp Ile Val Tyr Pro Gly Tyr Thr Tyr Ile Phe Phe Gly Met
370                 375                 380

Pro Glu Val Glu Phe Phe Met Val Asn Gln Leu Asn Asn Thr Arg Lys
385                 390                 395                 400

Thr Leu Lys Tyr Asn Pro Val Ser Lys Asp Ile Ile Ala Ser Thr Arg
                405                 410                 415

Asp Ser Glu Leu Glu Leu Pro Pro Glu Thr Ser Asp Gln Pro Asn Tyr
                420                 425                 430

Glu Ser Tyr Ser His Arg Leu Cys His Ile Thr Ser Ile Pro Ala Thr
            435                 440                 445

Gly Asn Thr Thr Gly Leu Val Pro Val Phe Ser Trp Thr His Arg Ser
450                 455                 460

Ala Asp Leu Asn Asn Thr Ile Tyr Ser Asp Lys Ile Thr Gln Ile Pro
465                 470                 475                 480

Ala Val Lys Cys Trp Asp Asn Leu Pro Phe Val Pro Val Val Lys Gly
                485                 490                 495

Pro Gly His Thr Gly Gly Asp Leu Leu Gln Tyr Asn Arg Ser Thr Gly
                500                 505                 510

Ser Val Gly Thr Leu Phe Leu Ala Arg Tyr Gly Leu Ala Leu Glu Lys
            515                 520                 525

Ala Gly Lys Tyr Arg Val Arg Leu Arg Tyr Ala Thr Asp Ala Asp Ile
530                 535                 540

Val Leu His Val Asn Asp Ala Gln Ile Gln Met Pro Lys Thr Met Asn
545                 550                 555                 560

Pro Gly Glu Asp Leu Thr Ser Lys Thr Phe Lys Val Ala Asp Ala Ile
                565                 570                 575

Thr Thr Leu Asn Leu Ala Thr Asp Ser Ser Leu Ala Leu Lys His Asn
            580                 585                 590

Leu Gly Glu Asp Pro Asn Ser Thr Leu Ser Gly Ile Val Tyr Val Asp
            595                 600                 605

Arg Ile Glu Phe Ile Pro Val Asp
610                 615

<210> SEQ ID NO 21
<211> LENGTH: 2022
<212> TYPE: DNA
```

<213> ORGANISM: Bacillus thuringiensis (mutated)
<220> FEATURE:
<221> NAME/KEY: misc_feature
<223> OTHER INFORMATION: LKMS.N1218-1
<220> FEATURE:
<221> NAME/KEY: CDS
<222> LOCATION: (1)..(2022)

<400> SEQUENCE: 21

| | | | | | | | | | | | | | | | | |
|---|---|---|---|---|---|---|---|---|---|---|---|---|---|---|---|---|
| atg | agt | cca | aat | aat | caa | aat | gaa | tat | gaa | att | ata | gat | gcg | aca | cct | 48 |
| Met | Ser | Pro | Asn | Asn | Gln | Asn | Glu | Tyr | Glu | Ile | Ile | Asp | Ala | Thr | Pro | |
| 1 | | | | 5 | | | | | 10 | | | | | 15 | | |
| tct | act | tct | gta | tcc | aat | gat | tct | aac | aga | tac | cct | ttt | gcg | aat | gag | 96 |
| Ser | Thr | Ser | Val | Ser | Asn | Asp | Ser | Asn | Arg | Tyr | Pro | Phe | Ala | Asn | Glu | |
| | | | 20 | | | | | 25 | | | | | 30 | | | |
| cca | aca | aat | gcg | cta | caa | aat | atg | gat | tat | aaa | gat | tat | tta | aaa | atg | 144 |
| Pro | Thr | Asn | Ala | Leu | Gln | Asn | Met | Asp | Tyr | Lys | Asp | Tyr | Leu | Lys | Met | |
| | | 35 | | | | | 40 | | | | | 45 | | | | |
| tct | gcg | gga | aat | gct | agt | gaa | tac | cct | ggt | tca | cct | gaa | gta | ctt | gtt | 192 |
| Ser | Ala | Gly | Asn | Ala | Ser | Glu | Tyr | Pro | Gly | Ser | Pro | Glu | Val | Leu | Val | |
| | 50 | | | | | 55 | | | | | 60 | | | | | |
| agc | gga | caa | gat | gca | gct | aag | gcc | gca | att | gat | ata | gta | ggt | aaa | tta | 240 |
| Ser | Gly | Gln | Asp | Ala | Ala | Lys | Ala | Ala | Ile | Asp | Ile | Val | Gly | Lys | Leu | |
| 65 | | | | | 70 | | | | | 75 | | | | | 80 | |
| cta | tca | ggt | tta | ggg | gtc | cca | ttt | gtt | ggg | ccg | ata | gtg | agt | ctt | tat | 288 |
| Leu | Ser | Gly | Leu | Gly | Val | Pro | Phe | Val | Gly | Pro | Ile | Val | Ser | Leu | Tyr | |
| | | | | 85 | | | | | 90 | | | | | 95 | | |
| act | caa | ctt | att | gat | att | ctg | tgg | cct | tca | ggg | gaa | aag | agt | caa | tgg | 336 |
| Thr | Gln | Leu | Ile | Asp | Ile | Leu | Trp | Pro | Ser | Gly | Glu | Lys | Ser | Gln | Trp | |
| | | | 100 | | | | | 105 | | | | | 110 | | | |
| gaa | att | ttt | atg | gaa | caa | gta | gaa | gaa | ctc | att | aat | caa | aaa | ata | gca | 384 |
| Glu | Ile | Phe | Met | Glu | Gln | Val | Glu | Glu | Leu | Ile | Asn | Gln | Lys | Ile | Ala | |
| | | 115 | | | | | 120 | | | | | 125 | | | | |
| gaa | tat | gca | agg | aat | aaa | gcg | ctt | tcg | gaa | tta | gaa | gga | tta | ggt | aat | 432 |
| Glu | Tyr | Ala | Arg | Asn | Lys | Ala | Leu | Ser | Glu | Leu | Glu | Gly | Leu | Gly | Asn | |
| | 130 | | | | | 135 | | | | | 140 | | | | | |
| aat | tac | caa | tta | tat | cta | act | gcg | ctt | gaa | gaa | tgg | gaa | gaa | aat | cca | 480 |
| Asn | Tyr | Gln | Leu | Tyr | Leu | Thr | Ala | Leu | Glu | Glu | Trp | Glu | Glu | Asn | Pro | |
| 145 | | | | | 150 | | | | | 155 | | | | | 160 | |
| tta | aaa | atg | tct | aat | ggt | tca | aga | gcc | tta | cga | gat | gtg | cga | aat | cga | 528 |
| Leu | Lys | Met | Ser | Asn | Gly | Ser | Arg | Ala | Leu | Arg | Asp | Val | Arg | Asn | Arg | |
| | | | | 165 | | | | | 170 | | | | | 175 | | |
| ttt | gaa | atc | ctg | gat | agt | tta | ttt | acg | caa | tat | atg | cca | tct | ttt | aga | 576 |
| Phe | Glu | Ile | Leu | Asp | Ser | Leu | Phe | Thr | Gln | Tyr | Met | Pro | Ser | Phe | Arg | |
| | | | 180 | | | | | 185 | | | | | 190 | | | |
| gtg | aca | aat | ttt | gaa | gta | cca | ttc | ctt | act | gta | tat | gca | atg | gca | gcc | 624 |
| Val | Thr | Asn | Phe | Glu | Val | Pro | Phe | Leu | Thr | Val | Tyr | Ala | Met | Ala | Ala | |
| | | 195 | | | | | 200 | | | | | 205 | | | | |
| aac | ctt | cat | tta | ctg | tta | tta | aag | gac | gcg | tca | att | ttt | gga | gaa | gaa | 672 |
| Asn | Leu | His | Leu | Leu | Leu | Leu | Lys | Asp | Ala | Ser | Ile | Phe | Gly | Glu | Glu | |
| | 210 | | | | | 215 | | | | | 220 | | | | | |
| tgg | gga | tgg | tca | aca | act | act | att | aat | aac | tat | tat | gat | cgt | caa | atg | 720 |
| Trp | Gly | Trp | Ser | Thr | Thr | Thr | Ile | Asn | Asn | Tyr | Tyr | Asp | Arg | Gln | Met | |
| 225 | | | | | 230 | | | | | 235 | | | | | 240 | |
| aaa | ctt | act | gca | gaa | tat | tct | gat | cac | tgt | gta | aag | tgg | tat | gaa | act | 768 |
| Lys | Leu | Thr | Ala | Glu | Tyr | Ser | Asp | His | Cys | Val | Lys | Trp | Tyr | Glu | Thr | |
| | | | | 245 | | | | | 250 | | | | | 255 | | |
| ggt | tta | gca | aaa | tta | aaa | ggc | acg | agc | gct | aaa | caa | tgg | gtt | gac | tat | 816 |
| Gly | Leu | Ala | Lys | Leu | Lys | Gly | Thr | Ser | Ala | Lys | Gln | Trp | Val | Asp | Tyr | |
| | | | 260 | | | | | 265 | | | | | 270 | | | |
| aac | caa | ttc | cgt | aga | gaa | atg | aca | ctg | gcg | gtt | tta | gat | gtt | gtt | gca | 864 |
| Asn | Gln | Phe | Arg | Arg | Glu | Met | Thr | Leu | Ala | Val | Leu | Asp | Val | Val | Ala | |

|  |  |
|---|---:|
| tta ttc cca aat tat gac aca cgc acg tac cca atg gaa acg aaa gca<br>Leu Phe Pro Asn Tyr Asp Thr Arg Thr Tyr Pro Met Glu Thr Lys Ala<br>290                  295                      300 | 912 |
| caa cta aca agg gaa gta tat aca gat cca ctg ggc gcg gta aac gtg<br>Gln Leu Thr Arg Glu Val Tyr Thr Asp Pro Leu Gly Ala Val Asn Val<br>305                  310                      315                  320 | 960 |
| tct tca att ggt tcc tgg tat gac aaa gca cct tct ttc gga gtg ata<br>Ser Ser Ile Gly Ser Trp Tyr Asp Lys Ala Pro Ser Phe Gly Val Ile<br>                325                      330                  335 | 1008 |
| gaa tca tcc gtt att cga cca ccc cat gta ttt gat tat ata acg gga<br>Glu Ser Ser Val Ile Arg Pro Pro His Val Phe Asp Tyr Ile Thr Gly<br>            340                      345                      350 | 1056 |
| ctc aca gtg tat aca caa tca aga agc att tct tcc gct cgc tat ata<br>Leu Thr Val Tyr Thr Gln Ser Arg Ser Ile Ser Ser Ala Arg Tyr Ile<br>                355                      360                  365 | 1104 |
| aga cat tgg gct ggt cat caa ata agc tac cat cgt gtc agt agg ggt<br>Arg His Trp Ala Gly His Gln Ile Ser Tyr His Arg Val Ser Arg Gly<br>370                  375                      380 | 1152 |
| agt aat ctt caa caa atg tat gga act aat caa aat cta cac agc act<br>Ser Asn Leu Gln Gln Met Tyr Gly Thr Asn Gln Asn Leu His Ser Thr<br>385                  390                      395                  400 | 1200 |
| agt acc ttt gat ttt acg aat tat gat att tac aag act cta tca aag<br>Ser Thr Phe Asp Phe Thr Asn Tyr Asp Ile Tyr Lys Thr Leu Ser Lys<br>                405                      410                  415 | 1248 |
| gat gca gta ctc ctt gat att gtt tac cct ggt tat acg tat ata ttt<br>Asp Ala Val Leu Leu Asp Ile Val Tyr Pro Gly Tyr Thr Tyr Ile Phe<br>            420                      425                      430 | 1296 |
| ttt gga atg cca gaa gtc gag ttt ttc atg gta aac caa ttg aat aat<br>Phe Gly Met Pro Glu Val Glu Phe Phe Met Val Asn Gln Leu Asn Asn<br>                435                      440                  445 | 1344 |
| acc aga aag acg tta aag tat aat cca gtt tcc aaa gat att ata gcg<br>Thr Arg Lys Thr Leu Lys Tyr Asn Pro Val Ser Lys Asp Ile Ile Ala<br>450                  455                      460 | 1392 |
| agt aca aga gat tcg gaa tta gaa tta cct cca gaa act tca gat caa<br>Ser Thr Arg Asp Ser Glu Leu Glu Leu Pro Pro Glu Thr Ser Asp Gln<br>465                  470                      475                  480 | 1440 |
| cca aat tat gag tca tat agc cat aga tta tgt cat atc aca agt att<br>Pro Asn Tyr Glu Ser Tyr Ser His Arg Leu Cys His Ile Thr Ser Ile<br>                485                      490                  495 | 1488 |
| ccc gcg acg ggt aac act acc gga tta gta cct gta ttt tct tgg aca<br>Pro Ala Thr Gly Asn Thr Thr Gly Leu Val Pro Val Phe Ser Trp Thr<br>            500                      505                      510 | 1536 |
| cat cga agt gca gat tta aac aat aca ata tat tca gat aaa atc act<br>His Arg Ser Ala Asp Leu Asn Asn Thr Ile Tyr Ser Asp Lys Ile Thr<br>                515                      520                  525 | 1584 |
| caa att ccg gcc gtt aaa tgt tgg gat aat tta ccg ttt gtt cca gtg<br>Gln Ile Pro Ala Val Lys Cys Trp Asp Asn Leu Pro Phe Val Pro Val<br>530                  535                      540 | 1632 |
| gta aaa gga cca gga cat aca gga ggg gat tta tta cag tat aat aga<br>Val Lys Gly Pro Gly His Thr Gly Gly Asp Leu Leu Gln Tyr Asn Arg<br>545                  550                      555                  560 | 1680 |
| agt act ggt tct gta gga acc tta ttt cta gct cga tat ggc cta gca<br>Ser Thr Gly Ser Val Gly Thr Leu Phe Leu Ala Arg Tyr Gly Leu Ala<br>                565                      570                  575 | 1728 |
| tta gaa aaa gca ggg aaa tat cgt gta aga ctg aga tat gct act gat<br>Leu Glu Lys Ala Gly Lys Tyr Arg Val Arg Leu Arg Tyr Ala Thr Asp<br>            580                      585                      590 | 1776 |
| gca gat att gta ttg cat gta aac gat gct cag att cag atg cca aaa<br>Ala Asp Ile Val Leu His Val Asn Asp Ala Gln Ile Gln Met Pro Lys | 1824 |

-continued

```
              595                 600                 605
aca atg aac cca ggt gag gat ctg aca tct aaa act ttt aaa gtt gca    1872
Thr Met Asn Pro Gly Glu Asp Leu Thr Ser Lys Thr Phe Lys Val Ala
    610                 615                 620 gat gct atc aca aca tta aat tta gca aca gat agt tcg cta gca ttg    1920
Asp Ala Ile Thr Thr Leu Asn Leu Ala Thr Asp Ser Ser Leu Ala Leu
625                 630                 635                 640 aaa cat aat tta ggt gaa gac cct aat tca aca tta tct ggt ata gtt    1968
Lys His Asn Leu Gly Glu Asp Pro Asn Ser Thr Leu Ser Gly Ile Val
                645                 650                 655 tac gtt gac cga atc gaa ttc atc cca gta gat gag aca tat gaa gcg    2016
Tyr Val Asp Arg Ile Glu Phe Ile Pro Val Asp Glu Thr Tyr Glu Ala
            660                 665                 670 gaa taa                                                            2022
Glu
```

<210> SEQ ID NO 22
<211> LENGTH: 673
<212> TYPE: PRT
<213> ORGANISM: Bacillus thuringiensis (mutated)

<400> SEQUENCE: 22

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
                20                  25                  30

Pro Thr Asn Ala Leu Gln Asn Met Asp Tyr Lys Asp Tyr Leu Lys Met
            35                  40                  45

Ser Ala Gly Asn Ala Ser Glu Tyr Pro Gly Ser Pro Glu Val Leu Val
        50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
145                 150                 155                 160

Leu Lys Met Ser Asn Gly Ser Arg Ala Leu Arg Asp Val Arg Asn Arg
                165                 170                 175

Phe Glu Ile Leu Asp Ser Leu Phe Thr Gln Tyr Met Pro Ser Phe Arg
            180                 185                 190

Val Thr Asn Phe Glu Val Pro Phe Leu Thr Val Tyr Ala Met Ala Ala
        195                 200                 205

Asn Leu His Leu Leu Leu Leu Lys Asp Ala Ser Ile Phe Gly Glu Glu
    210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
            260                 265                 270

```
Asn Gln Phe Arg Arg Glu Met Thr Leu Ala Val Leu Asp Val Val Ala
    275                 280                 285

Leu Phe Pro Asn Tyr Asp Thr Arg Thr Tyr Pro Met Glu Thr Lys Ala
290                 295                 300

Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
                325                 330                 335

Glu Ser Ser Val Ile Arg Pro Pro His Val Phe Asp Tyr Ile Thr Gly
                340                 345                 350

Leu Thr Val Tyr Thr Gln Ser Arg Ser Ile Ser Ser Ala Arg Tyr Ile
                355                 360                 365

Arg His Trp Ala Gly His Gln Ile Ser Tyr His Arg Val Ser Arg Gly
370                 375                 380

Ser Asn Leu Gln Gln Met Tyr Gly Thr Asn Gln Asn Leu His Ser Thr
385                 390                 395                 400

Ser Thr Phe Asp Phe Thr Asn Tyr Asp Ile Tyr Lys Thr Leu Ser Lys
                405                 410                 415

Asp Ala Val Leu Leu Asp Ile Val Tyr Pro Gly Tyr Thr Tyr Ile Phe
                420                 425                 430

Phe Gly Met Pro Glu Val Glu Phe Phe Met Val Asn Gln Leu Asn Asn
                435                 440                 445

Thr Arg Lys Thr Leu Lys Tyr Asn Pro Val Ser Lys Asp Ile Ile Ala
                450                 455                 460

Ser Thr Arg Asp Ser Glu Leu Glu Leu Pro Pro Glu Thr Ser Asp Gln
465                 470                 475                 480

Pro Asn Tyr Glu Ser Tyr Ser His Arg Leu Cys His Ile Thr Ser Ile
                485                 490                 495

Pro Ala Thr Gly Asn Thr Thr Gly Leu Val Pro Val Phe Ser Trp Thr
                500                 505                 510

His Arg Ser Ala Asp Leu Asn Asn Thr Ile Tyr Ser Asp Lys Ile Thr
                515                 520                 525

Gln Ile Pro Ala Val Lys Cys Trp Asp Asn Leu Pro Phe Val Pro Val
530                 535                 540

Val Lys Gly Pro Gly His Thr Gly Gly Asp Leu Leu Gln Tyr Asn Arg
545                 550                 555                 560

Ser Thr Gly Ser Val Gly Thr Leu Phe Leu Ala Arg Tyr Gly Leu Ala
                565                 570                 575

Leu Glu Lys Ala Gly Lys Tyr Arg Val Arg Leu Arg Tyr Ala Thr Asp
                580                 585                 590

Ala Asp Ile Val Leu His Val Asn Asp Ala Gln Ile Gln Met Pro Lys
                595                 600                 605

Thr Met Asn Pro Gly Glu Asp Leu Thr Ser Lys Thr Phe Lys Val Ala
610                 615                 620

Asp Ala Ile Thr Thr Leu Asn Leu Ala Thr Asp Ser Ser Leu Ala Leu
625                 630                 635                 640

Lys His Asn Leu Gly Glu Asp Pro Asn Ser Thr Leu Ser Gly Ile Val
                645                 650                 655

Tyr Val Asp Arg Ile Glu Phe Ile Pro Val Asp Glu Thr Tyr Glu Ala
                660                 665                 670

Glu

<210> SEQ ID NO 23
<211> LENGTH: 2013
```

```
<212> TYPE: DNA
<213> ORGANISM: Bacillus thuringiensis (mutated)
<220> FEATURE:
<221> NAME/KEY: misc_feature
<223> OTHER INFORMATION: LKMS.R1218-1
<220> FEATURE:
<221> NAME/KEY: CDS
<222> LOCATION: (1)..(2013)

<400> SEQUENCE: 23 atg agt cca aat aat caa aat gaa tat gaa att ata gat gcg aca cct      48
Met Ser Pro Asn Asn Gln Asn Glu Tyr Glu Ile Ile Asp Ala Thr Pro
 1               5                  10                  15 tct act tct gta tcc aat gat tct aac aga tac cct ttt gcg aat gag      96
Ser Thr Ser Val Ser Asn Asp Ser Asn Arg Tyr Pro Phe Ala Asn Glu
             20                  25                  30 cca aca aat gcg cta caa aat atg gat tat aaa gat tat tta aaa atg     144
Pro Thr Asn Ala Leu Gln Asn Met Asp Tyr Lys Asp Tyr Leu Lys Met
         35                  40                  45 tct gcg gga aat gct agt gaa tac cct ggt tca cct gaa gta ctt gtt     192
Ser Ala Gly Asn Ala Ser Glu Tyr Pro Gly Ser Pro Glu Val Leu Val
     50                  55                  60 agc gga caa gat gca gct aag gcc gca att gat ata gta ggt aaa tta     240
Ser Gly Gln Asp Ala Ala Lys Ala Ala Ile Asp Ile Val Gly Lys Leu
 65                  70                  75                  80 cta tca ggt tta ggg gtc cca ttt gtt ggg ccg ata gtg agt ctt tat     288
Leu Ser Gly Leu Gly Val Pro Phe Val Gly Pro Ile Val Ser Leu Tyr
                 85                  90                  95 act caa ctt att gat att ctg tgg cct tca ggg gaa aag agt caa tgg     336
Thr Gln Leu Ile Asp Ile Leu Trp Pro Ser Gly Glu Lys Ser Gln Trp
            100                 105                 110 gaa att ttt atg gaa caa gta gaa gaa ctc att aat caa aaa ata gca     384
Glu Ile Phe Met Glu Gln Val Glu Glu Leu Ile Asn Gln Lys Ile Ala
        115                 120                 125 gaa tat gca agg aat aaa gcg ctt tcg gaa tta gaa gga tta ggt aat     432
Glu Tyr Ala Arg Asn Lys Ala Leu Ser Glu Leu Glu Gly Leu Gly Asn
    130                 135                 140 aat tac caa tta tat cta act gcg ctt gaa gaa tgg gaa gaa aat cca     480
Asn Tyr Gln Leu Tyr Leu Thr Ala Leu Glu Glu Trp Glu Glu Asn Pro
145                 150                 155                 160 tta aaa atg tct aga gcc tta cga gat gtg cga aat cga ttt gaa atc     528
Leu Lys Met Ser Arg Ala Leu Arg Asp Val Arg Asn Arg Phe Glu Ile
                165                 170                 175 ctg gat agt tta ttt acg caa tat atg cca tct ttt aga gtg aca aat     576
Leu Asp Ser Leu Phe Thr Gln Tyr Met Pro Ser Phe Arg Val Thr Asn
            180                 185                 190 ttt gaa gta cca ttc ctt act gta tat gca atg gca gcc aac ctt cat     624
Phe Glu Val Pro Phe Leu Thr Val Tyr Ala Met Ala Ala Asn Leu His
        195                 200                 205 tta ctg tta tta aag gac gcg tca att ttt gga gaa gaa tgg gga tgg     672
Leu Leu Leu Leu Lys Asp Ala Ser Ile Phe Gly Glu Glu Trp Gly Trp
    210                 215                 220 tca aca act act att aat aac tat tat gat cgt caa atg aaa ctt act     720
Ser Thr Thr Thr Ile Asn Asn Tyr Tyr Asp Arg Gln Met Lys Leu Thr
225                 230                 235                 240 gca gaa tat tct gat cac tgt gta aag tgg tat gaa act ggt tta gca     768
Ala Glu Tyr Ser Asp His Cys Val Lys Trp Tyr Glu Thr Gly Leu Ala
                245                 250                 255 aaa tta aaa ggc acg agc gct aaa caa tgg gtt gac tat aac caa ttc     816
Lys Leu Lys Gly Thr Ser Ala Lys Gln Trp Val Asp Tyr Asn Gln Phe
            260                 265                 270 cgt aga gaa atg aca ctg gcg gtt tta gat gtt gtt gca tta ttc cca     864
```

```
                            -continued

Arg Arg Glu Met Thr Leu Ala Val Leu Asp Val Val Ala Leu Phe Pro
        275                 280                 285 aat tat gac aca cgc acg tac cca atg gaa acg aaa gca caa cta aca         912
Asn Tyr Asp Thr Arg Thr Tyr Pro Met Glu Thr Lys Ala Gln Leu Thr
290                 295                 300 agg gaa gta tat aca gat cca ctg ggc gcg gta aac gtg tct tca att         960
Arg Glu Val Tyr Thr Asp Pro Leu Gly Ala Val Asn Val Ser Ser Ile
    305                 310                 315                 320 ggt tcc tgg tat gac aaa gca cct tct ttc gga gtg ata gaa tca tcc        1008
Gly Ser Trp Tyr Asp Lys Ala Pro Ser Phe Gly Val Ile Glu Ser Ser
                325                 330                 335 gtt att cga cca ccc cat gta ttt gat tat ata acg gga ctc aca gtg        1056
Val Ile Arg Pro Pro His Val Phe Asp Tyr Ile Thr Gly Leu Thr Val
            340                 345                 350 tat aca caa tca aga agc att tct tcc gct cgc tat ata aga cat tgg        1104
Tyr Thr Gln Ser Arg Ser Ile Ser Ser Ala Arg Tyr Ile Arg His Trp
        355                 360                 365 gct ggt cat caa ata agc tac cat cgt gtc agt agg ggt agt aat ctt        1152
Ala Gly His Gln Ile Ser Tyr His Arg Val Ser Arg Gly Ser Asn Leu
    370                 375                 380 caa caa atg tat gga act aat caa aat cta cac agc act agt acc ttt        1200
Gln Gln Met Tyr Gly Thr Asn Gln Asn Leu His Ser Thr Ser Thr Phe
385                 390                 395                 400 gat ttt acg aat tat gat att tac aag act cta tca aag gat gca gta        1248
Asp Phe Thr Asn Tyr Asp Ile Tyr Lys Thr Leu Ser Lys Asp Ala Val
                405                 410                 415 ctc ctt gat att gtt tac cct ggt tat acg tat ata ttt ttt gga atg        1296
Leu Leu Asp Ile Val Tyr Pro Gly Tyr Thr Tyr Ile Phe Phe Gly Met
            420                 425                 430 cca gaa gtc gag ttt ttc atg gta aac caa ttg aat aat acc aga aag        1344
Pro Glu Val Glu Phe Phe Met Val Asn Gln Leu Asn Asn Thr Arg Lys
        435                 440                 445 acg tta aag tat aat cca gtt tcc aaa gat att ata gcg agt aca aga        1392
Thr Leu Lys Tyr Asn Pro Val Ser Lys Asp Ile Ile Ala Ser Thr Arg
    450                 455                 460 gat tcg gaa tta gaa tta cct cca gaa act tca gat caa cca aat tat        1440
Asp Ser Glu Leu Glu Leu Pro Pro Glu Thr Ser Asp Gln Pro Asn Tyr
465                 470                 475                 480 gag tca tat agc cat aga tta tgt cat atc aca agt att ccc gcg acg        1488
Glu Ser Tyr Ser His Arg Leu Cys His Ile Thr Ser Ile Pro Ala Thr
                485                 490                 495 ggt aac act acc gga tta gta cct gta ttt tct tgg aca cat cga agt        1536
Gly Asn Thr Thr Gly Leu Val Pro Val Phe Ser Trp Thr His Arg Ser
            500                 505                 510 gca gat tta aac aat aca ata tat tca gat aaa atc act caa att ccg        1584
Ala Asp Leu Asn Asn Thr Ile Tyr Ser Asp Lys Ile Thr Gln Ile Pro
        515                 520                 525 gcc gtt aaa tgt tgg gat aat tta ccg ttt gtt cca gtg gta aaa gga        1632
Ala Val Lys Cys Trp Asp Asn Leu Pro Phe Val Pro Val Val Lys Gly
    530                 535                 540 cca gga cat aca gga ggg gat tta tta cag tat aat aga agt act ggt        1680
Pro Gly His Thr Gly Gly Asp Leu Leu Gln Tyr Asn Arg Ser Thr Gly
545                 550                 555                 560 tct gta gga acc tta ttt cta gct cga tat ggc cta gca tta gaa aaa        1728
Ser Val Gly Thr Leu Phe Leu Ala Arg Tyr Gly Leu Ala Leu Glu Lys
                565                 570                 575 gca ggg aaa tat cgt gta aga ctg aga tat gct act gat gca gat att        1776
Ala Gly Lys Tyr Arg Val Arg Leu Arg Tyr Ala Thr Asp Ala Asp Ile
            580                 585                 590 gta ttg cat gta aac gat gct cag att cag atg cca aaa aca atg aac        1824
```

```
Val Leu His Val Asn Asp Ala Gln Ile Gln Met Pro Lys Thr Met Asn
        595                 600                 605 cca ggt gag gat ctg aca tct aaa act ttt aaa gtt gca gat gct atc      1872
Pro Gly Glu Asp Leu Thr Ser Lys Thr Phe Lys Val Ala Asp Ala Ile
610                 615                 620 aca aca tta aat tta gca aca gat agt tcg cta gca ttg aaa cat aat      1920
Thr Thr Leu Asn Leu Ala Thr Asp Ser Ser Leu Ala Leu Lys His Asn
625                 630                 635                 640 tta ggt gaa gac cct aat tca aca tta tct ggt ata gtt tac gtt gac      1968
Leu Gly Glu Asp Pro Asn Ser Thr Leu Ser Gly Ile Val Tyr Val Asp
        645                 650                 655 cga atc gaa ttc atc cca gta gat gag aca tat gaa gcg gaa taa           2013
Arg Ile Glu Phe Ile Pro Val Asp Glu Thr Tyr Glu Ala Glu
                660                 665                 670

<210> SEQ ID NO 24
<211> LENGTH: 670
<212> TYPE: PRT
<213> ORGANISM: Bacillus thuringiensis (mutated)

<400> SEQUENCE: 24

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
                20                  25                  30

Pro Thr Asn Ala Leu Gln Asn Met Asp Tyr Lys Asp Tyr Leu Lys Met
            35                  40                  45

Ser Ala Gly Asn Ala Ser Glu Tyr Pro Gly Ser Pro Glu Val Leu Val
50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Glu Glu Asn Pro
145                 150                 155                 160

Leu Lys Met Ser Arg Ala Leu Arg Asp Val Arg Asn Arg Phe Glu Ile
                165                 170                 175

Leu Asp Ser Leu Phe Thr Gln Tyr Met Pro Ser Phe Arg Val Thr Asn
            180                 185                 190

Phe Glu Val Pro Phe Leu Thr Val Tyr Ala Met Ala Ala Asn Leu His
        195                 200                 205

Leu Leu Leu Leu Lys Asp Ala Ser Ile Phe Gly Glu Glu Trp Gly Trp
210                 215                 220

Ser Thr Thr Thr Ile Asn Asn Tyr Tyr Asp Arg Gln Met Lys Leu Thr
225                 230                 235                 240

Ala Glu Tyr Ser Asp His Cys Val Lys Trp Tyr Glu Thr Gly Leu Ala
                245                 250                 255

Lys Leu Lys Gly Thr Ser Ala Lys Gln Trp Val Asp Tyr Asn Gln Phe
            260                 265                 270

Arg Arg Glu Met Thr Leu Ala Val Leu Asp Val Val Ala Leu Phe Pro
        275                 280                 285
```

Asn Tyr Asp Thr Arg Thr Tyr Pro Met Glu Thr Lys Ala Gln Leu Thr
    290                 295                 300

Arg Glu Val Tyr Thr Asp Pro Leu Gly Ala Val Asn Val Ser Ser Ile
305                 310                 315                 320

Gly Ser Trp Tyr Asp Lys Ala Pro Ser Phe Gly Val Ile Glu Ser Ser
                325                 330                 335

Val Ile Arg Pro Pro His Val Phe Asp Tyr Ile Thr Gly Leu Thr Val
            340                 345                 350

Tyr Thr Gln Ser Arg Ser Ile Ser Ser Ala Arg Tyr Ile Arg His Trp
        355                 360                 365

Ala Gly His Gln Ile Ser Tyr His Arg Val Ser Arg Gly Ser Asn Leu
    370                 375                 380

Gln Gln Met Tyr Gly Thr Asn Gln Asn Leu His Ser Thr Ser Thr Phe
385                 390                 395                 400

Asp Phe Thr Asn Tyr Asp Ile Tyr Lys Thr Leu Ser Lys Asp Ala Val
                405                 410                 415

Leu Leu Asp Ile Val Tyr Pro Gly Tyr Thr Tyr Ile Phe Phe Gly Met
            420                 425                 430

Pro Glu Val Glu Phe Phe Met Val Asn Gln Leu Asn Asn Thr Arg Lys
        435                 440                 445

Thr Leu Lys Tyr Asn Pro Val Ser Lys Asp Ile Ile Ala Ser Thr Arg
450                 455                 460

Asp Ser Glu Leu Glu Leu Pro Pro Glu Thr Ser Asp Gln Pro Asn Tyr
465                 470                 475                 480

Glu Ser Tyr Ser His Arg Leu Cys His Ile Thr Ser Ile Pro Ala Thr
                485                 490                 495

Gly Asn Thr Thr Gly Leu Val Pro Val Phe Ser Trp Thr His Arg Ser
            500                 505                 510

Ala Asp Leu Asn Asn Thr Ile Tyr Ser Asp Lys Ile Thr Gln Ile Pro
        515                 520                 525

Ala Val Lys Cys Trp Asp Asn Leu Pro Phe Val Pro Val Lys Gly
    530                 535                 540

Pro Gly His Thr Gly Gly Asp Leu Leu Gln Tyr Asn Arg Ser Thr Gly
545                 550                 555                 560

Ser Val Gly Thr Leu Phe Leu Ala Arg Tyr Gly Leu Ala Leu Glu Lys
                565                 570                 575

Ala Gly Lys Tyr Arg Val Arg Leu Arg Tyr Ala Thr Asp Ala Asp Ile
            580                 585                 590

Val Leu His Val Asn Asp Ala Gln Ile Gln Met Pro Lys Thr Met Asn
        595                 600                 605

Pro Gly Glu Asp Leu Thr Ser Lys Thr Phe Lys Val Ala Asp Ala Ile
    610                 615                 620

Thr Thr Leu Asn Leu Ala Thr Asp Ser Ser Leu Ala Leu Lys His Asn
625                 630                 635                 640

Leu Gly Glu Asp Pro Asn Ser Thr Leu Ser Gly Ile Val Tyr Val Asp
                645                 650                 655

Arg Ile Glu Phe Ile Pro Val Asp Glu Thr Tyr Glu Ala Glu
            660                 665                 670

<210> SEQ ID NO 25
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: LKMS Insert
<220> FEATURE:
<221> NAME/KEY: CDS
<222> LOCATION: (1)..(12)

<400> SEQUENCE: 25 tta aaa atg tct 12
Leu Lys Met Ser
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Construct

<400> SEQUENCE: 26

Leu Lys Met Ser
1

<210> SEQ ID NO 27
<211> LENGTH: 4874
<212> TYPE: DNA
<213> ORGANISM: Bacillus thuringiensis
<220> FEATURE:
<221> NAME/KEY: misc_feature
<223> OTHER INFORMATION: Genomic DNA 1218-1

<400> SEQUENCE: 27
ggtttccatt cccaccggtt ttcactttca aaaaccccaa tacaccgaaa cttgtctatg 60
atgtgagtca tttatcttat ggcaaaagag atgtgtaaac gaacgattga cgtagaggat 120
tgtgggcaaa ttgagataga tttacatgtc ttaaaaatta aaggtgtttt accgtttatc 180
gtgaacgtat ccattgaacc gcttagtatg gaacatgtat ataccacaag tggtagagac 240
acatccttat ttttaagttg tcaagaaacg gtatatgtgg atcatatttt aaaatatagt 300
gttgatcatg tcccatatta tgtaattgat ggccatcata ttcaagtgcg tgatgtatcg 360
attaaattga tggaagaaaa cccacaaact gctcaaatat cgggtgtttt ttattttgat 420
tatgcataat tataaaaaat caaaaaatat tttgtgaaga atccctaaaa ttatcacaac 480
attgtttatt ataaaataac tcatttcaag aaaaatcgta atattttttt atctaacagg 540
aattttatca tctacagaag aatattctta tcatggtaat gaggagggag agtgacagag 600
aggggataga caatcaaaag agtatctaga agagtttgtc atgtaagaac aaaaggaatc 660
tatcgtatat gctactcaaa agaaagtgta aaaaatcttt gtatcttgta tatgtatagg 720
aggaaaatag atgagtccaa ataatcaaaa tgaatatgaa attatagatg cgacaccttc 780
tacttctgta tccaatgatt ctaacagata cccttttgcg aatgagccaa caaatgcgct 840
acaaaatatg gattataaag attatttaaa aatgtctgcg ggaaatgcta gtgaataccc 900
tggttcacct gaagtacttg ttagcggaca agatgcagct aaggccgcaa ttgatatagt 960
aggtaaatta ctatcaggtt taggggtccc atttgttggg ccgatagtga gtctttatac 1020
tcaacttatt gatattctgt ggccttcagg ggaaaagagt caatgggaaa tttttatgga 1080
acaagtagaa gaactcatta atcaaaaaat agcagaatat gcaaggaata aagcgctttc 1140
ggaattagaa ggattaggta ataattacca attatatcta actgcgcttg aagaatggga 1200
agaaaatcca aatggttcaa gagccttacg agatgtgcga aatcgatttg aaatcctgga 1260
tagtttattt acgcaatata tgccatcttt tagagtgaca aattttgaag taccattcct 1320

```
tactgtatat gcaatggcag ccaaccttca tttactgtta ttaaaggacg cgtcaatttt    1380
tggagaagaa tggggatggt caacaactac tattaataac tattatgatc gtcaaatgaa    1440
acttactgca gaatattctg atcactgtgt aaagtggtat gaaactggtt tagcaaaatt    1500
aaaaggcacg agcgctaaac aatgggttga ctataaccaa ttccgtagag aaatgacact    1560
ggcggtttta gatgttgttg cattattccc aaattatgac acacgcacgt acccaatgga    1620
aacgaaagca caactaacaa gggaagtata tacagatcca ctgggcgcgg taaacgtgtc    1680
ttcaattggt tcctggtatg acaaagcacc ttctttcgga gtgatagaat catccgttat    1740
tcgaccaccc catgtatttg attatataac gggactcaca gtgtatacac aatcaagaag    1800
catttcttcc gctcgctata aagacattg ggctggtcat caaataagct accatcgtgt    1860 cagtagggt agtaatcttc aacaaatgta tggaactaat caaaatctac acagcactag    1920 taccttgat tttacgaatt atgatattta caagactcta tcaaggatg cagtactcct    1980 tgatattgtt taccctggtt atacgtatat attttttgga atgccagaag tcgagttttt    2040
catggtaaac caattgaata ataccagaaa gacgttaaag tataatccag tttccaaaga    2100
tattatagcg agtacaagag attcggaatt agaattacct ccagaaactt cagatcaacc    2160
aaattatgag tcatatagcc atagattatg tcatatcaca agtattcccg cgacgggtaa    2220
cactaccgga ttagtacctg tattttcttg gacacatcga agtgcagatt taacaaatac    2280
aatatattca gataaaatca ctcaaattcc ggccgttaaa tgttgggata atttaccgtt    2340
tgttccagtg gtaaaaggac caggacatac aggagggga ttattacagt ataatagaag    2400
tactggttct gtaggaacct tatttctagc tcgatatggc ctagcattag aaaaagcagg    2460
gaaatatcgt gtaagactga gatatgctac tgatgcagat attgtattgc atgtaaacga    2520
tgctcagatt cagatgccaa aaacaatgaa cccaggtgag gatctgacat ctaaaacttt    2580
taaagttgca gatgctatca caacattaaa tttagcaaca gatagttcgc tagcattgaa    2640
acataattta ggtgaagacc ctaattcaac attatctggt atagtttacg ttgaccgaat    2700
cgaattcatc ccagtagatg agacatatga agcggaacaa gatttagaag cagcgaagaa    2760
agcagtgaat gccttgttta cgaatacaaa agatggctta cgaccaggcg taacggatta    2820
tgaagtgaat caagcggcaa acttagtgga atgcctatcg gatgatttgt atccaaatga    2880
aaaacgattg ttatttgatg cagtgagaga ggcaaaacgc ctcagtgagg cacgtaattt    2940
gcttcaagat ccagatttcc aagagataaa tggagaaaat ggctggacgg caagtacggg    3000
aattgaggtt atagaagggg atgctttatt caaagggcgt tatctacgcc taccaggtgc    3060
gagagaaata gatacggaaa cgtatccaac gtatctgtat caaaaagtag aggaaggtgt    3120
attaaaacca tacacaagat atagattgag agggtttgtc ggaagcagtc aaggattgga    3180
aattttcaca attcgtcatc aaacgaaccg aattgtaaaa aatgtaccgg atgatttgct    3240
gccagatgta tctcctgtta actcggatgg tagtatcaat cgatgcagcg aacaaaagta    3300
tgtgaatagc cgtttagaag tagaaaaccg ttctggtgaa gcgcatgagt tctctattcc    3360
tattgataca ggtgaaatcg attacaatga aaatgcagga atatgggttg gatttaagat    3420
tacggaccca gagggatatg caacactcgg aaacctagaa ttggtcgaag agggaccttt    3480
atcaggagac gcattagaac gcttgcaaag agaagaacaa cagtggaaga ttcaaatgac    3540
aagaagacgt gaagaaacag atagaaggta tatggcatcg aaacaagcgg tagatcgttt    3600
atatgccgat tatcaggatc agcaactgaa tcctgatgta gagattacag atcttactgc    3660
ggcccaagat ctgatacagt ccattcctta cgtatataac gaaatgttcc cagaaatacc    3720
```

-continued

```
agggatgaac tatacgaagt ttacagaatt aacagatcga ctccaacaag cgtggagttt    3780
gtatgatcag cgaaatgcca taccaaatgg tgattttcga aatgggttaa gtaattggaa    3840
tgcaacgcct ggcgtagaag tacaacaaat caatcataca tctgtccttg tgattccaaa    3900
ctgggatgag caagtttcgc aacagtttac agttcaaccg aatcaaagat atgtgttacg    3960
agttactgcg agaaaagaag gggtaggaaa tggatatgta agtatccgtg atggtggaaa    4020
tcaaacagaa acgcttactt ttagtgcaag cgattatgat acaaatggaa tgtataatac    4080
gcaagtgtcc aatacaaatg gatataacac aaataatgcg tataatacac aagcatcgag    4140
tacaaacgga tataacgcaa ataatatgta taatacgcaa gcatcgaata caaacggata    4200
taacacaaat agtgtgtaca atgatcaaac cggctatatc acaaaaacag tgacattcat    4260
cccgtataca gatcaaatgt ggattgagat gagtgagaca gaaggtacat tctatataga    4320
aagtgtagaa ttgattgtag acgtagagta atagtagtac ccctccagat gaaacctgta    4380
tctggagggg ttttttatgc aaaagagtct tttcatacag aatatattgg ttttacccgg    4440
attacatatt ttgtgaatag gactatggtt ggttaccttg cggtaccttt ttatatccac    4500
cggcattgga aaatgtaaga gggaggataa tcatatatag tcccttccct acacatcaaa    4560
ttccttcgaa agtttctcgt gaatgagagt gaatatttct ttttgtactt tattcaggtc    4620
ttgtaagaaa ggaatggtat tcacacaaat gatgggtgtg gatacgtctg ttaaacctga    4680
gatatttgta ataatcaagt catagttttt tgcaatctgt ttaaatgagc tgagatgtaa    4740
tacatcaatc ttagatagtt gaatcatatg accaaattga tactgcataa tattacgaat    4800
aaatagggta tgttccatat ctgaatcaca aaaaatgccg acatgaagaa caggaacctt    4860
ctgttttaaa gctt                                                      4874
```

<210> SEQ ID NO 28
<211> LENGTH: 6613
<212> TYPE: DNA
<213> ORGANISM: Bacillus thuringiensis
<220> FEATURE:
<221> NAME/KEY: misc_feature
<223> OTHER INFORMATION: Genomic DNA 1218-2

<400> SEQUENCE: 28

```
ttttaggtat tctttttaagt tctttataga gacagattaa cgaaaaacta ataagaaat      60 tcaatccctt gatacatgat gcatcggatg ccaaattatt agtacgtatc ttgcgtatat     120
tgtacgaggt cgaattgacg taacagggca ccttttttggt caaattgacc aaagaatcca    180
tcctttgcat gagcacttct cgaaaccact tcccatagtg cacttcttat cttttgtata    240
tatttcctaa ggtatcgta atccctattt ctgataagag gattttgtca gtgtaggaag     300
agcgaatgtc ttttcgtatt tcaaacaaaa aataaaggat gtttatgcac ggaaataatc    360
atcatattaa taatgcccag tacataaaga tagatggggg tcattttttg aaatgattcg    420
aaaagactcc gttgactcga taggaggtgc acagaaaaat ggaagaaaga tatgcatcgc    480
aagatcagtc ggatgtagaa gtttctaatc gcaaggggaa gaaaaaccat acagttccct    540
ttcaatgtat ggtttccatt ccaacaggtt ttcaaattca aaacccaat acaccgaaac     600 ttgtctatga tgtgagtcat ttatctatgg caaaagagat gtgtaaacga acgattgacg    660
tagaggattg tgggcaaatt gagatagatt tacatgtctt aaaaattaaa ggtgttttac    720
cgtttatcgt gaacgtatcc attgaaccgc ttagtatgaa catgtatata ccacaagtgg    780
tagagacaca tccttatttt taagttgtca agaaacggta tatgtggatc atattttaaa    840
```

```
atatagtgtt gatcatgtcc cgtattatgt aattgatggc catcatattc aagtgcgtga    900
tgtatcgatt aaattgatgg aagaaaaccc acaaactgct caaatatcgg gtgtttttta    960
ttttgattat gcataatttt aaaaaatcaa aaatatttt gtgaagaatc cctaaaatta   1020
tcacaacatt gtttattata aaataactca tttcaagaaa aatcgtaata tttttttatc   1080
taacaggaat tttatcatct acagaagaat attcttatca tggtaatgag gagggagagt   1140
gacagtcaaa agagtacctg gtttgtcgtg taagaaaaaa gaatcgatcg tacaggaaag   1200
ttaaaaaaag tgtaagaaat tttatatctt ttgtatgtat aggaggaaaa tagatgagtc   1260
caaataatca aaatgaatat gaaattatag atgcgacacc ttctacttct gtatccaatg   1320
attctaacag ataccctttt gcgaatgagc caacaaatgc gctacaaaat atggattata   1380
aagattattt aaaaatgtct gcgggaaatg ctagtaaata ccctggttca cctgaagtac   1440
ttgttagcgg acaagatgca gctaaggccg caattgatat agtaggtaaa ttactatcag   1500
gtttaggggt cccatttgtt gggccgatag tgagtcttta tactcaactt attgatattc   1560
tgtggccttc agggcaaaag agtcaatggg agatttttat ggaacaagta aagaactca    1620
taaatcaaaa aatagcagaa tatgcaagga ataaagcgct ttcggaatta aaggattag    1680
gtaataatta ccaattatat ctaactgcgc ttgaagaatg gaaagaaaat ccaaatggtt   1740
caagagcctt acgagatgtg cgaaatcgat ttgaaatcct ggatagttta tttacgcaat   1800
acatgccatc ttttcgagtg acaaattttg aagtaccatt ccttacagta tatacacagg   1860
cagccaacct tcatttactg ttattaaagg acgcttcaat ttttggagaa gaatggggat   1920
ggtctacaac cactattaat aactattatg atcgtcaaat gaaacttact gcagaatatt   1980
ctgatcactg tgtaaagtgg tatgaaactg gtttagcaaa attaaaaggc acgagcgcta   2040
aacaatgggt cgactataac caattccgta gagaaatgac actgacggtt ttagatgttg   2100
ttgcattatt cccaaattat gacacacgca cgtacccaat ggaaacgaaa gcacaactaa   2160
caagggaagt atatacagat ccactgggcg cggtaaacgt gtcttcaatt ggttcctggt   2220
atgacaaagc accttctttc ggagtgtatag aatcatccgt tattcgacca ccccatgtat   2280
ttgattatat aacgggactc acagtgtata cacaatcaag aagcatttct tccgctcgct   2340
atataagaca ttgggctggt catcaaataa gctatcatcg gatttttagt gataatatta   2400
taaaacagat gtatggaact aatcaaaatc tacacagcac tagtaccttt gattttacga   2460
attatgatat ttacaagacg ttatcaaaag atgcggtgct ccttgatatt gtttttcctg   2520
gttatacgta tatatttttt ggaatgccag aagtcgagtt tttcatggta aaccaattga   2580
ataataccag aaagacgtta agtataatc cggtttccaa agatattata gcggggacaa   2640
gagattcgga attagaatta cctccagaaa cttcagatca accaaattat gagtcatata   2700
gccatagatt atgtcatatc acaagtattc ccgcgacggg ttcaactacc ggattagtac   2760
ctgtattttc ttggacacat cggagtgccg atcttataaa tgcagttcat tcagataaaa   2820
ttactcagat tccggtcgta aaggtttctg atttggctcc ctctataaca ggagggccaa   2880
ataataccgt tgtatcgggt cctggattta caggggggg gataataaaa gtaataagaa   2940
atggagtaat tatatcacat atgcgtgtta aaatttcaga cattaacaaa gaatatagta   3000
tgaggattcg gtatgcttcc gctaataata ctgaatttta tataaatcct tctgaagaaa   3060
acgttaaatc tcacgctcaa aaaactatga atagaggtga agctttaaca tataataaat   3120
ttaattatgc gactttgccc cctattaaat ttacgacaac cgaacctttc attactctag   3180
gggctatatt tgaagcggaa gactttcttg gaattgaagc ttatatagac cgaatcgaat   3240
```

```
ttatcccagt agatgagaca tatgaagcgg aacaagattt agaagcagcg aagaaagcag    3300
tgaatgcctt gtttacgaat acaaaagatg gcttacgacc aggcgtaacg gattatgaag    3360
tgaatcaagc ggcaaactta gtggaatgcc tatcggatga tttgtatcca aatgaaaaac    3420
gattgttatt tgatgcagtg agagaggcaa acgcctcag tgaggcacgt aatttgcttc     3480
aagatccaga tttccaagag ataaatggag aaaatggctg gacggcaagt acgggaattg    3540
aggttataga aggggatgct ttattcaaag ggcgttatct acgcctacca ggtgcgagag    3600
aaatagatac ggaaacgtat ccaacgtatc tgtatcaaaa agtagaggaa ggtgtattaa    3660
aaccatacac aagatataga ttgagagggt ttgtcggaag cagtcaagga ttggaaattt    3720
tcacaattcg tcatcaaacg aaccgaattg taaaaaatgt accggatgat ttgctgccag    3780
atgtatctcc tgttaactcg gatggtagta tcaatcgatg cagcgaacaa agtatgtga    3840 atagccgttt agaagtagaa aaccgttctg gtgaagcgca tgagttctct attcctattg    3900
atacaggtga aatcgattac aatgaaaatg caggaatatg ggttggattt aagattacgg    3960
acccagaggg atatgcaaca ctcggaaacc tagaattggt cgaagaggga cctttatcag    4020
gagacgcatt agaacgcttg caaagagaag aacaacagtg gaagattcaa atgacaagaa    4080
gacgtgaaga aacagataga aggtatatgg catcgaaaca agcggtagat cgtttatatg    4140
ccgattatca ggatcagcaa ctgaatcctg atgtagagat tacagatctt actgcggccc    4200
aagatctgat acagtccatt ccttacgtat ataacgaaat gttcccagaa ataccaggga    4260
tgaactatac gaagtttaca gaattaacag atcgactcca acaagcgtgg agtttgtatg    4320
atcagcgaaa tgccatacca aatggtgatt ttcgaaatgg gttaagtaat tggaatgcaa    4380
cgcctggcgt agaagtacaa caaatcaatc atacatctgt ccttgtgatt ccaaactggg    4440
atgagcaagt ttcgcaacag tttacagttc aaccgaatca aagatatgtg ttacgagtta    4500
ctgcgagaaa agaaggggta ggaaatggat atgtaagtat ccgtgatggt ggaaatcaaa    4560
cagaaacgct tactttagt gcaagcgatt atgatacaaa tggaatgtat aatacgcaag    4620
tgtccaatac aaatggatat aacacaaata atgcgtataa tacacaagca tcgagtacaa    4680
acggatataa cgcaaataat atgtataata cgcaagcatc gaatacaaac ggatataaca    4740
caaatagtgt gtacaatgat caaaccggct atatcacaaa aacagtgaca ttcatcccgt    4800
atacagatca aatgtggatt gagatgagtg agacagaagg tacattctat atagaaagtg    4860
tagaattgat tgtagacgta gagtaatagt agtacccctc cagatgaaac ctgtatctgg    4920
aggggttttt tatgcaaaag agtctttca tacagaatat attggtttta cccggattac     4980
atattttgtg aataggacta tggttggtta ccttacggta ccttttata tccaccggca    5040 ttggaaaatg taagagggag gataatcata tatagtccct tccctacaca tcaaattcct    5100
tcgaaagttt ctcgtgaatg agagtgaata tttcttttg tactttattc aggtcttgta    5160
agaaaggaat ggtattcaca caaatgatgg gtgtggatac gtctgttaaa cctgagatat    5220
ttgtaataat caagtcatag ttttttgcaa tctgtttaaa tgagctgaga tgtaatacat    5280
caatcttaga tagttgaatc atatgaccaa attgatactg cataatatta cgaataaata    5340
gggtatgttc catatctgaa tcacaaaaaa tgccgacatg aagaacagga accttctgtt    5400
ttaaagcttg taataagttt gtccaatgta tgattaaaat atataatgtt ccgtaaaaa     5460 catgctcgtc ccatttgaac tgttcatgat agtgaaagtg agttaattct tctttaaaa     5520 gcaagacaaa gtatgaaaat tcgtgagaat gatgctcgga aaaaaaacgt cttttatcat    5580
gtaaaataaa actacgtcca taattcatgg tttgtaaatt gtataactcc aaaatgattt    5640
```

-continued

```
tttgtttatt ttggagaggc acatgtagtt tgtcggatag tctatgcaat aagtttagaa     5700
tttcaggaac aattttccat gcgtcatttg attttgttg taccatagtt tctaattgct      5760
catacgtaaa tgcataatga tgattaaaaa aaacagagaa gagttggtaa acagtctcat     5820
gattaaaatc aagagaaaag gtatcccgga acaattgaca aaatgagctg ttctcaaaaa     5880
tacttacatc caaaggattg gaaaaatctt ctgaaatggt tttcatatgc tggtgttgta     5940
aacgaatcac attcaccatt gtccaatacc gaatccgtat gaggtctgga aaatttagtt     6000
gtatctgatt ttttgggtg acatatagaa agagttgatc caatgcctgt agttggttgt     6060
ctgggaaagg agtatgagtc acaccatatt tttcataaaa aaactggacc ataatacttc     6120
taatatgttg ttcatttcct atgattttac aaggatttgt ttgaatgtgt atctcatatt     6180
gttcgagata cacattcaat tttgtgataa tccgccttag ggtggaagta ctaagaaata     6240
attcctccgc gattgtctct atgtcatctc tttcatcaaa aaatatccgt tcgataaagg     6300
aaaactcagg acttacagat aagaccttt gatatataaa atcaatagaa tactgagaag      6360
gataggttaa cataatccct tttatagatg tctcaatctg aaaaggttga aattcttgat     6420
taataaattt aatgtcatct ctcaaaaattc tttcggaaca atttagtgtt tgtgcactca    6480
ctcctaacgt atgccatcca tcttgttcat atagtagttc taagaattgt agttgtctgc    6540
gtaaattgtt atttaaaaga gaacgcatga gtagacacct tctttcattt ataaaatatc    6600
actgatggaa ttc                                                       6613
```

<210> SEQ ID NO 29
<211> LENGTH: 1863
<212> TYPE: DNA
<213> ORGANISM: Bacillus thuringiensis (mutated)
<220> F

```
cga ttt gaa atc ctg gat agt tta ttt acg caa tat atg cca tct ttt       432
Arg Phe Glu Ile Leu Asp Ser Leu Phe Thr Gln Tyr Met Pro Ser Phe
    130                 135                 140 aga gtg aca aat ttt gaa gta cca ttc ctt act gta tat gca atg gca       480
Arg Val Thr Asn Phe Glu Val Pro Phe Leu Thr Val Tyr Ala Met Ala
145                 150                 155                 160 gcc aac ctt cat tta ctg tta tta aag gac gcg tca att ttt gga gaa       528
Ala Asn Leu His Leu Leu Leu Leu Lys Asp Ala Ser Ile Phe Gly Glu
                165                 170                 175 gaa tgg gga tgg tca aca act act att aat aac tat tat gat cgt caa       576
Glu Trp Gly Trp Ser Thr Thr Thr Ile Asn Asn Tyr Tyr Asp Arg Gln
            180                 185                 190 atg aaa ctt act gca gaa tat tct gat cac tgt gta aag tgg tat gaa       624
Met Lys Leu Thr Ala Glu Tyr Ser Asp His Cys Val Lys Trp Tyr Glu
        195                 200                 205 act ggt tta gca aaa tta aaa ggc acg agc gct aaa caa tgg gtt gac       672
Thr Gly Leu Ala Lys Leu Lys Gly Thr Ser Ala Lys Gln Trp Val Asp
    210                 215                 220 tat aac caa ttc cgt aga gaa atg aca ctg gcg gtt tta gat gtt gtt       720
Tyr Asn Gln Phe Arg Arg Glu Met Thr Leu Ala Val Leu Asp Val Val
225                 230                 235                 240 gca tta ttc cca aat tat gac aca cgc acg tac cca atg gaa acg aaa       768
Ala Leu Phe Pro Asn Tyr Asp Thr Arg Thr Tyr Pro Met Glu Thr Lys
                245                 250                 255 gca caa cta aca agg gaa gta tat aca gat cca ctg ggc gcg gta aac       816
Ala Gln Leu Thr Arg Glu Val Tyr Thr Asp Pro Leu Gly Ala Val Asn
            260                 265                 270 gtg tct tca att ggt tcc tgg tat gac aaa gca cct tct ttc gga gtg       864
Val Ser Ser Ile Gly Ser Trp Tyr Asp Lys Ala Pro Ser Phe Gly Val
        275                 280                 285 ata gaa tca tcc gtt att cga cca ccc cat gta ttt gat tat ata acg       912
Ile Glu Ser Ser Val Ile Arg Pro Pro His Val Phe Asp Tyr Ile Thr
    290                 295                 300 gga ctc aca gtg tat aca caa tca aga agc att tct tcc gct cgc tat       960
Gly Leu Thr Val Tyr Thr Gln Ser Arg Ser Ile Ser Ser Ala Arg Tyr
305                 310                 315                 320 ata aga cat tgg gct ggt cat caa ata agc tac cat cgt gtc agt agg      1008
Ile Arg His Trp Ala Gly His Gln Ile Ser Tyr His Arg Val Ser Arg
                325                 330                 335 ggt agt aat ctt caa caa atg tat gga act aat caa aat cta cac agc      1056
Gly Ser Asn Leu Gln Gln Met Tyr Gly Thr Asn Gln Asn Leu His Ser
            340                 345                 350 act agt acc ttt gat ttt acg aat tat gat att tac aag act cta tca      1104
Thr Ser Thr Phe Asp Phe Thr Asn Tyr Asp Ile Tyr Lys Thr Leu Ser
        355                 360                 365 aag gat gca gta ctc ctt gat att gtt tac cct ggt tat acg tat ata      1152
Lys Asp Ala Val Leu Leu Asp Ile Val Tyr Pro Gly Tyr Thr Tyr Ile
    370                 375                 380 ttt ttt gga atg cca gaa gtc gag ttt ttc atg gta aac caa ttg aat      1200
Phe Phe Gly Met Pro Glu Val Glu Phe Phe Met Val Asn Gln Leu Asn
385                 390                 395                 400 aat acc aga aag acg tta aag tat aat cca gtt tcc aaa gat att ata      1248
Asn Thr Arg Lys Thr Leu Lys Tyr Asn Pro Val Ser Lys Asp Ile Ile
                405                 410                 415 gcg agt aca aga gat tcg gaa tta gaa tta cct cca gaa act tca gat      1296
Ala Ser Thr Arg Asp Ser Glu Leu Glu Leu Pro Pro Glu Thr Ser Asp
            420                 425                 430 caa cca aat tat gag tca tat agc cat aga tta tgt cat atc aca agt      1344
Gln Pro Asn Tyr Glu Ser Tyr Ser His Arg Leu Cys His Ile Thr Ser
        435                 440                 445
```

```
att ccc gcg acg ggt aac act acc gga tta gta cct gta ttt tct tgg      1392
Ile Pro Ala Thr Gly Asn Thr Thr Gly Leu Val Pro Val Phe Ser Trp
450                 455                 460 aca cat cga agt gca gat tta aac aat aca ata tat tca gat aaa atc      1440
Thr His Arg Ser Ala Asp Leu Asn Asn Thr Ile Tyr Ser Asp Lys Ile
465                 470                 475                 480 act caa att ccg gcc gtt aaa tgt tgg gat aat tta ccg ttt gtt cca      1488
Thr Gln Ile Pro Ala Val Lys Cys Trp Asp Asn Leu Pro Phe Val Pro
                485                 490                 495 gtg gta aaa gga cca gga cat aca gga ggg gat tta tta cag tat aat      1536
Val Val Lys Gly Pro Gly His Thr Gly Gly Asp Leu Leu Gln Tyr Asn
            500                 505                 510 aga agt act ggt tct gta gga acc tta ttt cta gct cga tat ggc cta      1584
Arg Ser Thr Gly Ser Val Gly Thr Leu Phe Leu Ala Arg Tyr Gly Leu
        515                 520                 525 gca tta gaa aaa gca ggg aaa tat cgt gta aga ctg aga tat gct act      1632
Ala Leu Glu Lys Ala Gly Lys Tyr Arg Val Arg Leu Arg Tyr Ala Thr
    530                 535                 540 gat gca gat att gta ttg cat gta aac gat gct cag att cag atg cca      1680
Asp Ala Asp Ile Val Leu His Val Asn Asp Ala Gln Ile Gln Met Pro
545                 550                 555                 560 aaa aca atg aac cca ggt gag gat ctg aca tct aaa act ttt aaa gtt      1728
Lys Thr Met Asn Pro Gly Glu Asp Leu Thr Ser Lys Thr Phe Lys Val
                565                 570                 575 gca gat gct atc aca aca tta aat tta gca aca gat agt tcg cta gca      1776
Ala Asp Ala Ile Thr Thr Leu Asn Leu Ala Thr Asp Ser Ser Leu Ala
            580                 585                 590 ttg aaa cat aat tta ggt gaa gac cct aat tca aca tta tct ggt ata      1824
Leu Lys His Asn Leu Gly Glu Asp Pro Asn Ser Thr Leu Ser Gly Ile
        595                 600                 605 gtt tac gtt gac cga atc gaa ttc atc cca gta gat taa                  1863
Val Tyr Val Asp Arg Ile Glu Phe Ile Pro Val Asp
    610                 615                 620

<210> SEQ ID NO 30
<211> LENGTH: 620
<212> TYPE: PRT
<213> ORGANISM: Bacillus thuringiensis (mutated)

<400> SEQUENCE: 30

Met Ser Ala Gly Asn Ala Ser Glu Tyr Pro Gly Ser Pro Glu Val Leu
1               5                   10                  15

Val Ser Gly Gln Asp Ala Ala Lys Ala Ala Ile Asp Ile Val Gly Lys
            20                  25                  30

Leu Leu Ser Gly Leu Gly Val Pro Phe Val Gly Pro Ile Val Ser Leu
        35                  40                  45

Tyr Thr Gln Leu Ile Asp Ile Leu Trp Pro Ser Gly Glu Lys Ser Gln
    50                  55                  60

Trp Glu Ile Phe Met Glu Gln Val Glu Glu Leu Ile Asn Gln Lys Ile
65                  70                  75                  80

Ala Glu Tyr Ala Arg Asn Lys Ala Leu Ser Glu Leu Glu Gly Leu Gly
                85                  90                  95

Asn Asn Tyr Gln Leu Tyr Leu Thr Ala Leu Glu Glu Trp Glu Glu Asn
            100                 105                 110

Pro Asn Gly Ser Arg Asn Gly Ser Arg Ala Leu Arg Asp Val Arg Asn
        115                 120                 125

Arg Phe Glu Ile Leu Asp Ser Leu Phe Thr Gln Tyr Met Pro Ser Phe
    130                 135                 140

Arg Val Thr Asn Phe Glu Val Pro Phe Leu Thr Val Tyr Ala Met Ala
```

```
                145                 150                 155                 160
        Ala Asn Leu His Leu Leu Leu Lys Asp Ala Ser Ile Phe Gly Glu
                        165                 170                 175

Glu Trp Gly Trp Ser Thr Thr Thr Ile Asn Asn Tyr Tyr Asp Arg Gln
                            180                 185                 190

Met Lys Leu Thr Ala Glu Tyr Ser Asp His Cys Val Lys Trp Tyr Glu
                        195                 200                 205

Thr Gly Leu Ala Lys Leu Lys Gly Thr Ser Ala Lys Gln Trp Val Asp
                        210                 215                 220

Tyr Asn Gln Phe Arg Arg Glu Met Thr Leu Ala Val Leu Asp Val Val
        225                 230                 235                 240

Ala Leu Phe Pro Asn Tyr Asp Thr Arg Thr Tyr Pro Met Glu Thr Lys
                        245                 250                 255

Ala Gln Leu Thr Arg Glu Val Tyr Thr Asp Pro Leu Gly Ala Val Asn
                        260                 265                 270

Val Ser Ser Ile Gly Ser Trp Tyr Asp Lys Ala Pro Ser Phe Gly Val
                        275                 280                 285

Ile Glu Ser Ser Val Ile Arg Pro Pro His Val Phe Asp Tyr Ile Thr
                290                 295                 300

Gly Leu Thr Val Tyr Thr Gln Ser Arg Ser Ile Ser Ser Ala Arg Tyr
        305                 310                 315                 320

Ile Arg His Trp Ala Gly His Gln Ile Ser Tyr His Arg Val Ser Arg
                        325                 330                 335

Gly Ser Asn Leu Gln Gln Met Tyr Gly Thr Asn Gln Asn Leu His Ser
                        340                 345                 350

Thr Ser Thr Phe Asp Phe Thr Asn Tyr Asp Ile Tyr Lys Thr Leu Ser
                        355                 360                 365

Lys Asp Ala Val Leu Leu Asp Ile Val Tyr Pro Gly Tyr Thr Tyr Ile
            370                 375                 380

Phe Phe Gly Met Pro Glu Val Glu Phe Met Val Asn Gln Leu Asn
        385                 390                 395                 400

Asn Thr Arg Lys Thr Leu Lys Tyr Asn Pro Val Ser Lys Asp Ile Ile
                        405                 410                 415

Ala Ser Thr Arg Asp Ser Glu Leu Glu Leu Pro Pro Glu Thr Ser Asp
                        420                 425                 430

Gln Pro Asn Tyr Glu Ser Tyr Ser His Arg Leu Cys His Ile Thr Ser
                        435                 440                 445

Ile Pro Ala Thr Gly Asn Thr Thr Gly Leu Val Pro Val Phe Ser Trp
            450                 455                 460

Thr His Arg Ser Ala Asp Leu Asn Asn Thr Ile Tyr Ser Asp Lys Ile
        465                 470                 475                 480

Thr Gln Ile Pro Ala Val Lys Cys Trp Asp Asn Leu Pro Phe Val Pro
                        485                 490                 495

Val Val Lys Gly Pro Gly His Thr Gly Gly Asp Leu Leu Gln Tyr Asn
                        500                 505                 510

Arg Ser Thr Gly Ser Val Gly Thr Leu Phe Leu Ala Arg Tyr Gly Leu
                        515                 520                 525

Ala Leu Glu Lys Ala Gly Lys Tyr Arg Val Arg Leu Arg Tyr Ala Thr
                530                 535                 540

Asp Ala Asp Ile Val Leu His Val Asn Asp Ala Gln Ile Gln Met Pro
        545                 550                 555                 560

Lys Thr Met Asn Pro Gly Glu Asp Leu Thr Ser Lys Thr Phe Lys Val
                        565                 570                 575
```

```
Ala Asp Ala Ile Thr Thr Leu Asn Leu Ala Thr Asp Ser Ser Leu Ala
            580                 585                 590

Leu Lys His Asn Leu Gly Glu Asp Pro Asn Ser Thr Leu Ser Gly Ile
        595                 600                 605

Val Tyr Val Asp Arg Ile Glu Phe Ile Pro Val Asp
    610                 615                 620

<210> SEQ ID NO 31
<211> LENGTH: 1863
<212> TYPE: DNA
<213> ORGANISM: Bacillus thuringiensis (mutated)
<220> FEATURE:
<221> NAME/KEY: misc_feature
<223> OTHER INFORMATION: LKMS.N49PVD
<220> FEATURE:
<221> NAME/KEY: CDS
<222> LOCATION: (1)..(1863)

<400> SEQUENCE: 31 atg tct gcg gga aat gct agt gaa tac cct ggt tca cct gaa gta ctt    48
Met Ser Ala Gly Asn Ala Ser Glu Tyr Pro Gly Ser Pro Glu Val Leu
1               5                   10                  15 gtt agc gga caa gat gca gct aag gcc gca att gat ata gta ggt aaa    96
Val Ser Gly Gln Asp Ala Ala Lys Ala Ala Ile Asp Ile Val Gly Lys
            20                  25                  30 tta cta tca ggt tta ggg gtc cca ttt gtt ggg ccg ata gtg agt ctt   144
Leu Leu Ser Gly Leu Gly Val Pro Phe Val Gly Pro Ile Val Ser Leu
        35                  40                  45 tat act caa ctt att gat att ctg tgg cct tca ggg gaa aag agt caa   192
Tyr Thr Gln Leu Ile Asp Ile Leu Trp Pro Ser Gly Glu Lys Ser Gln
    50                  55                  60 tgg gaa att ttt atg gaa caa gta gaa gaa ctc att aat caa aaa ata   240
Trp Glu Ile Phe Met Glu Gln Val Glu Glu Leu Ile Asn Gln Lys Ile
65                  70                  75                  80 gca gaa tat gca agg aat aaa gcg ctt tcg gaa tta gaa gga tta ggt   288
Ala Glu Tyr Ala Arg Asn Lys Ala Leu Ser Glu Leu Glu Gly Leu Gly
                85                  90                  95 aat aat tac caa tta tat cta act gcg ctt gaa gaa tgg gaa gaa aat   336
Asn Asn Tyr Gln Leu Tyr Leu Thr Ala Leu Glu Glu Trp Glu Glu Asn
            100                 105                 110 cca tta aaa atg tct aat ggt tct aga gcc tta cga gat gtg cga aat   384
Pro Leu Lys Met Ser Asn Gly Ser Arg Ala Leu Arg Asp Val Arg Asn
        115                 120                 125 cga ttt gaa atc ctg gat agt tta ttt acg caa tat atg cca tct ttt   432
Arg Phe Glu Ile Leu Asp Ser Leu Phe Thr Gln Tyr Met Pro Ser Phe
    130                 135                 140 aga gtg aca aat ttt gaa gta cca ttc ctt act gta tat gca atg gca   480
Arg Val Thr Asn Phe Glu Val Pro Phe Leu Thr Val Tyr Ala Met Ala
145                 150                 155                 160 gcc aac ctt cat tta ctg tta tta aag gac gcg tca att ttt gga gaa   528
Ala Asn Leu His Leu Leu Leu Lys Asp Ala Ser Ile Phe Gly Glu
                165                 170                 175 gaa tgg gga tgg tca aca act act att aat aac tat tat gat cgt caa   576
Glu Trp Gly Trp Ser Thr Thr Thr Ile Asn Asn Tyr Tyr Asp Arg Gln
            180                 185                 190 atg aaa ctt act gca gaa tat tct gat cac tgt gta aag tgg tat gaa   624
Met Lys Leu Thr Ala Glu Tyr Ser Asp His Cys Val Lys Trp Tyr Glu
        195                 200                 205 act ggt tta gca aaa tta aaa ggc acg agc gct aaa caa tgg gtt gac   672
Thr Gly Leu Ala Lys Leu Lys Gly Thr Ser Ala Lys Gln Trp Val Asp
    210                 215                 220 tat aac caa ttc cgt aga gaa atg aca ctg gcg gtt tta gat gtt gtt   720
```

-continued

| | | | | | | | | | | | | |
|---|---|---|---|---|---|---|---|---|---|---|---|---|
| Tyr | Asn | Gln | Phe | Arg | Arg | Glu | Met | Thr | Leu | Ala | Val | Leu | Asp | Val | Val |
| 225 | | | | | 230 | | | | | 235 | | | | | 240 |

```
gca tta ttc cca aat tat gac aca cgc acg tac cca atg gaa acg aaa      768
Ala Leu Phe Pro Asn Tyr Asp Thr Arg Thr Tyr Pro Met Glu Thr Lys
                    245                 250                 255 gca caa cta aca agg gaa gta tat aca gat cca ctg ggc gcg gta aac      816
Ala Gln Leu Thr Arg Glu Val Tyr Thr Asp Pro Leu Gly Ala Val Asn
                260                 265                 270 gtg tct tca att ggt tcc tgg tat gac aaa gca cct tct ttc gga gtg      864
Val Ser Ser Ile Gly Ser Trp Tyr Asp Lys Ala Pro Ser Phe Gly Val
            275                 280                 285 ata gaa tca tcc gtt att cga cca ccc cat gta ttt gat tat ata acg      912
Ile Glu Ser Ser Val Ile Arg Pro Pro His Val Phe Asp Tyr Ile Thr
        290                 295                 300 gga ctc aca gtg tat aca caa tca aga agc att tct tcc gct cgc tat      960
Gly Leu Thr Val Tyr Thr Gln Ser Arg Ser Ile Ser Ser Ala Arg Tyr
305                 310                 315                 320 ata aga cat tgg gct ggt cat caa ata agc tac cat cgt gtc agt agg     1008
Ile Arg His Trp Ala Gly His Gln Ile Ser Tyr His Arg Val Ser Arg
                    325                 330                 335 ggt agt aat ctt caa caa atg tat gga act aat caa aat cta cac agc     1056
Gly Ser Asn Leu Gln Gln Met Tyr Gly Thr Asn Gln Asn Leu His Ser
                340                 345                 350 act agt acc ttt gat ttt acg aat tat gat att tac aag act cta tca     1104
Thr Ser Thr Phe Asp Phe Thr Asn Tyr Asp Ile Tyr Lys Thr Leu Ser
            355                 360                 365 aag gat gca gta ctc ctt gat att gtt tac cct ggt tat acg tat ata     1152
Lys Asp Ala Val Leu Leu Asp Ile Val Tyr Pro Gly Tyr Thr Tyr Ile
        370                 375                 380 ttt ttt gga atg cca gaa gtc gag ttt ttc atg gta aac caa ttg aat     1200
Phe Phe Gly Met Pro Glu Val Glu Phe Phe Met Val Asn Gln Leu Asn
385                 390                 395                 400 aat acc aga aag acg tta aag tat aat cca gtt tcc aaa gat att ata     1248
Asn Thr Arg Lys Thr Leu Lys Tyr Asn Pro Val Ser Lys Asp Ile Ile
                    405                 410                 415 gcg agt aca aga gat tcg gaa tta gaa tta cct cca gaa act tca gat     1296
Ala Ser Thr Arg Asp Ser Glu Leu Glu Leu Pro Pro Glu Thr Ser Asp
                420                 425                 430 caa cca aat tat gag tca tat agc cat aga tta tgt cat atc aca agt     1344
Gln Pro Asn Tyr Glu Ser Tyr Ser His Arg Leu Cys His Ile Thr Ser
            435                 440                 445 att ccc gcg acg ggt aac act acc gga tta gta cct gta ttt tct tgg     1392
Ile Pro Ala Thr Gly Asn Thr Thr Gly Leu Val Pro Val Phe Ser Trp
        450                 455                 460 aca cat cga agt gca gat tta aac aat aca ata tat tca gat aaa atc     1440
Thr His Arg Ser Ala Asp Leu Asn Asn Thr Ile Tyr Ser Asp Lys Ile
465                 470                 475                 480 act caa att ccg gcc gtt aaa tgt tgg gat aat tta ccg ttt gtt cca     1488
Thr Gln Ile Pro Ala Val Lys Cys Trp Asp Asn Leu Pro Phe Val Pro
                    485                 490                 495 gtg gta aaa gga cca gga cat aca ggg ggt gat tta tta cag tat aat     1536
Val Val Lys Gly Pro Gly His Thr Gly Gly Asp Leu Leu Gln Tyr Asn
                500                 505                 510 aga agt act ggt tct gta gga acc tta ttt cta gct cga tat ggc cta     1584
Arg Ser Thr Gly Ser Val Gly Thr Leu Phe Leu Ala Arg Tyr Gly Leu
            515                 520                 525 gca tta gaa aaa gca ggg aaa tat cgt gta aga ctg aga tat gct act     1632
Ala Leu Glu Lys Ala Gly Lys Tyr Arg Val Arg Leu Arg Tyr Ala Thr
        530                 535                 540 gat gca gat att gta ttg cat gta aac gat gct cag att cag atg cca     1680
```

```
Asp Ala Asp Ile Val Leu His Val Asn Asp Ala Gln Ile Gln Met Pro
545                 550                 555                 560 aaa aca atg aac cca ggt gag gat ctg aca tct aaa act ttt aaa gtt   1728
Lys Thr Met Asn Pro Gly Glu Asp Leu Thr Ser Lys Thr Phe Lys Val
                565                 570                 575 gca gat gct atc aca aca tta aat tta gca aca gat agt tcg cta gca   1776
Ala Asp Ala Ile Thr Thr Leu Asn Leu Ala Thr Asp Ser Ser Leu Ala
                580                 585                 590 ttg aaa cat aat tta ggt gaa gac cct aat tca aca tta tct ggt ata   1824
Leu Lys His Asn Leu Gly Glu Asp Pro Asn Ser Thr Leu Ser Gly Ile
            595                 600                 605 gtt tac gtt gac cga atc gaa ttc atc cca gta gat taa               1863
Val Tyr Val Asp Arg Ile Glu Phe Ile Pro Val Asp
610                 615                 620
```

<210> SEQ ID NO 32
<211> LENGTH: 620
<212> TYPE: PRT
<213> ORGANISM: Bacillus thuringiensis (mutated)

<400> SEQUENCE: 32

```
Met Ser Ala Gly Asn Ala Ser Glu Tyr Pro Gly Ser Pro Glu Val Leu
1               5                   10                  15

Val Ser Gly Gln Asp Ala Ala Lys Ala Ala Ile Asp Ile Val Gly Lys
                20                  25                  30

Leu Leu Ser Gly Leu Gly Val Pro Phe Val Gly Pro Ile Val Ser Leu
            35                  40                  45

Tyr Thr Gln Leu Ile Asp Ile Leu Trp Pro Ser Gly Glu Lys Ser Gln
50                  55                  60

Trp Glu Ile Phe Met Glu Gln Val Glu Glu Leu Ile Asn Gln Lys Ile
65                  70                  75                  80

Ala Glu Tyr Ala Arg Asn Lys Ala Leu Ser Glu Leu Glu Gly Leu Gly
                85                  90                  95

Asn Asn Tyr Gln Leu Tyr Leu Thr Ala Leu Glu Glu Trp Glu Glu Asn
            100                 105                 110

Pro Leu Lys Met Ser Asn Gly Ser Arg Ala Leu Arg Asp Val Arg Asn
        115                 120                 125

Arg Phe Glu Ile Leu Asp Ser Leu Phe Thr Gln Tyr Met Pro Ser Phe
130                 135                 140

Arg Val Thr Asn Phe Glu Val Pro Phe Leu Thr Val Tyr Ala Met Ala
145                 150                 155                 160

Ala Asn Leu His Leu Leu Leu Lys Asp Ala Ser Ile Phe Gly Glu
                165                 170                 175

Glu Trp Gly Trp Ser Thr Thr Thr Ile Asn Asn Tyr Tyr Asp Arg Gln
            180                 185                 190

Met Lys Leu Thr Ala Glu Tyr Ser Asp His Cys Val Lys Trp Tyr Glu
        195                 200                 205

Thr Gly Leu Ala Lys Leu Lys Gly Thr Ser Ala Lys Gln Trp Val Asp
210                 215                 220

Tyr Asn Gln Phe Arg Arg Glu Met Thr Leu Ala Val Leu Asp Val Val
225                 230                 235                 240

Ala Leu Phe Pro Asn Tyr Asp Thr Arg Thr Tyr Pro Met Glu Thr Lys
                245                 250                 255

Ala Gln Leu Thr Arg Glu Val Tyr Thr Asp Pro Leu Gly Ala Val Asn
            260                 265                 270

Val Ser Ser Ile Gly Ser Trp Tyr Asp Lys Ala Pro Ser Phe Gly Val
        275                 280                 285
```

Ile Glu Ser Ser Val Ile Arg Pro Pro His Val Phe Asp Tyr Ile Thr
290                 295                 300

Gly Leu Thr Val Tyr Thr Gln Ser Arg Ser Ile Ser Ser Ala Arg Tyr
305                 310                 315                 320

Ile Arg His Trp Ala Gly His Gln Ile Ser Tyr His Arg Val Ser Arg
            325                 330                 335

Gly Ser Asn Leu Gln Gln Met Tyr Gly Thr Asn Gln Asn Leu His Ser
            340                 345                 350

Thr Ser Thr Phe Asp Phe Thr Asn Tyr Asp Ile Tyr Lys Thr Leu Ser
            355                 360                 365

Lys Asp Ala Val Leu Leu Asp Ile Val Tyr Pro Gly Tyr Thr Tyr Ile
370                 375                 380

Phe Phe Gly Met Pro Glu Val Glu Phe Phe Met Val Asn Gln Leu Asn
385                 390                 395                 400

Asn Thr Arg Lys Thr Leu Lys Tyr Asn Pro Val Ser Lys Asp Ile Ile
            405                 410                 415

Ala Ser Thr Arg Asp Ser Glu Leu Glu Leu Pro Pro Glu Thr Ser Asp
            420                 425                 430

Gln Pro Asn Tyr Glu Ser Tyr Ser His Arg Leu Cys His Ile Thr Ser
            435                 440                 445

Ile Pro Ala Thr Gly Asn Thr Thr Gly Leu Val Pro Val Phe Ser Trp
450                 455                 460

Thr His Arg Ser Ala Asp Leu Asn Asn Thr Ile Tyr Ser Asp Lys Ile
465                 470                 475                 480

Thr Gln Ile Pro Ala Val Lys Cys Trp Asp Asn Leu Pro Phe Val Pro
            485                 490                 495

Val Val Lys Gly Pro Gly His Thr Gly Gly Asp Leu Leu Gln Tyr Asn
            500                 505                 510

Arg Ser Thr Gly Ser Val Gly Thr Leu Phe Leu Ala Arg Tyr Gly Leu
            515                 520                 525

Ala Leu Glu Lys Ala Gly Lys Tyr Arg Val Arg Leu Arg Tyr Ala Thr
530                 535                 540

Asp Ala Asp Ile Val Leu His Val Asn Asp Ala Gln Ile Gln Met Pro
545                 550                 555                 560

Lys Thr Met Asn Pro Gly Glu Asp Leu Thr Ser Lys Thr Phe Lys Val
            565                 570                 575

Ala Asp Ala Ile Thr Thr Leu Asn Leu Ala Thr Asp Ser Ser Leu Ala
            580                 585                 590

Leu Lys His Asn Leu Gly Glu Asp Pro Asn Ser Thr Leu Ser Gly Ile
            595                 600                 605

Val Tyr Val Asp Arg Ile Glu Phe Ile Pro Val Asp
610                 615                 620

<210> SEQ ID NO 33
<211> LENGTH: 1854
<212> TYPE: DNA
<213> ORGANISM: Bacillus thuringiensis (mutated)
<220> FEATURE:
<221> NAME/KEY: misc_feature
<223> OTHER INFORMATION: LKMS.R49PVD
<220> FEATURE:
<221> NAME/KEY: CDS
<222> LOCATION: (1)..(1854)

<400> SEQUENCE: 33 atg tct gcg gga aat gct agt gaa tac cct ggt tca cct gaa gta ctt     48
Met Ser Ala Gly Asn Ala Ser Glu Tyr Pro Gly Ser Pro Glu Val Leu -continued

```
1               5                   10                  15
gtt agc gga caa gat gca gct aag gcc gca att gat ata gta ggt aaa     96
Val Ser Gly Gln Asp Ala Ala Lys Ala Ala Ile Asp Ile Val Gly Lys
            20                  25                  30 tta cta tca ggt tta ggg gtc cca ttt gtt ggg ccg ata gtg agt ctt    144
Leu Leu Ser Gly Leu Gly Val Pro Phe Val Gly Pro Ile Val Ser Leu
        35                  40                  45 tat act caa ctt att gat att ctg tgg cct tca ggg gaa aag agt caa    192
Tyr Thr Gln Leu Ile Asp Ile Leu Trp Pro Ser Gly Glu Lys Ser Gln
    50                  55                  60 tgg gaa att ttt atg gaa caa gta gaa gaa ctc att aat caa aaa ata    240
Trp Glu Ile Phe Met Glu Gln Val Glu Glu Leu Ile Asn Gln Lys Ile
65                  70                  75                  80 gca gaa tat gca agg aat aaa gcg ctt tcg gaa tta gaa gga tta ggt    288
Ala Glu Tyr Ala Arg Asn Lys Ala Leu Ser Glu Leu Glu Gly Leu Gly
                85                  90                  95 aat aat tac caa tta tat cta act gcg ctt gaa gaa tgg gaa gaa aat    336
Asn Asn Tyr Gln Leu Tyr Leu Thr Ala Leu Glu Glu Trp Glu Glu Asn
            100                 105                 110 cca tta aaa atg tct aga gcc tta cga gat gtg cga aat cga ttt gaa    384
Pro Leu Lys Met Ser Arg Ala Leu Arg Asp Val Arg Asn Arg Phe Glu
        115                 120                 125 atc ctg gat agt tta ttt acg caa tat atg cca tct ttt aga gtg aca    432
Ile Leu Asp Ser Leu Phe Thr Gln Tyr Met Pro Ser Phe Arg Val Thr
    130                 135                 140 aat ttt gaa gta cca ttc ctt act gta tat gca atg gca gcc aac ctt    480
Asn Phe Glu Val Pro Phe Leu Thr Val Tyr Ala Met Ala Ala Asn Leu
145                 150                 155                 160 cat tta ctg tta tta aag gac gcg tca att ttt gga gaa gaa tgg gga    528
His Leu Leu Leu Leu Lys Asp Ala Ser Ile Phe Gly Glu Glu Trp Gly
                165                 170                 175 tgg tca aca act act att aat aac tat tat gat cgt caa atg aaa ctt    576
Trp Ser Thr Thr Thr Ile Asn Asn Tyr Tyr Asp Arg Gln Met Lys Leu
            180                 185                 190 act gca gaa tat tct gat cac tgt gta aag tgg tat gaa act ggt tta    624
Thr Ala Glu Tyr Ser Asp His Cys Val Lys Trp Tyr Glu Thr Gly Leu
        195                 200                 205 gca aaa tta aaa ggc acg agc gct aaa caa tgg gtt gac tat aac caa    672
Ala Lys Leu Lys Gly Thr Ser Ala Lys Gln Trp Val Asp Tyr Asn Gln
    210                 215                 220 ttc cgt aga gaa atg aca ctg gcg gtt tta gat gtt gtt gca tta ttc    720
Phe Arg Arg Glu Met Thr Leu Ala Val Leu Asp Val Val Ala Leu Phe
225                 230                 235                 240 cca aat tat gac aca cgc acg tac cca atg gaa acg aaa gca caa cta    768
Pro Asn Tyr Asp Thr Arg Thr Tyr Pro Met Glu Thr Lys Ala Gln Leu
                245                 250                 255 aca agg gaa gta tat aca gat cca ctg ggc gcg gta aac gtg tct tca    816
Thr Arg Glu Val Tyr Thr Asp Pro Leu Gly Ala Val Asn Val Ser Ser
            260                 265                 270 att ggt tcc tgg tat gac aaa gca cct tct ttc gga gtg ata gaa tca    864
Ile Gly Ser Trp Tyr Asp Lys Ala Pro Ser Phe Gly Val Ile Glu Ser
        275                 280                 285 tcc gtt att cga cca ccc cat gta ttt gat tat ata acg gga ctc aca    912
Ser Val Ile Arg Pro Pro His Val Phe Asp Tyr Ile Thr Gly Leu Thr
    290                 295                 300 gtg tat aca caa tca aga agc att tct tcc gct cgc tat ata aga cat    960
Val Tyr Thr Gln Ser Arg Ser Ile Ser Ser Ala Arg Tyr Ile Arg His
305                 310                 315                 320 tgg gct ggt cat caa ata agc tac cat cgt gtc agt agg ggt agt aat   1008
Trp Ala Gly His Gln Ile Ser Tyr His Arg Val Ser Arg Gly Ser Asn
```

```
                325                 330                 335
ctt caa caa atg tat gga act aat caa aat cta cac agc act agt acc    1056
Leu Gln Gln Met Tyr Gly Thr Asn Gln Asn Leu His Ser Thr Ser Thr
            340                 345                 350 ttt gat ttt acg aat tat gat att tac aag act cta tca aag gat gca    1104
Phe Asp Phe Thr Asn Tyr Asp Ile Tyr Lys Thr Leu Ser Lys Asp Ala
                355                 360                 365 gta ctc ctt gat att gtt tac cct ggt tat acg tat ata ttt ttt gga    1152
Val Leu Leu Asp Ile Val Tyr Pro Gly Tyr Thr Tyr Ile Phe Phe Gly
        370                 375                 380 atg cca gaa gtc gag ttt ttc atg gta aac caa ttg aat aat acc aga    1200
Met Pro Glu Val Glu Phe Phe Met Val Asn Gln Leu Asn Asn Thr Arg
385                 390                 395                 400 aag acg tta aag tat aat cca gtt tcc aaa gat att ata gcg agt aca    1248
Lys Thr Leu Lys Tyr Asn Pro Val Ser Lys Asp Ile Ile Ala Ser Thr
                405                 410                 415 aga gat tcg gaa tta gaa tta cct cca gaa act tca gat caa cca aat    1296
Arg Asp Ser Glu Leu Glu Leu Pro Pro Glu Thr Ser Asp Gln Pro Asn
            420                 425                 430 tat gag tca tat agc cat aga tta tgt cat atc aca agt att ccc gcg    1344
Tyr Glu Ser Tyr Ser His Arg Leu Cys His Ile Thr Ser Ile Pro Ala
                435                 440                 445 acg ggt aac act acc gga tta gta cct gta ttt tct tgg aca cat cga    1392
Thr Gly Asn Thr Thr Gly Leu Val Pro Val Phe Ser Trp Thr His Arg
        450                 455                 460 agt gca gat tta aac aat aca ata tat tca gat aaa atc act caa att    1440
Ser Ala Asp Leu Asn Asn Thr Ile Tyr Ser Asp Lys Ile Thr Gln Ile
465                 470                 475                 480 ccg gcc gtt aaa tgt tgg gat aat tta ccg ttt gtt cca gtg gta aaa    1488
Pro Ala Val Lys Cys Trp Asp Asn Leu Pro Phe Val Pro Val Val Lys
                485                 490                 495 gga cca gga cat aca gga ggg gat tta tta cag tat aat aga agt act    1536
Gly Pro Gly His Thr Gly Gly Asp Leu Leu Gln Tyr Asn Arg Ser Thr
            500                 505                 510 ggt tct gta gga acc tta ttt cta gct cga tat ggc cta gca tta gaa    1584
Gly Ser Val Gly Thr Leu Phe Leu Ala Arg Tyr Gly Leu Ala Leu Glu
        515                 520                 525 aaa gca ggg aaa tat cgt gta aga ctg aga tat gct act gat gca gat    1632
Lys Ala Gly Lys Tyr Arg Val Arg Leu Arg Tyr Ala Thr Asp Ala Asp
530                 535                 540 att gta ttg cat gta aac gat gct cag att cag atg cca aaa aca atg    1680
Ile Val Leu His Val Asn Asp Ala Gln Ile Gln Met Pro Lys Thr Met
545                 550                 555                 560 aac cca ggt gag gat ctg aca tct aaa act ttt aaa gtt gca gat gct    1728
Asn Pro Gly Glu Asp Leu Thr Ser Lys Thr Phe Lys Val Ala Asp Ala
                565                 570                 575 atc aca aca tta aat tta gca aca gat agt tcg cta gca ttg aaa cat    1776
Ile Thr Thr Leu Asn Leu Ala Thr Asp Ser Ser Leu Ala Leu Lys His
        580                 585                 590 aat tta ggt gaa gac cct aat tca aca tta tct ggt ata gtt tac gtt    1824
Asn Leu Gly Glu Asp Pro Asn Ser Thr Leu Ser Gly Ile Val Tyr Val
            595                 600                 605 gac cga atc gaa ttc atc cca gta gat taa                            1854
Asp Arg Ile Glu Phe Ile Pro Val Asp
        610                 615
```

<210> SEQ ID NO 34
<211> LENGTH: 617
<212> TYPE: PRT
<213> ORGANISM: Bacillus thuringiensis (mutated)

```
<400> SEQUENCE: 34

Met Ser Ala Gly Asn Ala Ser Glu Tyr Pro Gly Ser Pro Glu Val Leu
1               5                   10                  15

Val Ser Gly Gln Asp Ala Ala Lys Ala Ala Ile Asp Ile Val Gly Lys
            20                  25                  30

Leu Leu Ser Gly Leu Gly Val Pro Phe Val Gly Pro Ile Val Ser Leu
        35                  40                  45

Tyr Thr Gln Leu Ile Asp Ile Leu Trp Pro Ser Gly Glu Lys Ser Gln
    50                  55                  60

Trp Glu Ile Phe Met Glu Gln Val Glu Leu Ile Asn Gln Lys Ile
65                  70                  75                  80

Ala Glu Tyr Ala Arg Asn Lys Ala Leu Ser Glu Leu Glu Gly Leu Gly
                85                  90                  95

Asn Asn Tyr Gln Leu Tyr Leu Thr Ala Leu Glu Glu Trp Glu Glu Asn
                100                 105                 110

Pro Leu Lys Met Ser Arg Ala Leu Arg Asp Val Arg Asn Arg Phe Glu
            115                 120                 125

Ile Leu Asp Ser Leu Phe Thr Gln Tyr Met Pro Ser Phe Arg Val Thr
    130                 135                 140

Asn Phe Glu Val Pro Phe Leu Thr Val Tyr Ala Met Ala Ala Asn Leu
145                 150                 155                 160

His Leu Leu Leu Lys Asp Ala Ser Ile Phe Gly Glu Glu Trp Gly
                165                 170                 175

Trp Ser Thr Thr Thr Ile Asn Asn Tyr Tyr Asp Arg Gln Met Lys Leu
                180                 185                 190

Thr Ala Glu Tyr Ser Asp His Cys Val Lys Trp Tyr Glu Thr Gly Leu
            195                 200                 205

Ala Lys Leu Lys Gly Thr Ser Ala Lys Gln Trp Val Asp Tyr Asn Gln
    210                 215                 220

Phe Arg Arg Glu Met Thr Leu Ala Val Leu Asp Val Val Ala Leu Phe
225                 230                 235                 240

Pro Asn Tyr Asp Thr Arg Thr Tyr Pro Met Glu Thr Lys Ala Gln Leu
                245                 250                 255

Thr Arg Glu Val Tyr Thr Asp Pro Leu Gly Ala Val Asn Val Ser Ser
            260                 265                 270

Ile Gly Ser Trp Tyr Asp Lys Ala Pro Ser Phe Gly Val Ile Glu Ser
    275                 280                 285

Ser Val Ile Arg Pro Pro His Val Phe Asp Tyr Ile Thr Gly Leu Thr
    290                 295                 300

Val Tyr Thr Gln Ser Arg Ser Ile Ser Ser Ala Arg Tyr Ile Arg His
305                 310                 315                 320

Trp Ala Gly His Gln Ile Ser Tyr His Arg Val Ser Arg Gly Ser Asn
                325                 330                 335

Leu Gln Gln Met Tyr Gly Thr Asn Gln Asn Leu His Ser Thr Ser Thr
            340                 345                 350

Phe Asp Phe Thr Asn Tyr Asp Ile Tyr Lys Thr Leu Ser Lys Asp Ala
        355                 360                 365

Val Leu Leu Asp Ile Val Tyr Pro Gly Tyr Tyr Ile Phe Phe Gly
    370                 375                 380

Met Pro Glu Val Glu Phe Phe Met Val Asn Gln Leu Asn Asn Thr Arg
385                 390                 395                 400

Lys Thr Leu Lys Tyr Asn Pro Val Ser Lys Asp Ile Ile Ala Ser Thr
                405                 410                 415
```

```
Arg Asp Ser Glu Leu Glu Leu Pro Pro Glu Thr Ser Asp Gln Pro Asn
        420                 425                 430

Tyr Glu Ser Tyr Ser His Arg Leu Cys His Ile Thr Ser Ile Pro Ala
            435                 440                 445

Thr Gly Asn Thr Thr Gly Leu Val Pro Val Phe Ser Trp Thr His Arg
450                 455                 460

Ser Ala Asp Leu Asn Asn Thr Ile Tyr Ser Asp Lys Ile Thr Gln Ile
465                 470                 475                 480

Pro Ala Val Lys Cys Trp Asp Asn Leu Pro Phe Val Pro Val Val Lys
                485                 490                 495

Gly Pro Gly His Thr Gly Gly Asp Leu Leu Gln Tyr Asn Arg Ser Thr
            500                 505                 510

Gly Ser Val Gly Thr Leu Phe Leu Ala Arg Tyr Gly Leu Ala Leu Glu
        515                 520                 525

Lys Ala Gly Lys Tyr Arg Val Arg Leu Arg Tyr Ala Thr Asp Ala Asp
530                 535                 540

Ile Val Leu His Val Asn Asp Ala Gln Ile Gln Met Pro Lys Thr Met
545                 550                 555                 560

Asn Pro Gly Glu Asp Leu Thr Ser Lys Thr Phe Lys Val Ala Asp Ala
                565                 570                 575

Ile Thr Thr Leu Asn Leu Ala Thr Asp Ser Ser Leu Ala Leu Lys His
            580                 585                 590

Asn Leu Gly Glu Asp Pro Asn Ser Thr Leu Ser Gly Ile Val Tyr Val
        595                 600                 605

Asp Arg Ile Glu Phe Ile Pro Val Asp
    610                 615

<210> SEQ ID NO 35
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 5' forward primer

<400> SEQUENCE: 35
atgagtccaa ataatcaaaa tg                                              22

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 5' reverse primer

<400> SEQUENCE: 36
ccgcttctaa atcttgttcc                                                 20

<210> SEQ ID NO 37
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 3' forward primer
```

```
<400> SEQUENCE: 37
ggaacaagat ttagagg                                                    17

<210> SEQ ID NO 38
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 3' reverse primer

<400> SEQUENCE: 38
ctcatcgtct acaatcaatt catc                                            24

<210> SEQ ID NO 39
<211> LENGTH: 2022
<212> TYPE: DNA
<213> ORGANISM: Bacillus thuringiensis (mutated)
<220> FEATURE:
<221> NAME/KEY: misc_feature
<223> OTHER INFORMATION: LRNS.N

```
gtg aca aat ttt gaa gta cca ttc ctt act gta tat gca atg gca gcc    624
Val Thr Asn Phe Glu Val Pro Phe Leu Thr Val Tyr Ala Met Ala Ala
        195                 200                 205 aac ctt cat tta ctg tta tta aag gac gcg tca att ttt gga gaa gaa    672
Asn Leu His Leu Leu Leu Leu Lys Asp Ala Ser Ile Phe Gly Glu Glu
    210                 215                 220 tgg gga tgg tca aca act act att aat aac tat tat gat cgt caa atg    720
Trp Gly Trp Ser Thr Thr Thr Ile Asn Asn Tyr Tyr Asp Arg Gln Met
225                 230                 235                 240 aaa ctt act gca gaa tat tct gat cac tgt gta aag tgg tat gaa act    768
Lys Leu Thr Ala Glu Tyr Ser Asp His Cys Val Lys Trp Tyr Glu Thr
            245                 250                 255 ggt tta gca aaa tta aaa ggc acg agc gct aaa caa tgg gtt gac tat    816
Gly Leu Ala Lys Leu Lys Gly Thr Ser Ala Lys Gln Trp Val Asp Tyr
        260                 265                 270 aac caa ttc cgt aga gaa atg aca ctg gcg gtt tta gat gtt gtt gca    864
Asn Gln Phe Arg Arg Glu Met Thr Leu Ala Val Leu Asp Val Val Ala
    275                 280                 285 tta ttc cca aat tat gac aca cgc acg tac cca atg gaa acg aaa gca    912
Leu Phe Pro Asn Tyr Asp Thr Arg Thr Tyr Pro Met Glu Thr Lys Ala
290                 295                 300 caa cta aca agg gaa gta tat aca gat cca ctg ggc gcg gta aac gtg    960
Gln Leu Thr Arg Glu Val Tyr Thr Asp Pro Leu Gly Ala Val Asn Val
305                 310                 315                 320 tct tca att ggt tcc tgg tat gac aaa gca cct tct ttc gga gtg ata   1008
Ser Ser Ile Gly Ser Trp Tyr Asp Lys Ala Pro Ser Phe Gly Val Ile
            325                 330                 335 gaa tca tcc gtt att cga cca ccc cat gta ttt gat tat ata acg gga   1056
Glu Ser Ser Val Ile Arg Pro Pro His Val Phe Asp Tyr Ile Thr Gly
        340                 345                 350 ctc aca gtg tat aca caa tca aga agc att tct tcc gct cgc tat ata   1104
Leu Thr Val Tyr Thr Gln Ser Arg Ser Ile Ser Ser Ala Arg Tyr Ile
    355                 360                 365 aga cat tgg gct ggt cat caa ata agc tac cat cgt gtc agt agg ggt   1152
Arg His Trp Ala Gly His Gln Ile Ser Tyr His Arg Val Ser Arg Gly
370                 375                 380 agt aat ctt caa caa atg tat gga act aat caa aat cta cac agc act   1200
Ser Asn Leu Gln Gln Met Tyr Gly Thr Asn Gln Asn Leu His Ser Thr
385                 390                 395                 400 agt acc ttt gat ttt acg aat tat gat att tac aag act cta tca aag   1248
Ser Thr Phe Asp Phe Thr Asn Tyr Asp Ile Tyr Lys Thr Leu Ser Lys
            405                 410                 415 gat gca gta ctc ctt gat att gtt tac cct ggt tat acg tat ata ttt   1296
Asp Ala Val Leu Leu Asp Ile Val Tyr Pro Gly Tyr Thr Tyr Ile Phe
        420                 425                 430 ttt gga atg cca gaa gtc gag ttt ttc atg gta aac caa ttg aat aat   1344
Phe Gly Met Pro Glu Val Glu Phe Phe Met Val Asn Gln Leu Asn Asn
    435                 440                 445 acc aga aag acg tta aag tat aat cca gtt tcc aaa gat att ata gcg   1392
Thr Arg Lys Thr Leu Lys Tyr Asn Pro Val Ser Lys Asp Ile Ile Ala
450                 455                 460 agt aca aga gat tcg gaa tta gaa tta cct cca gaa act tca gat caa   1440
Ser Thr Arg Asp Ser Glu Leu Glu Leu Pro Pro Glu Thr Ser Asp Gln
465                 470                 475                 480 cca aat tat gag tca tat agc cat aga tta tgt cat atc aca agt att   1488
Pro Asn Tyr Glu Ser Tyr Ser His Arg Leu Cys His Ile Thr Ser Ile
            485                 490                 495 ccc gcg acg ggt aac act acc gga tta gta cct gta ttt tct tgg aca   1536
Pro Ala Thr Gly Asn Thr Thr Gly Leu Val Pro Val Phe Ser Trp Thr
        500                 505                 510
```

```
cat cga agt gca gat tta aac aat aca ata tat tca gat aaa atc act    1584
His Arg Ser Ala Asp Leu Asn Asn Thr Ile Tyr Ser Asp Lys Ile Thr
        515                 520                 525 caa att ccg gcc gtt aaa tgt tgg gat aat tta ccg ttt gtt cca gtg    1632
Gln Ile Pro Ala Val Lys Cys Trp Asp Asn Leu Pro Phe Val Pro Val
530                 535                 540 gta aaa gga cca gga cat aca gga ggg gat tta tta cag tat aat aga    1680
Val Lys Gly Pro Gly His Thr Gly Gly Asp Leu Leu Gln Tyr Asn Arg
545                 550                 555                 560 agt act ggt tct gta gga acc tta ttt cta gct cga tat ggc cta gca    1728
Ser Thr Gly Ser Val Gly Thr Leu Phe Leu Ala Arg Tyr Gly Leu Ala
                565                 570                 575 tta gaa aaa gca ggg aaa tat cgt gta aga ctg aga tat gct act gat    1776
Leu Glu Lys Ala Gly Lys Tyr Arg Val Arg Leu Arg Tyr Ala Thr Asp
            580                 585                 590 gca gat att gta ttg cat gta aac gat gct cag att cag atg cca aaa    1824
Ala Asp Ile Val Leu His Val Asn Asp Ala Gln Ile Gln Met Pro Lys
        595                 600                 605 aca atg aac cca ggt gag gat ctg aca tct aaa act ttt aaa gtt gca    1872
Thr Met Asn Pro Gly Glu Asp Leu Thr Ser Lys Thr Phe Lys Val Ala
610                 615                 620 gat gct atc aca aca tta aat tta gca aca gat agt tcg cta gca ttg    1920
Asp Ala Ile Thr Thr Leu Asn Leu Ala Thr Asp Ser Ser Leu Ala Leu
625                 630                 635                 640 aaa cat aat tta ggt gaa gac cct aat tca aca tta tct ggt ata gtt    1968
Lys His Asn Leu Gly Glu Asp Pro Asn Ser Thr Leu Ser Gly Ile Val
                645                 650                 655 tac gtt gac cga atc gaa ttc atc cca gta gat gag aca tat gaa gcg    2016
Tyr Val Asp Arg Ile Glu Phe Ile Pro Val Asp Glu Thr Tyr Glu Ala
            660                 665                 670 gaa taa                                                            2022
Glu

<210> SEQ ID NO 40
<211> LENGTH: 673
<212> TYPE: PRT
<213> ORGANISM: Bacillus thuringiensis (mutated)

<400> SEQUENCE: 40

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
```

```
            145                 150                 155                 160
Leu Arg Met Ser Asn Gly Ser Arg Ala Leu Arg Asp Val Arg Asn Arg
                    165                 170                 175

Phe Glu Ile Leu Asp Ser Leu Phe Thr Gln Tyr Met Pro Ser Phe Arg
                180                 185                 190

Val Thr Asn Phe Glu Val Pro Phe Leu Thr Val Tyr Ala Met Ala Ala
            195                 200                 205

Asn Leu His Leu Leu Leu Lys Asp Ala Ser Ile Phe Gly Glu Glu
        210                 215                 220

Trp Gly Trp Ser Thr Thr Thr Ile Asn Asn Tyr Tyr Asp Arg Gln Met
225                 230                 235                 240

Lys Leu Thr Ala Glu Tyr Ser Asp His Cys Val Lys Trp Tyr Glu Thr
                245                 250                 255

Gly Leu Ala Lys Leu Lys Gly Thr Ser Ala Lys Gln Trp Val Asp Tyr
                260                 265                 270

Asn Gln Phe Arg Arg Glu Met Thr Leu Ala Val Leu Asp Val Val Ala
                275                 280                 285

Leu Phe Pro Asn Tyr Asp Thr Arg Thr Tyr Pro Met Glu Thr Lys Ala
        290                 295                 300

Gln Leu Thr Arg Glu Val Tyr Thr Asp Pro Leu Gly Ala Val Asn Val
305                 310                 315                 320

Ser Ser Ile Gly Ser Trp Tyr Asp Lys Ala Pro Ser Phe Gly Val Ile
                325                 330                 335

Glu Ser Ser Val Ile Arg Pro Pro His Val Phe Asp Tyr Ile Thr Gly
            340                 345                 350

Leu Thr Val Tyr Thr Gln Ser Arg Ser Ile Ser Ser Ala Arg Tyr Ile
            355                 360                 365

Arg His Trp Ala Gly His Gln Ile Ser Tyr His Arg Val Ser Arg Gly
        370                 375                 380

Ser Asn Leu Gln Gln Met Tyr Gly Thr Asn Asn Leu His Ser Thr
385                 390                 395                 400

Ser Thr Phe Asp Phe Thr Asn Tyr Asp Ile Tyr Lys Thr Leu Ser Lys
                405                 410                 415

Asp Ala Val Leu Leu Asp Ile Val Tyr Pro Gly Tyr Thr Tyr Ile Phe
                420                 425                 430

Phe Gly Met Pro Glu Val Glu Phe Phe Met Val Asn Gln Leu Asn Asn
            435                 440                 445

Thr Arg Lys Thr Leu Lys Tyr Asn Pro Val Ser Lys Asp Ile Ile Ala
        450                 455                 460

Ser Thr Arg Asp Ser Glu Leu Glu Leu Pro Pro Glu Thr Ser Asp Gln
465                 470                 475                 480

Pro Asn Tyr Glu Ser Tyr Ser His Arg Leu Cys His Ile Thr Ser Ile
                485                 490                 495

Pro Ala Thr Gly Asn Thr Gly Leu Val Pro Val Phe Ser Trp Thr
            500                 505                 510

His Arg Ser Ala Asp Leu Asn Asn Thr Ile Tyr Ser Asp Lys Ile Thr
        515                 520                 525

Gln Ile Pro Ala Val Lys Cys Trp Asp Asn Leu Pro Phe Val Pro Val
        530                 535                 540

Val Lys Gly Pro Gly His Thr Gly Gly Asp Leu Leu Gln Tyr Asn Arg
545                 550                 555                 560

Ser Thr Gly Ser Val Gly Thr Leu Phe Leu Ala Arg Tyr Gly Leu Ala
                565                 570                 575
```

```
Leu Glu Lys Ala Gly Lys Tyr Arg Val Arg Leu Arg Tyr Ala Thr Asp
            580                 585                 590

Ala Asp Ile Val Leu His Val Asn Asp Ala Gln Ile Gln Met Pro Lys
595                 600                 605

Thr Met Asn Pro Gly Glu Asp Leu Thr Ser Lys Thr Phe Lys Val Ala
    610                 615                 620

Asp Ala Ile Thr Thr Leu Asn Leu Ala Thr Ser Ser Leu Ala Leu
625                 630                 635                 640

Lys His Asn Leu Gly Glu Asp Pro Asn Ser Thr Leu Ser Gly Ile Val
                645                 650                 655

Tyr Val Asp Arg Ile Glu Phe Ile Pro Val Asp Glu Tyr Glu Ala
            660                 665                 670

Glu

<210> SEQ ID NO 41
<211> LENGTH: 1863
<212> TYPE: DNA
<213> ORGANISM: Bacillus thuringiensis (mutated)
<220> FEATURE:
<221> NAME/KEY: misc_feature
<223> OTHER INFORMATION: LRMS.N49PVD
<220> FEATURE:
<221> NAME/KEY: CDS
<222> LOCATION: (1)..(1863)

<400> SEQUENCE: 41 atg tct gcg gga aat gct agt gaa tac cct ggt tca cct gaa gta ctt      48
Met Ser Ala Gly Asn Ala Ser Glu Tyr Pro Gly Ser Pro Glu Val Leu
1               5                   10                  15 gtt agc gga caa gat gca gct aag gcc gca att gat ata gta ggt aaa      96
Val Ser Gly Gln Asp Ala Ala Lys Ala Ala Ile Asp Ile Val Gly Lys
            20                  25                  30 tta cta tca ggt tta ggg gtc cca ttt gtt ggg ccg ata gtg agt ctt     144
Leu Leu Ser Gly Leu Gly Val Pro Phe Val Gly Pro Ile Val Ser Leu
        35                  40                  45 tat act caa ctt att gat att ctg tgg cct tca ggg gaa aag agt caa     192
Tyr Thr Gln Leu Ile Asp Ile Leu Trp Pro Ser Gly Glu Lys Ser Gln
50                  55                  60 tgg gaa att ttt atg gaa caa gta gaa gaa ctc att aat caa aaa ata     240
Trp Glu Ile Phe Met Glu Gln Val Glu Glu Leu Ile Asn Gln Lys Ile
65                  70                  75                  80 gca gaa tat gca agg aat aaa gcg ctt tcg gaa tta gaa gga tta ggt     288
Ala Glu Tyr Ala Arg Asn Lys Ala Leu Ser Glu Leu Glu Gly Leu Gly
                85                  90                  95 aat aat tac caa tta tat cta act gcg ctt gaa gaa tgg gaa gaa aat     336
Asn Asn Tyr Gln Leu Tyr Leu Thr Ala Leu Glu Glu Trp Glu Glu Asn
            100                 105                 110 cca tta aga atg tct aat ggt tcc cgg gcc tta cga gat gtg cga aat     384
Pro Leu Arg Met Ser Asn Gly Ser Arg Ala Leu Arg Asp Val Arg Asn
        115                 120                 125 cga ttt gaa atc ctg gat agt tta ttt acg caa tat atg cca tct ttt     432
Arg Phe Glu Ile Leu Asp Ser Leu Phe Thr Gln Tyr Met Pro Ser Phe
130                 135                 140 aga gtg aca aat ttt gaa gta cca ttc ctt act gta tat gca atg gca     480
Arg Val Thr Asn Phe Glu Val Pro Phe Leu Thr Val Tyr Ala Met Ala
145                 150                 155                 160 gcc aac ctt cat tta ctg tta tta aag gac gcg tca att ttt gga gaa     528
Ala Asn Leu His Leu Leu Leu Leu Lys Asp Ala Ser Ile Phe Gly Glu
                165                 170                 175 gaa tgg gga tgg tca aca act act att aat aac tat tat gat cgt caa     576
Glu Trp Gly Trp Ser Thr Thr Thr Ile Asn Asn Tyr Tyr Asp Arg Gln
```

```
                   180                 185                 190
atg aaa ctt act gca gaa tat tct gat cac tgt gta aag tgg tat gaa       624
Met Lys Leu Thr Ala Glu Tyr Ser Asp His Cys Val Lys Trp Tyr Glu
    195                 200                 205 act ggt tta gca aaa tta aaa ggc acg agc gct aaa caa tgg gtt gac       672
Thr Gly Leu Ala Lys Leu Lys Gly Thr Ser Ala Lys Gln Trp Val Asp
210                 215                 220 tat aac caa ttc cgt aga gaa atg aca ctg gcg gtt tta gat gtt gtt       720
Tyr Asn Gln Phe Arg Arg Glu Met Thr Leu Ala Val Leu Asp Val Val
225                 230                 235                 240 gca tta ttc cca aat tat gac aca cgc acg tac cca atg gaa acg aaa       768
Ala Leu Phe Pro Asn Tyr Asp Thr Arg Thr Tyr Pro Met Glu Thr Lys
                245                 250                 255 gca caa cta aca agg gaa gta tat aca gat cca ctg ggc gcg gta aac       816
Ala Gln Leu Thr Arg Glu Val Tyr Thr Asp Pro Leu Gly Ala Val Asn
            260                 265                 270 gtg tct tca att ggt tcc tgg tat gac aaa gca cct tct ttc gga gtg       864
Val Ser Ser Ile Gly Ser Trp Tyr Asp Lys Ala Pro Ser Phe Gly Val
        275                 280                 285 ata gaa tca tcc gtt att cga cca ccc cat gta ttt gat tat ata acg       912
Ile Glu Ser Ser Val Ile Arg Pro Pro His Val Phe Asp Tyr Ile Thr
    290                 295                 300 gga ctc aca gtg tat aca caa tca aga agc att tct tcc gct cgc tat       960
Gly Leu Thr Val Tyr Thr Gln Ser Arg Ser Ile Ser Ser Ala Arg Tyr
305                 310                 315                 320 ata aga cat tgg gct ggt cat caa ata agc tac cat cgt gtc agt agg      1008
Ile Arg His Trp Ala Gly His Gln Ile Ser Tyr His Arg Val Ser Arg
                325                 330                 335 ggt agt aat ctt caa caa atg tat gga act aat caa aat cta cac agc      1056
Gly Ser Asn Leu Gln Gln Met Tyr Gly Thr Asn Gln Asn Leu His Ser
            340                 345                 350 act agt acc ttt gat ttt acg aat tat gat att tac aag act cta tca      1104
Thr Ser Thr Phe Asp Phe Thr Asn Tyr Asp Ile Tyr Lys Thr Leu Ser
        355                 360                 365 aag gat gca gta ctc ctt gat att gtt tac cct ggt tat acg tat ata      1152
Lys Asp Ala Val Leu Leu Asp Ile Val Tyr Pro Gly Tyr Thr Tyr Ile
    370                 375                 380 ttt ttt gga atg cca gaa gtc gag ttt tca atg gta aac caa ttg aat      1200
Phe Phe Gly Met Pro Glu Val Glu Phe Phe Met Val Asn Gln Leu Asn
385                 390                 395                 400 aat acc aga aag acg tta aag tat aat cca gtt tcc aaa gat att ata      1248
Asn Thr Arg Lys Thr Leu Lys Tyr Asn Pro Val Ser Lys Asp Ile Ile
                405                 410                 415 gcg agt aca aga gat tcg gaa tta gaa tta cct cca gaa act tca gat      1296
Ala Ser Thr Arg Asp Ser Glu Leu Glu Leu Pro Pro Glu Thr Ser Asp
            420                 425                 430 caa cca aat tat gag tca tat agc cat aga tta tgt cat atc aca agt      1344
Gln Pro Asn Tyr Glu Ser Tyr Ser His Arg Leu Cys His Ile Thr Ser
        435                 440                 445 att ccc gcg acg ggt aac act acc gga tta gta cct gta ttt tct tgg      1392
Ile Pro Ala Thr Gly Asn Thr Thr Gly Leu Val Pro Val Phe Ser Trp
    450                 455                 460 aca cat cga agt gca gat tta aac aat aca ata tat tca gat aaa atc      1440
Thr His Arg Ser Ala Asp Leu Asn Asn Thr Ile Tyr Ser Asp Lys Ile
465                 470                 475                 480 act caa att ccg gcc gtt aaa tgt tgg gat aat tta ccg ttt gtt cca      1488
Thr Gln Ile Pro Ala Val Lys Cys Trp Asp Asn Leu Pro Phe Val Pro
                485                 490                 495 gtg gta aaa gga cca gga cat aca gga ggg gat tta tta cag tat aat      1536
Val Val Lys Gly Pro Gly His Thr Gly Gly Asp Leu Leu Gln Tyr Asn
```

```
                500                  505                  510
aga agt act ggt tct gta gga acc tta ttt cta gct cga tat ggc cta      1584
Arg Ser Thr Gly Ser Val Gly Thr Leu Phe Leu Ala Arg Tyr Gly Leu
        515                  520                  525 gca tta gaa aaa gca ggg aaa tat cgt gta aga ctg aga tat gct act      1632
Ala Leu Glu Lys Ala Gly Lys Tyr Arg Val Arg Leu Arg Tyr Ala Thr
    530                  535                  540 gat gca gat att gta ttg cat gta aac gat gct cag att cag atg cca      1680
Asp Ala Asp Ile Val Leu His Val Asn Asp Ala Gln Ile Gln Met Pro
545                  550                  555                  560 aaa aca atg aac cca ggt gag gat ctg aca tct aaa act ttt aaa gtt      1728
Lys Thr Met Asn Pro Gly Glu Asp Leu Thr Ser Lys Thr Phe Lys Val
                565                  570                  575 gca gat gct atc aca aca tta aat tta gca aca gat agt tcg cta gca      1776
Ala Asp Ala Ile Thr Thr Leu Asn Leu Ala Thr Asp Ser Ser Leu Ala
            580                  585                  590 ttg aaa cat aat tta ggt gaa gac cct aat tca aca tta tct ggt ata      1824
Leu Lys His Asn Leu Gly Glu Asp Pro Asn Ser Thr Leu Ser Gly Ile
        595                  600                  605 gtt tac gtt gac cga atc gaa ttc atc cca gta gat taa                  1863
Val Tyr Val Asp Arg Ile Glu Phe Ile Pro Val Asp
    610                  615                  620

<210> SEQ ID NO 42
<211> LENGTH: 620
<212> TYPE: PRT
<213> ORGANISM: Bacillus thuringiensis (mutated)

<400> SEQUENCE: 42

Met Ser Ala Gly Asn Ala Ser Glu Tyr Pro Gly Ser Pro Glu Val Leu
1               5                   10                  15

Val Ser Gly Gln Asp Ala Ala Lys Ala Ala Ile Asp Ile Val Gly Lys
            20                  25                  30

Leu Leu Ser Gly Leu Gly Val Pro Phe Val Gly Pro Ile Val Ser Leu
        35                  40                  45

Tyr Thr Gln Leu Ile Asp Ile Leu Trp Pro Ser Gly Glu Lys Ser Gln
    50                  55                  60

Trp Glu Ile Phe Met Glu Gln Val Glu Glu Leu Ile Asn Gln Lys Ile
65                  70                  75                  80

Ala Glu Tyr Ala Arg Asn Lys Ala Leu Ser Glu Leu Glu Gly Leu Gly
                85                  90                  95

Asn Asn Tyr Gln Leu Tyr Leu Thr Ala Leu Glu Glu Trp Glu Glu Asn
            100                 105                 110

Pro Leu Arg Met Ser Asn Gly Ser Arg Ala Leu Arg Asp Val Arg Asn
        115                 120                 125

Arg Phe Glu Ile Leu Asp Ser Leu Phe Thr Gln Tyr Met Pro Ser Phe
    130                 135                 140

Arg Val Thr Asn Phe Glu Val Pro Phe Leu Thr Val Tyr Ala Met Ala
145                 150                 155                 160

Ala Asn Leu His Leu Leu Leu Leu Lys Asp Ala Ser Ile Phe Gly Glu
                165                 170                 175

Glu Trp Gly Trp Ser Thr Thr Thr Ile Asn Asn Tyr Tyr Asp Arg Gln
            180                 185                 190

Met Lys Leu Thr Ala Glu Tyr Ser Asp His Cys Val Lys Trp Tyr Glu
        195                 200                 205

Thr Gly Leu Ala Lys Leu Lys Gly Thr Ser Ala Lys Gln Trp Val Asp
    210                 215                 220
```

```
Tyr Asn Gln Phe Arg Arg Glu Met Thr Leu Ala Val Leu Asp Val Val
225                 230                 235                 240

Ala Leu Phe Pro Asn Tyr Asp Thr Arg Thr Tyr Pro Met Glu Thr Lys
            245                 250                 255

Ala Gln Leu Thr Arg Glu Val Tyr Thr Asp Pro Leu Gly Ala Val Asn
        260                 265                 270

Val Ser Ser Ile Gly Ser Trp Tyr Asp Lys Ala Pro Ser Phe Gly Val
    275                 280                 285

Ile Glu Ser Ser Val Ile Arg Pro Pro His Val Phe Asp Tyr Ile Thr
290                 295                 300

Gly Leu Thr Val Tyr Thr Gln Ser Arg Ser Ile Ser Ala Arg Tyr
305                 310                 315                 320

Ile Arg His Trp Ala Gly His Gln Ile Ser Tyr His Arg Val Ser Arg
            325                 330                 335

Gly Ser Asn Leu Gln Gln Met Tyr Gly Thr Asn Gln Asn Leu His Ser
        340                 345                 350

Thr Ser Thr Phe Asp Phe Thr Asn Tyr Asp Ile Tyr Lys Thr Leu Ser
    355                 360                 365

Lys Asp Ala Val Leu Leu Asp Ile Val Tyr Pro Gly Tyr Thr Tyr Ile
370                 375                 380

Phe Phe Gly Met Pro Glu Val Glu Phe Phe Met Val Asn Gln Leu Asn
385                 390                 395                 400

Asn Thr Arg Lys Thr Leu Lys Tyr Asn Pro Val Ser Lys Asp Ile Ile
            405                 410                 415

Ala Ser Thr Arg Asp Ser Glu Leu Glu Leu Pro Pro Glu Thr Ser Asp
        420                 425                 430

Gln Pro Asn Tyr Glu Ser Tyr Ser His Arg Leu Cys His Ile Thr Ser
    435                 440                 445

Ile Pro Ala Thr Gly Asn Thr Thr Gly Leu Val Pro Val Phe Ser Trp
450                 455                 460

Thr His Arg Ser Ala Asp Leu Asn Asn Thr Ile Tyr Ser Asp Lys Ile
465                 470                 475                 480

Thr Gln Ile Pro Ala Val Lys Cys Trp Asp Asn Leu Pro Phe Val Pro
            485                 490                 495

Val Val Lys Gly Pro Gly His Thr Gly Gly Asp Leu Leu Gln Tyr Asn
        500                 505                 510

Arg Ser Thr Gly Ser Val Gly Thr Leu Phe Leu Ala Arg Tyr Gly Leu
    515                 520                 525

Ala Leu Glu Lys Ala Gly Lys Tyr Arg Val Arg Leu Arg Tyr Ala Thr
530                 535                 540

Asp Ala Asp Ile Val Leu His Val Asn Asp Ala Gln Ile Gln Met Pro
545                 550                 555                 560

Lys Thr Met Asn Pro Gly Glu Asp Leu Thr Ser Lys Thr Phe Lys Val
            565                 570                 575

Ala Asp Ala Ile Thr Thr Leu Asn Leu Ala Thr Asp Ser Ser Leu Ala
        580                 585                 590

Leu Lys His Asn Leu Gly Glu Asp Pro Asn Ser Thr Leu Ser Gly Ile
    595                 600                 605

Val Tyr Val Asp Arg Ile Glu Phe Ile Pro Val Asp
610                 615                 620

<210> SEQ ID NO 43
<211> LENGTH: 2013
<212> TYPE: DNA
<213> ORGANISM: Bacillus thuringiensis (mutated)
```

```
<220> FEATURE:
<221> NAME/KEY: misc_feature
<223> OTHER INFORMATION: LRMS.R1218-1
<220> FEATURE:
<221> NAME/KEY: CDS
<222> LOCATION: (1)..(2013)

<400> SEQUENCE: 43
```

| | | | | | | | | | | | | | | | | |
|---|---|---|---|---|---|---|---|---|---|---|---|---|---|---|---|---|
| atg | agt | cca | aat | aat | caa | aat | gaa | tat | gaa | att | ata | gat | gcg | aca | cct | 48 |
| Met | Ser | Pro | Asn | Asn | Gln | Asn | Glu | Tyr | Glu | Ile | Ile | Asp | Ala | Thr | Pro | |
| 1 | | | | 5 | | | | | 10 | | | | | 15 | | |
| tct | act | tct | gta | tcc | aat | gat | tct | aac | aga | tac | cct | ttt | gcg | aat | gag | 96 |
| Ser | Thr | Ser | Val | Ser | Asn | Asp | Ser | Asn | Arg | Tyr | Pro | Phe | Ala | Asn | Glu | |
| | | | 20 | | | | | 25 | | | | | 30 | | | |
| cca | aca | aat | gcg | cta | caa | aat | atg | gat | tat | aaa | gat | tat | tta | aaa | atg | 144 |
| Pro | Thr | Asn | Ala | Leu | Gln | Asn | Met | Asp | Tyr | Lys | Asp | Tyr | Leu | Lys | Met | |
| | | 35 | | | | | 40 | | | | | 45 | | | | |
| tct | gcg | gga | aat | gct | agt | gaa | tac | cct | ggt | tca | cct | gaa | gta | ctt | gtt | 192 |
| Ser | Ala | Gly | Asn | Ala | Ser | Glu | Tyr | Pro | Gly | Ser | Pro | Glu | Val | Leu | Val | |
| 50 | | | | | 55 | | | | | 60 | | | | | | |
| agc | gga | caa | gat | gca | gct | aag | gcc | gca | att | gat | ata | gta | ggt | aaa | tta | 240 |
| Ser | Gly | Gln | Asp | Ala | Ala | Lys | Ala | Ala | Ile | Asp | Ile | Val | Gly | Lys | Leu | |
| 65 | | | | | 70 | | | | | 75 | | | | | 80 | |
| cta | tca | ggt | tta | ggg | gtc | cca | ttt | gtt | ggg | ccg | ata | gtg | agt | ctt | tat | 288 |
| Leu | Ser | Gly | Leu | Gly | Val | Pro | Phe | Val | Gly | Pro | Ile | Val | Ser | Leu | Tyr | |
| | | | | 85 | | | | | 90 | | | | | 95 | | |
| act | caa | ctt | att | gat | att | ctg | tgg | cct | tca | ggg | gaa | aag | agt | caa | tgg | 336 |
| Thr | Gln | Leu | Ile | Asp | Ile | Leu | Trp | Pro | Ser | Gly | Glu | Lys | Ser | Gln | Trp | |
| | | | 100 | | | | | 105 | | | | | 110 | | | |
| gaa | att | ttt | atg | gaa | caa | gta | gaa | gaa | ctc | att | aat | caa | aaa | ata | gca | 384 |
| Glu | Ile | Phe | Met | Glu | Gln | Val | Glu | Glu | Leu | Ile | Asn | Gln | Lys | Ile | Ala | |
| | | 115 | | | | | 120 | | | | | 125 | | | | |
| gaa | tat | gca | agg | aat | aaa | gcg | ctt | tcg | gaa | tta | gaa | gga | tta | ggt | aat | 432 |
| Glu | Tyr | Ala | Arg | Asn | Lys | Ala | Leu | Ser | Glu | Leu | Glu | Gly | Leu | Gly | Asn | |
| 130 | | | | | 135 | | | | | 140 | | | | | | |
| aat | tac | caa | tta | tat | cta | act | gcg | ctt | gaa | gaa | tgg | gaa | gaa | aat | cca | 480 |
| Asn | Tyr | Gln | Leu | Tyr | Leu | Thr | Ala | Leu | Glu | Glu | Trp | Glu | Glu | Asn | Pro | |
| 145 | | | | | 150 | | | | | 155 | | | | | 160 | |
| tta | aga | atg | tct | aga | gcc | tta | cga | gat | gtg | cga | aat | cga | ttt | gaa | atc | 528 |
| Leu | Arg | Met | Ser | Arg | Ala | Leu | Arg | Asp | Val | Arg | Asn | Arg | Phe | Glu | Ile | |
| | | | | 165 | | | | | 170 | | | | | 175 | | |
| ctg | gat | agt | tta | ttt | acg | caa | tat | atg | cca | tct | ttt | aga | gtg | aca | aat | 576 |
| Leu | Asp | Ser | Leu | Phe | Thr | Gln | Tyr | Met | Pro | Ser | Phe | Arg | Val | Thr | Asn | |
| | | | 180 | | | | | 185 | | | | | 190 | | | |
| ttt | gaa | gta | cca | ttc | ctt | act | gta | tat | gca | atg | gca | gcc | aac | ctt | cat | 624 |
| Phe | Glu | Val | Pro | Phe | Leu | Thr | Val | Tyr | Ala | Met | Ala | Ala | Asn | Leu | His | |
| | | 195 | | | | | 200 | | | | | 205 | | | | |
| tta | ctg | tta | tta | aag | gac | gcg | tca | att | ttt | gga | gaa | gaa | tgg | gga | tgg | 672 |
| Leu | Leu | Leu | Leu | Lys | Asp | Ala | Ser | Ile | Phe | Gly | Glu | Glu | Trp | Gly | Trp | |
| | | 210 | | | | | 215 | | | | | 220 | | | | |
| tca | aca | act | act | att | aat | aac | tat | tat | gat | cgt | caa | atg | aaa | ctt | act | 720 |
| Ser | Thr | Thr | Thr | Ile | Asn | Asn | Tyr | Tyr | Asp | Arg | Gln | Met | Lys | Leu | Thr | |
| 225 | | | | | 230 | | | | | 235 | | | | | 240 | |
| gca | gaa | tat | tct | gat | cac | tgt | gta | aag | tgg | tat | gaa | act | ggt | tta | gca | 768 |
| Ala | Glu | Tyr | Ser | Asp | His | Cys | Val | Lys | Trp | Tyr | Glu | Thr | Gly | Leu | Ala | |
| | | | | 245 | | | | | 250 | | | | | 255 | | |
| aaa | tta | aaa | ggc | acg | agc | gct | aaa | caa | tgg | gtt | gac | tat | aac | caa | ttc | 816 |
| Lys | Leu | Lys | Gly | Thr | Ser | Ala | Lys | Gln | Trp | Val | Asp | Tyr | Asn | Gln | Phe | |
| | | | 260 | | | | | 265 | | | | | 270 | | | |
| cgt | aga | gaa | atg | aca | ctg | gcg | gtt | tta | gat | gtt | gtt | gca | tta | ttc | cca | 864 |
| Arg | Arg | Glu | Met | Thr | Leu | Ala | Val | Leu | Asp | Val | Val | Ala | Leu | Phe | Pro | |
| | | 275 | | | | | 280 | | | | | 285 | | | | |

-continued

| | |
|---|---|
| aat tat gac aca cgc acg tac cca atg gaa acg aaa gca caa cta aca<br>Asn Tyr Asp Thr Arg Thr Tyr Pro Met Glu Thr Lys Ala Gln Leu Thr<br>290                                  295                                300 | 912 |
| agg gaa gta tat aca gat cca ctg ggc gcg gta aac gtg tct tca att<br>Arg Glu Val Tyr Thr Asp Pro Leu Gly Ala Val Asn Val Ser Ser Ile<br>305                                310                            315                    320 | 960 |
| ggt tcc tgg tat gac aaa gca cct tct ttc gga gtg ata gaa tca tcc<br>Gly Ser Trp Tyr Asp Lys Ala Pro Ser Phe Gly Val Ile Glu Ser Ser<br>                        325                            330                            335 | 1008 |
| gtt att cga cca ccc cat gta ttt gat tat ata acg gga ctc aca gtg<br>Val Ile Arg Pro Pro His Val Phe Asp Tyr Ile Thr Gly Leu Thr Val<br>            340                            345                            350 | 1056 |
| tat aca caa tca aga agc att tct tcc gct cgc tat ata aga cat tgg<br>Tyr Thr Gln Ser Arg Ser Ile Ser Ser Ala Arg Tyr Ile Arg His Trp<br>355                                360                            365 | 1104 |
| gct ggt cat caa ata agc tac cat cgt gtc agt agg ggt agt aat ctt<br>Ala Gly His Gln Ile Ser Tyr His Arg Val Ser Arg Gly Ser Asn Leu<br>370                                375                            380 | 1152 |
| caa caa atg tat gga act aat caa aat cta cac agc act agt acc ttt<br>Gln Gln Met Tyr Gly Thr Asn Gln Asn Leu His Ser Thr Ser Thr Phe<br>385                                390                            395                    400 | 1200 |
| gat ttt acg aat tat gat att tac aag act cta tca aag gat gca gta<br>Asp Phe Thr Asn Tyr Asp Ile Tyr Lys Thr Leu Ser Lys Asp Ala Val<br>                        405                            410                            415 | 1248 |
| ctc ctt gat att gtt tac cct ggt tat acg tat ata ttt ttt gga atg<br>Leu Leu Asp Ile Val Tyr Pro Gly Tyr Thr Tyr Ile Phe Phe Gly Met<br>            420                            425                            430 | 1296 |
| cca gaa gtc gag ttt ttc atg gta aac caa ttg aat aat acc aga aag<br>Pro Glu Val Glu Phe Phe Met Val Asn Gln Leu Asn Asn Thr Arg Lys<br>                        435                            440                            445 | 1344 |
| acg tta aag tat aat cca gtt tcc aaa gat att ata gcg agt aca aga<br>Thr Leu Lys Tyr Asn Pro Val Ser Lys Asp Ile Ile Ala Ser Thr Arg<br>450                                455                            460 | 1392 |
| gat tcg gaa tta gaa tta cct cca gaa act tca gat caa cca aat tat<br>Asp Ser Glu Leu Glu Leu Pro Pro Glu Thr Ser Asp Gln Pro Asn Tyr<br>465                                470                            475                    480 | 1440 |
| gag tca tat agc cat aga tta tgt cat atc aca agt att ccc gcg acg<br>Glu Ser Tyr Ser His Arg Leu Cys His Ile Thr Ser Ile Pro Ala Thr<br>                        485                            490                            495 | 1488 |
| ggt aac act acc gga tta gta cct gta ttt tct tgg aca cat cga agt<br>Gly Asn Thr Thr Gly Leu Val Pro Val Phe Ser Trp Thr His Arg Ser<br>            500                            505                            510 | 1536 |
| gca gat tta aac aat aca ata tat tca gat aaa atc act caa att ccg<br>Ala Asp Leu Asn Asn Thr Ile Tyr Ser Asp Lys Ile Thr Gln Ile Pro<br>                515                            520                            525 | 1584 |
| gcc gtt aaa tgt tgg gat aat tta ccg ttt gtt cca gtg gta aaa gga<br>Ala Val Lys Cys Trp Asp Asn Leu Pro Phe Val Pro Val Val Lys Gly<br>530                                535                            540 | 1632 |
| cca gga cat aca gga ggg gat tta tta cag tat aat aga agt act ggt<br>Pro Gly His Thr Gly Gly Asp Leu Leu Gln Tyr Asn Arg Ser Thr Gly<br>545                                550                            555                    560 | 1680 |
| tct gta gga acc tta ttt cta gct cga tat ggc cta gca tta gaa aaa<br>Ser Val Gly Thr Leu Phe Leu Ala Arg Tyr Gly Leu Ala Leu Glu Lys<br>                565                            570                            575 | 1728 |
| gca ggg aaa tat cgt gta aga ctg aga tat gct act gat gca gat att<br>Ala Gly Lys Tyr Arg Val Arg Leu Arg Tyr Ala Thr Asp Ala Asp Ile<br>                        580                            585                            590 | 1776 |
| gta ttg cat gta aac gat gct cag att cag atg cca aaa aca atg aac<br>Val Leu His Val Asn Asp Ala Gln Ile Gln Met Pro Lys Thr Met Asn<br>            595                            600                            605 | 1824 |

```
cca ggt gag gat ctg aca tct aaa act ttt aaa gtt gca gat gct atc    1872
Pro Gly Glu Asp Leu Thr Ser Lys Thr Phe Lys Val Ala Asp Ala Ile
        610                 615                 620 aca aca tta aat tta gca aca gat agt tcg cta gca ttg aaa cat aat    1920
Thr Thr Leu Asn Leu Ala Thr Asp Ser Ser Leu Ala Leu Lys His Asn
625                 630                 635                 640 tta ggt gaa gac cct aat tca aca tta tct ggt ata gtt tac gtt gac    1968
Leu Gly Glu Asp Pro Asn Ser Thr Leu Ser Gly Ile Val Tyr Val Asp
                645                 650                 655 cga atc gaa ttc atc cca gta gat gag aca tat gaa gcg gaa taa        2013
Arg Ile Glu Phe Ile Pro Val Asp Glu Thr Tyr Glu Ala Glu
            660                 665                 670

<210> SEQ ID NO 44
<211> LENGTH: 670
<212> TYPE: PRT
<213> ORGANISM: Bacillus thuringiensis (mutated)

<400> SEQUENCE: 44

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
145                 150                 155                 160

Leu Arg Met Ser Arg Ala Leu Arg Asp Val Arg Asn Arg Phe Glu Ile
                165                 170                 175

Leu Asp Ser Leu Phe Thr Gln Tyr Met Pro Ser Phe Arg Val Thr Asn
            180                 185                 190

Phe Glu Val Pro Phe Leu Thr Val Tyr Ala Met Ala Ala Asn Leu His
        195                 200                 205

Leu Leu Leu Leu Lys Asp Ala Ser Ile Phe Gly Glu Glu Trp Gly Trp
    210                 215                 220

Ser Thr Thr Thr Ile Asn Asn Tyr Tyr Asp Arg Gln Met Lys Leu Thr
225                 230                 235                 240

Ala Glu Tyr Ser Asp His Cys Val Lys Trp Tyr Glu Thr Gly Leu Ala
                245                 250                 255

Lys Leu Lys Gly Thr Ser Ala Lys Gln Trp Val Asp Tyr Asn Gln Phe
            260                 265                 270

Arg Arg Glu Met Thr Leu Ala Val Leu Asp Val Val Ala Leu Phe Pro
        275                 280                 285

Asn Tyr Asp Thr Arg Thr Tyr Pro Met Glu Thr Lys Ala Gln Leu Thr
```

```
            290                 295                 300
Arg Glu Val Tyr Thr Asp Pro Leu Gly Ala Val Asn Val Ser Ser Ile
305                 310                 315                 320

Gly Ser Trp Tyr Asp Lys Ala Pro Ser Phe Gly Val Ile Glu Ser Ser
                325                 330                 335

Val Ile Arg Pro Pro His Val Phe Asp Tyr Ile Thr Gly Leu Thr Val
                340                 345                 350

Tyr Thr Gln Ser Arg Ser Ile Ser Ala Arg Tyr Ile Arg His Trp
                355                 360                 365

Ala Gly His Gln Ile Ser Tyr His Arg Val Ser Arg Gly Ser Asn Leu
        370                 375                 380

Gln Gln Met Tyr Gly Thr Asn Gln Asn Leu His Ser Thr Ser Thr Phe
385                 390                 395                 400

Asp Phe Thr Asn Tyr Asp Ile Tyr Lys Thr Leu Ser Lys Asp Ala Val
                405                 410                 415

Leu Leu Asp Ile Val Tyr Pro Gly Tyr Thr Tyr Ile Phe Phe Gly Met
                420                 425                 430

Pro Glu Val Glu Phe Phe Met Val Asn Gln Leu Asn Asn Thr Arg Lys
                435                 440                 445

Thr Leu Lys Tyr Asn Pro Val Ser Lys Asp Ile Ile Ala Ser Thr Arg
450                 455                 460

Asp Ser Glu Leu Glu Leu Pro Pro Glu Thr Ser Asp Gln Pro Asn Tyr
465                 470                 475                 480

Glu Ser Tyr Ser His Arg Leu Cys His Ile Thr Ser Ile Pro Ala Thr
                485                 490                 495

Gly Asn Thr Thr Gly Leu Val Pro Val Phe Ser Trp Thr His Arg Ser
                500                 505                 510

Ala Asp Leu Asn Asn Thr Ile Tyr Ser Asp Lys Ile Thr Gln Ile Pro
        515                 520                 525

Ala Val Lys Cys Trp Asp Asn Leu Pro Phe Val Pro Val Lys Gly
                530                 535                 540

Pro Gly His Thr Gly Gly Asp Leu Leu Gln Tyr Asn Arg Ser Thr Gly
545                 550                 555                 560

Ser Val Gly Thr Leu Phe Leu Ala Arg Tyr Gly Leu Ala Leu Glu Lys
                565                 570                 575

Ala Gly Lys Tyr Arg Val Arg Leu Arg Tyr Ala Thr Asp Ala Asp Ile
                580                 585                 590

Val Leu His Val Asn Asp Ala Gln Ile Gln Met Pro Lys Thr Met Asn
        595                 600                 605

Pro Gly Glu Asp Leu Thr Ser Lys Thr Phe Lys Val Ala Asp Ala Ile
610                 615                 620

Thr Thr Leu Asn Leu Ala Thr Asp Ser Ser Leu Ala Leu Lys His Asn
625                 630                 635                 640

Leu Gly Glu Asp Pro Asn Ser Thr Leu Ser Gly Ile Val Tyr Val Asp
                645                 650                 655

Arg Ile Glu Phe Ile Pro Val Asp Glu Thr Tyr Glu Ala Glu
                660                 665                 670

<210> SEQ ID NO 45
<211> LENGTH: 1854
<212> TYPE: DNA
<213> ORGANISM: Bacillus thuringiensis (mutated)
<220> FEATURE:
<221> NAME/KEY: misc_feature
<223> OTHER INFORMATION: LRMS.R49PVD
<220> FEATURE:
```

<221> NAME/KEY: CDS
<222> LOCATION: (1)..(1854)

<400> SEQUENCE: 45

| | | | | | | | | | | | | | | | | |
|---|---|---|---|---|---|---|---|---|---|---|---|---|---|---|---|---|
| atg | tct | gcg | gga | aat | gct | agt | gaa | tac | cct | ggt | tca | cct | gaa | gta | ctt | 48 |
| Met | Ser | Ala | Gly | Asn | Ala | Ser | Glu | Tyr | Pro | Gly | Ser | Pro | Glu | Val | Leu | |
| 1 | | | | 5 | | | | | 10 | | | | | 15 | | |
| gtt | agc | gga | caa | gat | gca | gct | aag | gcc | gca | att | gat | ata | gta | ggt | aaa | 96 |
| Val | Ser | Gly | Gln | Asp | Ala | Ala | Lys | Ala | Ala | Ile | Asp | Ile | Val | Gly | Lys | |
| | | | 20 | | | | | 25 | | | | | 30 | | | |
| tta | cta | tca | ggt | tta | ggg | gtc | cca | ttt | gtt | ggg | ccg | ata | gtg | agt | ctt | 144 |
| Leu | Leu | Ser | Gly | Leu | Gly | Val | Pro | Phe | Val | Gly | Pro | Ile | Val | Ser | Leu | |
| | | 35 | | | | | 40 | | | | | 45 | | | | |
| tat | act | caa | ctt | att | gat | att | ctg | tgg | cct | tca | ggg | gaa | aag | agt | caa | 192 |
| Tyr | Thr | Gln | Leu | Ile | Asp | Ile | Leu | Trp | Pro | Ser | Gly | Glu | Lys | Ser | Gln | |
| 50 | | | | | 55 | | | | | 60 | | | | | | |
| tgg | gaa | att | ttt | atg | gaa | caa | gta | gaa | gaa | ctc | att | aat | caa | aaa | ata | 240 |
| Trp | Glu | Ile | Phe | Met | Glu | Gln | Val | Glu | Glu | Leu | Ile | Asn | Gln | Lys | Ile | |
| 65 | | | | 70 | | | | | 75 | | | | | 80 | | |
| gca | gaa | tat | gca | agg | aat | aaa | gcg | ctt | tcg | gaa | tta | gaa | gga | tta | ggt | 288 |
| Ala | Glu | Tyr | Ala | Arg | Asn | Lys | Ala | Leu | Ser | Glu | Leu | Glu | Gly | Leu | Gly | |
| | | | | 85 | | | | | 90 | | | | | 95 | | |
| aat | aat | tac | caa | tta | tat | cta | act | gcg | ctt | gaa | gaa | tgg | gaa | gaa | aat | 336 |
| Asn | Asn | Tyr | Gln | Leu | Tyr | Leu | Thr | Ala | Leu | Glu | Glu | Trp | Glu | Glu | Asn | |
| | | | 100 | | | | | 105 | | | | | 110 | | | |
| cca | tta | aga | atg | tct | aga | gcc | tta | cga | gat | gtg | cga | aat | cga | ttt | gaa | 384 |
| Pro | Leu | Arg | Met | Ser | Arg | Ala | Leu | Arg | Asp | Val | Arg | Asn | Arg | Phe | Glu | |
| | | 115 | | | | | 120 | | | | | 125 | | | | |
| atc | ctg | gat | agt | tta | ttt | acg | caa | tat | atg | cca | tct | ttt | aga | gtg | aca | 432 |
| Ile | Leu | Asp | Ser | Leu | Phe | Thr | Gln | Tyr | Met | Pro | Ser | Phe | Arg | Val | Thr | |
| 130 | | | | | 135 | | | | | 140 | | | | | | |
| aat | ttt | gaa | gta | cca | ttc | ctt | act | gta | tat | gca | atg | gca | gcc | aac | ctt | 480 |
| Asn | Phe | Glu | Val | Pro | Phe | Leu | Thr | Val | Tyr | Ala | Met | Ala | Ala | Asn | Leu | |
| 145 | | | | 150 | | | | | 155 | | | | | 160 | | |
| cat | tta | ctg | tta | tta | aag | gac | gcg | tca | att | ttt | gga | gaa | gaa | tgg | gga | 528 |
| His | Leu | Leu | Leu | Leu | Lys | Asp | Ala | Ser | Ile | Phe | Gly | Glu | Glu | Trp | Gly | |
| | | | | 165 | | | | | 170 | | | | | 175 | | |
| tgg | tca | aca | act | act | att | aat | aac | tat | tat | gat | cgt | caa | atg | aaa | ctt | 576 |
| Trp | Ser | Thr | Thr | Thr | Ile | Asn | Asn | Tyr | Tyr | Asp | Arg | Gln | Met | Lys | Leu | |
| | | | 180 | | | | | 185 | | | | | 190 | | | |
| act | gca | gaa | tat | tct | gat | cac | tgt | gta | aag | tgg | tat | gaa | act | ggt | tta | 624 |
| Thr | Ala | Glu | Tyr | Ser | Asp | His | Cys | Val | Lys | Trp | Tyr | Glu | Thr | Gly | Leu | |
| | | 195 | | | | | 200 | | | | | 205 | | | | |
| gca | aaa | tta | aaa | ggc | acg | agc | gct | aaa | caa | tgg | gtt | gac | tat | aac | caa | 672 |
| Ala | Lys | Leu | Lys | Gly | Thr | Ser | Ala | Lys | Gln | Trp | Val | Asp | Tyr | Asn | Gln | |
| 210 | | | | | 215 | | | | | 220 | | | | | | |
| ttc | cgt | aga | gaa | atg | aca | ctg | gcg | gtt | tta | gat | gtt | gtt | gca | tta | ttc | 720 |
| Phe | Arg | Arg | Glu | Met | Thr | Leu | Ala | Val | Leu | Asp | Val | Val | Ala | Leu | Phe | |
| 225 | | | | 230 | | | | | 235 | | | | | 240 | | |
| cca | aat | tat | gac | aca | cgc | acg | tac | cca | atg | gaa | acg | aaa | gca | caa | cta | 768 |
| Pro | Asn | Tyr | Asp | Thr | Arg | Thr | Tyr | Pro | Met | Glu | Thr | Lys | Ala | Gln | Leu | |
| | | | | 245 | | | | | 250 | | | | | 255 | | |
| aca | agg | gaa | gta | tat | aca | gat | cca | ctg | ggc | gcg | gta | aac | gtg | tct | tca | 816 |
| Thr | Arg | Glu | Val | Tyr | Thr | Asp | Pro | Leu | Gly | Ala | Val | Asn | Val | Ser | Ser | |
| | | | 260 | | | | | 265 | | | | | 270 | | | |
| att | ggt | tcc | tgg | tat | gac | aaa | gca | cct | tct | ttc | gga | gtg | ata | gaa | tca | 864 |
| Ile | Gly | Ser | Trp | Tyr | Asp | Lys | Ala | Pro | Ser | Phe | Gly | Val | Ile | Glu | Ser | |
| | | 275 | | | | | 280 | | | | | 285 | | | | |
| tcc | gtt | att | cga | cca | ccc | cat | gta | ttt | gat | tat | ata | acg | gga | ctc | aca | 912 |
| Ser | Val | Ile | Arg | Pro | Pro | His | Val | Phe | Asp | Tyr | Ile | Thr | Gly | Leu | Thr | |
| | | | | 290 | | | | | 295 | | | | | 300 | | |

-continued

| | |
|---|---|
| gtg tat aca caa tca aga agc att tct tcc gct cgc tat ata aga cat<br>Val Tyr Thr Gln Ser Arg Ser Ile Ser Ser Ala Arg Tyr Ile Arg His<br>305                      310                      315                      320 | 960 |
| tgg gct ggt cat caa ata agc tac cat cgt gtc agt agg ggt agt aat<br>Trp Ala Gly His Gln Ile Ser Tyr His Arg Val Ser Arg Gly Ser Asn<br>                325                      330                      335 | 1008 |
| ctt caa caa atg tat gga act aat caa aat cta cac agc act agt acc<br>Leu Gln Gln Met Tyr Gly Thr Asn Gln Asn Leu His Ser Thr Ser Thr<br>            340                      345                      350 | 1056 |
| ttt gat ttt acg aat tat gat att tac aag act cta tca aag gat gca<br>Phe Asp Phe Thr Asn Tyr Asp Ile Tyr Lys Thr Leu Ser Lys Asp Ala<br>355                      360                      365 | 1104 |
| gta ctc ctt gat att gtt tac cct ggt tat acg tat ata ttt ttt gga<br>Val Leu Leu Asp Ile Val Tyr Pro Gly Tyr Thr Tyr Ile Phe Phe Gly<br>370                      375                      380 | 1152 |
| atg cca gaa gtc gag ttt ttc atg gta aac caa ttg aat aat acc aga<br>Met Pro Glu Val Glu Phe Phe Met Val Asn Gln Leu Asn Asn Thr Arg<br>385                      390                      395                      400 | 1200 |
| aag acg tta aag tat aat cca gtt tcc aaa gat att ata gcg agt aca<br>Lys Thr Leu Lys Tyr Asn Pro Val Ser Lys Asp Ile Ile Ala Ser Thr<br>                      405                      410                      415 | 1248 |
| aga gat tcg gaa tta gaa tta cct cca gaa act tca gat caa cca aat<br>Arg Asp Ser Glu Leu Glu Leu Pro Pro Glu Thr Ser Asp Gln Pro Asn<br>            420                      425                      430 | 1296 |
| tat gag tca tat agc cat aga tta tgt cat atc aca agt att ccc gcg<br>Tyr Glu Ser Tyr Ser His Arg Leu Cys His Ile Thr Ser Ile Pro Ala<br>                      435                      440                      445 | 1344 |
| acg ggt aac act acc gga tta gta cct gta ttt tct tgg aca cat cga<br>Thr Gly Asn Thr Thr Gly Leu Val Pro Val Phe Ser Trp Thr His Arg<br>450                      455                      460 | 1392 |
| agt gca gat tta aac aat aca ata tat tca gat aaa atc act caa att<br>Ser Ala Asp Leu Asn Asn Thr Ile Tyr Ser Asp Lys Ile Thr Gln Ile<br>465                      470                      475                      480 | 1440 |
| ccg gcc gtt aaa tgt tgg gat aat tta ccg ttt gtt cca gtg gta aaa<br>Pro Ala Val Lys Cys Trp Asp Asn Leu Pro Phe Val Pro Val Val Lys<br>                      485                      490                      495 | 1488 |
| gga cca gga cat aca gga ggg gat tta tta cag tat aat aga agt act<br>Gly Pro Gly His Thr Gly Gly Asp Leu Leu Gln Tyr Asn Arg Ser Thr<br>            500                      505                      510 | 1536 |
| ggt tct gta gga acc tta ttt cta gct cga tat ggc cta gca tta gaa<br>Gly Ser Val Gly Thr Leu Phe Leu Ala Arg Tyr Gly Leu Ala Leu Glu<br>                      515                      520                      525 | 1584 |
| aaa gca ggg aaa tat cgt gta aga ctg aga tat gct act gat gca gat<br>Lys Ala Gly Lys Tyr Arg Val Arg Leu Arg Tyr Ala Thr Asp Ala Asp<br>530                      535                      540 | 1632 |
| att gta ttg cat gta aac gat gct cag att cag atg cca aaa aca atg<br>Ile Val Leu His Val Asn Asp Ala Gln Ile Gln Met Pro Lys Thr Met<br>545                      550                      555                      560 | 1680 |
| aac cca ggt gag gat ctg aca tct aaa act ttt aaa gtt gca gat gct<br>Asn Pro Gly Glu Asp Leu Thr Ser Lys Thr Phe Lys Val Ala Asp Ala<br>                      565                      570                      575 | 1728 |
| atc aca aca tta aat tta gca aca gat agt tcg cta gca ttg aaa cat<br>Ile Thr Thr Leu Asn Leu Ala Thr Asp Ser Ser Leu Ala Leu Lys His<br>            580                      585                      590 | 1776 |
| aat tta ggt gaa gac cct aat tca aca tta tct ggt ata gtt tac gtt<br>Asn Leu Gly Glu Asp Pro Asn Ser Thr Leu Ser Gly Ile Val Tyr Val<br>                      595                      600                      605 | 1824 |
| gac cga atc gaa ttc atc cca gta gat taa<br>Asp Arg Ile Glu Phe Ile Pro Val Asp<br>            610                      615 | 1854 |

<210> SEQ ID NO 46
<211> LENGTH: 617
<212> TYPE: PRT
<213> ORGANISM: Bacillus thuringiensis (mutated)

<400> SEQUENCE: 46

```
Met Ser Ala Gly Asn Ala Ser Glu Tyr Pro Gly Ser Pro Glu Val Leu
1               5                   10                  15

Val Ser Gly Gln Asp Ala Ala Lys Ala Ile Asp Ile Val Gly Lys
            20                  25                  30

Leu Leu Ser Gly Leu Gly Val Pro Phe Val Gly Pro Ile Val Ser Leu
            35                  40                  45

Tyr Thr Gln Leu Ile Asp Ile Leu Trp Pro Ser Gly Glu Lys Ser Gln
50                  55                  60

Trp Glu Ile Phe Met Glu Gln Val Glu Glu Leu Ile Asn Gln Lys Ile
65                  70                  75                  80

Ala Glu Tyr Ala Arg Asn Lys Ala Leu Ser Glu Leu Glu Gly Leu Gly
                85                  90                  95

Asn Asn Tyr Gln Leu Tyr Leu Thr Ala Leu Glu Glu Trp Glu Glu Asn
            100                 105                 110

Pro Leu Arg Met Ser Arg Ala Leu Arg Asp Val Arg Asn Arg Phe Glu
            115                 120                 125

Ile Leu Asp Ser Leu Phe Thr Gln Tyr Met Pro Ser Phe Arg Val Thr
130                 135                 140

Asn Phe Glu Val Pro Phe Leu Thr Val Tyr Ala Met Ala Ala Asn Leu
145                 150                 155                 160

His Leu Leu Leu Leu Lys Asp Ala Ser Ile Phe Gly Glu Glu Trp Gly
                165                 170                 175

Trp Ser Thr Thr Thr Ile Asn Asn Tyr Tyr Asp Arg Gln Met Lys Leu
            180                 185                 190

Thr Ala Glu Tyr Ser Asp His Cys Val Lys Trp Tyr Glu Thr Gly Leu
            195                 200                 205

Ala Lys Leu Lys Gly Thr Ser Ala Lys Gln Trp Val Asp Tyr Asn Gln
            210                 215                 220

Phe Arg Arg Glu Met Thr Leu Ala Val Leu Asp Val Val Ala Leu Phe
225                 230                 235                 240

Pro Asn Tyr Asp Thr Arg Thr Tyr Pro Met Glu Thr Lys Ala Gln Leu
                245                 250                 255

Thr Arg Glu Val Tyr Thr Asp Pro Leu Gly Ala Val Asn Val Ser Ser
            260                 265                 270

Ile Gly Ser Trp Tyr Asp Lys Ala Pro Ser Phe Gly Val Ile Glu Ser
            275                 280                 285

Ser Val Ile Arg Pro Pro His Val Phe Asp Tyr Ile Thr Gly Leu Thr
290                 295                 300

Val Tyr Thr Gln Ser Arg Ser Ile Ser Ser Ala Arg Tyr Ile Arg His
305                 310                 315                 320

Trp Ala Gly His Gln Ile Ser Tyr His Arg Val Ser Arg Gly Ser Asn
                325                 330                 335

Leu Gln Gln Met Tyr Gly Thr Asn Gln Asn Leu His Ser Thr Ser Thr
            340                 345                 350

Phe Asp Phe Thr Asn Tyr Asp Ile Tyr Lys Thr Leu Ser Lys Asp Ala
            355                 360                 365

Val Leu Leu Asp Ile Val Tyr Pro Gly Tyr Thr Tyr Ile Phe Phe Gly
370                 375                 380
```

Met Pro Glu Val Glu Phe Phe Met Val Asn Gln Leu Asn Asn Thr Arg
385                 390                 395                 400

Lys Thr Leu Lys Tyr Asn Pro Val Ser Lys Asp Ile Ile Ala Ser Thr
            405                 410                 415

Arg Asp Ser Glu Leu Glu Leu Pro Pro Glu Thr Ser Asp Gln Pro Asn
        420                 425                 430

Tyr Glu Ser Tyr Ser His Arg Leu Cys His Ile Thr Ser Ile Pro Ala
    435                 440                 445

Thr Gly Asn Thr Thr Gly Leu Val Pro Val Phe Ser Trp Thr His Arg
450                 455                 460

Ser Ala Asp Leu Asn Asn Thr Ile Tyr Ser Asp Lys Ile Thr Gln Ile
465                 470                 475                 480

Pro Ala Val Lys Cys Trp Asp Asn Leu Pro Phe Val Pro Val Val Lys
            485                 490                 495

Gly Pro Gly His Thr Gly Gly Asp Leu Leu Gln Tyr Asn Arg Ser Thr
        500                 505                 510

Gly Ser Val Gly Thr Leu Phe Leu Ala Arg Tyr Gly Leu Ala Leu Glu
    515                 520                 525

Lys Ala Gly Lys Tyr Arg Val Arg Leu Arg Tyr Ala Thr Asp Ala Asp
530                 535                 540

Ile Val Leu His Val Asn Asp Ala Gln Ile Gln Met Pro Lys Thr Met
545                 550                 555                 560

Asn Pro Gly Glu Asp Leu Thr Ser Lys Thr Phe Lys Val Ala Asp Ala
            565                 570                 575

Ile Thr Thr Leu Asn Leu Ala Thr Asp Ser Ser Leu Ala Leu Lys His
        580                 585                 590

Asn Leu Gly Glu Asp Pro Asn Ser Thr Leu Ser Gly Ile Val Tyr Val
    595                 600                 605

Asp Arg Ile Glu Phe Ile Pro Val Asp
    610                 615

<210> SEQ ID NO 47
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: LRMS Insert
<220> FEATURE:
<221> NAME/KEY: CDS
<222> LOCATION: (1)..(12)

<400> SEQUENCE: 47 tta aga atg tct                                                        12
Leu Arg Met Ser
1

<210> SEQ ID NO 48
<211> LENGTH: 4
<212> TYPE: PRT
<213> ORGANISM: Artificial Sequence
<220> FEATURE:
<223> OTHER INFORMATION: Synthetic Construct

<400> SEQUENCE: 48

Leu Arg Met Ser
1

GENES ENCODING NOVEL PROTEINS WITH PESTICIDAL ACTIVITY AGAINST COLEOPTERANS

CROSS-REFERENCE PARAGRAPH

This application is a divisional of U.S. application Ser. No. 10/032,717, filed Oct. 23, 2001 now U.S. Pat. No. 7,605,304, which claims the benefit of U.S. Provisional Application No. 60/242,838, filed Oct. 24, 2000, which are hereby incorporated herein in their entirety by reference.

REFERENCE TO A SEQUENCE LISTING SUBMITTED AS A TEXT FILE VIA EFS-WEB

An official copy of the Sequence Listing is submitted concurrently with the Specification as a text file via EFS-Web, in compliance with the American Standard Code for Information Interchange (ASCII), with a file name of 371815SequenceListing.txt, a creation date of May 21, 2009, and a size of 69 Kb. The Sequence Listing filed via EFS-Web is part of the Specification and is incorporated herein by reference as if set forth in its entirety.

FIELD OF THE INVENTION

The present invention relates to naturally occurring and recombinant nucleic acids obtained from *Bacillus thuringiensis* Cry8-like genes that encode δ-endotoxins characterized by pesticidal activity against pests of the order Coleoptera. Compositions and methods of the invention utilize the disclosed nucleic acids, and their encoded pesticidal polypetides, to control plant pests.

BACKGROUND OF THE INVENTION

Insect pests are a major factor in the loss of the world's agricultural crops. Insect pest-related crop loss from corn rootworm alone has reached one billion dollars a year. For example, corn rootworm feeding can be economically devastating to agricultural producers. The western corn rootworm is a major insect pest of corn or maize in many regions of the world. While not as important a pest as the western corn rootworm, the southern corn rootworm may occasionally cause significant economic damage to corn. Damage from western and southern corn rootworms may result in increased lodging, reduced drought tolerance and ultimately, crop yield reductions.

Traditionally, the primary methods for impacting corn rootworm populations are crop rotation and the application of broad-spectrum chemical insecticides. Unfortunately, some species of pests have developed resistance to the chemical insecticides. Furthermore, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative. Generally speaking, the use of biopesticides presents a lower risk of pollution and environmental hazards, and they provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* and *Bacillus papilliae* are among the most successful biocontrol agents discovered to date. Insect pathogenicity has also been attributed to strains of: *B. larvae, B. lentimorbus, B. papilliae, B. sphaericus, B. thuringiensis* (Harwook, ed., ((1989) *Bacillus*, Plenum Press), 306) and *B. cereus* (WO 96/10083). Pesticidal activity appears to be concentrated in parasporal crystalline protein inclusions, and several genes encoding these pesticidal proteins have been isolated and characterized (see, for example U.S. Pat. No. 5,366,892).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants genetically engineered to produce pesticidal proteins isolated from strains of *B. thuringiensis*, known as δ-endotoxins or Cry toxins, are now widely used in American agriculture and have provided the farmer with an environmentally friendly alternative to traditional insect-control methods. In addition, potatoes genetically engineered to contain pesticidal Cry toxins have been sold to the American farmer. However, while they have proven to be very successful commercially, these genetically engineered, insect-resistant crop plants provide resistance to only a narrow range of the economically important insect pests. Some insects, such as Western corn rootworm, have proven to be recalcitrant, and the level of Bt-toxin resistance is increasing in formerly susceptible populations of some important insect pests.

Although numerous investigators have attempted to make mutant endotoxin proteins with improved insecticidal activity, few have succeeded. In fact, the majority of genetically engineered *B. thuringiensis* toxins that have been reported in the literature report endotoxin activity that is no better than that of the wild-type protein, and in many cases, the activity is decreased or destroyed altogether. Thus, new microbial insecticides having altered specificity and/or improved pesticidal activity are desired for use in pest-management strategies.

SUMMARY OF THE INVENTION

Compositions and methods are provided for impacting plant pests, particularly Coleopteran insect pests. More specifically, the invention relates to methods of impacting insects utilizing nucleic acids derived from δ-endotoxin genes to produce transformed microorganisms and plants that express a pesticidal polypeptide of the invention. The compositions and methods of the invention find use in agriculture for controlling pests of crop plants.

The invention provides nucleic acids, and fragments and variants thereof, which encode polypeptides that possess pesticidal activity against pests of the order Coleoptera. The wild-type (e.g., naturally occurring) nucleotide sequences of the invention, which were obtained from strains of *Bacillus thuringiensis*, encode Cry-8-like δ-endotoxins.

The invention further provides fragments and variants of Cry-8 like nucleotide sequences that encode biologically active (e.g., pesticidal) polypeptides. In particular embodiments, the disclosed nucleotide sequences encode polypeptides that are pesticidal for at least one insect belonging to the order Coleoptera (e.g., Colorado potato beetle, southern corn rootworm, and western corn rootworm).

Other embodiments of the invention provide nucleic acid encoding truncated versions of a Cry8 endotoxin that are characterized by pesticidal activity that is either equivalent to, or improved, relative to the activity of the corresponding full-length endotoxin. Some of the truncated nucleic acids of the invention can be referred to as either fragments or variants. In particular embodiments, some of the nucleic acid fragments/variants of the invention are truncated at the 3' end of a wild-type coding sequence; in alternative embodiments, other nucleic acids of the invention comprise a contiguous sequence of nucleic acid residues, derived from another coding sequence of the invention, that have been truncated at both the 5' and 3' ends.

The invention also provides recombinant Cry8-like nucleic acids comprising mutagenized nucleic acid sequence variants encoding *B. thuringiensis* endotoxins that have been engineered to have improved and/or altered pesticidal activities. More specifically, the invention provides mutagenized nucleic acids encoding pesticidal polypeptides that comprise an additional, or an alternative, protease-sensitive site located in domain 1 of the polypeptide variant in a region that is located between alpha-helices 3 and 4 of the encoded polypeptide.

As demonstrated herein, the presence of an additional, and/or alternative, protease-sensitive site in the amino acid sequence of the encoded polypeptide can improve the pesticidal activity and/or specificity of the variant polypeptide encoded by the nucleic acid variants of the invention. Accordingly, the Cry8-nucleotide sequences of the invention can be recombinantly engineered or manipulated to produce endotoxins having improved or altered activity and/or specificity compared to that of an unmodified wild-type δ-endotoxin.

For example, one type of variant nucleic acid (e.g., mutagenized Cry8-like nucleotide sequence) disclosed herein provides additional mutants that comprise additional codons that introduce a second trypsin-sensitive amino acid sequence (in addition to the naturally occurring trypsin site) into its encoded polypeptide. An alternative addition variant of the invention comprises additional codons designed to introduce a chymotrypsin-sensitive site located immediately 5' of the naturally occurring trypsin site.

A second alternative type of variant nucleic acid of the invention provides substitution mutants in which at least one codon of the nucleic acid that encodes the naturally occurring protease-sensitive site is destroyed, and alternative codons are introduced into the variant nucleic acid sequence in order to introduce a different (e.g., substitute) protease-sensitive site in its place. In a particular embodiment of this variant polynucleotide, a replacement mutant is disclosed in which the naturally occurring trypsin cleavage site present in the encoded polypeptide is destroyed and a chymotrypsin cleavage site is introduced into in its place.

It is to be recognized that any of the disclosed mutations can be engineered in any polynucleotide sequence of the invention that comprises the amino acid residues providing the trypsin cleavage site that is targeted for modification. Accordingly, variants of either full-length endotoxins or fragments thereof can be modified to contain additional or alternative cleavage sites.

The nucleic acids of the invention can be used to produce expression cassettes that can be used to produce transformed microorganisms comprising a nucleic acid of the invention. The resulting transformants can be used in the preparation of pesticidal compositions comprising a transformed microorganism, or for the production and isolation of pesticidal proteins. Thus, the invention further provides pesticidal compositions, comprising either pesticidal polypeptides or transformed microorganisms, and methods for producing such compositions. The pesticidal compositions of the invention find use in agricultural methods for impacting pests. For example, the compositions can be used in a method that involves placing an effective amount of the pesticidal composition in the environment of the pest by a procedure selected from the group consisting of spraying, dusting, broadcasting, or seed coating.

The invention further provides isolated pesticidal (e.g., insecticidal) polypeptides encoded by either a naturally occurring, or a modified (e.g., mutagenized or manipulated) nucleic acid of the invention. In particular examples, pesticidal proteins of the invention include full-length δ-endotoxin proteins, fragments of full-length δ-endotoxins, and variant polypeptides that are produced from mutagenized nucleic acids designed to introduce particular amino acid sequences into the polypeptides of the invention. In particular embodiments, the polypeptide fragments and polypeptide variants of the invention have enhanced pesticidal activity relative to the activity of the naturally occurring δ-endotoxin from which they are derived. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

The nucleic acids of the invention can also be used to produce transgenic (e.g., transformed) plants that are characterized by genomes that comprise at least one stably incorporated nucleotide construct comprising a coding sequence of the invention operably linked to a promoter that drives expression of the encoded pesticidal polypeptide. Accordingly, transformed plant cells, plant tissues, plants, and seeds thereof are also provided.

In a particular embodiment, a transformed plant of the invention can be produced using a nucleic acid that has been optimized for increased expression in a host plant. For example, one of the pesticidal polypeptides of the invention can be back-translated to produce a nucleic acid comprising codons optimized for expression in a particular host, for example a plant, more specifically for expression in a *Zea mays* plant. Expression of a coding sequence by such a transformed plant (e.g., dicot or monocot) will result in the production of a pesticidal polypeptide and confer increased insect resistance to the plant. In a particular embodiment, the invention provides transgenic plants expressing pesticidal polypeptides that find use in methods for impacting the Colorado potato beetle, western corn rootworm, and southern corn rootworm.

DETAILED DESCRIPTION OF THE INVENTION

The invention is drawn to compositions and methods for impacting pests, particularly plant pests, more specifically insect pests of the order Coleoptera. More specifically, the isolated nucleic acids of the invention, and fragments and variants thereof, comprise nucleotide sequences that encode pesticidal polypeptides (e.g., proteins). The disclosed pesticidal proteins are biologically active (e.g., pesticidal) against insect pests, particularly the Colorado potato beetle (*Leptinotarsa decemlineata*), the western corn rootworm (*Diabrotica virgifera virgifera*), and the southern corn rootworm (*Diabrotica undecimpunctata howardi*).

The compositions of the invention comprise isolated nucleic acids, and fragments and variants thereof, that encode pesticidal polypeptides, expression cassettes comprising nucleotide sequences of the invention, isolated pesticidal proteins, and pesticidal compositions. In some embodiments, the invention provides modified Cry8-like δ-endotoxin proteins characterized by improved insecticidal activity against Coleopterans relative to the pesticidal activity of the corresponding wild-type parental protein. The invention further provides plants and microorganisms transformed with these novel nucleic acids, and methods involving the use of such nucleic acids, pesticidal compositions, and transformed organisms in impacting insect pests.

In the description that follows, a number of terms are used extensively. The following definitions are provided to facilitate understanding of the invention.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein the terms "encoding" or "encoded," when used in the context of a specified nucleic acid, means that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid, or may lack such intervening non-translated sequences (e.g., as in cDNA).

As used herein "full-length sequence" in reference to a specified polynucleotide or its encoded protein means having the entire nucleic acid sequence or the entire amino acid sequence of, a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively, "protein"). The amino acid may be a naturally occurring amino acid and, unless otherwise limited, may encompass known analogues of natural amino acids that can function in a similar manner as naturally occurring amino acids.

As used herein the terms "isolated" and "purified" are used interchangeably to refer to nucleic acids, or polypeptides, or biologically active portion thereof, that are substantially or essentially free from components that normally accompany or interact with the nucleic acid or polypeptide as found in its naturally occurring environment. Thus, an isolated or purified nucleic acid or polypeptide is substantially free of other cellular material, or culture medium when produced by recombinant techniques, or substantially free of chemical precursors or other chemicals when chemically synthesized.

As used herein the term "impacting insect pests" refers to effecting changes in insect feeding, growth, and/or behavior at any stage of development, including, but not limited to, killing the insect, retarding growth, preventing reproductive capability, and the like.

As used herein the terms "pesticidal activity" and "insecticidal activity" are used synonymously to refer to activity of an organism or a substance, such as, for example, a protein, that can be measured by, but is not limited to, pest mortality, pest weight loss, pest attraction, pest repellency, and other behavioral and physical changes of a pest after feeding and exposure for an appropriate length of time. For example "pesticidal proteins" are proteins that display pesticidal activity by themselves or in combination with other proteins.

The term "pesticidally effective amount" connotes a quantity of a substance or organism that has pesticidal activity when present in the environment of a pest. For each substance or organism, the pesticidally effective amount is determined empirically for each pest affected in a specific environment. Similarly an "insecticidally effective amount" may be used to refer to a "pesticidally effective amount" when the pest is an insect pest.

As used herein the term "recombinantly engineered" connotes the utilization of recombinant DNA technology to introduce (e.g., engineer) a change in the protein structure based on an understanding of the protein's mechanism of action and a consideration of the amino acids being introduced, deleted or substituted.

As used herein the term "mutagenized nucleotide sequence" connotes a nucleotide sequence that has been mutagenized or altered to contain one or more nucleotide residues (e.g., base pair) that is not present in the corresponding wild-type sequence, and which encodes a mutant δ-endotoxin showing improved insecticidal activity.

As used herein the term "improved insecticidal activity" characterizes a δ-endotoxin of the invention that either has enhanced anti-Coleopteran pesticidal activity relative to the activity of its corresponding wild-type protein, and/or an endotoxin that is effective against either a broader range of insects, or acquires a specificity for an insect that is not susceptible to the toxicity of the wild-type protein. A finding of enhanced pesticidal activity requires a demonstration of an increase of toxicity of at least 30% against the insect target, and more preferably 35%, 40%, 45%, or 50% relative to the insecticidal activity of the wild-type endotoxin determined against the same insect.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The nucleotide sequences of the invention may be used to transform any organism to produce the encoded pesticidal proteins. Methods are provided that involve the use of such transformed organisms to impact or control plant pests. The invention further relates to the identification of fragments and variants of the naturally occurring coding sequence that encode biologically active pesticidal proteins. All of the nucleotide sequences of the invention find direct use in methods for impacting pests, particularly insect pests, more particularly pests of the order Coleoptera, including, for example, the Colorado potato beetle, western corn rootworm, and southern corn rootworm. Accordingly, the present invention provides new approaches for impacting insect pests that do not depend on the use of traditional, synthetic chemical insecticides. The invention involves the discovery of naturally occurring, biodegradable pesticides and the genes that encode them.

The invention further provides fragments and variants of the naturally occurring coding sequences that also encode biologically active (e.g., pesticidal) polypeptides. The nucleic acids of the invention encompass nucleic acid sequences that have been optimized for expression by the cells of a particular organism, for example nucleic acid sequences that have been back-translated using plant-preferred codons based on the amino acid sequence of a polypeptide having enhanced pesticidal activity.

The nucleotide sequences of the invention were isolated from strains of the bacterium, Bacillus thuringiensis. Crude lysates prepared from cultures of the strains were discovered to have pesticidal activity against Colorado potato beetle, western corn rootworm, and southern corn rootworm. Crystal proteins were isolated from cultures of the strains. The isolated crystal proteins were tested for pesticidal activity in insect feeding assays. The results of the assays revealed that the isolated crystal proteins possessed Coleopteran pesticidal activity. An effort was undertaken to identify nucleotide sequences encoding crystal proteins from the strains, and the naturally occurring coding sequences and genomic nucleic acids of the invention were discovered.

The nucleotide sequences of the isolated nucleic acids were demonstrated to encode pesticidal proteins by transforming Escherichia coli with such nucleotide sequences. Lysates prepared from the transformed E. coli had pesticidal activity against corn rootworms and Colorado potato beetles in feeding assays, demonstrating that the isolated nucleotide sequences of the invention encode pesticidal proteins. Depending upon the characteristics of a given lysate preparation, it was recognized that the demonstration of pesticidal activity sometimes required trypsin pretreatment to activate the pesticidal proteins.

Subsequently, nucleic acid variants and fragments encoding biologically active pesticidal polypeptides were identified. Some of the encoded pesticidal proteins require protease (e.g., trypsin) activation and other proteins were observed to be biologically active (e.g., pesticidal) in the absence of activation. In some embodiments, the nucleic acid encodes a truncated version of the naturally occurring polypeptide and as such, can be classified either as a variant or a fragment. In addition, second generation nucleic acid sequences were engineered to comprise nucleotide sequences that encode Cry8-like polypeptides characterized by improved or altered pesticidal activity relative to the pesticidal activity of the naturally occurring polypeptide.

The nucleic acids of the invention comprise isolated polynucleotides, and variants and fragments thereof, that encode biologically active (e.g., pesticidal) polypeptides, including, but not limited to, the Cry8-like nucleotide sequences set forth in SEQ ID NOS: 1, 3, 5, 7, 9, 11, 15, 17, 19, 21, 23, 27, 28, 29, 31, 33, 39, 41, 43, and 45. The nucleotide sequences disclosed herein provide two background sequences referred to herein as 1218-1 and 49PVD into which mutations are introduced. In some instances, the sequences also provide variants of two distinct clones referred to herein as 1218-1 and 1218-2. More specifically, SEQ ID NO: 15 (1218-1A) represents a variant of SEQ ID NO: 5, each of which represent alternative embodiments of the 1218-1 clone. In addition, SEQ ID NO: 17 (1218-2A) represents a variant of SEQ ID NO: 7, each of which represent alternative embodiments of the 1218-2 clone.

The polynucleotides of the invention also include any synthetic or recombinant nucleotide sequence that encodes a pesticidal polypeptide comprising the amino acid sequences set forth in SEQ ID NOS: 2, 4, 6, 8, 10, 12, 16, 18, 20, 22, 24, 30, 32, 34, 40, 42, 44, and 46.

An "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

The present invention provides isolated nucleic acids comprising nucleotide sequences which encode the amino acid sequences set forth in SEQ ID NOS: 2, 4, 6, 8, 10, 12, 16, 18, 20, 22, 24, 30, 32, 34, 40, 42, 44, and 46. In particular embodiments, the invention provides nucleic acids comprising the nucleotide sequences set forth in SEQ ID NOS: 1 (Cry1218-1 CDS) and 3 (Cry1218-2 CDS), the maize-optimized nucleic acid set forth in SEQ ID NO: 9 (mo1218-1), and the native genomic sequences set forth in SEQ ID NO: 27 (genomic Cry1218-1) and SEQ ID NO: 28 (genomic Cry 1218-2). The coding sequence (CDS) for SEQ ID NO: 27 runs from base pair 731-4348. The CDS for SEQ ID NO: 28 runs from base pair 1254-4883. Plasmids comprising each of these five nucleic acids were deposited on May 5, 2000 and Oct. 20, 2000 with the Patent Depository of the American Type Culture Collection (ATCC), Manassas, Va., and assigned Patent Deposit Nos. PTA-1821 (corresponding to SEQ ID NO: 1); PTA-1817 (corresponding to SEQ ID NO: 3); PTA-2635 (corresponding to SEQ ID NO: 9); PTA-2634 (comprising SEQ ID NO:27); and PTA-2636 (comprising SEQ ID NO:28).

Patent Deposits PTA-1821 and PTA-1817 comprise a mixture of 2 clones, each of which contains a part of the entire coding sequence. More specifically, the deposited plasmids encode nucleic acid molecules cloned into a TA vector (Invitrogen, Carlsbad, Calif.) that encode two overlapping fragments of the coding sequence. The full length coding sequence can be produced using an overlapping PCR strategy. A first PCR reaction should comprise forward and reverse primers designed to correspond to the 5' and the 3' ends of the full-length coding sequence. Suitable primers for use in PCR reactions are set forth in SEQ ID NOS: 35 through 38. More specifically, SEQ ID NOS: 35 and 36 provide a first primer set "(a)" comprising a forward primer SEQ ID NO: 35 (5'-ATGAGTCCAAATAATCAAAATG) and a reverse primer SEQ ID NO: 36 (5'-CCGCTTCTAAATCTTGTTCC) for the 5' end of the coding sequence. SEQ ID NOS: 37 and 38 provide a second primer set "(b)" comprising a forward primer SEQ ID NO: 37 (5'-GGAACAAGATTTAGAGG) and a reverse primer SEQ ID NO: 38 (5'-CTCATCGTCTACAATCAATTCATC) for the 3' end of the coding sequence. The two DNA bands generated by the first PCR reaction performed with the above-identified primer sets should be purified and a second round of PCR, set for 7 cycles, should be performed utilizing the purified DNA isolated from the first PCR reaction in the absence of any primers. The 3' end of the nucleic acid generated by primer set (a) and the 5' end of the nucleic acid generated by primer set (b) will overlap and prime the generation of the full-length coding sequence. A third and final PCR reaction is performed to generate the full-length coding sequence. This reaction is performed using 1 μl of the second PCR reaction product and a primer set comprising SEQ ID NO: 35 (forward primer of set (a)) and SEQ ID NO: 39 (reverse primer of set (b)).

The above-referenced deposits (e.g., PTA-1821; PTA-1817; PTA-2635; PTA-2634; and PTA-2636) will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Of particular interest are optimized nucleotide sequences encoding the pesticidal proteins of the invention. As used herein the phrase "optimized nucleotide sequences" refers to nucleic acids that are optimized for expression in a particular organism, for example a plant. Optimized nucleotide sequences may be prepared for any organism of interest using methods known in the art. For example, SEQ ID NO: 9 discloses an optimized nucleic acid sequence encoding the pesticidal protein set forth in SEQ ID NO: 16 (truncated 1218-1A). More specifically, the nucleotide sequence of SEQ ID NO: 9 comprising maize-preferred codons SEQ ID NO: 9 was prepared by reverse-translating the amino acid sequence set forth in SEQ ID NO: 16 to comprise maize-preferred codons as described by Murray et al. (1989) *Nucleic Acids Res.* 17:477-498. Optimized nucleotide sequences find use in increasing expression of a pesticidal protein in a plant, particularly a monocot plant, more particularly a plant of the Gramineae (Poaceae) family, most particularly a maize or corn plant.

The invention further provides isolated pesticidal (e.g., insecticidal) polypeptides encoded by either a naturally occurring, or a modified (e.g., mutagenized or truncated) nucleic acid of the invention. More specifically, the invention provides polypeptides comprising an amino acid sequence set forth in SEQ ID NOS: 2, 4, 6, 8, 10, 12, 16, 18, 20, 22, 24, 30, 32, 34, 40, 42, 44, and 46 and the polypeptides encoded by a nucleic acid described herein, for example those set forth in SEQ ID NOS: 1, 3, 5, 7, 9, 11, 15, 17, 19, 21, 23, 27, 28, 29, 31, 33, 39, 41, 43, and 45, and fragments and variants thereof.

In particular embodiments, pesticidal proteins of the invention provide full-length δ-endotoxin proteins, fragments of full-length δ-endotoxins, and variant polypeptides that are produced from mutagenized nucleic acids designed to introduce particular amino acid sequences into polypeptides of the invention. In particular embodiments, the amino acid sequences that are introduced into the polypeptides comprise a sequence that provides a cleavage site for an enzyme or protease.

Some of the polypeptides of the invention, for example SEQ ID NOS: 2 and 4 comprise full-length δ-endotoxins; other polypeptides such as SEQ ID NOS: 6, 8, 10, 16, 18, and 20 embody fragments of a full-length δ-endotoxin; and SEQ ID NOS: 12, 22, 24, 30, 32, 34, 40, 42, 44, and 46 provide polypeptide variants. Some of the polypeptide fragments and variants of the invention have enhanced pesticidal activity relative to the activity of the naturally occurring δ-endotoxin from which they are derived, particularly in the absence of in vitro activation of the endotoxin with a protease prior to screening for activity. For example, the data presented herein in Table 1 of Example 6 indicates that the NGRS addition mutant (SEQ ID NO: 12) of SEQ ID NO: 16 (truncated 1218-1A endotoxin) is characterized by increased pesticidal activity against Colorado potato beetle.

SEQ ID NOS: 6, 10, 16 and 20 provide polypeptides that embody truncated versions of the 1218-1 polypeptide set forth in SEQ ID NO: 2. SEQ ID NO: 16 provides a variant, referred to herein as 1218-1A of the polypeptide set forth in SEQ ID NO: 6 and referred to herein as 1218-1. Three of the above-mentioned sequences, SEQ ID NOS: 6, and 16 represent a polypeptide that is shortened (truncated) at the 3' end of the amino acid sequence set forth in SEQ ID NO: 2. In contrast, the fourth polypeptide variant set forth in SEQ ID NO: 20 provides a variant that is truncated at both the 5' and 3' ends of the full-length protein set forth in SEQ ID NO: 2. SEQ ID NOS: 8 and 18 (1218-2 and 1218-2A, respectively) provide polypeptides that embody truncated versions of the polypeptides set forth in SEQ ID NO: 4. Each of these two polypeptides provide a protein that is truncated at the 3' end of the full-length 1218-2 polypeptide set forth in SEQ ID NO: 4.

SEQ ID NOS: 12, 22, 24, 40, and 44 provide a family of polypeptides that embody variants of the 1218-1A truncated polypeptides set forth in SEQ ID NO: 16, thus SEQ ID NOS: 12, 22, 24, 40, and 44 provide variants (or mutants) of the biologically active fragment of the Cry8-like polypeptide set forth in SEQ ID NO: 2. More specifically, SEQ ID NO: 12 provides a mutant, referred to herein as NGSR.N1218-1, that comprises an additional trypsin-sensitive cleavage site; SEQ ID NO: 22 provides a second mutant, referred to herein as LKMS.N1218-1, that comprises a chymotrypsin-sensitive cleavage site that is not present in the wild-type 1218-1 or 1218-1A polypeptide; and SEQ ID NO: 24 provides a replacement mutant, referred to herein as LKMS.R1218-1, in which an existing trypsin cleavage-site is destroyed and a chymotrypsin site is introduced in its place. SEQ ID NO: 40 provides a second chymotrypsin-addition mutant, referred to herein as LRMS.N1218-1, that comprises the alternative chymotrypsin cleavage site LRMS (SEQ ID NO: 48). SEQ ID NO: 44 provides a second replacement or substitution mutant, referred to herein as LRMS.R1218-1, in which the native trypsin site is replaced with the chymotrypsin cleavage site LRMS.

SEQ ID NOS: 30, 32, 34, 42, and 46 provide a second family of polypeptides that embody variants or mutants of the truncated polypeptide set forth in SEQ ID NO: 20. Thus, SEQ ID NOS: 30, 32, 34, 42, and 46 provide variants of the pesticidal fragment of SEQ ID NO: 2 that is set forth in SEQ ID NO: 20. More specifically, SEQ ID NO: 30 provides a mutant, referred to herein as NGSR.N49PVD, that comprises an additional trypsin-sensitive cleavage site; SEQ ID NO: 32 provides a second mutant, referred to herein as LKMS.N49PVD, that comprises a chymotrypsin-sensitive cleavage site that is not present in the wild-type 1218-1 or 1218-1A polypeptide; and SEQ ID NO: 34 provides a replacement mutant, referred to herein as LKMS.R49PVD, in which an existing trypsin cleavage site is destroyed and a chymotrypsin site is introduced in its place. SEQ ID NO: 42 provides a second chymotrypsin addition mutant, referred to herein as LRMS.N49PVD, that comprises the alternative chymotrypsin cleavage site LRMS (SEQ ID NO: 48). SEQ ID NO: 46 (LRMS.R49PVD) provides a second replacement or substitution mutant in which the native trypsin site is replaced with the chymotrypsin cleavage site LRMS.

It is to be understood that the polypeptides of the invention can be produced either by expression of a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification of a purified wild-type protein.

As used herein the term "isolated" or "purified" as it is used to refer to a polypeptide of the invention means that the isolated protein is substantially free of cellular material and includes preparations of protein having less than about 30%, 20%, 10%, or 5% (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

It is recognized that the pesticidal proteins may be oligomeric and will vary in molecular weight, number of residues, component peptides, activity against particular pests, and in other characteristics. However, by the methods set forth herein, proteins active against a variety of pests may be isolated and characterized. The pesticidal proteins of the invention can be used in combination with Bt endotoxins or other insecticidal proteins to increase insect target range. Furthermore, the use of the pesticidal proteins of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase, and peroxidase.

Fragments and variants of the nucleotide and amino acid sequences and the polypeptides encoded thereby are also encompassed by the present invention. As used herein the term "fragment" refers to a portion of a nucleotide sequence of a polynucleotide or a portion of an amino acid sequence of a polypeptide of the invention. Fragments of a nucleotide sequence may encode protein fragments that retain the biological activity of the native protein and hence possess pesticidal activity. Thus, it is acknowledged that some of the polynucleotide and amino acid sequences of the invention can correctly be referred to as either fragments or variants. This is particularly true of truncated sequences that are biologically active.

It is to be understood that the term "fragment," as it is used to refer to nucleic acid sequences of the invention, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Cry8-like nucleotide sequence that encodes a biologically active portion of a pesticidal protein of the invention will encode at least 15, 25, 30, 50, 100, 200, 300, 400, 500, 600, 700, 800, 900, 1,000, 1,100, or 1,200 contiguous amino acids, or up to the total number of amino acids present in a pesticidal polypeptide of the invention (for example, 1,206, 1,210, 667, 667, and 669 amino acids for SEQ ID NOS: 2, 4, 6, 8, and 10, respectively). Fragments of a Cry8-like nucleotide sequence that are useful as hybridization probes or PCR primers generally need not encode a biologically active portion of a pesticidal protein.

Thus, a fragment of a Cry8-like nucleic acid may encode a biologically active portion of a pesticidal protein, or it may be a fragment that can be used as a hybridization probe or PCR primer using methods disclosed below. A biologically active portion of a pesticidal protein can be prepared by isolating a portion of one of the Cry8-like nucleotide sequences of the invention, expressing the encoded portion of the pesticidal protein (e.g., by recombinant expression in vitro), and assessing the activity of the encoded portion of the pesticidal protein.

Nucleic acids that are fragments of a Cry8-like nucleotide sequence comprise at least 16, 20, 50, 75, 100, 150, 200, 250, 300, 350, 400, 450, 500, 600, 700, 800, 1,000, 1,200, 1,400, 1,600, 1,800, 2,000, 2,200, 2,400, 2,600, 2,800, 3,000, 3,200, 3,400, or 3,600 nucleotides, or up to the number of nucleotides present in a Cry8-like nucleotide sequence disclosed herein (for example, 3,621, 3,633, 2,003, 2,003, 2,010, and 2010 and 2022 nucleotides for SEQ ID NOS: 1, 3, 5, 7, 9, 15 and 17 respectively).

For example, SEQ ID NOS: 5, 9, 15, and 19 represent fragments of SEQ ID NO: 1 and SEQ ID NOS: 7 and 17 represent fragments of SEQ ID NO: 3. More specifically, particular embodiments of the nucleic acids of the invention disclose fragments derived from (e.g., produced from) a first nucleic acid of the invention, wherein the fragment encodes a truncated Cry8-like endotoxin characterized by pesticidal activity. The truncated polypeptide encoded by the polynucleotide fragments of the invention are characterized by pesticidal activity that is either equivalent to, or improved, relative to the activity of the corresponding full-length polypeptide encoded by the first nucleic acid from which the fragment is derived.

In specific embodiments, some of the nucleic acid fragments of the invention are truncated at the 3' end of the wild-type coding sequence. For example, SEQ ID NOS: 5 and 15 represent fragments of SEQ ID NO: 1 that are truncated at the 3' end. In an alternative embodiment, one of the polynucleotides of the invention, SEQ ID NO: 19, comprises a nucleic acid sequence that is truncated at both the 5' and 3' end of the truncated 1218-1 and 1218-1A toxin domain encoded by SEQ ID NOS: 5 and 15, respectively.

By "variants" is intended substantially similar sequences. For nucleotide sequences, conservative variants include those sequences that, because of the degeneracy of the genetic code, encode the amino acid sequence of one of the pesticidal polypeptides of the invention. Naturally occurring allelic variants such as these can be identified with the use of well-known molecular biology techniques, as, for example, with polymerase chain reaction (PCR) and hybridization techniques as outlined below.

Variant nucleotide sequences also include synthetically derived nucleotide sequences, such as those generated, for example, by using site-directed mutagenesis but which still encode a pesticidal protein of the invention. Generally, variants of a particular nucleotide sequence of the invention will have at least about 40%, 50%, 60%, 65%, 70%, generally at least about 75%, 80%, 85%, preferably at least about 87%, 88%, 89%, 90%, 91%, 92%, 93%, 94%, 95%, 96%, 97%, and more preferably at least about 98%, 99%, or more sequence identity to that particular nucleotide sequence as determined by sequence alignment programs described elsewhere herein using default parameters.

As used herein the term "variant protein" encompasses polypeptides that are derived from a native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term variant protein encompasses biologically active fragments of a native protein that comprise a sufficient number of contiguous amino acid residues to retain the biological activity of the native protein.

Variant proteins encompassed by the present invention are biologically active, that is they continue to possess the desired biological activity of the native protein, that is, pesticidal activity as described herein. Such variants may result from, for example, genetic polymorphism or from human manipulation. Biologically active variants of a native pesticidal protein of the invention will have at least about 40%, 50%, 60%, 65%, 70%, generally at least about 75%, 80%, 85%, preferably at least about 86%, 87%, 88%, 89%, 90%, 91%, 92%, 93%, 94%, 95%, 96%, 97%, and more preferably at least about 98%, 99%, or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

It is recognized that the nucleic acid sequence of any one of the polynucleotides of the invention can be altered or mutagenized to alter (e.g., improve) the biological activity and/or specificity of its encoded pesticidal polypeptide. For example, SEQ ID NO: 11 represents a Cry8-like nucleotide sequence that has been mutagenized to comprise 12 additional nucleotides (SEQ ID NO: 13) that are not present in the wild-type nucleic acid sequence (SEQ ID NO: 15) that is being altered. The nucleotide sequence inserted into the coding region of SEQ ID NO: 15 was designed to encode an NGRS addition mutant that comprises an additional trypsin cleavage site (NGSR) (SEQ ID NO: 14) in the amino acid sequence of the encoded polypeptide.

More specifically, the amino acid sequence set forth in SEQ ID NO: 14 was introduced between amino acid 164 and 165 of the Cry8 δ-endotoxin set forth in SEQ ID NO: 16. This particular amino acid sequence was chosen because it duplicates the endogenous sequence present in the naturally occurring full-length protein (SEQ ID NO: 2), and creates a second protease-sensitive site. More specifically, the modification introduces a second trypsin-like site. It is well known to those of skill in the art that trypsin cleaves bonds immediately C-terminal to arginine and lysine. As demonstrated herein the recombinantly engineered protein (SEQ ID NO: 12, NGSRN 1218-1) encoded by SEQ ID NO: 11 is characterized by improved activity against Coleopterans, particularly against Colorado potato beetle (see Example 6, Table 1, L-M), southern corn rootworm (see Example 7, Tables 2 through 4 and 6, NGSRN 1218-1), and western corn rootworm (see Example 7, Table 5, NGSRN 1218-1).

SEQ ID NO: 21 represents a Cry8-like nucleotide sequence that has been mutagenized to comprise 12 additional nucleotides (SEQ ID NO: 25) that are not present in the wild-type endotoxin. The inserted nucleotide sequence was designed to encode an LKMS addition mutant that comprises a chymotrypsin cleavage site (LKMS) (SEQ ID NO: 26) in the amino acid sequence of the encoded polypeptide. More specifically, the LKMS addition mutant (LKMS.N1218-1, SEQ ID NO:22) comprises a nucleotide sequence insert that introduces the amino acid sequence LKMS between amino acids 160 and 161 of SEQ ID NO: 6. The LKMS replacement mutant LKMS.R1218-1 (SEQ ID NO:24) comprises a polypeptide in which the amino acid sequence LKMS is introduced between amino acid 160 and 161 of SEQ ID NO: 16 and the amino acids NGS are removed from amino acid positions 161-163 of SEQ ID NO: 16. This modification removes a trypsin site and introduces a chymotrypsin site. Chymotrypsin cleaves bonds immediately C-terminal to Methionine.

The LRMS addition mutant (LRMS.N1218-1, SEQ ID NO:40) and replacement mutant (LRMS.R1218-1, SEQ ID NO:44) provide alternative embodiments of polypeptides comprising an additional or alternative chymotrypsin cleavage site, but the LRMS mutants differ in the specific amino acid sequence (SEQ ID NO: 48) and nucleotide sequence (SEQ ID NO: 47) that is used to introduce the chymotrypsin cleavage site into the nucleic acid sequence that encodes the mutant polypeptides.

SEQ ID NO: 30 (NGSR.N49PVD), SEQ ID NO: 32 (LKMS.N49PVD), SEQ ID NO: 34 (LKMS.R49PVD), SEQ ID NO: 42 (LRMS.N49PVD), and SEQ ID NO: 46 (LRMS.R49PVD) provide mutants of the truncated pesticidal polypeptide 49PVD (SEQ ID NO:20). The amino acid sequence of 49PVD is provided in SEQ ID NO: 20. The basic design of these polypeptides and their nomenclature follow the same pattern discussed above for the 1218-1 truncated polypeptide, and are explained more fully elsewhere herein.

The LRMS addition mutant (LRMS.N1218-1) and replacement mutant (LRMS.R1218-1) provide alternative embodiments of polypeptides comprising an additional or alternative chymotrypsin cleavage site, but the LRMS mutants differ in the specific amino acid sequence (SEQ ID NO: 48) and nucleotide sequence (SEQ ID NO: 47) that is used to introduce the chymotrypsin cleavage site into the nucleic acid sequence that encodes the mutant polypeptides.

SEQ ID NO: 30 (NGSR.N49PVD), SEQ ID NO: 32 (LKMS.N49PVD), SEQ ID NO: 34 (LKMS.R49PVD), SEQ ID NO: 42 (LRMS.N49PVD), and SEQ ID NO: 46 (LRMS.R49PVD) provide mutants of the truncated pesticidal polypeptide 49PVD. The amino acid sequence of 49PVD is provided in SEQ ID NO: 20. The basic design of the these polypeptides and their nomenclature follow the same pattern discussed above for the 1218-1 truncated polypeptide, and are explained more fully elsewhere herein.

It is recognized that any nucleotide sequence encoding the amino acid sequences NGSR fSEQ ID NO:14), LKMS fSEQ ID NO:26), or LRMS fSEQ ID NO:48) can be used and that the exact identity of the codons used to introduce any of these cleavage sites into a variant polypeptide may vary depending on the use, i.e., expression in particular plant species. It is also recognized that any of the disclosed mutations can be introduced into any polynucleotide sequence of the invention that comprises the codons for amino acid residues that provide the native trypsin cleavage site that is targeted for modification. Accordingly, variants of either full-length endotoxins or fragments thereof can be modified to contain additional or alternative cleavage sites, and these embodiments are intended to be encompassed by the scope of the invention disclosed and claimed herein.

The invention further encompasses a microorganism that is transformed with at least one nucleic acid of the invention, with an expression cassette comprising the nucleic acid, or with a vector comprising the expression cassette. Preferably, the microorganism is one that multiplies on plants. More preferably, the microorganism is a root-colonizing bacterium. An embodiment of the invention relates to an encapsulated pesticidal protein, which comprises a transformed microorganism comprising at least one pesticidal protein of the invention.

The invention provides pesticidal compositions comprising a transformed organism of the invention. Preferably the transformed microorganism is present in the pesticidal composition in a pesticidally effective amount, together with a suitable carrier. The invention also encompasses pesticidal compositions comprising an isolated protein of the invention, alone or in combination with a transformed organism of the invention and/or an encapsulated pesticidal protein of the invention, in an insecticidally effective amount, together with a suitable carrier.

The invention further provides a method of increasing insect target range by using a pesticidal protein of the invention in combination with at least one second pesticidal protein that is different from the pesticidal protein of the invention. Any pesticidal protein known in the art can be employed in the methods of the present invention. Such pesticidal proteins include, but are not limited to, Bt δ-endotoxins, protease inhibitors, lectins, α-amylases, and peroxidases.

The invention also encompasses transformed or transgenic plants comprising at least one nucleotide sequence of the invention. Preferably, the plant is stably transformed with a nucleotide construct comprising at least one nucleotide sequence of the invention operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, and plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants. A preferred plant is *Solanum tuberosum*. A particularly preferred plant is *Zea mays*.

While the invention does not depend on a particular biological mechanism for increasing the resistance of a plant to a plant pest, expression of the nucleotide sequences of the invention in a plant can result in the production of the pesticidal proteins of the invention and in an increase in the resistance of the plant to a plant pest. The plants of the invention find use in agriculture in methods for impacting insect pests. Certain embodiments of the invention provide transformed maize plants, which find use in methods for impacting western and southern corn rootworms. Another embodiment of the invention provides transformed potato plants, which find use in methods for impacting the Colorado potato beetle.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences, of proteins of agricultural interest. Thus, the Cry8-like proteins of the invention may be altered in various ways including amino acid substitutions, deletions, truncations, and insertions. Methods for such manipulations are generally known in the art.

For example, amino acid sequence variants of the pesticidal proteins can be prepared by introducing mutations into a synthetic nucleic acid (e.g, DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker & Gaastra, eds. (1983) *Techniques in Molecular Biology* (MacMillan Publishing Company, New York), and the references cited therein.

The wild-type (e.g., naturally occurring) nucleotide sequences of the invention were obtained from strains of *Bacillus thuringiensis* encoding Cry8-like δ-endotoxins. It is well known that naturally occurring δ-endotoxins are synthesized by *B. thuringiensis* sporulating cells as a proteinaceous crystalline inclusion protoxin. Upon being ingested by susceptible insect larvae, the microcrystals dissolve in the midgut, and the protoxin is transformed into a biologically active moiety by proteases characteristic of digestive enzymes located in the insect gut. The activated δ-endotoxin binds with high affinity to protein receptors on brush-border membrane vesicles. The epithelial cells lining the midgut are the primary target of the endotoxin and are rapidly destroyed as a consequence of membrane perforation resulting from the formation of gated, cation-selective channels by the toxin.

A comparison of the amino acid sequences of Cry toxins of different specificities reveals five highly conserved sequence blocks. Structurally, the δ-endotoxins comprise three distinct domains, which are, from the N- to C-termini: a cluster of seven alpha-helices implicated in pore formation, three antiparallel beta sheets implicated in cell binding, and a beta sandwich.

The mutant Cry8 polypeptides of the present invention were generally prepared by a process that involved the steps of: obtaining a nucleic acid sequence encoding a Cry8 polypeptide; analyzing the structure of the polypeptide to identify particular "target" sites for mutagenesis of the underlying gene sequence, based on a consideration of the proposed function of the target domain in the mode of action of the endotoxin; introducing one or more mutations into the nucleic acid sequence to produce a desired change in one or more amino acid residues of the encoded polypeptide sequence, wherein the change is designed to add a protease-sensitive cleavage site to the target region or to remove the original protease-sensitive site and to add a protease-sensitive site that is sensitive to the activity of a different protease; and expressing the mutagenized nucleic acid sequence that encodes the recombinantly engineered protein of the invention in a transformed host cell under conditions effective to obtain expression of the modified Cry8 polypeptide.

Many of the δ-endotoxins are related to various degrees by similarities in their amino acid sequences and tertiary structure, and means for obtaining the crystal structures of *B. thuringiensis* endotoxins are well known. Exemplary high-resolution crystal structure solution of both the Cry3A and Cry3B polypeptides is available in the literature. The inventors of the present invention used the solved structure of the Cry3A gene (Li et al. (1991) *Nature* 353:815-821) to produce a homology model of the Cry8 δ-endotoxin disclosed and claimed herein as SEQ ID NO: 2 to gain insight into the relationship between structure and function of the endotoxin, and to design the recombinantly engineered proteins disclosed and claimed herein. A combined consideration of the published structural analyses of *B. thuringiensis* endotoxins and the reported function associated with particular structures, motifs, and the like indicates that specific regions of the endotoxin are correlated with particular functions and discrete steps of the mode of action of the protein. For example, δ-endotoxins isolated from *B. thuringiensis* are generally described as comprising three domains, a seven-helix bundle that is involved in pore formation, a three-sheet domain that has been implicated in receptor binding, and a beta-sandwich motif (Li et al. (1991) *Nature,* 305:815-821).

The inventors reasoned that the toxicity of Cry8-like proteins, and specifically the toxicity of the Cry8 protein, could be improved by targeting the region located between alpha helices 3 and 4 of domain 1 of the endotoxin protein. This theory was premised both on the knowledge that alpha helices 4 and 5 of domain 1 of Cry3A δ-endotoxins had been reported to insert into the lipid bilayer of cells lining the midgut of susceptible insects (Gazit et al., (1998) *PNAS USA* 95:12289-12294); the inventors' knowledge of the location of trypsin and chymotrypsin cleavage cites within the amino acid sequence of the wild-type protein; and the observation reported herein that the protein encoded by 1218-1 (i.e., SEQ ID NO: 2) was more active against certain Coleopterans following in vitro activation by trypsin or chymotrypsin treatment. Accordingly, the inventors engineered a mutant Cry8-like protein that would comprise at least one additional trypsin cleavage site in the region located between helices 3 and 4 of domain 1.

More specifically, the inventors produced mutagenized Cry8-like nucleotide sequences that encode mutant Cry8 endotoxins (e.g., polypeptides) that comprise either additional, or alternative protease-sensitive sites. The invention provides mutant polypeptides that have been constructed in either a 1218-1 (SEQ ID NOS: 6 or 16), or a 49PVD (SEQ ID NO: 20) background. It should be understood that the designation 1218-1 as used herein encompasses two embodiments (e.g., 1218-1 and 1218-1A) of the 1218-1 nucleotide and amino acid sequences presented herein. This is particularly true in the context of the disclosed addition and replacement mutants that have been created in either the 1218-1 or 49PVD background. It is to be understood that the nomenclature used herein to refer to a mutant such as, for example the NGSR.N1218-1 mutant described contemplates mutants created in either the 1218-1 and/or the 1218-1A background. For the sake of consistency, the sequences presented in the sequence listing for the 1218-1 mutants embody mutants created in the 1218-1A sequences (SEQ ID NOS: 15 and 16).

Generally speaking, all of the mutant polypeptides described herein are designed to comprise at least one proteolytic cleavage site located between helix 3 and 4 of domain 1 that is not present in the wild-type polypeptide. All of the mutants disclosed herein were cloned into the pET expression system, expressed in *E. coli*, and tested for pesticidal activity first against southern corn rootworm (SCRW) and then western corn rootworm (WCRW). Additionally, the 49PVD variant (SEQ ID NO: 20) and the NGSR.N1218-1 mutant (SEQ ID NO: 12) were tested for pesticidal activity against the Colorado potato beetle (CPB).

Briefly, the mutants provided herein include: mutants comprising a second trypsin cleavage site (i.e., NGSR (SEQ ID NO: 14)) introduced into the amino acid sequence of the fragment presented in either SEQ ID NO: 6 (1218-1) or SEQ ID NO: 16 (1218-1A) or the fragment presented in SEQ ID NO: 20 (49PVD). Mutants that comprise a chymotrypsin cleavage site comprising either the amino acid sequence LKMS (SEQ ID NO: 26) or LRMS (SEQ ID NO: 48) introduced in front of (e.g., directly 5' of) the trypsin cleavage site that is naturally present in the modified polypeptide sequence; and replacement mutants in which the native trypsin site that occurs in the toxin domain of the modified polypeptide is destroyed and a chymotrypsin site (e.g., LKMS or LRMS) is introduced in its place.

The 1218-1 series of mutants disclosed herein are referred to as NGSR.N1218-1, LKMS.N1218-1, LKMS.R1218-1, LRMS.N1218-1, and LRMS.R1218-1. The amino acid sequences of these mutant polypeptides are set forth in SEQ ID NOS: 12, 22, 24, 42, and 44 respectively. The invention also provides a second series of mutant polypeptides (SEQ ID NOS: 30, 32, 34, 42, and 46) in which the above-described addition (trypsin or chymotrypsin cleavage sites) and replacement (a chymotrypsin cleavage site instead of the trypsin site) mutations were introduced into the truncated polypeptide (e.g., 49PVD) set forth in SEQ ID NO: 20. This series of mutants are referred to as NGSR.N49PVD, LKMS.N49PVD, LKMS.R49PVD, LRMS.N49PVD, and LRMS.R49PVD. The amino acid sequences of each of the 49PVD mutant polypeptides are set forth in SEQ ID NOS: 30, 32, 34, 42, and 46 respectively.

The NGSR mutants (e.g., SEQ ID NO:12 and SEQ ID NO:30) disclosed herein comprise an additional trypsin-sensitive protease site in a region of the amino acid sequence that encodes domain 1 of the polypeptide. For example, the NGSR.N1218-1 mutant (SEQ ID NO:12) comprises an NGSR sequence (SEQ ID NO:13) introduced between amino acid residues 164 and 165 of the wild-type protein (SEQ ID NO:2). This amino acid sequence provides a second trypsin-sensitive cleavage site into the mutant endotoxin encoded by SEQ ID NO: 11. More specifically, the NGSR (e.g., SEQ ID NO: 14) sequence duplicates the endogenous trypsin cleavage site that is present at the target location, thereby introducing a second protease-sensitive sight into the loop region located between alpha helices 3 and 4 of domain 1. Thus, the amino acid sequence of SEQ ID NO: 14, beginning at residue 160, reads NGSRNGSR. In contrast, amino acid positions 160-164 of the wild-type protein comprise the sequence NGSR.

While not bound by theory, it is believed that the presence of a second protease-sensitive (e.g., trypsin or chymotrypsin) site facilitates intramolecular proteolytic cleavage by enhancing the ability of helices 4 and 5 to separate from the rest of the toxin. The effects of enhancing the ability of helices 4 and 5 to separate from the rest of the toxin would be manifest as a more efficient pore-forming process and hence confer an increase in the insecticidal activity of the toxin. Indeed, the Cry8 mutants described herein (e.g., SEQ ID NO:12, 22, 24, 40, 44, 30, 32, 34, 42, and 46) show improved toxicity towards several Coleopteran pests. The data further suggests that the presence of the second protease-sensitive site produces a polypeptide that is more amenable to activation by the digestive processes of susceptible insects.

The mutagenized Cry8-like nucleotide sequences of the invention may be modified so as to change about 1, 2, 3, 4, 5, 6, 8, 10, 12 or more of the amino acids present in the primary sequence of the encoded polypeptide. Alternatively even more changes from the native sequence may be introduced, such that the encoded protein may have at least about 1% or 2%, or alternatively about 3% or about 4%, or even about 5% or more of the codons altered, or otherwise modified. It should be understood that the mutagenized Cry8-like nucleotide sequences (e.g., SEQ ID NO:12, 22, 24, 40, 44, 30, 32, 34, 42, and 46) of the present invention are intended to encompass biologically functional, equivalent peptides. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations (e.g., truncated polypeptides) and modified (e.g., mutant) forms thereof. Such variants will continue to possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78:290-293 and Czapla & Lang (1990) *J. Econ. Entomol.* 83:2480-2485, herein incorporated by reference.

Variant nucleotide sequences and proteins also encompass sequences and proteins derived from a mutagenic and recombinogenic procedure such as DNA shuffling. With such a procedure, one or more different Cry8-like coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequences of the invention may be shuffled between the Cry8-like nucleotide sequences of the invention and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the invention. The invention is not bound by a particular shuffling strategy, only that at least one nucleotide sequence of the invention, or part thereof, is involved in such a shuffling strategy. Shuffling may involve only nucleotide sequences disclosed herein or may additionally involve shuffling of any other nucleotide sequences known in the art including, but not limited to, GenBank Accession Nos. U04364, U04365, and U04366. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences isolated based on their sequence identity to the entire Cry8-like sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also, Innis et al., eds. (1990) *PCR Protocols: A Guide to Methods and Applications* (Academic Press, New York); Innis & Gelfand, eds. (1995) *PCR Strategies* (Academic Press, New York); and Innis & Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the Cry8-like sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire Cry8-like sequence disclosed herein, or one or more portions thereof, may be used as a probe capable of specifically hybridizing to corresponding Cry8-like sequences and messenger RNAs. To achieve specific hybridization under a variety of conditions, such probes include sequences that are unique among Cry8-like sequences and are preferably at least about 10 nucleotides in length, and most preferably at least about 20 nucleotides in length. Such probes may be used to amplify corresponding Cry8-like sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/ or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). Thus, isolated sequences that encode a Cry8-like protein of the invention and hybridize under stringent conditions to the Cry8-like sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence, for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers & Miller (1988) CABIOS 4:11-17; the local homology algorithm of Smith et al. (1981) *Adv. Appl. Math.* 2:482; the homology alignment algorithm of Needleman & Wunsch (1970) *J. Mol. Biol.* 48:443-453; the search-for-similarity-method of Pearson & Lipman (1988) *Proc. Natl. Acad. Sci.* 85:2444-2448; the algorithm of Karlin & Altschul (1990) *Proc. Natl. Acad. Sci. USA* 87:2264, modified as in Karlin & Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) *Meth. Mol. Biol.* 24:307-331. The ALIGN program is based on the algorithm of Myers & Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin & Altschul (1990) supra. BLAST nucleotide searches can be performed with the BLASTN program, score=100, word length=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See information available on the website ncbi.hlm.nih.gov available on the world wide web. Alignment may also be performed manually by inspection.

Unless otherwise stated, nucleotide sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. For amino acid sequences, amino acid sequence identity values provided herein refer to the value obtained using GAP Version 10 using the following parameters: % identity using GAP Weight of 8 and Length Weight of 2, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman & Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

For purposes of the present invention, comparison of nucleotide or protein sequences for determination of percent sequence identity to the Cry8-like sequences disclosed herein is preferably made using the GAP program in the Wisconsin Genetics Software Package (Version 8 or later) or any equivalent program. For GAP analyses of nucleotide sequences, a GAP Weight of 50 and a Length of 3 was used.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman & Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. The nucleotide constructs, nucleic acid, and nucleotide sequences of the invention additionally encompass all complementary forms of such constructs, molecules, and sequences. Further, the nucleotide constructs, nucleotide molecules, and nucleotide sequences of the present invention encompass all nucleotide constructs, molecules, and sequences which can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the invention also encompass all forms of nucleotide constructs including, but not limited to, single-stranded forms, double-stranded forms, hairpins, stem-and-loop structures, and the like.

A further embodiment of the invention relates to a transformed organism, preferably a transformed organism selected from the group consisting of plant and insect cells, bacteria, yeast, baculoviruses, protozoa, nematodes, and algae, comprising a DNA molecule of the invention, an expression cassette comprising the said DNA molecule, or a vector comprising the said expression cassette, preferably stably incorporated into the genome of the transformed organism.

The Cry8-like sequences of the invention are provided in expression cassettes for expression in the organism of interest. The cassette will include 5' and 3' regulatory sequences operably linked to a Cry8-like sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the Cry8-like sequence to be under the transcriptional regulation of the regulatory regions. The expression cassette may additionally contain selectable marker genes.

The expression cassette will include in the 5'-3' direction of transcription, a transcriptional and translational initiation region, a Cry8-like DNA sequence of the invention, and a transcriptional and translational termination region functional in the organism serving as a host. The transcriptional initiation region, the promoter, may be native or analogous or foreign or heterologous to the host organism. Additionally, the promoter may be the natural sequence or alternatively a synthetic sequence. By "foreign" is intended that the transcriptional initiation region is not found in the native organism into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell & Gowri (1990) *Plant Physiol.* 92: 1-11 for a discussion of host-preferred codon usage. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants are listed in Table 4 of Murray et al., supra. Methods are available in the art for synthesizing plant-preferred genes. See, for example, U.S. Pat. Nos. 5,380, 831, and 5,436,391, and Murray et al. (1989) *Nucleic Acids Res.* 17:477-498; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledenous plant cells. A particularly preferred monocotolydenous host cell is a maize host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165 (2): 233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608, 144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the present invention in plants are wound-inducible promoters. Such wound-inducible promoters, may respond to damage caused by insect feeding, and include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323: 73-76); MPI gene (Corderok et al. (1994) *Plant J.* 6(2):141-150); and the like, herein incorporated by reference.

Additionally, pathogen-inducible promoters may be employed in the methods and nucleotide constructs of the present invention. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2) 255-265; Kawamata et al. (1997) *Plant Cell Physiol.* 38(7): 792-803; Hansen et al. (1997) *Mol. Gen. Genet.* 254(3): 337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505. Such promoters can be modified, if necessary, for weak expression.

Leaf-specific promoters are known in the art. See, for example, Yamamoto et al. (1997) *Plant J.* 12(2): 255-265; Kwon et al. (1994) *Plant Physiol.* 105:357-67; Yamamoto et al. (1994) *Plant Cell Physiol.* 35(5): 773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20): 9586-9590.

Root-specific promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3): 433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents*

Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926); and Lec1 transformation (WO 00/28058). For potato transformation see Tu et al. (1998) Plant Molecular Biology 37:829-838 and Chong et al. (2000) Transgenic Research 9:71-78. Additional transformation procedures can be found in Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer & McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The nucleotide sequences of the invention may be provided to the plant by contacting the plant with a virus or viral nucleic acids. Generally, such methods involve incorporating the nucleotide construct of interest within a viral DNA or RNA molecule. It is recognized that the recombinant proteins of the invention may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the invention, may have the desired pesticidal activity. Such viral polyproteins and the nucleotide sequences that encode for them are encompassed by the present invention. Methods for providing plants with nucleotide constructs and producing the encoded proteins in the plants which involve viral DNA or RNA molecules are known in the art. See, for example, U.S. Pat. Nos. 5,889,191, 5,889,190, 5,866,785, 5,589,367 and 5,316,931; herein incorporated by reference.

The invention further relates to plant propagating material of a transformed plant of the invention including, but not limited to, seeds, tubers, corms, bulbs, leaves, and cuttings of roots and shoots.

The present invention may be used for transformation of any plant species, including, but not limited to, monocots and dicots. Examples of plants of interest include, but are not limited to, corn (Zea mays), Brassica sp. (e.g., B. napus, B. rapa, B. juncea), particularly those Brassica species useful as sources of seed oil, alfalfa (Medicago sativa), rice (Oryza sativa), rye (Secale cereale), sorghum (Sorghum bicolor, Sorghum vulgare), millet (e.g., pearl millet (Pennisetum glaucum), proso millet (Panicum miliaceum), foxtail millet (Setaria italica), finger millet (Eleusine coracana)), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Coffea spp.), coconut (Cocos nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), macadamia (Macadamia integrifolia), almond (Prunus amygdalus), sugar beets (Beta vulgaris), sugarcane (Saccharum spp.), oats, barley, vegetables, ornamentals, and conifers.

Vegetables include tomatoes (Lycopersicon esculentum), lettuce (e.g., Lactuca sativa), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo). Ornamentals include azalea (Rhododendron spp.), hydrangea (Macrophylla hydrangea), hibiscus (Hibiscus rosasanensis), roses (Rosa spp.), tulips (Tulipa spp.), daffodils (Narcissus spp.), petunias (Petunia hybrida), carnation (Dianthus caryophyllus), poinsettia (Euphorbia pulcherrima), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding a pesticidal protein of the invention may be treated with a seed protectant coating comprising a seed treatment compound, such as, for example, captan, carboxin, thiram, methalaxyl, pirimiphosmethyl, and others that are commonly used in seed treatment. In one embodiment within the scope of the invention, a seed protectant coating comprising a pesticidal composition of the invention is used alone or in combination with one of the seed protectant coatings customarily used in seed treatment.

It is recognized that the genes encoding the pesticidal proteins can be used to transform insect pathogenic organisms. Such organisms include Baculoviruses, fungi, protozoa, bacteria, and nematodes.

A gene encoding a pesticidal protein of the invention may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) *Molecular Cloning: A Laboratory Manual*, ed. Maniatis et al. (Cold Spring Harbor Laboratory Press, Cold Spring Harbor, N.Y.); Davis et al., eds. (1980) *Advanced Bacterial Genetics* (Cold Spring Harbor Laboratory Press), Cold Spring Harbor, N.Y.; and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as Rhizobium; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae.

Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* sp., *Aureobasidium* sp., *Saccharomyces* sp., and *Sporobolomyces* sp., phylloplane organisms such as *Pseudomonas* sp., *Erwinia* Sp., and *Flavobacterium* sp., and other such organisms, including *Pseudomonas aeurginosa, Pseudomonas fluorescens, Saccharomyces cerevisiae, Bacillus thuringiensis, Escherichia coli, Bacillus subtilis*, and the like.

Genes encoding the pesticidal proteins of the invention can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the invention can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60:211-218). The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60:211-218).

Expression systems can be designed so that pesticidal proteins are secreted outside the cytoplasm of gram-negative bacteria, *E. coli*, for example. Advantages of having pesticidal proteins secreted are: (1) avoidance of potential cytotoxic effects of the pesticidal protein expressed, and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153:492).

Pesticidal proteins of the invention can be fermented in a bacterial host and the resulting bacteria processed and used as a microbial spray in the same manner that *Bacillus thuringiensis* strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express *Bacillus thuringiensis* endotoxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EPA 0192319, and the references cited therein.

In the present invention, a transformed microorganism, which includes whole organisms, cells, spore(s), pesticidal protein(s), pesticidal component(s), pest-impacting component(s), mutant(s); preferably living or dead cells and cell components, including mixtures of living and dead cells and cell components, and including broken cells and cell components, or an isolated pesticidal protein, can be formulated with an acceptable carrier into a pesticidal composition(s) that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematocides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluant before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb-5.0 lb. per acre when in dry form and at about 0.01 pts.-10 pts. per acre when in liquid form.

In a further embodiment, the compositions, as well as the transformed microorganisms and pesticidal proteins, of the invention can be treated prior to formulation to prolong the pesticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as iso-propanol and ethanol; and histological fixatives, such as Bouin's fixative and Helly's fixative (see, for example, Humason, (1967) *Animal Tissue Techniques* (W.H. Freeman and Co.).

In other embodiments of the invention, it may be advantageous to treat the Cry8-like polypeptides with a protease, for example trypsin, to activate the protein prior to application of a pesticidal protein composition of the invention to the environment of the target pest. Methods for the activation of protoxin by a serine protease are well known in the art. See, for example, Cooksey (1968) *Biochem. J.* 6:445-454 and Carroll & Ellar (1989) *Biochem. J.* 261:99-105, the teachings of which are herein incorporated by reference. For example, a suitable activation protocol includes, but is not limited to, combining a polypeptide to be activated, for example a purified 1218-1 polypeptide, and trypsin at a 1/100 weight ratio 1218-1 protein/trypsin in 20 nM NaHCO3, pH 8 and digesting the sample at 36° C. for 3 hours.

The compositions, as well as the transformed microorganisms and pesticidal proteins, of the invention can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. It is generally important to obtain good control of pests in the early stages of plant growth, as this is the time when the plant can be most severely damaged. The compositions of the invention can conveniently contain another insecticide if this is thought necessary. In an embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, an inert carrier, and dead cells of a *Bacillus* strain or transformed microorganism of the invention.

The embodiments of the present invention may be effective against a variety of pests. For purposes of the present invention, pests include, but are not limited to, insects, fungi, bacteria, nematodes, acarids, protozoan pathogens, animal-parasitic liver flukes, and the like. Preferred pests are insect pests, particularly insect pests that cause significant damage, most particularly insect pests that cause significant damage to agricultural plants. By "insect pests" is intended insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens,*

*Hemileuca oliviae, Homoeosoma electellum, Hyphantia cunea, Keiferia lycopersicella, Lambdinafiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails,* and *Yponomeuta padella.*

Also, the embodiments of the present invention may be effective against insect pests including insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, especially *Diabrotica virgifera* and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus* leucopterus, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn bloth leafminer; *Anaphothrips obscrurus*, grass thrips; *Solenopsis milesta*, thief ant; *Tetranychus urticae*, two spotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, two-spotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus feurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; *Anthonomus grandis* grandis, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; Potato: *Leptinotarsa decemlineata*, Colorado potato beetle.

Furthermore, embodiments of the present invention may be effective against Hemiptera such as *Lygus hesperus, Lygus lineolaris, Lygus pratensis, Lygus rugulipennis Popp, Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster,* Coreidae, Pyrrhocoridae, Tinidae, Blostomatidae, Reduviidae, and Cimicidae.

Nematodes include plant-parasitic nematodes such as rootknot, cyst, and lesion nematodes, including *Heterodera* and *Globodera* spp; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode).

The preferred developmental stage for testing for pesticidal activity is larvae or immature forms of these above mentioned insect pests. The insects may be reared in total darkness at from about 20° C. to about 30° C. and from about 30% to about 70% relative humidity. Bioassays may be performed as described in Czapla & Lang (1990) *J. Econ. Entomol.* 83(6): 2480-2485. Methods of rearing insect larvae and performing bioassays are well known to one of ordinary skill in the art.

A wide variety of bioassay techniques is known to one skilled in the art. General procedures include addition of the experimental compound or organism to the diet source in an enclosed container. Pesticidal activity can be measured by, but is not limited to, mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTAL

Example 1

Bioassay for Testing the Pesticidal Activity of *B. thuringiensis* Strains Against Western Corn Rootworm and Southern Corn Rootworm Insect diets for Colorado potato beetle (CPB), southern corn rootworm (SCRW), and western corn rootworm (WCRW) larvae are known in the art. See, for example, Rose & McCabe (1973) *J. Econ. Entomology* 66:393, herein incorporated by reference. The insect diet is prepared and poured onto a Pittman tray. Generally 1.5 mL of diet is dispensed into each cell with an additional 150 µL of sample preparation applied to the diet surface.

Bacterial colonies from an original plate of transformants expressing the pesticidal proteins of interest are spotted on replica plates and inoculated in 5 mL 2×YT broth with 500 µL/1000 mL kanamycin antibiotic. The tubes are grown overnight. If no growth is present, the tubes are incubated for an additional 24 hours. Following incubation, the tubes are centrifuged at 3500 rpms for 5-8 minutes. The supernatant is discarded and the pellet resuspended in 1000 µL PBS. The sample is then transferred to 1.5 mL eppendorf tubes and incubated on ice until the temperature is 3 to 4° C., followed by sonication for 12-15 seconds.

Microbial culture broths (150 µL) or other samples (150 µL) are overlayed onto 1.5 mL artificial diets with a 2.54 cm² surface area. For the screening of pesticidal activity against rootworms, 25 µL of a 0.8% egg agar solution is applied to lids of the trays. The trays and lids are allowed to dry under a hood. After drying, the lids are placed on trays and incubated for 4-7 days at a temperature of 26° C. The bioassays are then scored by counting "live" versus "dead" larvae. Mortality is calculated as percentage of dead larvae out of the total larvae tested.

Example 2

Pesticidal Activity of *B. thuringiensis* Strain 1218 Lysates

Samples prepared from cultures of *B. thuringiensis* strains 1218 were tested for the presence of pesticidal activity against CPB, WCRW, and SCRW as described in Example 1. As a control, the diet was treated with phosphate-buffered saline (PBS).

To prepare each sample, an individual colony of a strain growing on an LB plate was selected and used to inoculate a tube containing 50 mL of TB medium. The tube was incubated overnight at 28° C. and 250 rpm. Following the incubation, the tube was centrifuged at 4300×g for 15 minutes. The supernatant was discarded and the pellet resuspended in 50 mL of sporulation medium. The tube was centrifuged again at 4300×g for 15 minutes. The second supernatant was discarded, and the second pellet resuspended in 50 mL of sporulation medium. The tube was then incubated for 48 hours at 28° C. and 250 rpm. Following this incubation, the tube was centrifuged at 4300×g for 15 minutes. The supernatant was discarded, and the pellet was resuspended in 10 mL of 1×M9 medium. The sample was then transferred to a 1.5 mL microfuge tube, incubated on ice until the temperature was about 3 to 4° C., and then sonicated for 12-15 seconds. For bioassays, 150 µL of a sonicated sample was used.

Sporulation medium comprises 200 mL of 5×M9 salts solution, 5 mL of salts solution, 5 mL of $CaCl_2$ solution, and $dH_2O$ to a final volume of 1 L. The solution of 5×M9 salts comprises: 64 g, $Na_2HPO_4.7H_2O$; 15 g, $KH_2PO_4$; 2.5 g, NaCl; 5 g, $NH_4Cl$; and dH2O to a final volume of 1.0 L. Salts solution comprises: 2.46 g, $MgSO_4.7H_2O$; 0.04 g, $MnSO_4.H2O$; 0.28 g, $ZnSO_4.7H2O$; 0.40 g, $FeSO_4.7H2O$; and $dH_2O$ to a final volume of 1.0 L. $CaCl_2$ solution comprises 3.66 g $CaCl_2.2H_2O$ and dH2O to a final volume of 100 ml.

Samples were tested with and without heating to determine whether the component(s) responsible for the pesticidal activity is heat stable. For the heat treatment, the samples were boiled for 15 minutes prior to use in the bioassay. Unheated samples prepared from strain 1218 exhibited pesticidal activity against western corn rootworm, with lesser pesticidal activity against southern corn rootworm. The samples prepared from strain 1218 lysates caused moderate stunting in the southern corn rootworm larvae. Following heating, the samples had greatly reduced pesticidal activity against both species of rootworms.

The reduction in pesticidal activity following heating indicated that the one or more components of the sample from strain 1218 that is responsible for the pesticidal activity is heat labile. Such a reduction is consistent with one or more of the components being a protein.

Example 3

Pesticidal Activity of Crystal Proteins Isolated from *B. thuringiensis* Strain 1218

Using samples of sporulated cultures of *B. thuringiensis* strain 1218 prepared as described in Example 2, crystal proteins were isolated and then trypsin-treated using methods known in the art. Briefly, after purification (zonal gradient centrifugation, Renografin-76), the purified crystals were dissolved in alkaline buffer (50 mM $Na_2CO_3$, 10 mM dithiothreitol, pH 10). Prior to use in the assays, the dissolved crystal proteins were concentrated by filtration with Centriprep® (Millipore Corp.) centrifugal filter units with a MW cutoff of 10,000.

It is recognized that under some experimental conditions, it may be advantageous to treat the Cry8-like polypeptides with a protease, for example trypsin, to activate the protein prior to determining the pesticidal activity of a particular sample. Methods for the activation of protoxin by a serine protease are well known in the art. See, for example, Cooksey (1968) *Biochem J.* 6:445-454 and Carroll and Ellar (1989) *Biochem J.* 261:99-105; herein incorporated by reference. Isolated crystal proteins were screened for pesticidal activity against western corn rootworm larvae as described in Example 1. Both a new crystal protein preparation and a previously made preparation ("old preparation") from strain 1218 possessed substantial pesticidal activity against western corn rootworms. Dissolved crystal proteins were stored at −80° C. for 20 days before use in the assays.

A skilled artisan will acknowledge that there are numerous indicators of pesticidal activity and that variables such as number of dead insects, or average weight of treated insects can be monitored. For example, pesticidal activity can be conveniently expressed as % mortality, which is the percentage of dead rootworm larvae out of the total number of larvae.

Example 4

Nucleotide Sequences Isolated from *B. thuringiensis* Strain 1218

An effort was undertaken to isolate the nucleotide sequences that encode the crystal proteins from *B. thuringiensis* strain 1218. Two nucleotide sequences were isolated from 1218 that have nucleotide sequence and amino acid sequence homology to Cry8Ba1 (GenBank Accession No. U04365). The two Cry8-like coding sequences isolated from strain 1218 have been designated Cry1218-1 (SEQ ID NO: 1) and Cry1218-2 (SEQ ID NO: 3). SEQ ID NO: 27 and SEQ ID NO: 28 provide the nucleic acid sequences of native genomic clones of Cry1218-1 and Cry1218-2, respectively.

To determine if the proteins encoded by variant or mutant polynucleotides of the invention encode proteins with pesticidal activity, each of the nucleic acid sequence was expressed in *Escherichia coli*. For example, to determine if the 1218-1 or 1218-2 polynucleotide sequences provided herein encode polypeptides with pesticidal activity, truncated nucleotide sequences were prepared. SEQ ID NO: 15 corresponds to nucleotides 1 through 2007 of the nucleotide sequence of Cry1218-1 (SEQ ID NO: 1). SEQ ID NO: 17 corresponds to nucleotides 1 through 2019 of the nucleotide sequence of Cry1218-2 (SEQ ID NO: 3).

SEQ ID NOS: 15 and 17 encode truncated Cry8-like polypeptides having the amino acid sequences set forth in SEQ ID NO: 16 and 18, respectively. Each of the truncated nucleotide sequences (SEQ ID NOs: 15 and 17) was separately cloned into a pET28a expression vector and then used to transform *E. coli*. Transformed colonies were selected and grown in liquid culture as described in Example 1. The expressed, N-terminal-His-tagged, truncated Cry8-like proteins were isolated from *E. coli* lysates by affinity chromatography using a Nickel affinity column. The column fractions with the protein of interest were dialyzed extensively against 10 mM Tris-HCl (pH 8.5) and then concentrated using Centriprep® (Millipore Corp.) centrifugal filter units with a MW cutoff of 10,000 according to the manufacturer's directions. The concentrated Cry8-like protein samples were tested for the presence of pesticidal activity against western corn rootworm as described in Example 1.

Bioassays evaluating the pesticidal activity of recombinant Cry8-like proteins purified from *E. coli-expressed* preparations were conducted as described in Example 1 with the aqueous protein samples overlaid on the surface of the rootworm diet. The pesticidal activity of wild-type (e.g., native) and mutant endotoxin were assessed against southern corn rootworms. As expected, it was observed that the pesticidal activity decreased as the concentration of the truncated Cry8-like proteins applied to the diet decreased.

Pesticidal activity was also assessed by incorporating the pesticidal proteins into the rootworm diet, as opposed to the method described above, which involved incorporating a protein-containing solution into the diet mixture. For example, sample diets comprising 1000, 500, 400, 300, 200, or 100 ppm of a pesticidal polypeptide incorporated into the diet were assessed.

Example 5

Preparation of a Plant-Preferred Nucleotide Sequence Encoding a Pesticidal Protein Because codon usage is different between plants and bacteria, the expression in a plant of a protein encoded by nucleotide sequence of bacterial origin can be limited due to translational inefficiency in the plant. It is known in the art that expression can be increased in a plant by altering the coding sequence of the protein to contain plant-preferred codons. For optimal expression of a protein in a plant, a synthetic nucleotide sequence may be prepared using the amino acid sequence of the protein and back-translating the sequence using plant-preferred codons.

Using such an approach, a portion of the amino acid sequence of the protein encoded by Cry1218-1 (SEQ ID NO: 2) was back-translated using maize-preferred codons. The resulting plant-preferred nucleotide sequence is set forth in SEQ ID NO: 9. The nucleotide sequence set forth in SEQ ID NO: 9 encodes a polypeptide (SEQ ID NO: 10) that comprises the first 669 amino acids of the amino acid sequence set forth in SEQ ID NO: 2. Thus, SEQ ID NOS: 10 and 16 encode polypeptides comprising the same amino acid sequence, and SEQ ID NO: 15 provides a second polynucleotide that encodes the amino acid sequences set forth in SEQ ID NO: 10.

Example 6

Bioassay for Testing the Pesticidal Activity of Mutant Cry8-Like Polypeptides against Colorado Potato Beetle (*Leptinotarsa decemlineata*)

Protocol

Briefly, bioassay parameters were as follows: Bio-Serv diet (catalog number F9800B, from: BIOSERV, Entomology Division, One 8$^{th}$ Street, Suite 1, Frenchtown, N.J. 08825) was dispensed in 128-well Pitman trays (catalog number BIO-BA-128 from CD International, Pitman, N.J. 08071) having a surface area of 2.4 cm$^2$. Cry 8-like samples (1218-1A, 49PVD, and NGSR1218-1) were applied topically to the diet surface at a rate of 50 μl/well. Enough sample material was supplied to provide for 4 observations/sample. After the sample dried, 2 Colorado potato beetle neonates were added to each well. Therefore, there was a total of 8 larvae/sample. A lid was placed on each tray (catalog number BIO-CV-16, CD International, Pitman, N.J., 08071) and the trays were placed in an incubator at 25° C.

The assay trays showed no surface contamination present in the buffer controls or the wells that contained Cry8-like samples. The test was scored for mortality on the 4$^{th}$ day following live infesting.

TABLE 1

Pesticidal Activity of Truncated 1218-1 Polypeptides and a Trypsin Addition-Mutant against Colorado Potato Beetle

| Code | Samples | Protein (mg/ml) | Mortality | |
|------|---------|-----------------|-----------|------|
| A | a-buffer | | 1/8 | 13% |
| B | b-1218-1A | 0.05 | 7/8 | 88% |
| C | c-1218-1A | 0.025 | 7/8 | 88% |
| D | d-1218-1A | 0.013 | 4/6 | 67% |
| F | f-49PVD | 0.1 | 8/8 | 100% |
| G | g-49PVD | 0.05 | 4/8 | 50% |
| H | h-49PVD | 0.025 | 8/8 | 89% |
| L | l-NGSR1218-1 | 0.1 | 8/8 | 100% |
| M | m-NGSR1218-1 | 0.05 | 8/8 | 100% |
| N | n-NGSR1218-1 | 0.025 | 8/8 | 100% |

Results

The sample labeled "A" in Table 1 is a control sample consisting of 10 mM carbonate buffer at pH 10. All of the truncated and mutant protein samples 1218-1A (b-d), 49PVD (f-h), and NGSR1218-1 (1-n) were solubilized in 10 mM carbonate buffer at pH 10.

The 1218-1A samples, b-d, comprise a truncated polypeptide sequence comprising the amino acid sequence set forth in SEQ ID NO: 16. More specifically, the 1218-1A samples comprise the truncated toxin domain represented by amino acid (aa) residue 1 to aa 669 (from M to E) of the amino acid sequences set forth in SEQ ID NO: 2.

The 49PVD samples, f-h, comprise a mutant polypeptide sequence having an amino acid sequence that is set forth in SEQ ID NO: 20. 49PVD was generated by trimming sequence from both the N-terminus and the C-terminus of the sequence set forth in SEQ ID NO: 16. More specifically, the N-terminus of the 49PVD mutant was trimmed by 47 residues; thus, the polypeptide starts at aa residue 48(M) and the C-terminus was trimmed by 6 residues up to aa 663(D). Therefore mutant 49PVD is 1218-1A (SEQ ID NO: 16) from aa residue 48 to aa 663.

The NGSR samples, l-m, comprise a 1218-1 mutant polypeptide sequence that is set forth in SEQ ID NO: 12. NGSR1218-1 was generated by the addition of an NGSR motif to the amino acid sequence set forth in SEQ ID NO: 16 after aa 164. More specifically, the NGSR mutant provides a 1218-1A mutant that includes the amino acid sequence NGSR between aa 164 and aa 165 of the sequence set forth in SEQ ID NO: 16. The addition of 4 residues to 1218-1A generated a protein with 673 aa. Bioassays of 1218-1A, 49PVD, and NGSR1218-1 indicated that all three protein samples are efficacious against Colorado potato beetle (CPB). Mutant NGSR1218-1 was found to be more potent that the parent 1218-1A and 49PVD mutant. The modified (e.g., truncated or mutant) 1218-1 polypeptides (49PVD, NGSR1218-1) were at least as active as the relevant 1218-1 or 1218-1A control sample.

Example 7

Bioassay for Testing the Pesticidal Activity of Mutant Cry8-Like Polypeptides against Southern Corn Rootworm and Western Corn Rootworm Protocol Briefly, the assay parameters described above in Example 6 were modified to allow for the evaluation of the pesticidal activity of additional 1218-1, 1218-1A or 49PVD mutants against western corn rootworm (WCRW) and southern corn rootworm (SCRW). Briefly, Bio-Serv diet (catalog number F9800B, from: BIOSERV, Entomology Division, One $8^{th}$ Street, Suite 1, Frenchtown, N.J. 08825) was dispensed in 128-well Pitman trays (catalog number BIO-BA-128 from CD International, Pitman, N.J. 08071) having a surface area of 2.4 $cm^2$.

Cry 8-like samples were applied topically to the diet surface at a volume of 50 μl/well. Enough sample material was supplied to provide for replicate observations/sample. For the screening of pesticidal activity against rootworms, 25 μL of a 0.8% egg agar solution is applied to lids of the trays. The trays and lids are allowed to dry under a hood. After drying, the lids are placed on trays and incubated for 4-7 days at a temperature of 26° C. A lid was placed on each tray (catalog number BIO-CV-16, CD International, Pitman, N.J., 08071), and the trays were placed in an incubator at 25° C.

For the evaluation of pesticidal activity against SCRW, insects were exposed to a solution comprising either buffer (50 mM carbonate buffer (pH 10) or a 1218-1 or 1218-1A mutant polypeptide (e.g., 1218-1A), LKMS.N1218-1 (SEQ ID NO:22), LKMS.R1218-1 (SEQ ID NO:24), NGSR.N1218-1 (SEQ ID NO: 12), LKMS.N49PVD (SEQ ID NO:32), LKMS.R49PVD (SEQ ID NO:34), or NGSR.N49PVD (SEQ ID NO:30) at a doses of either 36 or 3.6 .mu.g/cm.sup.2.

For the evaluation of pesticidal activity against WCRW, insects were exposed to a solution comprising either buffer (50 mM carbonate buffer (pH 10) or to a limited number of the mutant 1218-1 polypeptides (LKMS.R1218-1 (SEQ ID NO:24), NGSR.N1218-1 (SEQ ID NO:12), LKMS.N49PVD (SEQ ID NO:32), LKMS.R49PVD (SEQ ID NO:34), or NGSR.N49PVD (SEQ ID NO:30) at 88.mu.g/cm.sup.2. The bioassays are then scored by counting "live" versus "dead" larvae. Mortality is calculated as percentage of dead larvae out of the total larvae tested.

TABLE 2

Pesticidal Activity of Cry1218-1 Mutant Polypeptides against Southern Corn Rootworm- Replicate 1

| POLYPEPTIDE | DOSE | % MORTALITY | DOSE | % MORTALITY |
|---|---|---|---|---|
| 1218-1A | 36 μg/$cm^2$ | 0 | 3.6 μg/$cm^2$ | 3 |
| LKMS.N 1218-1 | 36 μg/$cm^2$ | 6 (no protein) | 3.6 μg/$cm^2$ | 4 |
| LKMS.R 1218-1 | 36 μg/$cm^2$ | 89 | 3.6 μg/$cm^2$ | 27 |
| NGSR.N 1218-1 | 36 μg/$cm^2$ | 80 | 3.6 μg/$cm^2$ | 8 |
| 50 mM Carbonate Buffer (pH 10) | — | 0 | — | 0 |
| 49PVD | 36 μg/$cm^2$ | 3 | 3.6 μg/$cm^2$ | 3 |
| LKMS.N49PVD | 36 μg/$cm^2$ | 69 | 3.6 μg/$cm^2$ | 11 |
| LKMS.R49PVD | 36 μg/$cm^2$ | 60 | 3.6 μg/$cm^2$ | 17 |

TABLE 3

Pesticidal Activity of Cry1218-1 Mutant Polypeptides against Southern Corn Rootworm- Replicate 2

| POLYPEPTIDE | DOSE | % MORTALITY | DOSE | % MORTALITY |
|---|---|---|---|---|
| 1218-1A | 36 μg/$cm^2$ | 3 | 3.6 μg/$cm^2$ | 0 |
| LKMS.N 1218-1 | 36 μg/$cm^2$ | 75 | 3.6 μg/$cm^2$ | 20 |
| LKMS.R 1218-1 | 36 μg/$cm^2$ | 77 | 3.6 μg/$cm^2$ | 23 |
| NGSR.N 1218-1 | | | | |
| 50 mM Carbonate Buffer (pH 10) | — | 0 | — | 0 |
| 49PVD | 36 μg/$cm^2$ | 0 | 3.6 μg/$cm^2$ | 2 |
| LKMS.N49PVD | 36 μg/$cm^2$ | 83 | 3.6 μg/$cm^2$ | 0 |
| LKMS.R49PVD | 36 μg/$cm^2$ | 62 | 3.6 μg/$cm^2$ | 3 |
| NGSR.N49PVD | 36 μg/$cm^2$ | 81 | 3.6 μg/$cm^2$ | 25 |

TABLE 4

Pesticidal Activity of Cry1218-1 Mutant Polypeptides against Southern Corn Rootworm- Replicate 3

| POLYPEPTIDE | DOSE | % MORTALITY | DOSE | % MORTALITY |
|---|---|---|---|---|
| 1218-1A | 36 μg/cm² | 2 | 3.6 μg/cm² | 0 |
| LKMS.N 1218-1 | — | — | — | — |
| LKMS.R 1218-1 | 36 μg/cm² | 74 | 3.6 μg/cm² | 15 |
| NGSR.N 1218-1 | 36 μg/cm² | 65 | 3.6 μg/cm² | 17 |
| 50 mM Carbonate Buffer (pH 10) | — | 0 | — | 0 |
| 49PVD | 36 μg/cm² | 0 | 3.6 μg/cm² | 0 |
| LKMS.N49PVD | 36 μg/cm² | 70 | 3.6 μg/cm² | 5 |
| LKMS.R49PVD | 36 μg/cm² | 57 | 3.6 μg/cm² | 4 |
| NGSR.N49PVD | 36 μg/cm² | 81 | 3.6 μg/cm² | 28 |

TABLE 5

Pesticidal Activity of Cry1218-1 Mutant Polypeptides against Western Corn Rootworm

| POLYPEPTIDE | DOSE | % MORTALITY |
|---|---|---|
| 1218-1A | | |
| LKMS.N 1218-1 | | |
| LKMS.R 1218-1 | 88 μg/cm² | 16 |
| NGSR.N 1218-1 | 88 μg/cm² | 14 |
| 50 mM Carbonate Buffer (pH 10) | — | 4 |
| 49PVD | 88 μg/cm² | |
| LKMS.N49PVD | 88 μg/cm² | 7 |
| LKMS.R49PVD | 88 μg/cm² | 12 |
| NGSR.N49PVD | 88 μg/cm² | 10 |

TABLE 6

Pesticidal Activity of Cry1218-1 Mutant Polypeptides against Western Corn Rootwoom

| POLYPEPTIDE | DOSE (μg/cm²) | AVERAGE LARVAE WT (μg) TRAY 1 | TRAY 2 | AVG | NUMBER OF LARVAE WEIGHED TRAY 1 | TRAY 2 | AVG | % MORTALITY TRAY 1 | TRAY 2 | AVG |
|---|---|---|---|---|---|---|---|---|---|---|
| 1218-1A | 193 | 161 | 140 | 150.5 | 74 | 65 | 69.5 | 9 | 9 | 9 |
| NGSR.N 1218-1 | 193 | 92 | 83 | 99 | 60 | 60 | 60 | 24 | 12 | 18 |
| LKMS.R 1218-1 | 193 | 92 | 106 | 99 | 48 | 49 | 48.5 | 20 | 13 | 16.5 |
| 49PVD | 220 | 129 | 166 | 147.5 | 79 | 71 | 75 | 6 | 2 | 4 |
| NGSR.N 49PVD | 220 | 67 | 76 | 71.5 | 39 | 58 | 48.5 | 22 | 7 | 14.5 |
| LKMS.R 49PVD | 220 | 92 | 94 | 93 | 49 | 32 | 40.5 | 20 | 17 | 18.5 |
| LKMS.N 49PVD | 220 | 82 | 80 | 81 | 44 | 41 | 42.5 | 28 | 16 | 22 |
| 50 Mm Carbonate | 220 | 165 | 164 | 164.5 | 80 | 95 | 87.5 | 4 | 0 | 2 |
| Diet | 220 | 171 | 132 | 151.5 | 78 | 78 | 78 | 1 | 6 | 3.5 |

Example 8

Transformation of Maize by Particle Bombardment and Regeneration of Transgenic Plants Immature maize embryos from greenhouse donor plants are bombarded with a plasmid containing the plant-optimized Cry1218-1 nucleotide sequence (SEQ ID NO: 9) operably linked to a ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the plant-optimized Cry1218-1 nucleotide sequence (SEQ ID NO: 9) operably linked to a ubiquitin promoter is made. For example, a suitable transformation vector comprises a UBI1 promoter from *Zea mays*, a 5' UTR from UBI1 and a UBI1 intron, in combination with a PinII terminator. A plasmid DNA comprising the plant-optimized nucleotide sequence and a second plasmid DNA containing a PAT selectable marker (e.g., CAMV35S (ACK) promoter driving PAT with a CAMV35S terminator) is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to a tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total often aliquots taken from each tube of prepared particles/DNA.

Subsequent Treatment Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5° pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the Cry1218-1 protein by assays known in the art, such as, for example, immunoassays and western blotting with an antibody that binds to the Cry1218-1 protein.

Bombardment and Culture Media

Bombardment medium (560Y) comprises 4.0 g/l N6 basal salts (SIGMA C-1416), 1.0 ml/l Eriksson's Vitamin Mix (100× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-1$H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-1$H_2O$ following adjustment to pH 5.8 with KOH); 3.0 g/l Gelrite (added after bringing to volume with D-1$H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l Glycine brought to volume with polished D-1$H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-1$H_2O$ after adjusting to pH 5.6); 3.0 g/l Gelrite (added after bringing to volume with D-1$H_2O$); and 1.0 mg/l indoleacetic acid and 3.0 mg/l Bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l Glycine brought to volume with polished D-1$H_2O$), 0.1 g/l myo-inositol, and 40.0 g/l sucrose (brought to volume with polished D-1$H_2O$ after adjusting pH to 5.6); and 6 g/l bacto-agar (added after bringing to volume with polished D-1$H_2O$), sterilized and cooled to 60° C.

Example 9

*Agrobacterium*-Mediated Transformation of Maize and Regeneration of Transgenic Plants For *Agrobacterium*-mediated transformation of maize with a plant-optimized Cry1218-1 nucleotide sequence (SEQ ID NO: 9), preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the plant-optimized Cry 218-1 nucleotide sequence (SEQ ID NO: 9) to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

That which is claimed:

1. An isolated pesticidal polypeptide comprising at least 90% sequence identity to the amino acid sequence set forth in SEQ ID NO: 6, 20, 12, 22, 24, 40, 44, 30, 32, 34, 42, or 46, and wherein said polypeptide encoded by said amino acid sequences is pesticidal for at least one pest selected from the group consisting of western corn rootworm, southern corn rootworm, and Colorado potato beetle.

2. A pesticidal composition comprising at least one polypeptide according to claim 1 in combination with a carrier.

3. A method for impacting an insect pest comprising applying the pesticidal composition according to claim 2 to an environment of the insect pest by a procedure comprising spraying, dusting, broadcasting, or seed coating.

4. The method according to claim 1, wherein said insect pest is selected from the group consisting of Colorado potato beetle, western corn rootworm, and southern corn rootworm.

5. The isolated pesticidal polypeptide of claim 1, wherein said polypeptide comprises at least 95% sequence identity to the amino acid sequence set forth in SEQ ID NO: 6, 20, 12, 22, 24, 40, 44, 30, 32, 34, 42, or 46.

6. The isolated pesticidal polypeptide of claim 1, wherein said polypeptide comprises the amino acid sequence set forth in SEQ ID NO: 6, 20, 12, 22, 24, 40, 44, 30, 32, 34, 42, or 46.

7. The pesticidal composition of claim 2, wherein said pesticidal composition comprises at least one polypeptide comprising 95% sequence identity to SEQ ID NO: 6, 20, 12, 22, 24, 40, 44, 30, 32, 34, 42, or 46.

8. The pesticidal composition of claim 2, wherein said pesticidal composition comprises at least one polypeptide comprising the amino acid sequence set forth in SEQ ID NO: 6, 20, 12, 22, 24, 40, 44, 30, 32, 34, 42, or 46.

9. The method of claim 3, wherein said pesticidal composition comprises at least one polypeptide comprising 95% sequence identity to SEQ ID NO: 6, 20, 12, 22, 24, 40, 44, 30, 32, 34, 42, or 46.

10. The method of claim 3, wherein said pesticidal composition comprises at least one polypeptide comprising the amino acid sequence set forth in SEQ ID NO: 6, 20, 12, 22, 24, 40, 44, 30, 32, 34, 42, or 46.

11. The method according to claim 9, wherein said insect pest is selected from the group consisting of Colorado potato beetle, western corn rootworm, and southern corn rootworm.

12. The method according to claim 10, wherein said insect pest is selected from the group consisting of Colorado potato beetle, western corn rootworm, and southern corn rootworm.

* * * * *